United States Patent
Dorwald et al.

(10) Patent No.: US 7,208,497 B2
(45) Date of Patent: Apr. 24, 2007

(54) SUBSTITUTED PIPERAZINES AND DIAZEPANES

(75) Inventors: Florencio Zaragoza Dorwald, Ballerup (DK); Knud Erik Andersen, Brøndby (DK); Jan Lindy Sørensen, Brøndby (DK)

(73) Assignee: Novo Nordisk A/S, Bagsvaerd (DK)

(*) Notice: Subject to any disclaimer, the term of this patent is extended or adjusted under 35 U.S.C. 154(b) by 113 days.

(21) Appl. No.: 10/185,861

(22) Filed: Jun. 27, 2002

(65) Prior Publication Data

US 2004/0019039 A1 Jan. 29, 2004

Related U.S. Application Data

(60) Provisional application No. 60/342,871, filed on Dec. 17, 2001, provisional application No. 60/304,371, filed on Jul. 10, 2001.

(30) Foreign Application Priority Data

Jul. 2, 2001 (DK) .................. 2001 01046
Dec. 14, 2001 (DK) .................. 2001 01878

(51) Int. Cl.
A61K 31/495 (2006.01)
A61K 31/496 (2006.01)
C07D 295/185 (2006.01)
C07D 405/06 (2006.01)
C07D 401/04 (2006.01)
C07D 405/04 (2006.01)
C07D 405/14 (2006.01)

(52) U.S. Cl. ............... 514/254.11; 514/255.01; 514/254.01; 514/218; 540/575; 544/360; 544/364; 544/371; 544/372; 544/376; 544/377; 544/387; 544/388; 544/390; 544/391

(58) Field of Classification Search ............ 544/372, 544/377, 387–388, 391; 514/254.01, 254.11, 514/255.01
See application file for complete search history.

(56) References Cited

U.S. PATENT DOCUMENTS

| | | | | |
|---|---|---|---|---|
| 2,724,713 A | | 11/1955 | Goldman et al. | ......... 260/268 |
| 3,957,779 A | * | 5/1976 | Seng et al. | ......... 544/183 |
| 4,241,062 A | * | 12/1980 | Hannah | ......... 514/197 |
| 4,308,382 A | | 12/1981 | Zenitz | ......... 544/162 |
| 4,474,783 A | * | 10/1984 | Robba et al. | ......... 514/252.12 |
| 5,756,730 A | * | 5/1998 | Terada et al. | ......... 544/60 |
| 6,316,475 B1 | | 11/2001 | Bennani et al. | ......... 514/343 |
| 6,723,730 B2 | * | 4/2004 | Bakthavatchalam et al. | ......... 514/284 |

FOREIGN PATENT DOCUMENTS

| | | |
|---|---|---|
| DE | 2 141 634 | 2/1972 |
| DE | 2 360 362 | 6/1974 |
| DE | 2304155 | 8/1974 |
| DE | 19621221 A1 | 11/1997 |
| EP | 0203743 B1 | 2/1991 |
| EP | 0978512 A1 | 2/2000 |
| JP | 57-7459 * | 1/1982 |
| WO | WO 81/02421 | 9/1981 |
| WO | WO 92/02498 | 2/1992 |
| WO | WO 95/00512 | 5/1995 |
| WO | WO 97/17345 | 5/1997 |
| WO | WO 99/42458 | 8/1999 |
| WO | WO 00/51984 | 9/2000 |
| WO | WO 00/76970 A2 | 12/2000 |
| WO | WO 01/44191 A2 | 6/2001 |
| WO | WO 01/66534 A2 | 9/2001 |
| WO | WO 01/74773 A2 | 10/2001 |
| WO | WO 01/74810 A2 | 10/2001 |
| WO | WO 01/74813 A2 | 10/2001 |
| WO | WO 01/74814 A2 | 10/2001 |
| WO | WO 01/74815 A2 | 10/2001 |
| WO | WO 02/012190 A3 | 2/2002 |

OTHER PUBLICATIONS

Phillips et al. Annual Reports in medicinal Chemistry, vol. 33, p. 31-40 (1998).*
Passani et al. Neuroscience and Biobehavioral Reviews, vol. 24, p. 107-113 (2000).*
Leurs et al. TIPS, vol. 19, p. 177-183 (1998).*
Kyoto Pharmaceutical, Chemical Abstract, vol. 96, No. 217485, (1982) Abstract for JP 57007459 (Jan. 14, 1982).*
Mignot et al. Nature Neuroscience Supplement, vol. 5, p. 1071-1075 (2002).*
Tozer et al., Ashley Publications Ltd., pp. 1045-1055 (2000).
Walczynski et al., Arch. Pharm. Pharm. Med. Chem., pp. 389-398 (1999).
Linney et al., J. Med. Chem., vol. 43, pp. 2362-2370 (2000).
Ganellin et al., Arch. Pharm. Pharm. Med. Chem., pp. 395-404 (1998).

(Continued)

*Primary Examiner*—Emily Bernhardt
(74) *Attorney, Agent, or Firm*—Rosemarie Wilk-Orescan; Reza Green; Richard W. Bork

(57) ABSTRACT

A novel class of substituted piperazines and diazepanes, pharmaceutical compositions comprising them and use thereof in the treatment of diseases and disorders related to the histamine H3 receptor. More particularly, the compounds are useful for the treatment of diseases and disorders in which an interaction with the histamine H3 receptor is beneficial.

28 Claims, No Drawings

OTHER PUBLICATIONS

Walczynski et al., Elsevier Science S.A., vol. 54, pp. 684-694 (1999).
Nishi et al., Chem. Pharm. Bull., vol. 31, pp. 852-860 (1983).
Dauzonne et al. Eur. J. Med. Chem., vol. 30, pp. 53-59 (1995).
Vejdelek et al., Collection Czechoslovak Chem. Commun., vol. 48, pp. 2977-2988 (1983).
Valenta et al., Collect. Czech. Chem. Commun., vol. 55, pp. 1613-1629 (1990).
Stark et al., Drugs of the Future, vol. 21, No. 5, pp. 507-520 (1996).
Leurs et al., Progress in Drug Research, vol. 45, pp. 107-165 (1995).
Lovenberg et al., Molecular Pharmacology, vol. 55, pp. 1101-1107 (1999).
Morisset et al., Letters to Nature, vol. 408, pp. 860-864 (2000).
Tiwari et al., Drug Design and Discovery, vol. 12, pp. 249-258 (1995).
Brown et al., J. Am. Chem. Soc., vol. 119, pp. 3288-3295 (1997).
Gayral et al., Arzneim.-Forsch./Drug Res. vol. 45 (II), No. 10, pp. 1122-1127 (1995).
Abstract CA 59:13982a (2002), Christensen et al.
Abstract JP Patent No. JP 57175168 A2.
Abstract JP Patent No. JP 57002274 A2.
Baba et al., J. Med. Chem., vol. 21, No. 6, pp. 525-529 (1978).
Dahlbom et al., Acta Chem Scand., vol. 15, No. 6, pp. 1367-1371 (1961).
Harfenist, J. Am. Chem. Soc., vol. 76, pp. 4991-4993 (1954).
Mndzhoyan et al., Chemical Abstracts, vol. 70, No. 21 (1969).
Petigara et al., J. Med. Chem., American Chemical Society, vol. 11, pp. 332-336 (1968).
Zlatoidsky et al. Eur. J. Med. Chem., vol. 31, No. 11, pp. 895-899 (1996).

* cited by examiner

SUBSTITUTED PIPERAZINES AND DIAZEPANES

CROSS-REFERENCE TO RELATED APPLICATIONS

This application claims priority of U.S. provisional application Nos. 60/304,371 filed Jul. 10, 2001 and 60/342,871 filed Dec. 17, 2001 and claims priority of Danish application Nos. PA 2001 01046 filed Jul. 2, 2001 and PA 2001 01878 filed Dec. 14, 2001, the contents of which are fully incorporated herein by reference.

FIELD OF THE INVENTION

The present invention relates to novel substituted piperazines and diazapanes, to the use of these compounds as pharmaceutical compositions, to pharmaceutical compositions comprising the compounds, and to a method of treatment employing these compounds and compositions. The present compounds show a high and selective binding affinity to the histamine H3 receptor indicating histamine H3 receptor antagonistic, inverse agonistic or agonistic activity. As a result, the compounds are useful for the treatment of diseases and disorders related to the histamine H3 receptor.

BACKGROUND OF THE INVENTION

The existence of the histamine H3 receptor has been known for several years and the receptor is of current interest for the development of new medicaments (see eg Stark, H.; Schlicker, E.; Schunack, W., *Drugs Fut.* 1996, 21, 507–520; Leurs, R.; Timmerman, H.; Vollinga, R. C., *Progress in Drug Research* 1995, 45, 107–165). Recently, the human histamine H3 receptor has been cloned, cf Lovenberg, T. W. et al, *Molecular Pharmacology*, June 1999, 55, 1101–1107. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor show intrinsic, constitutive activity, in vitro as well as in vivo (ie it is active in the absence of an agonist; see eg Morisset et al., *Nature* 2000, 408, 860–864). Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

Piperazines similar to the compounds of the present invention have previously been prepared, and their biological properties have been investigated.

JP 57175168, JP 01035827 and WO 81/02421 disclose the compound:

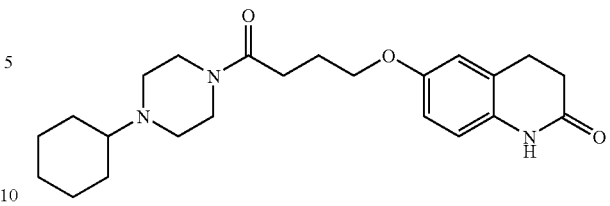

JP 63026754 discloses the compound:

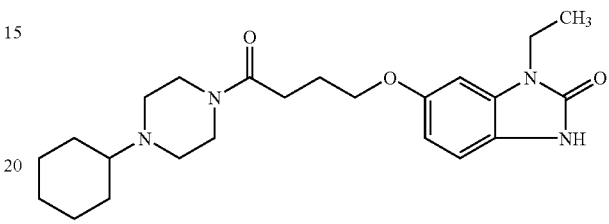

Nishi et al. (*Chem.Pharm.Bull.;* 31; 3; 1983; 852–860) disclose the compound:

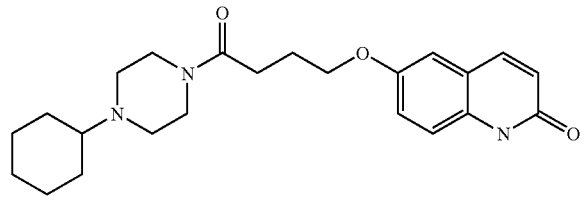

Tiwari et al. (*Drug Des. Discovery* 1995; 12(3); 249–58) and Meanwell et al. (*J. Med. Chem.* 1992; 35(14); 2688–96 disclose the compound:

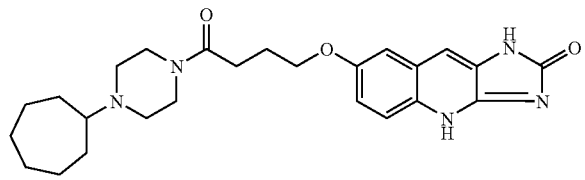

WO 95/00512 discloses the compound:

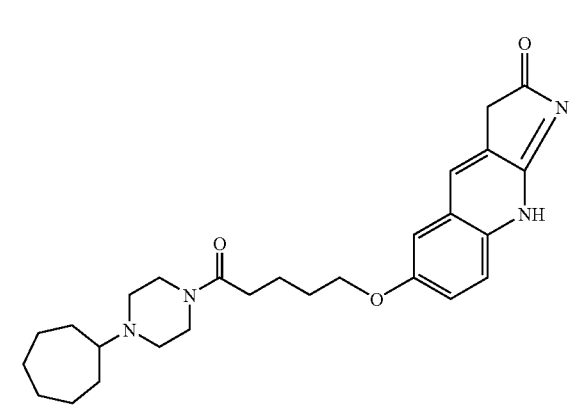

WO 00/51984 discloses indole-containing piperazine derivatives.

DE 19621221 discloses the compound:

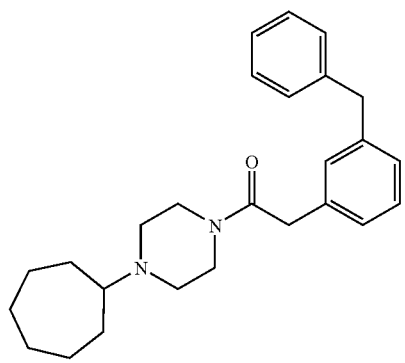

U.S. Pat. No. 2,724,713 discloses the following compound:

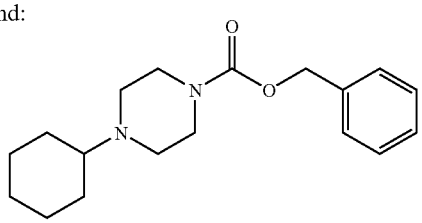

Dauzonne et al. (*J. Med. Chem. Chim. Ther.*; 30; 1; 1995; 53–60) disclose the compound:

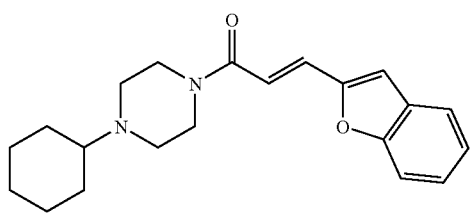

Vejdelek et al. (*Res. Inst. Pharm. Biochem. Commun.*; 48; 10; 1983; 2977–88) disclose the following compound as a potential antitussive:

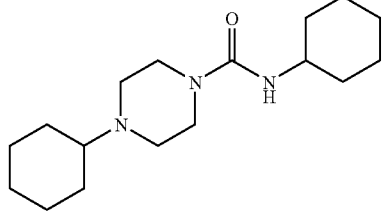

Brown et al. (*J. Am. Chem. Soc.*; 119; 14; 1997; 3288–3295) disclose the following compound:

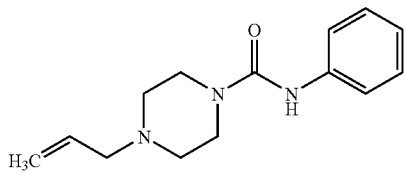

Gayral et al. (*Arzneim.-Forsch.*; 45; 10; 1995; 1122–1127) disclose the following compound:

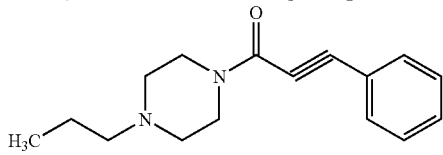

WO 00/76970 discloses the compound:

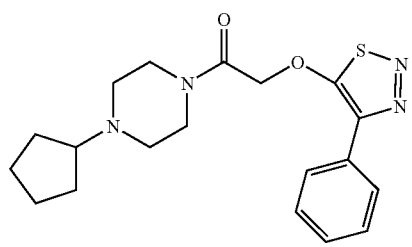

EP 0 203 743 discloses the compound:

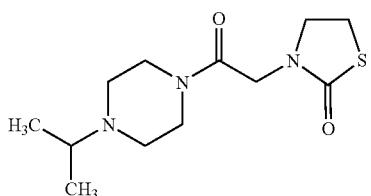

WO 92/02498 and Valenta et al. (*Collect. Czech. Chem. Commun.* 1990; 55(6); 1613–29) disclose the compound:

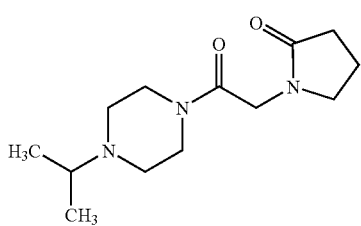

DE 2360362 discloses the compound:

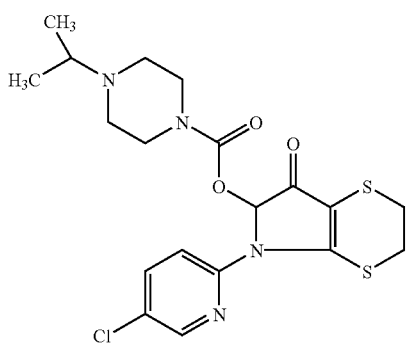

CA59:13982a discloses the compound:

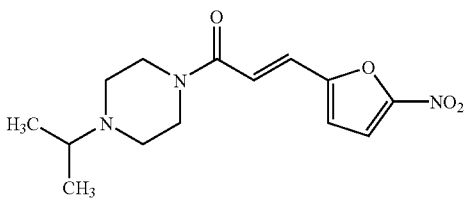

DE 2141634 discloses the compound:

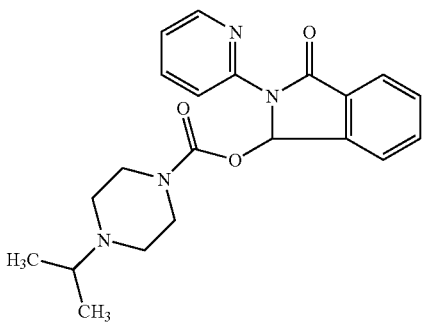

However, these references neither disclose nor suggest that these substituted piperazines may have a histamine H3 receptor antagonistic or agonistic activity.

Several publications disclose the preparation and use of histamine H3 agonists and antagonists. Most of these are imidazole derivatives (see eg Stark et al., *Drugs of the Future* 1996, 21, 507–520; Tozer, Kalinddjian, *Expert Opinion on Therapeutic Patents*, 2000, 10, 1045–1055). However, recently some imidazole-free ligands of the histamine H3 receptor have been described (see eg Walczynski et al., *Arch. Pharm. Pharm. Med. Chem.* 1999, 332, 389–398; Linney et al., *J. Med. Chem.* 2000, 43, 2362–2370; Ganellin et al., *Arch. Pharm. Pharm. Med. Chem.* 1998, 331, 395–404; Walczynski et al., *II Farmaco* 1999, 54, 684–694; WO 99/42458, EP 0 978 512, WO 97/17345, U.S. Pat. No. 6,316,475, WO 01/66534, WO 01/74810, WO 01/44191, WO 01/74815, WO 01/74773, WO 01/74813, WO 01/74814 and WO 02/12190.

However, these compounds differ structurally from the present compounds.

In view of the art's interest in histamine H3 receptor agonists, inverse agonists and antagonists, novel compounds which interact with the histamine H3 receptor would be a highly desirable contribution to the art. The present invention provides such a contribution to the art being based on the finding that a novel class of substituted piperazines has a high and specific affinity to the histamine H3 receptor.

Due to their interaction with the histamine H3 receptor, the present compounds are useful in the treatment of a wide range of conditions and disorders in which an interaction with the histamine H3 receptor is beneficial. Thus, the compounds may find use eg in the treatment of diseases of the central nervous system, the peripheral nervous system, the cardiovascular system, the pulmonary system, the gastrointestinal system and the endocrinological system.

DEFINITIONS

In the structural formulas given herein and throughout the present specification, the following terms have the indicated meaning:

The term "halogen" means F, Cl, Br or I.

The term "$C_{1-6}$-alkyl" as used herein represent a saturated, branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "$C_{3-9}$-alkyl" as used herein represent a saturated, branched or straight hydrocarbon group having from 3 to 9 carbon atoms. Typical $C_{3-9}$-alkyl groups include, but are not limited to, n-propyl, isopropyl, butyl, isobutyl, sec-butyl, tert-butyl, pentyl, isopentyl, hexyl, isohexyl, heptyl, octyl, nonyl and the like.

The term "$C_{2-6}$-alkenyl" as used herein represents a branched or straight hydrocarbon group having from 2 to 6 carbon atoms and at least one double bond. Examples of such groups include, but are not limited to, ethenyl, 1-propenyl, 2-propenyl, allyl, iso-propenyl, 1,3-butadienyl, 1-butenyl, 2-butenyl, 1-pentenyl, 2-pentenyl, 1-hexenyl, 2-hexenyl and the like.

The term "$C_{3-9}$-alkenyl" as used herein represents a branched or straight hydrocarbon group having from 3 to 9 carbon atoms and at least one double bond. Examples of such groups include, but are not limited to, 1-propenyl, 2-propenyl, allyl, iso-propenyl, 1,3-butadienyl, 1-butenyl, 2-butenyl, 1-pentenyl, 2-pentenyl, 1-hexenyl, 2-hexenyl, 1-heptenyl, 2-heptenyl, 1-octenyl, 2-octenyl, 1-nonenyl and the like.

The term "$C_{2-6}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 1-pentynyl, 2-pentynyl, 1-hexynyl, 2-hexynyl and the like.

The term "$C_{3-9}$-alkynyl" as used herein represents a branched or straight hydrocarbon group having from 3 to 9 carbon atoms and at least one triple bond. Examples of such groups include, but are not limited to, 1-propynyl, 2-propynyl, 1-butynyl, 2-butynyl, 1-pentynyl, 2-pentynyl, 1-hexynyl, 2-hexynyl, 1-heptynyl, 2-heptynyl, 1-octynyl, 2-octynyl, 1-nonynyl and the like.

The term "$C_{1-6}$-alkoxy" as used herein, alone or in combination, refers to the radical —O—$C_{1-6}$-alkyl where $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_{1-6}$-alkylthio" as used herein, alone or in combination, refers to the radical —S—$C_{1-6}$-alkyl where $C_{1-6}$-alkyl is as defined above. Representative examples are methylthio, ethylthio, isopropylthio, n-propylthio, butylthio, pentylthio and the like.

The term "$C_{1-6}$-alkylsulfonyl" as used herein, alone or in combination, refers to the radical —S(=O)$_2$—$C_{1-6}$-alkyl where $C_{1-6}$-alkyl is as defined above. Representative examples are methylsulfonyl, ethylsulfonyl, isopropylsulfonyl, n-propylsulfonyl, butylsulfonyl, pentylsulfonyl and the like.

The term "$C_{1-6}$-alkanoyl" as used herein, alone or in combination, refers to the radical —C(=O)H or —C(=O)$C_{1-6}$-alkyl where $C_{1-6}$-alkyl is as defined above. Representative examples are formyl, acetyl, propionyl, butanoyl, pentanoyl, hexanoyl, heptanoyl and the like.

The term "$C_{1-7}$-alkanoyl" as used herein, alone or in combination, refers to the radical —C(=O)H or —C(=O)$C_{1-6}$-alkyl where $C_{1-6}$-alkyl is as defined above. Representative examples are formyl, acetyl, propionyl, butanoyl, pentanoyl, hexanoyl, heptanoyl and the like.

The term "$C_{3-8}$-cycloalkyl" as used herein represents a saturated, monocyclic, carbocyclic group having from from 3 to 8 carbon atoms. Representative examples are cyclopropyl, cyclobutyl, cyclopentyl, cyclohexyl, cycloheptyl, cyclooctyl and the like.

The term "$C_{5-8}$-cycloalkenyl" as used herein represents a monocyclic, carbocyclic, non-aromatic group having from 5 to 8 carbon atoms and at least one double bond. Representative examples are cyclopentenyl, cyclohexenyl, cycloheptenyl, cyclooctenyl, and the like.

The term "aryl" as used herein is intended to include carbocyclic aromatic ring systems such as 6 membered monocyclic and 9 to 14 membered bi- and tricyclic, carbocyclic, aromatic ring systems. Representative examples are phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "aryloxy" as used herein refers to the radical —O-aryl where aryl is as defined above. Non-limiting examples are phenoxy, naphthoxy, anthracenyloxy, phenantrenyloxy, fluorenyloxy, indenyloxy and the like.

The term "heteroaryl" as used herein is intended to include heterocyclic aromatic ring systems containing one or more heteroatoms selected from nitrogen, oxygen and sulfur such as 5 to 7 membered monocyclic and 8 to 14 membered bi- and tricyclic aromatic, heterocyclic ring systems containing one or more heteroatoms selected from nitrogen, oxygen and sulfur. Representative examples are furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indanyl, indolinyl, oxazolidinyl, oxazolinyl, oxazepinyl and the like.

As used herein, the phrase "4 to 7 membered, saturated or unsaturated ring" is intended to include heterocyclic rings which are saturated or contain one or two double bonds.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

"Aryl-$C_{1-6}$-alkyl", "aryl-$C_{1-6}$-alkoxy" etc. mean $C_{1-6}$-alkyl or $C_{1-6}$-alkoxy as defined above, substituted by aryl as defined above, for example:

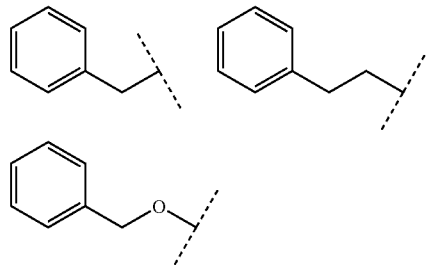

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

DESCRIPTION OF THE INVENTION

The present invention relates to a compound of the general formula (I):

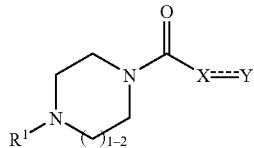

(I)

wherein

----- designates a single bond or a double bond, $R^1$ is (a) $C_3$–$C_9$-alkyl, $C_3$–$C_9$-alkenyl, $C_3$–$C_9$-alkynyl,
    which may optionally be substituted with one or more substituents selected from halogen and hydroxy, (b) $C_{3-8}$-cycloalkyl, $C_{5-8}$-cycloalkenyl, $C_{3-8}$-cycloalkyl-$C_{1-6}$-alkyl, di($C_{3-8}$-cycloalkyl)-$C_{1-6}$-alky, $C_{3-8}$-cycloalkyl-$C_{2-6}$-alkenyl, $C_{3-8}$-cycloalkyl-$C_{2-6}$-alkynyl, $C_{5-8}$-cycloalkenyl-$C_{1-6}$-alkyl, $C_{5-8}$-cycloalkenyl-$C_{2-6}$-alkenyl, $C_{5-8}$-cycloalkenyl-$C_{2-6}$-alkynyl, 4-pyridyl or tetrahydropyranyl,
    wherein the cyclic moieties may optionally be substituted with one or more substituents selected from $C_{1-6}$-alkyl, halogen, trifluoromethyl, 2,2,2-trifluoroethyl and $C_{3-8}$-cycloalkyl, X is —$(CH_2)_m$—$(Z)_n$—$(CR^2R^3)_o$—$(CH_2)_p$—$(V)_q$—, m and p independently are 0, 1, 2, 3 or 4, n, o and q independently are 0 or 1, Z and V independently are —O—, —NH—, —C(=O)—, —S—, —S(=O)—, —S(=O)$_2$—, —CH=CH— or —C≡C—, $R^2$ and $R^3$ independently are hydrogen, $C_{1-6}$-alkyl or hydroxy, Y is (a) aryl or heteroaryl, which may optionally be substituted with one or more substituents selected from
    halogen, nitro, cyano, oxo, hydroxy, $C_{1-7}$-alkanoyl, $C_{1-6}$alkylthio, $C_{1-6}$-alkylsulfonyl, $C_{1-6}$-alkyl, $C_{1-6}$-alkoxy, —C(=O)O—$C_{1-6}$-alkyl, $C_{3-8}$-cycloalkyl, trifluoromethyl, trifluoromethoxy, —$NR^4R^5$ and —O(C=O)$NR^4R^5$, or wherein two substituents in adjacent positions together form a radical —O—(CH$_2$)$_{1-3}$—O—, wherein R$^4$ and R$^5$ independently are hydrogen, C$_{1-6}$-alkyl, C$_{3-8}$-cycloalkyl, C$_{1-7}$-alkanoyl or aryl, or R$^4$ and R$^5$ together with the nitrogen atom to which they are attached form a 4 to 7 membered, saturated or unsaturated ring, aryl, aryl-C$_{1-6}$-alkyl, aryloxy and aryl-C$_{1-6}$-alkoxy, wherein the ring moieties optionally may be substituted with one or more substituents selected from halogen, nitro, cyano, hydroxy, C$_{1-7}$-alkanoyl, C$_{1-6}$-alkylthio, C$_{1-6}$-alkylsulfonyl, C$_{1-6}$-alkyl, C$_{1-5}$-alkoxy, C$_{3-8}$-cycloalkyl, trifluoromethyl, trifluoromethoxy, —NR$^8$R$^9$ and —O(C=O)NR$^6$R$^7$, or wherein two substituents in adjacent positions together form a radical —O—(CH$_2$)$_{1-3}$—O—, wherein R$^6$ and R$^7$ independently are hydrogen, C$_{1-6}$-alkyl, C$_{3-8}$-cycloalkyl, C$_{1-7}$-alkanoyl or aryl, or R$^6$ and R$^7$ together with the nitrogen atom to which they are attached form a 4 to 7 membered, saturated or unsaturated ring, (b) C$_{3-8}$-cycloalkyl or C$_{5-8}$-cycloalkenyl, which may optionally be substituted with one or more substituents selected from C$_{1-6}$-alkyl, C$_{1-6}$-alkoxy, C$_{1-6}$-alkylthio, cyano, trifluoromethyl, trifluoromethoxy and halogen, aryl and aryloxy, wherein the ring moieties optionally may be substituted with one or more substituents selected from halogen, nitro, cyano, hydroxy, C$_{1-7}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^8$R$^9$ and —O(C=O)NR$^8$R$^9$, or wherein two substituents in adjacent positions together form a radical —O—(CH$_2$)$_{1-3}$—O—, wherein R$^8$ and R$^9$ independently are hydrogen, C$_{1-6}$-alkyl, C$_{3-8}$-cycloalkyl, C$_{1-7}$-alkanoyl or aryl, or R$^8$ and R$^9$ together with the nitrogen atom to which they are attached form a 4 to 7 membered, saturated or unsaturated ring, with the proviso that when Y is selected from the group (a), the sum of m, n, o, p and q must be at least 1, and with the proviso that when R$^1$ is cyclohexyl and X is —(CH$_2$)$_3$—O—, Y must not be 1,2,3,4-tetrahydro-2-oxo-6-quinolinyl, -dihydro-2-oxo-6-quinolinyl or 3-ethyl-2,3-dihydro-2-oxo-1H-benzimidazol-5-yl, R$^1$ is cycloheptyl and X is —(CH$_2$)$_3$—O—, Y must not be 2,3-dihydro-2-oxo-1H-imidazo[4,5]-quinolin-7-yl, R$^1$ is cycloheptyl and X is —(CH$_2$)$_4$—O—, Y must not be 2,3-dihydro-2-oxo-1H-pyrrolo[2,3-b]quinolin-6-yl, Y must not be unsubstituted or substituted indolyl, R$^1$ is cycloheptyl and X is —CH$_2$—, Y must not be (3-benzyl)phenyl, R$^1$ is cyclohexyl and X is —O—CH$_2$—, Y must not be phenyl, R$^1$ is cyclohexyl and X is —CH=CH—, Y must not be benzofuran-2-yl, R$^1$ is cyclohexyl and X is —NH—, Y must not be cyclohexyl, R$^1$ is 2-propen-1-yl and X is —NH—, Y must not be phenyl, R$^1$ is n-propyl and X is —C≡C—, Y must not be phenyl, R$^1$ is cyclopentyl and X is —CH$_2$—O—, Y must not be 4-phenyl-1,2,3-thiadiazol-5-yl, R$^1$ is isopropyl and X is —CH$_2$—, Y must not be 4-oxothiazolidin-3-yl, R$^1$ is isopropyl and X is —CH$_2$—, Y must not be 2-oxopyrrolidin-1-yl, R$^1$ is isopropyl and X is —O—, Y must not be 6-(5-chloropyridin-2-yl)-2,3,6,7-tetrahydro-7-oxo-5H-1,4-dithiino[2,3-c]pyrrol-5-yl, R$^1$ is isopropyl and X is —CH=CH—, Y must not be 5-nitrofuran-2-yl, R$^1$ is isopropyl and X is —O—, Y must not be 3-oxo-2-pyridin-2-yl-2,3-dihydro-1H-isoindol-1 as well as any diastereomer or enantiomer or tautomeric form thereof including mixtures of these or a pharmaceutically acceptable salt thereof.

In one embodiment, the invention relates to a compound of the general formula (II):

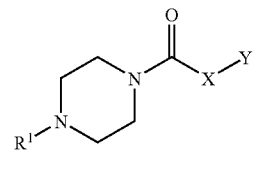

(I$_1$)

wherein R$^1$, X and Y are as defined for formula (I), as well as any diastereomer or enantiomer or tautomeric form thereof including mixtures of these or a pharmaceutically acceptable salt thereof.

In another embodiment, the invention relates to a compound of the general formula (12):

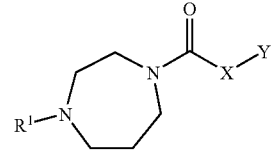

(I$_2$)

wherein R$^1$, X and Y are as defined for formula (I), as well as any diastereomer or enantiomer or tautomeric form thereof including mixtures of these or a pharmaceutically acceptable salt thereof.

In yet another embodiment, R$^1$ is C$_{3-8}$-cycloalkyl, which may optionally be substituted with one or two substituents selected from C$_{1-6}$-alkyl and C$_{3-8}$-cycloalkyl.

In still another embodiment, R$^1$ is 1-ethylcyclopropyl, 1-methylcyclopropyl, cyclopropyl, cyclobutyl, cyclopentyl or cyclohexyl.

In a further embodiment, R$^1$ is cyclopropyl, cyclobutyl, cyclopentyl or cyclohexyl.

In yet a further embodiment, R$^1$ is C$_{3-8}$-cycloalkyl-C$_{1-6}$-alkyl.

In still a further embodiment, R$^1$ is cyclopropylmethyl or 1-cyclopropyl-1-methylethyl.

In another embodiment, R$^1$ is 1-cyclopropyl-1-methylethyl.

In yet another embodiment, R$^1$ is 4-pyridyl.

In still another embodiment, R$^1$ is tetrahydropyranyl.

In still a further embodiment, R$^1$ is C$_{3-9}$-alkenyl, which may optionally be substituted with one or two halogen substituents.

In another embodiment, R$^1$ is allyl.

In yet another embodiment, R$^1$ is C$_{3-9}$-alkyl, which may optionally be substituted with one or more hydroxy substituents.

In still another embodiment, R$^1$ is 1-ethylpropyl, isopropyl, n-proyl or n-butyl.

In yet another embodiment, R$^1$ is C$_{5-8}$-cycloalkenyl.

In a further embodiment, X is —(CH$_2$)$_{0-4}$—, —(CH$_2$)$_{0-4}$—CH=CH—(CH$_2$)$_{0-4}$—, —(CH$_2$)$_{0-4}$—(CH$_2$)$_{0-4}$—, —(CH$_2$)$_{0-4}$—S—(CH$_2$)$_{0-4}$—, —(CH$_2$)$_{0-4}$—C(=O)—(CH$_2$)$_{0-4}$—, —(CH$_2$)$_{0-4}$—CH(OH)—, —CH(OH)—(CH$_2$)$_{0-4}$—, —CH(OH)—(CH$_2$)$_{0-4}$—C(=O)—, —CH=CH—CH(OH)—, —(CH$_2$)$_{0-4}$—O—(CH$_2$)$_{0-4}$—O— or —(CH$_2$)$_{0-4}$—CH=CH—(CH$_2$)$_{0-4}$—C(=O)—.

In another embodiment, X is —(CH$_2$)$_{1-4}$—, —CH=CH—, —CH=CH—CH$_2$—, —O—, —(CH$_2$)$_{1-4}$—O—, —O—(CH$_2$)$_{1-4}$—, —(CH$_2$)$_{1-4}$—S—(CH$_2$)$_{1-4}$—, —(CH$_2$)$_{1-4}$—S—, —(CH$_2$)$_{1-4}$—C(=O)—, —O—(CH$_2$)$_{2-3}$—O—, —CH=CH—C(=O)—, —CH=CH—CH(OH)—, —CH(OH)—CH$_2$—C(=O)— or —CH(OH)—CH$_2$—CH$_2$—.

In still another embodiment, X is —(CH$_2$)$_{1-4}$—, —CH=CH—, —(CH$_2$)$_{1-4}$—O—, —O—(CH$_2$)$_{1-4}$—, —(CH$_2$)$_{1-4}$—S—(CH$_2$)$_{1-4}$—, —(CH$_2$)$_{1-4}$—S—, —(CH$_2$)$_{1-4}$—C(=O)—, —O—(CH$_2$)$_{2-3}$—O— or —CH=CH—C(=O)—.

In a further embodiment, X is —CH$_2$—, —(CH$_2$)$_2$—, —(CH$_2$)$_3$—, —(CH$_2$)$_4$—, —CH=CH—, —CH$_2$—O—, —(CH$_2$)$_3$—O—, —O—(CH$_2$)$_2$—, —CH$_2$—S—CH$_2$—, —CH$_2$—S—, —(CH$_2$)$_2$—C(=O)— or —(CH$_2$)$_3$—C(=O)—.

In still a further embodiment, X is —CH$_2$—, —(CH$_2$)$_3$—, —CH=CH—, —O—(CH$_2$)$_2$— or —(CH$_2$)$_2$—C(=O)—.

In yet a further embodiment, X is —(CH$_2$)$_3$—, —(CH$_2$)$_2$—C(=O)— or —CH$_2$—.

In still a further embodiment, Y is phenyl, pyridyl, naphthyl, benzoxazolyl, indanyl, benzothienyl, benzthiazolyl, pyrazolyl or benzofuryl, which may optionally be substituted as defined for formula (I).

In yet a further embodiment, Y is phenyl or naphthyl, which may optionally be substituted as defined for formula (I).

In still a further embodiment, Y is phenyl, which may optionally be substituted as defined for formula (I).

In yet a further embodiment, Y is C$_{3-4}$-cycloalkyl, which may optionally be substituted as defined for formula (I).

In still a further embodiment, Y is cyclohexyl, which may optionally be substituted as defined for formula (I).

In yet another embodiment, Y is unsubstituted or substituted with one or more substituents selected from
halogen, nitro, cyano, hydroxy, C$_{1-7}$-alkanoyl, C$_{1-6}$-alkylsulfonyl, C$_{1-6}$-alkyl, C$_{1-6}$-alkoxy, —C(=O)O—C$_{1-6}$-alkyl, C$_{3-8}$-cycloalkyl, trifluoromethyl, trifluoromethoxy, —NR$^4$R$^5$ and —O(C=O)NR$^4$R$^5$, or wherein two substituents in adjacent positions together form a radical —O—(CH$_2$)$_{1-3}$—O—,
    wherein R$^4$ and R$^5$ independently are hydrogen, C$_{1-6}$-alkyl, C$_{3-8}$-cycloalkyl, C$_{1-7}$-alkanoyl or aryl, or R$^4$ and R$^5$ together with the nitrogen atom to which they are attached form a 4 to 7 membered, saturated or unsaturated ring,
phenyl, phenoxy and phenyl-C$_{1-6}$-alkoxy, wherein the ring moieties optionally may be substituted with one or more substituents selected from
    halogen, nitro, cyano, hydroxy, C$_{1-7}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^6$R$^7$ and —O(C=O)NR$^6$R$^7$, or wherein two substituents in adjacent position form a radical —O—(CH$_2$)$_{1-3}$—O—,
    wherein R$^6$ and R$^7$ independently are hydrogen, C$_{1-6}$-alkyl, C$_{3-8}$-cycloalkyl, C$_{1-7}$-alkanoyl or aryl, or R$^6$ and R$^7$ together with the nitrogen atom to which they are attached form a 4 to 7 membered, saturated or unsaturated ring.

In still another embodiment, Y is unsubstituted or substituted with one or more substituents selected from
halogen, nitro, hydroxy, C$_{1-7}$-alkanoyl, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^4$R$^5$ and —O(C=O)NR$^4$R$^5$, or wherein two substituents in adjacent positions together form a radical —O—(CH$_2$)$_{1-3}$—O—,
    wherein R$^4$ and R$^5$ are C$_{1-6}$-alkyl, or R$^4$ and R$^5$ together with the nitrogen atom to which they are attached form a 4 to 7 membered, saturated or unsaturated ring,
phenyl and phenyl-C$_{1-6}$-alkoxy, wherein the ring moieties optionally may be substituted with one or more substituents selected from halogen and C$_{1-6}$-alkyl.

In still another embodiment, Y is unsubstituted or substituted with one to three substituents selected from C$_{1-6}$-alkoxy, —CF$_3$, halogen, —N(C$_{1-6}$-alkyl)$_2$, phenyl and 4-fluorophenyl, or wherein two substituents in adjacent positions together form a radical —O—(CH$_2$)$_{1-3}$—O—.

In a further embodiment, Y is substituted with one halogen substituent.

In still a further embodiment, Y is substituted with one —N(C$_{1-6}$-alkyl)$_2$ substituent.

In yet a further embodiment, Y is unsubstituted or substituted with one or two substituents selected from
aryl and aryloxy, wherein the ring moieties optionally may be substituted with one or more substituents selected from
    halogen, nitro, cyano, hydroxy, C$_{1-7}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^8$R$^9$ and —O(C=O)NR$^8$R$^9$, or wherein two substituents in adjacent positions together form a radical —O—(CH$_2$)$_{1-3}$—O—,
    wherein R$^8$ and R$^9$ independently are hydrogen, C$_{1-6}$-alkyl, C$_{3-8}$-cycloalkyl, C$_{1-7}$-alkanoyl or aryl, or R$^8$ and R$^9$ together with the nitrogen atom to which they are attached form a 4 to 7 membered, saturated or unsaturated ring.

In another embodiment, Y is unsubstituted or substituted with one or two substituents selected from
phenyl and phenoxy, wherein the ring moieties optionally may be substituted with one or more substituents selected from
    halogen, nitro, cyano, hydroxy, C$_{1-7}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^8$R$^9$ and —O(C=O)NR$^8$R$^9$, or wherein two substituents in adjacent positions together form a radical —O—(CH$_2$)$_{1-3}$—O—,
    wherein R$^8$ and R$^9$ independently are hydrogen, C$_{1-6}$-alkyl, C$_{3-8}$-cycloalkyl, C$_{1-7}$-alkanoyl or aryl, or R$^8$ and R$^9$ together with the nitrogen atom to which they are attached form a 4 to 7 membered, saturated or unsaturated ring.

In yet another embodiment, Y is unsubstituted or substituted with phenyl, which is unsubstituted or substituted with halogen.

In another aspect, the present invention relates to a compound of the general formula (I"):

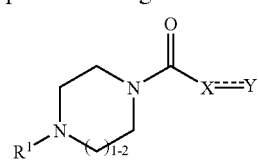

(I")

wherein

-----designates a single bond or a double bond, $R^1$ is (a) $C_3$–$C_9$-alkyl, $C_3$–$C_9$-alkenyl, $C_3$–$C_9$-alkynyl,
which may optionally be substituted with one or more substituents selected from halogen and hydroxy, (b) $C_{3-8}$-cycloalkyl, $C_{5-8}$-cycloalkenyl, $C_{3-8}$-cycloalkyl-$C_{1-6}$-alkyl, di($C_{3-8}$-cycloalkyl)-$C_{1-6}$-alky, $C_{3-8}$-cycloalkyl-$C_{2-6}$-alkenyl, $C_{3-8}$-cycloalkyl-$C_{2-6}$-alkynyl, $C_{5-8}$-cycloalkenyl-$C_{1-6}$-alkyl, $C_{5-8}$-cycloalkenyl-$C_{2-6}$-alkenyl, $C_{5-8}$-cycloalkenyl-$C_{2-6}$-alkynyl, 4-pyridyl or tetrahydropyranyl,
wherein the cyclic moieties may optionally be substituted with one or more substituents selected from $C_{1-6}$-alkyl, halogen, trifluoromethyl, 2,2,2-trifluoroethyl and $C_{3-8}$-cycloalkyl, X is —$(CH_2)_m$—$(Z)_n$—$(CR^2R^3)_o$—$(V)_p$—.

m and o independently are 0, 1, 2, 3 or 4, n and p independently are 0 or 1,

Z and V independently are —O—, —NH—, —C(=O)—, —S—, —S(=O)—, —S(=O)$_2$—, —CH=CH— or —C≡C—, $R^2$ and $R^3$ independently are hydrogen, $C_{1-6}$-alkyl or hydroxy, Y is (a) aryl or heteroaryl, which may optionally be substituted with one or more substituents selected from
halogen, nitro, cyano, oxo, hydroxy, $C_{1-6}$-alkanoyl, $C_{1-6}$-alkylthio, $C_{1-6}$-alkylsulfonyl, $C_{1-6}$-alkyl, $C_{1-4}$-alkoxy, $C_{3-8}$-cycloalkyl, trifluoromethyl, trifluoromethoxy, —$NR^4R^5$ and —$O(C=O)NR^4R^5$, or wherein two substituents in adjacent positions together form a radical —O—$(CH_2)_{1-3}$—O—,
wherein $R^4$ and $R^5$ independently are hydrogen, $C_{1-6}$-alkyl, $C_{3-8}$-cycloalkyl, $C_{1-6}$alkanoyl or aryl, or $R^4$ and $R^5$ together with the nitrogen atom to which they are attached form a 4 to 7 membered, saturated or unsaturated ring,
aryl, aryl-$C_{1-6}$-alkyl and aryl-$C_{1-6}$-alkoxy, wherein the ring moieties optionally may be substituted with one or more selected from
halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^6R^7$ and —$O(C=O)NR^6R^7$, or wherein two substituents in adjacent positions together form a radical —O—$(CH_2)_{1-3}$—O—,
wherein $R^6$ and $R^7$ independently are hydrogen, $C_{1-6}$-alkyl, $C_{3-8}$-cycloalkyl, $C_{1-6}$-alkanoyl or aryl, or $R^6$ and $R^7$ together with the nitrogen atom to which they are attached form a 4 to 7 membered, saturated or unsaturated ring, (b) $C_{3-8}$-cycloalkyl or $C_{5-8}$-cycloalkenyl, which may optionally be substituted with one or more substituents selected from
$C_{1-6}$-alkyl, $C_{1-6}$-alkoxy, $C_{1-6}$-alkylthio, cyano, trifluoromethyl, trifluoromethoxy and halogen,
aryl and aryloxy, wherein the ring moieties optionally may be substituted with one or more substituents selected from
halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^8R^9$ and —$O(C=O)NR^8R^9$, or wherein two substituents in adjacent positions together form a radical —O—$(CH_2)_{1-3}$—O—, wherein $R^8$ and $R^9$ independently are hydrogen, $C_{1-6}$-alkyl, $C_{3-8}$-cycloalkyl, $C_{1-6}$-alkanoyl or aryl, or $R^8$ and $R^9$ together with the nitrogen atom to which they are attached form a 4 to 7 membered, saturated or unsaturated ring, with the proviso that when Y is selected from the group (a), the sum of m, n, o and p must be at least 1, and with the proviso that when $R^1$ is cyclohexyl and X is —$(CH_2)_3$—O—, Y must not be 1,2,3,4-tetrahydro-2-oxo-6-quinolinyl, 1,2-dihydro-2-oxo-6-quinolinyl or 3-ethyl-2,3-dihydro-2-oxo-1H-benzimidazol-5-yl, $R^1$ is cycloheptyl and X is —$(CH_2)_3$—O—, Y must not be 2,3-dihydro-2-oxo-1H-imidazo[4,5-b]-quinolin-7-yl, $R^1$ is cycloheptyl and X is —$(CH_2)_4$—O—, Y must not be 2,3-dihydro-2-oxo-1H-pyrrolo[2,3-b]quinolin-6-yl, $R^1$ is cyclohexyl and X is —$(CH_2)_2$—, Y must not be 2-(4-chlorophenyl)-1H-indol-3-yl or 2-(4-bromophenyl)-1H-indol-3-yl, $R^1$ is cycloheptyl and X is —$CH_2$—, Y must not be (3-benzyl)phenyl, $R^1$ is cyclohexyl and X is —O—$CH_2$—, Y must not be phenyl, $R^1$ is cyclohexyl and X is —CH=CH—, Y must not be benzofuran-2-yl, $R^1$ is cyclohexyl and X is —NH—, Y must not be cyclohexyl, $R^1$ is 2-propen-1-yl and X is —NH—, Y must not be phenyl, $R^1$ is n-propyl and X is —C≡C—, Y must not be phenyl, $R^1$ is cyclopentyl and X is —$CH_2$—O—, Y must not be 4-phenyl-1,2,3-thiadiazol-5-yl, $R^1$ is isopropyl and X is —$CH_2$—, Y must not be 4-oxothiazolidin-3-yl, $R^1$ is isopropyl and X is —$CH_2$—, Y must not be 2-oxopyrrolidin-1-yl, $R^1$ is isopropyl and X is —O—, Y must not be 6-(5-chloropyridin-2-yl)-2,3,6,7-tetrahydro-7-oxo-5H-1,4-dithiino[2,3-c]pyrrol-5-yl, $R^1$ is isopropyl and X is —CH=CH—, Y must not be 5-nitrofuran-2-yl, $R^1$ is isopropyl and X is —O—, Y must not be 3-oxo-2-pyridin-2-yl-2,3-dihydro-1H-isoindol-1-yl, as well as any diastereomer or enantiomer or tautomeric form thereof including mixtures of these or a pharmaceutically acceptable salt thereof.

In one embodiment, the invention relates to a compound of the general formula (I$_1$):

(I$_1$)

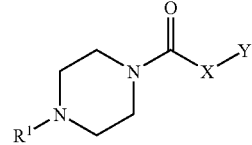

wherein $R^1$, X and Y are as defined for formula (I″).

In another embodiment, the invention relates to a compound of the general formula (I$_2$):

(I$_2$)

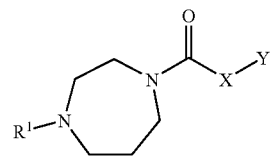

wherein $R^1$, X and Y are as defined for formula (I″).

In yet another embodiment, $R^1$ is $C_{3-8}$-cycloalkyl, which may optionally be substituted with one or two substituents selected from $C_{1-6}$-alkyl and $C_{3-8}$-cycloalkyl: Examples hereof are cyclopropyl, cyclobutyl, cyclopentyl or cyclohexyl.

In a further embodiment, $R^1$ is $C_{3-8}$-cycloalkyl-$C_{1-6}$-alkyl.

In still a further embodiment, $R^1$ is 4-pyridyl.

In yet a further embodiment, $R^1$ is $C_{3-9}$-alkenyl, which may optionally be substituted with one or two halogen substituents. An example hereof is allyl.

In another embodiment, $R^1$ is $C_{3-9}$-alkyl, which may optionally be substituted with one or more hydroxy substituents. Examples hereof are 1-ethylpropyl, isopropyl, n-proyl or n-butyl.

In yet another embodiment, X is $-(CH_2)_{0-4}-$, $-(CH_2)_{0-4}-CH=CH-(CH_2)_{0-4}-$, $-(CH_2)_{0-4}-O-(CH_2)_{0-4}-$, $-(CH_2)_{0-4}-S-(CH_2)_{0-4}-$, $-(CH_2)_{0-4}-C(=O)-(CH_2)_{0-4}-$, $-(CH_2)_{0-4}-CH(OH)-$, $-(CH_2)_{0-4}-O-(CH_2)_{1-4}-O-$ or $-(CH_2)_{0-4}-CH=CH-(CH_2)_{0-4}-C(=O)-$.

In still another X is $-(CH_2)_{1-4}-$, $-CH=CH-$, $-(CH_2)_{1-4}-O-$, $-O-(CH_2)_{1-4}-$, $-(CH_2)_{1-4}-S-(CH_2)_{1-4}-$, $-(CH_2)_{1-4}-S-$, $-(CH_2)_{1-4}-C(=O)-$, $-O-(CH_2)_{2-3}-O-$ or $-CH=CH-C(=O)-$.

In a further embodiment, X is $-CH_2-$, $-(CH_2)_2-$, $-(CH_2)_3-$, $-(CH_2)_4-$, $-CH=CH-$, $-CH_2-O-$, $-(CH_2)_3-O-$, $-O-(CH_2)_2-$, $-CH_2-S-CH_2-$, $-CH_2-S-$, $-(CH_2)_2-C(=O)-$ or $-(CH_2)_3-C(=O)-$, such as $-CH_2-$, $-(CH_2)_3-$, $-CH=CH-$, $-O-(CH_2)_2-$ or $-(CH_2)_2-C(=O)-$, eg $-(CH_2)_2-C(=O)-$ or $-CH_2-$.

In another embodiment, Y is phenyl, pyridyl, naphthyl, benzoxazolyl, indanyl, benzothienyl, benzthiazolyl or benzofuryl, which may optionally be substituted as defined for formula (I").

In another embodiment, Y is phenyl or naphthyl, which may optionally be substituted as defined for formula (I").

In yet another embodiment, Y is phenyl, which may optionally be substituted as defined for formula (I").

In still another embodiment, Y is $C_{3-4}$-cycloalkyl, such as cyclohexyl, which may optionally be substituted as defined for formula (I").

In one embodiment, Y is unsubstituted or substituted with one or more substituents selected from halogen, nitro, cyano, hydroxy, $C_{1-6}$-alkanoyl, $C_{1-6}$-alkylsulfonyl, $C_{1-6}$alkyl, $C_{1-6}$-alkoxy, $C_{3-8}$-cycloalkyl, trifluoromethyl, trifluoromethoxy, $-NR^4R^5$ and $-O(C=O)NR^4R^5$, or wherein two substituents in adjacent positions together form a radical $-O-(CH_2)_{1-3}-O-$,
  wherein $R^4$ and $R^5$ independently are hydrogen, $C_{1-6}$-alkyl, $C_{3-8}$-cycloalkyl, $C_{1-6}$-alkanoyl or aryl, or $R^4$ and $R^5$ together with the nitrogen atom to which they are attached form a 4 to 7 membered, saturated or unsaturated ring, phenyl and phenyl-$C_{1-6}$-alkoxy, wherein the ring moieties optionally may be substituted with one or more substituents selected from
  halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, $-NR^6R^7$ and $-O(C=O)NR^6R^7$, or wherein two substituents in adjacent position form a radical $-O-(CH_2)_{1-3}-O-$,
    wherein $R^6$ and $R^7$ independently are hydrogen, $C_{1-6}$-alkyl, $C_{3-8}$-cycloalkyl, $C_{1-6}$-alkanoyl or aryl, or $R^6$ and $R^7$ together with the nitrogen atom to which they are attached form a 4 to 7 membered, saturated or unsaturated ring.

In another embodiment, Y is unsubstituted or substituted with one or more substituents selected from
halogen, nitro, hydroxy, $C_{1-6}$-alkanoyl, $C_{1-6}$-alkylsulfonyl, $C_{1-6}$-alkyl, $C_{1-6}$alkoxy, $C_{3-8}$-cycloalkyl, trifluoromethyl, trifluoromethoxy, $-NR^4R^5$ and $-O(C=O)NR^4R^5$, or wherein two substituents in adjacent positions together form a radical $-O-(CH_2)_{1-3}-O-$,
  wherein $R^4$ and $R^5$ are $C_{1-6}$-alkyl, or $R^4$ and $R^5$ together with the nitrogen atom to which they are attached form a 4 to 7 membered, saturated or unsaturated ring, phenyl and phenyl-$C_{1-6}$-alkoxy, wherein the ring moieties optionally may be substituted with one or more substituents selected from halogen and $C_{1-6}$alkyl.

In another embodiment, Y is unsubstituted or substituted with one to three substituents selected from $C_{1-6}$-alkoxy, halogen, $-N(C_{1-6}$-alkyl$)_2$ and phenyl, or wherein two substituents in adjacent positions together form a radical $-O-(CH_2)_{1-3}-O-$.

In still another embodiment, Y is substituted with one halogen substituent.

In yet another embodiment, Y is substituted with one $-N(C_{1-6}$-alkyl$)_2$ substituent.

In a further embodiment, Y is unsubstituted or substituted with one or two substituents selected from
aryl and aryloxy, wherein the ring moieties optionally may be substituted with one or more substituents selected from
  halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, $-NR^8R^9$ and $-O(C=O)NR^8R^9$, or wherein two substituents in adjacent positions together form a radical $-O-(CH_2)_{1-3}-O-$,
    wherein $R^8$ and $R^9$ independently are hydrogen, $C_{1-6}$-alkyl, $C_{3-8}$-cycloalkyl, $C_{1-6}$-alkanoyl or aryl, or $R^8$ and $R^9$ together with the nitrogen atom to which they are attached form a 4 to 7 membered, saturated or unsaturated ring.

In yet a further embodiment, Y is unsubstituted or substituted with one or two substituents selected from
phenyl and phenoxy, wherein the ring moieties optionally may be substituted with one or more substituents selected from
  halogen, nitro, cyano, hydroxy, $C_{1-6}$alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, $-NR^8R^9$ and $-O(C=O)NR^8R^9$, or wherein two substituents in adjacent positions together form a radical $-O-(CH_2)_{1-3}-O-$,
    wherein $R^8$ and $R^9$ independently are hydrogen, $C_{1-6}$-alkyl, $C_{3-8}$-cycloalkyl, $C_{1-6}$-alkanoyl or aryl, or $R^8$ and $R^9$ together with the nitrogen atom to which they are attached form a 4 to 7 membered, saturated or unsaturated ring.

In still a further embodiment, Y is unsubstituted or substituted with phenyl, which is unsubstituted or substituted with halogen.

In a further aspect, the invention relates to a compound of the general formula (I'''):

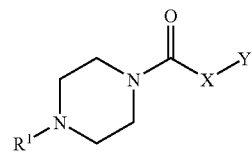

(I''')

wherein
R¹ is
(a) $C_3-C_9$-alkyl, $C_3-C_9$-alkenyl, $C_3-C_9$-alkynyl,
which may optionally be substituted with one or more halogen atoms,
(b) $C_{3-8}$-cycloalkyl, $C_{5-8}$-cycloalkenyl, $C_{3-8}$-cycloalkyl-$C_{1-6}$-alkyl, di($C_{3-8}$-cycloalkyl)-$C_{1-6}$-alkyl, $C_{3-8}$-cycloalkyl-$C_{2-6}$-alkenyl, $C_{3-8}$-cycloalkyl-$C_{2-6}$-alkynyl, $C_{5-8}$-cycloalkenyl-$C_{1-6}$-alkyl, $C_{5-8}$-cycloalkenyl-$C_{2-6}$-alkenyl, $C_{5-8}$-cycloalkenyl-$C_{2-6}$-alkynyl or 4-pyridyl,
wherein the cyclic moieties may optionally be substituted with one or more substituents selected from $C_{1-6}$-alkyl, halogen, trifluoromethyl and 2,2,2-trifluoroethyl, X is —$(CH_2)_m$—$(Z)_n$—$(CH_2)_o$—,
m and o independently are 0, 1, 2, 3 or 4,
n is 0 or 1,
Z is —O—, —NH—, —C(=O)—, —S—, —S(=O)—, —S(=O)$_2$—, —CH=CH— or —C≡C—,
Y is
(a) aryl or heteroaryl, which may optionally be substituted with one or more substituents selected from
halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —NR²R³ and —O(C=O)NR²R³, or wherein two substituents in adjacent positions form a radical —O—$(CH_2)_{1-3}$—O—,
wherein R² and R³ independently are hydrogen, $C_{1-6}$-alkyl, $C_{3-8}$-cycloalkyl, $C_{1-6}$-alkanoyl or aryl, or R² and R³ together with the nitrogen atom to which they are attached form a 4 to 7 membered, saturated or unsaturated ring,
aryl, aryl-$C_{1-6}$-alkyl and aryl-$C_{1-6}$-alkoxy, wherein the ring moieties optionally may be substituted with one or more substituents selected from
halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —NR⁴R⁵ and —O(C=O)NR⁴R⁵, or wherein two substituents in adjacent positions form a radical —O—$(CH_2)_{1-3}$—O—,
wherein R⁴ and R⁵ independently are hydrogen, $C_{1-6}$-alkyl, $C_{3-8}$-cycloalkyl, $C_{1-6}$-alkanoyl or aryl, or R⁴ and R⁵ together with the nitrogen atom to which they are attached form a 4 to 7 membered, saturated or unsaturated ring,
(b) $C_{3-8}$-cycloalkyl or $C_{5-8}$-cycloalkenyl, which may optionally be substituted with one or more substituents selected from
$C_{1-6}$-alkyl, $C_{1-6}$-alkoxy, $C_{1-6}$-alkylthio, cyano, trifluoromethyl, trifluoromethoxy and halogen,
aryl and aryloxy, wherein the ring moieties optionally may be substituted with one or more substituents selected from
halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —NR⁶R⁷ and —O(C=O)NR⁶R⁷, or wherein two substituents in adjacent positions form a radical —O—$(CH_2)_{1-3}$—O—,
wherein R⁶ and R⁷ independently are hydrogen, $C_{1-6}$-alkyl, $C_{3-8}$-cycloalkyl, $C_{1-6}$-alkanoyl or aryl, or R⁶ and R⁷ together with the nitrogen atom to which they are attached form a 4 to 7 membered, saturated or unsaturated ring,
with the proviso that when Y is selected from the group (a), the sum of m, n and o must be at least 1, and with the proviso that when
R¹ is cyclohexyl and X is —$(CH_2)_3$—O—, Y must not be 1,2,3,4-tetrahydro-2-oxo-6-quinolinyl, 1,2-dihydro-2-oxo-6-quinolinyl or 3-ethyl-2,3-dihydro-2-oxo-1H-benzimidazol-5-yl,
R¹ is cycloheptyl and X is —$(CH_2)_3$—O—, Y must not be 2,3-dihydro-2-oxo-1H-imidazo[4,5-b]-quinolin-7-yl,
R¹ is cycloheptyl and X is —$(CH_2)_4$—O—, Y must not be 2,3-dihydro-2-oxo-1H-pyrrolo[2,3-b]quinolin-6-yl,
R¹ is cyclohexyl and X is —$(CH_2)_2$—, Y must not be 2-(4-chlorophenyl)-1H-indol-3-yl or 2-(4-bromophenyl)-1H-indol-3-yl,
R¹ is cycloheptyl and X is —$CH_2$—, Y must not be (3-benzyl)phenyl,
R¹ is cyclohexyl and X is —O—$CH_2$—, Y must not be phenyl,
R¹ is cyclohexyl and X is —CH=CH—, Y must not be benzofuran-2-yl,
R¹ is cyclohexyl and X is —NH—, Y must not be cyclohexyl,
R¹ is 2-propen-1-yl and X is —NH—, Y must not be phenyl,
R¹ is n-propyl and X is —C≡C—, Y must not be phenyl,
R¹ is cyclopentyl and X is —$CH_2$—O—, Y must not be 4-phenyl-1,2,3-thiadiazol-5-yl,
R¹ is isopropyl and X is —$CH_2$—, Y must not be 4-oxothiazolidin-3-yl,
R¹ is isopropyl and X is —$CH_2$—, Y must not be 2-oxopyrrolidin-1-yl,
R¹ is isopropyl and X is —O—, Y must not be 6-(5-chloropyridin-2-yl)-2,3,6,7-tetrahydro-7-oxo-5H-1,4-dithiino[2,3-c]pyrrol-5-yl,
R¹ is isopropyl and X is —CH=CH—, Y must not be 5-nitrofuran-2-yl,
R¹ is isopropyl and X is —O—, Y must not be 3-oxo-2-pyridin-2-yl-2,3-dihydro-1H-isoindol-1-yl, as well as any diastereomer or enantiomer or tautomeric form thereof including mixtures of these or a pharmaceutically acceptable salt thereof.

In one embodiment, R¹ is $C_{3-8}$-cycloalkyl, such as cyclobutyl, cyclopentyl or cyclohexyl.

In another embodiment, R¹ is 4-pyridyl.

In yet another embodiment, R¹ is $C_{3-9}$-alkenyl, such as allyl.

In still another embodiment, R¹ is $C_{3-6}$-alkyl, such as 1-ethylpropyl, isopropyl, n-proyl or n-butyl.

In one embodiment, X is —$(CH_2)_{1-4}$—, —$(CH_2)_{0-4}$—CH=CH—$(CH_2)_{0-4}$—, —$(CH_2)_{0-4}$—O—$(CH_2)_{0-4}$—, —$(CH_2)_{0-4}$—S—$(CH_2)_{0-4}$— or —$(CH_2)_{0-4}$—C(=O)—$(CH_2)_{0-4}$—.

In another embodiment, X is —$(CH_2)_{1-4}$—, —CH=CH—, —$(CH_2)_{1-4}$—O—, —O—$(CH_2)_{1-4}$—, —$(CH_2)_{1-4}$—S—$(CH_2)_{1-4}$—, —$(CH_2)_{1-4}$—S— or —$(CH_2)_{1-4}$—C(=O)—.

In yet another embodiment, X is —$CH_2$—, —$(CH_2)_2$—, —$(CH_2)_3$—, —$(CH_2)_4$—$(CH_2)_3$—O—, —O—$(CH_2)_2$—, —$CH_2$—S—$CH_2$—, —$CH_2$—S—, —$(CH_2)_2$—C(=O)— or —$(CH_2)_3$—C(=O)—.

In still another embodiment, X is —$(CH_2)_3$—, —CH=CH—, —O—$(CH_2)_2$— or —$(CH_2)_2$—C(=O)—, such as —$(CH_2)_2$—C(=O)—.

In one embodiment, Y is phenyl, pyridyl, naphthyl, benzoxazolyl, indanyl or benzothiophenyl, which may optionally be substituted as defined for formula (I'''), such as phenyl or naphthyl, which may optionally be substituted as defined for formula (I''').

In another embodiment, Y is $C_{3-8}$-cycloalkyl, which may optionally be substituted as defined for formula (I'''), such as cyclohexyl, which may optionally be substituted as defined for formula (I''').

In one embodiment, Y is unsubstituted or substituted with one or more substituents selected from halogen, nitro, hydroxy, $C_{1-6}$-alkanoyl, $C_{1-6}$-alkylsulfonyl, $C_{1-6}$-alkyl, $C_{1-6}$alkoxy, $C_{3-8}$-cycloalkyl, trifluoromethyl, trifluoromethoxy, $-NR^2R^3$ and $-O(C=O)NR^2R^3$, or wherein two substituents in adjacent positions form a radical $-O-(CH_2)_{1-3}-O-$, wherein $R^2$ and $R^3$ independently are hydrogen, $C_{1-6}$alkyl, $C_{3-8}$-cycloalkyl, $C_{1-6}$-alkanoyl or aryl, or $R^2$ and $R^3$ together with the nitrogen atom to which they are attached form a 4 to 7 membered, saturated or unsaturated ring, phenyl and phenyl-$C_{1-6}$-alkoxy, wherein the ring moieties optionally may be substituted with one or more substituents selected from halogen, nitro, cyano, hydroxy, $C_{1-6}$-alkanoyl, $C_{1-6}$alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, $-NR^4R^5$ and $-O(C=O)NR^4R^5$, or wherein two substituents in adjacent position form a radical $-O-(CH_2)_{1-3}-O-$, wherein $R^4$ and $R^5$ independently are hydrogen, $C_{1-6}$-alkyl, $C_{3-8}$-cycloalkyl, $C_{1-6}$-alkanoyl or aryl, or $R^4$ and $R^5$ together with the nitrogen atom to which they are attached form a 4 to 7 membered, saturated or unsaturated ring.

In another embodiment, Y is unsubstituted or substituted with one or more substituents selected from halogen, nitro, hydroxy, $C_{1-6}$-alkanoyl, $C_{1-6}$-alkylsulfonyl, $C_{1-6}$-alkyl, $C_{1-6}$-alkoxy, $C_{3-8}$-cycloalkyl, trifluoromethyl, trifluoromethoxy, $-NR^2R^3$ and $-O(C=O)NR^2R^3$, or wherein two substituents in adjacent positions form a radical $-O-(CH_2)_{1-3}-O-$, wherein $R^2$ and $R^3$ are $C_{1-6}$-alkyl, or $R^2$ and $R^3$ together with the nitrogen atom to which they are attached form a 4 to 7 membered, saturated or unsaturated ring, phenyl and phenyl-$C_{1-6}$-alkoxy, wherein the ring moieties optionally may be substituted with one or more substituents selected from halogen and $C_{1-6}$-alkyl.

In yet another embodiment, Y is unsubstituted or substituted with one to three substituents selected from $C_{1-6}$-alkoxy, halogen and phenyl, or wherein two substituents in adjacent positions form a radical $-O-(CH_2)_{1-3}-O-$.

In still another embodiment, Y is substituted with one halogen substituent.

In yet another embodiment, Y is unsubstituted or substituted with one or two substituents selected from aryl and aryloxy, wherein the ring moieties optionally may be substituted with one or more substituents selected from halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, $-NR^6R^7$ and $-O(C=O)NR^6R^7$, or wherein two substituents in adjacent positions form a radical $-O-(CH_2)_{1-3}-O-$, wherein $R^6$ and $R^7$ independently are hydrogen, $C_{1-6}$-alkyl, $C_{3-8}$-cycloalkyl, $C_{1-6}$-alkanoyl or aryl, or $R^6$ and $R^7$ together with the nitrogen atom to which they are attached form a 4 to 7 membered, saturated or unsaturated ring.

In another embodiment, Y is unsubstituted or substituted with one or two substituents selected from phenyl and phenoxy, wherein the ring moieties optionally may be substituted with one or more substituents selected from halogen, nitro, cyano, hydroxy, $C_{1-6}$-alkanoyl, $C_{1-6}$alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, $-NR^6R^7$ and $-O(C=O)NR^6R^7$, or wherein two substituents in adjacent positions form a radical $-O-(CH_2)_{1-3}-O-$, wherein $R^6$ and $R^7$ independently are hydrogen, $C_{1-6}$-alkyl, $C_{3-8}$-cycloalkyl, $C_{1-6}$-alkanoyl or aryl, or $R^6$ and $R^7$ together with the nitrogen atom to which they are attached form a 4 to 7 membered, saturated or unsaturated ring.

In yet another embodiment, Y is unsubstituted or substituted with phenyl, which is unsubstituted or substituted with halogen.

The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates, which the present compounds are able to form.

The acid addition salts may be obtained as the direct products of compound synthesis.

In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds of the present invention interact with the histamine H3 receptor and are accordingly useful for the treatment of a wide variety of conditions and disorders in which histamine H3 receptor interactions are beneficial.

Accordingly, in another aspect the present invention relates to a compound of the general formula (I) as well as any diastereomer or enantiomer or tautomeric form thereof including mixtures of these or a pharmaceutically acceptable salt thereof for use as a pharmaceutical composition.

The invention also relates to pharmaceutical compositions comprising, as an active ingredient, at least one compound of the formula (I) or any diastereomer or enantiomer or tautomeric form thereof including mixtures of these or a pharmaceutically acceptable salt thereof together with one or more pharmaceutically acceptable carriers or diluents.

Furthermore, the invention relates to the use of a compound of the general formula (I'):

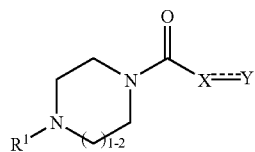

(I')

wherein

- - - - designates a single bond or a double bond, $R^1$ is (a) $C_3$–$C_9$-alkyl, $C_3$–$C_9$-alkenyl, $C_3$–$C_9$-alkynyl,
which may optionally be substituted with one or more substituents selected from halogen and hydroxy, (b) $C_{3-8}$-cycloalkyl, $C_{5-8}$-cycloalkenyl, $C_{3-8}$-cycloalkyl-$C_{1-6}$-alkyl, di($C_{3-8}$-cycloalkyl)-$C_{1-6}$-alkyl, $C_{3-8}$-cycloalkyl-$C_{2-6}$-alkenyl, $C_{3-8}$-cycloalkyl-$C_{2-6}$-alkynyl, $C_{5-8}$-cycloalkenyl-$C_{1-6}$-alkyl, $C_{5-8}$-cyclo-alkenyl-$C_{2-6}$-alkenyl, $C_{5-8}$-cycloalkenyl-$C_{2-6}$-alkynyl, 4-pyridyl or tetrahydropyranyl,
wherein the cyclic moieties may optionally be substituted with one or more substituents selected from $C_{1-6}$-alkyl, halogen, trifluoromethyl, 2,2,2-trifluoroethyl and $C_{3-8}$-cycloalkyl, X is —$(CH_2)_m$—$(Z)_n$—$(CR^2R^3)_o$—$(CH_2)_p$—$(V)_q$—.

m and p independently are 0, 1, 2, 3 or 4, n, o and q independently are 0 or 1,

Z and V independently are —O—, —NH—, —C(=O)—, —S—, —S(=O)—, —S(=O)$_2$—, —CH=CH— or —C≡C—, $R^2$ and $R^3$ independently are hydrogen, $C_{1-6}$-alkyl or hydroxy, Y is (a) aryl or heteroaryl, which may optionally be substituted with one or more substituents selected from
halogen, nitro, cyano, oxo, hydroxy, $C_{1-7}$-alkanoyl, $C_{1-6}$-alkylthio, $C_{1-6}$-alkylsulfonyl, $C_{1-6}$-alkyl, $C_{1-6}$-alkoxy, —C(=O)O—$C_{1-6}$-alkyl, $C_{3-8}$-cycloalkyl, trifluoromethyl, trifluoromethoxy, —$NR^4R^5$ and —O(C=O)$NR^4R^5$, or wherein two substituents in adjacent positions together form a radical —O—$(CH_2)_{1-3}$—O—,
wherein $R^4$ and $R^5$ independently are hydrogen, $C_{1-6}$-alkyl, $C_{3-8}$-cycloalkyl, $C_{1-7}$-alkanoyl or aryl, or $R^4$ and $R^5$ together with the nitrogen atom to which they are attached form a 4 to 7 membered, saturated or unsaturated ring,
aryl, aryl-$C_{1-6}$-alkyl, aryloxy and aryl-$C_{1-6}$-alkoxy, wherein the ring moieties optionally may be substituted with one or more substituents selected from
halogen, nitro, cyano, hydroxy, $C_{1-7}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^6R^7$ and —O(C=O)$NR^6R^7$, or wherein two substituents in adjacent positions together form a radical —O—$(CH_2)_{1-3}$—O—,
wherein $R^6$ and $R^7$ independently are hydrogen, $C_{1-6}$-alkyl, $C_{3-8}$-cycloalkyl, $C_{1-7}$-alkanoyl or aryl, or $R^6$ and $R^7$ together with the nitrogen atom to which they are attached form a 4 to 7 membered, saturated or unsaturated ring, (b) $C_{3-8}$-cycloalkyl or $C_{5-8}$-cycloalkenyl, which may optionally be substituted with one or more substituents selected from
$C_{1-6}$-alkyl, $C_{1-6}$-alkoxy, $C_{1-6}$-alkylthio, cyano, trifluoromethyl, trifluoromethoxy and halogen,
aryl and aryloxy, wherein the ring moieties optionally may be substituted with one or more substituents selected from
halogen, nitro, cyano, hydroxy, $C_{1-7}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^8R^9$ and —O(C=O)$NR^8R^9$, or wherein two substituents in adjacent positions together form a radical —O—$(CH_2)_{1-3}$—O—,
wherein $R^8$ and $R^9$ independently are hydrogen, $C_{1-6}$-alkyl, $C_{3-8}$-cycloalkyl, $C_{1-7}$-alkanoyl or aryl, or $R^8$ and $R^9$ together with the nitrogen atom to which they are attached form a 4 to 7 membered, saturated or unsaturated ring, with the proviso that when Y is selected from the group (a), the sum of m, n, o, p and q must be at least 1, as well as any diastereomer or enantiomer or tautomeric form thereof including mixtures of these or a pharmaceutically acceptable salt thereof for the preparation of a pharmaceutical composition for the treatment of disorders and diseases related to the histamine H3 receptor.

In still another aspect, the invention relates to a method for the treatment of diseases and disorders related to the histamine H3 receptor the method comprising administering to a subject in need thereof an effective amount of a compound of the formula (I') or any diastereomer or enantiomer or tautomeric form thereof including mixtures of these or a pharmaceutically acceptable salt thereof or a pharmaceutical composition comprising the same.

In one aspect the invention relates to compounds with histamine H3 receptor antagonistic activity or inverse agonistic activity which may accordingly be useful in the treatment of a wide range of conditions and disorders in which histamine H3 receptor blockade is beneficial.

In another aspect the invention relates to compounds with histamine H3 receptor agonistic activity and which may accordingly be useful in the treatment of a wide range of conditions and disorders in which histamine H3 receptor activation is beneficial.

In a preferred embodiment of the invention, the present compounds are used for the preparation of a pharmaceutical composition for the reduction of weight.

In a preferred embodiment of the invention, the present compounds are used for the preparation of a pharmaceutical composition for the treatment of overweight or obesity.

In another preferred embodiment of the invention, the present compounds are used for the preparation of a pharmaceutical composition for the suppression of appetite or satiety induction.

In a further preferred embodiment of the invention, the present compounds are used for the preparation of a pharmaceutical composition for the prevention and/or treatment of disorders and diseases related to overweight or obesity such as atherosclerosis, hypertension, IGT (impaired glucose tolerance), diabetes, especially Type 2 diabetes (NIDDM (non-insulin dependent diabetes mellitus)), dyslipidaemia, coronary heart disease, gallbladder disease, osteoarthritis and various types of cancer such as endometrial, breast, prostate and colon cancers.

In yet a further preferred embodiment of the invention, the present compounds are used for the preparation of a pharmaceutical composition for the prevention and/or treatment of eating disorders such as bulimia and binge eating.

In a further preferred embodiment of the invention, the present compounds are used for the preparation of a pharmaceutical composition for the treatment of IGT.

In a further preferred embodiment of the invention, the present compounds are used for the preparation of a pharmaceutical composition for the treatment of Type 2 diabetes.

In another preferred embodiment of the invention, the present compounds are used for the preparation of a pharmaceutical composition for the delaying or prevention of the progression from IGT to Type 2 diabetes.

In a further preferred embodiment of the invention, the present compounds are used for the preparation of a pharmaceutical composition for the delaying or prevention of the progression from non-insulin requiring Type 2 diabetes to insulin requiring Type 2 diabetes.

The compounds of the present invention may also be used for the treatment of airway disorders such as asthma, as anti-diarrhoeals and for the modulation of gastric acid secretion.

Furthermore, the compounds of the present invention may be used for the treatment of diseases associated with the regulation of sleep and wakefulness and for the treatment of narcolepsy and attention deficit disorder.

Moreover, the compounds of the invention may be used as CNS stimulants or as sedatives.

The present compounds may also be used for the treatment of conditions associated with epilepsy. Additionally, the present compounds may be used for the treatment of motion sickness and vertigo. Furthermore, they may be useful as regulators of hypothalamo-hypophyseal secretion, antidepressants, modulators of cerebral circulation, and in the treatment of irritable bowel syndrome.

Further, the compounds of the present invention may be used for the treatment of dementia and Alzheimer's disease.

The compounds of the present invention may also be useful for the treatment of allergic rhinitis, ulcer or anorexia.

The compounds of the present invention may furthermore be useful for the treatment of migraine, see R. L. McLeod et al., *The Journal of Pharmacology and Experimental Therapeutics* 287 (1998), 43–50, and for the treatment of myocardial infarction, see C. J. Mackins and R. Levi, *Expert Opinion on Investigational Drugs* 9 (2000), 2537–2542.

In a further aspect of the invention the present compounds are combined with diet and/or exercise.

In a further aspect of the invention the present compounds may be administered in combination with one or more further pharmacologically active substances in any suitable ratios. Such further active agents may be selected from antiobesity agents, antidiabetics, antihypertensive agents, agents for the treatment of complications resulting from or associated with diabetes and agents for the treatment of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention, the antiobesity agent is leptin.

In another embodiment, the antiobesity agent is dexamphetamine or amphetamine.

In another embodiment, the antiobesity agent is fenfluramine or dexfenfluramine.

In still another embodiment, the antiobesity agent is sibutramine.

In a further embodiment, the antiobesity agent is orlistat.

In another embodiment, the antiobesity agent is mazindol or phentermine.

In still another embodiment, the antiobesity agent is phendimetrazine, diethylpropion, fluoxetine, bupropion, topiramate or ecopipam.

Suitable antidiabetics comprise insulin, GLP-1 (glucagon like peptide-1) derivatives such as those disclosed in WO 98/08871 (Novo Nordisk A/S), which is incorporated herein by reference as well as orally active hypoglycaemic agents.

The orally active hypoglycaemic agents preferably comprise imidazolines, sulphonylureas, biguamides, meglitinides, oxadiazolidinediones, thiazolidinediones, insulin sensitizers, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S), which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk A/S and Agouron Pharmaceuticals, Inc.), which is incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention, the present compounds are administered in combination with insulin.

In a further embodiment of the invention, the present compounds are administered in combination with a sulphonylurea eg tolbutamide, chlorpropamide, tolazamide, glibenclamide, glipizide, glimepiride, glicazide or glyburide.

In another embodiment of the invention, the present compounds are administered in combination with a biguamide eg metformin.

In yet another embodiment of the invention, the present compounds are administered in combination with a meglitinide eg repaglinide or nateglinide.

In still another embodiment of the invention, the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention, the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention, the present compounds are administered in combination with an α-glucosidase inhibitor eg voglibose, emiglitate, miglitol or acarbose.

In another embodiment of the invention, the present compounds are administered in combination with an agent acting on the ATP-dependent potassium channel of the β-cells eg tolbutamide, glibenclamide, glipizide, glicazide, BTS-67582 or repaglinide.

In yet another embodiment of the invention, the present compounds may be administered in combination with nateglinide.

In still another embodiment of the invention, the present compounds are administered in combination with an antilipidemic agent eg cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds eg in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet, which may be prepared by conventional tabletting techniques, may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

EXAMPLES

In the examples the following terms are intended to have the following, general meanings:

| | |
|---|---|
| DCM: | dichloromethane, methylenechloride |
| DMA: | N,N-dimethylacetamide |
| DMF: | N,N-dimethyl formamide |
| DMSO: | dimethyl sulphoxide |
| EDC: | N-ethyl-N'-(3-dimethylaminopropyl)carbodiimide hydrochloride |
| HOBt: | N-hydroxybenzotriazole, 1-hydroxybenzotriazole |
| NMP: | N-methylpyrrolidone |

NMR spectra were recorded on Bruker 300 MHz and 400 MHz instruments. HPLC-MS was performed on a Perkin Elmer instrument (API 100).

HPLC was conducted on a reversed-phase x-Terra column from Waters (5 µm, 50 mm×3 mm), eluting with 5%–90% acetonitrile in 0.05% TFA during 7.5 min at 1.5 ml/min.

General Procedure (A)

The compounds of formula (Ia) according to the invention may be prepared by the general procedure (A):

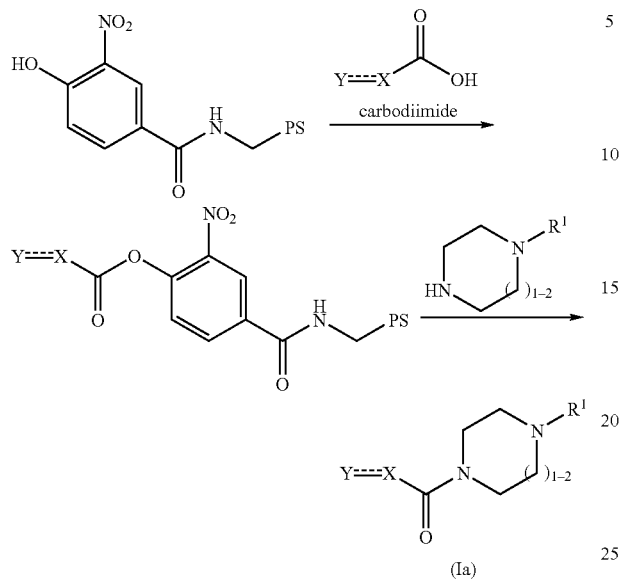

wherein X, Y and $R^1$ are as defined for formula (I) with the proviso that X must not start with —O— or —NH—.

The insoluble nitrophenol is prepared by acylating commercially available aminomethyl polystyrene (1% cross-linked with divinyl benzene, 0.8 mmol/g) with 4-hydroxy-3-nitrobenzoic acid. The resulting support is acylated with a carboxylic acid (DCM/DMF, diisopropyl carbodiimides, 2 hours, room temperature), filtered and washed with DCM (3 hours), and then treated with less than one equivalent of an amine (DCM/acetonitrile, room temperature, overnight). Filtration and concentration yield the pure products, which are tested directly, or further purified by recrystallization or column chromatography and/or transformed into appropriate salts. The products are analyzed by $^1$H NMR and HPLC-MS.

General Procedure (B)

The carbamates of formula (Ib) according to the invention may be prepared by the general procedure (B):

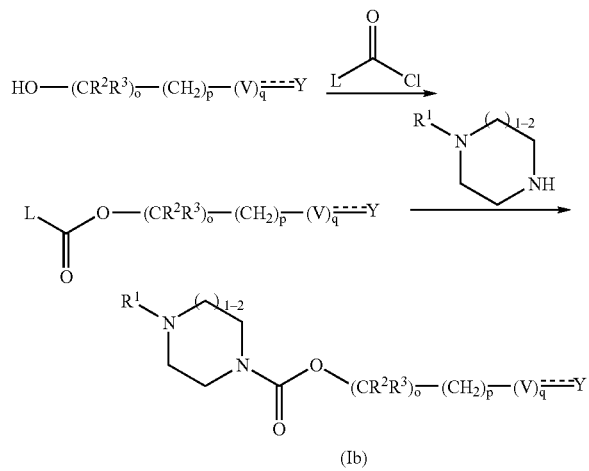

wherein L is chloro or nitrophenol, and $R^1$, $R^2$, $R^3$, o, p and Y are as defined for formula (I).

The carbamates of formula (Ib) are prepared by activating an alcohol with phosgene or 4-nitrophenyl chloroformate, and treating the resulting chloroformate or 4-nitrophenyl carbonate with an amine.

General Procedure (C)

The ureas of formula (Ic) according to the invention may be prepared by the general procedure (C):

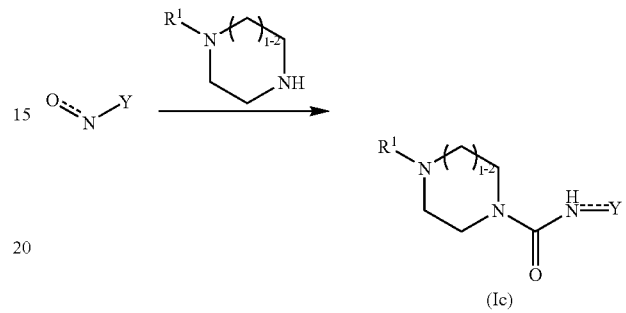

wherein Y and $R^1$ are as defined for formula (I).

The ureas of formula (Ic) are prepared by treating an amine with a suitable isocyanate.

General Procedure (D)

The amides of formula (Ia) can also be prepared in homogeneous phase without the use of a polymeric support:

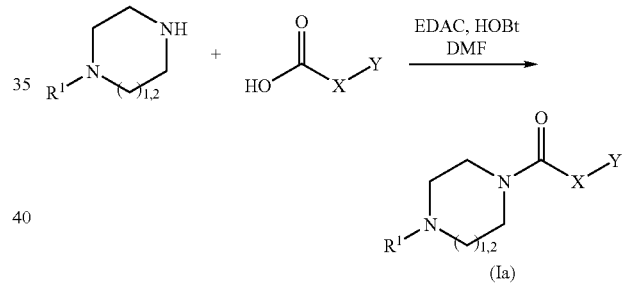

wherein X, Y and $R^1$ are as defined for formula (I) with the proviso that X must not start with —O— or —NH—.

To a mixture of the acid (150 mmol), DMF (200 ml), and N-hydroxybenzotriazole (40.6 g, 301 mmol) is added a solution of N-ethyl-N'-(3-dimethylaminopropyl)carbodiimide hydrochloride (28.8 g, 150 mmol) in DMF (100 ml). The mixture is stirred at room temperature for 1.5 hour, and a solution of the diamine (150 mmol) in DCM (100 ml) is added. The mixture is stirred at room temperature for 4 hours, concentrated under reduced pressure, and the residue is distributed between ethyl acetate (1.0 l) and a saturated, aqueous $NaHCO_3$ solution (1.0 l). The phases are separated, the organic layer is dried ($MgSO_4$), and concentrated, and the residue is re-dissolved in 1 M aqueous hydrochloric acid (150 ml) or in a solution of another suitable acid. The solution is concentrated, and the residue is dried by co-evaporation with ethanol. Re-crystallization of the residue from ethanol yields the title compound.

Starting Materials

Most of the 1-alkylpiperazines used were commercially available. Non-commercially available 1-alkylpiperazines were prepared by alkylation of 1-tert-butyloxycarbonylpiperazine, followed by tert-butyloxycarbonyl-group removal by treatment with 50% trifluoroacetic acid in dichloromethane at room temperature for one hour.

4-(1,1-Dimethylprop-2-ynyl)piperazine-1-carboxylic acid tert-butyl ester

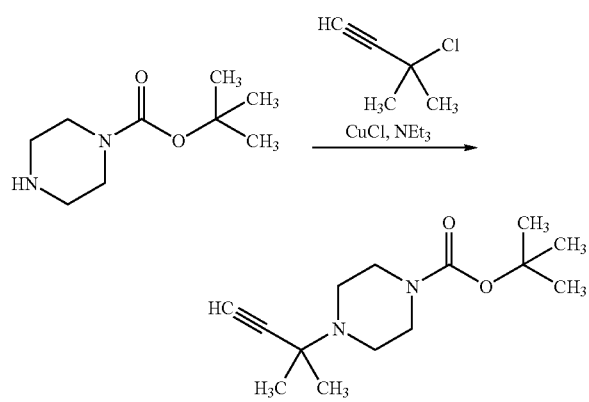

To a stirred mixture of 1-tert-butyloxycarbonylpiperazine (1.10 g, 5.91 mmol), 3-chloro-3-methyl-1-butyne (0.88 ml, 7.81 mmol), THF (10 ml), and NEt$_3$ (1.10 ml, 7.91 mmol) under nitrogen was added copper(I) chloride (45 mg, 0.46 mmol). An exothermic reaction ensued and a precipitate formed. After stirring for 0.5 hours at room temperature water (20 ml) and 1 N aqueous hydrochloric acid (8 ml) were added and the mixture was concentrated under reduced pressure to ⅔ of its original volume. The mixture was washed with ethyl acetate (2×20 ml) and made basic by addition of potassium carbonate (approx. 4 g). Extraction with ethyl acetate (3×20 ml), washing of the combined extracts (30 ml brine), drying with magnesium sulphate, and concentration under reduced pressure yielded 1.15 g (77%) of the title compound as a colourless solid.

$^1$H NMR (CDCl$_3$) δ 1.39 (s, 6H), 1.47 (s, 9H), 2.29 (s, 1H), 2.58 (m, 4H), 3.47 (m, 4H); HPCL-MS: m/z 253 (MH$^+$).

4-Cyclobutylpiperazine-1-carboxylic acid tert-butyl ester

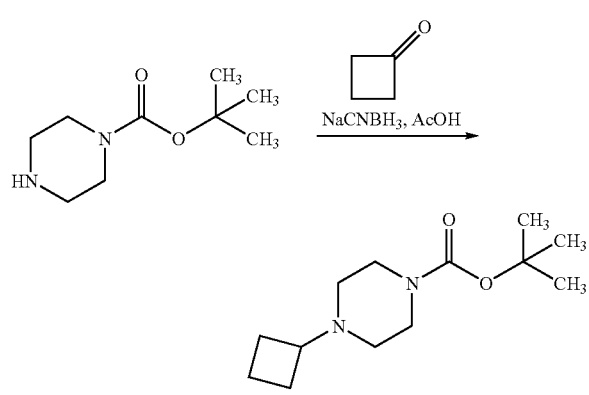

To a solution of 1-tert-butyloxycarbonylpiperazine (2.24 g, 12.0 mmol) in THF (20 ml) were added water (0.2 ml), cyclobutanone (1.35 ml, 18.1 mmol), acetic acid (2.20 ml) and sodium cyanoborohydride (18 ml of a 1M solution in THF, 18 mmol). The mixture was stirred at 60° C. over night, concentrated, and the residue was mixed with water (50 ml) and 1N aqueous hydrochloric acid (15 ml). The solution was washed with ethyl acetate (2×30 ml), made basic by addition of potassium carbonate, extracted (2×20 ml ethyl acetate), and the combined extracts were washed with brine, dried with magnesium sulphate, and concentrated. 1.1 g (38%) of the title compound was obtained as a colourless oil.

$^1$H NMR (DMSO-d$_6$) δ 1.38 (s, 6H), 1.60 (m, 2H), 1.73 (m, 2H), 1.94 (m, 2H), 2.13 (m, 4), 2.67 (m, 1H), 3.27 (m, 4H); HPLC-MS: m/z 241 (MH$^+$).

4-Cyclopropylpiperazine-1-carboxylic acid tert-butyl ester

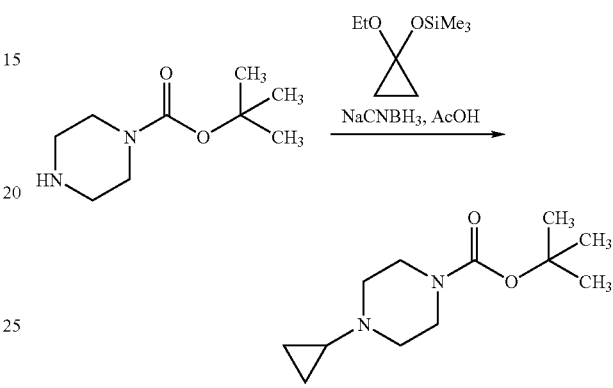

To a solution of 1-tert-butyloxycarbonylpiperazine (1.16 g, 6.23 mmol) in THF (10 ml) and methanol (5 ml) were added 1-ethoxy-1-trimethylsilyloxycyclopropane (2.40 ml, 12.0 mmol), acetic acid (0.75 ml), and sodium cyanoborohydride (7.8 ml of a 1M solution in THF, 7.8 mmol), and the mixture was stirred at 63° C. for 16 hours. The mixture was concentrated under reduced pressure, and the residue was mixed with water (20 ml) and potassium carbonate (6.6 g). The product was extracted with ethyl acetate (3×30 ml), the combined extracts were dried over magnesium sulphate, and concentrated under reduced pressure. 1.79 g (100%) of the title compound was obtained as an oil, which completely crystallized after a few hours.

$^1$H NMR (DMSO-d$_6$) δ 0.29 (m, 2H), 0.42 (m, 2H), 1.38 (s, 9H), 1.60 (m, 1H), 2.43 (m, 4H), 3.23 (m, 4H); HPLC-MS: m/z 227 (MH$^+$).

4-Cyclopropylmethyl piperazine-1-carboxylic acid tert-butyl ester

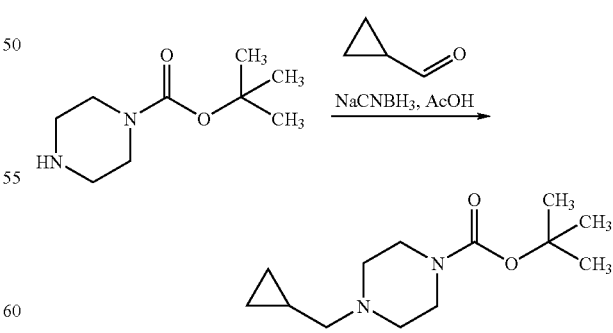

To a solution of 1-tert-butyloxycarbonylpiperazine (2.24 g, 12.0 mmol) in THF (10 ml) were added water (0.15 ml), acetic acid (3.60 ml), formylcyclopropane (1.35 ml, 18.1 mmol), and sodium cyanoborohydride (18 ml of a 1M solution in THF, 18 mmol). The mixture was stirred at 20°

C. for 14 hours. The mixture is concentrated under reduced pressure, and the residue is mixed with water (80 ml) and 1 N aqueous hydrochloric acid (40 ml). After washing with ethyl acetate (20 ml) the aqueous phase is made basic by addition of potassium carbonate (approx. 20 g) and extracted with ethyl acetate (4×30 ml). The combined extracts were dried with magnesium sulphate and concentrated under reduced pressure, to yield 2.3 g (80%) of the title compound as a colourless oil.

$^1$H NMR (DMSO-$d_6$) δ 0.05 (m, 2H), 0.43 (m, 2H), 0.79 (m, 1H), 1.38 (s, 9H), 2.16 (d, J=7 Hz, 2H), 2.33 (m, 4H), 3.30 (m, 4H); HPLC-MS: m/z 241 (MH$^+$).

Example 44

General Procedure (A)

1-(3-Fluoro-4-methoxyphenyl)-4-(4-pyridin-4-ylpiperazin-1-yl)butane-1,4-dione

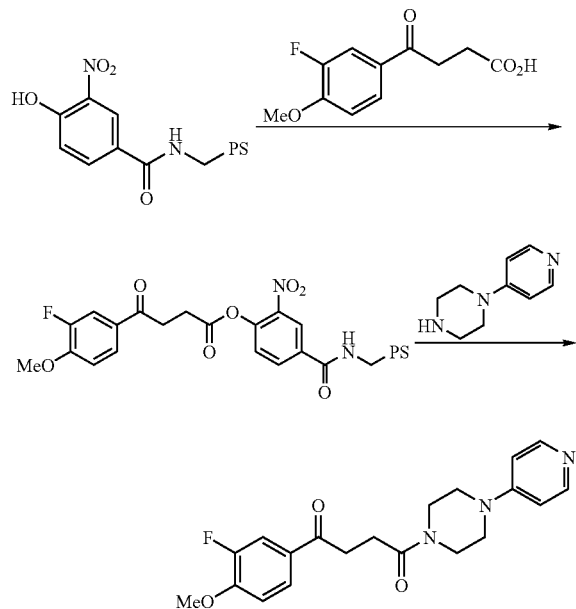

To the polymeric nitrophenol (1.5 g, approx. 1 mmol) was added a solution of 3-(4-methoxy-3-fluorobenzoyl)propionic acid (1.66 g, 7.34 mmol) in a mixture of 1,2-dichloropropane (15 ml) and DMF (6 ml), followed by the addition of DIC (0.78 ml, 5.01 mmol). The mixture was shaken at room temperature for 13 hours, filtered, and the polymer was extensively washed with DCM, DMF, and 1,2-dichloropropane. To the polymer was added 1,2-dichloropropane (5 ml), a solution of 1-(4-pyridyl)piperazine (116 mg, 0.71 mmol) in 1,2-dichloropropane (10 ml), and triethylamine (0.2 ml). The resulting mixture was shaken at room temperature for 21 hours, filtered, and the polymer was carefully washed with DCM and methanol. The combined filtrates were concentrated to yield the crude product as an oil (0.38 g). Crystallization from acetonitrile (2 ml) at –20° C. yielded 0.19 g (5.1 mmol, 72%) of the title compound as almost colourless solid.

$^1$H NMR (400 MHz, DMSO): δ 2.73 (m, 2H), 3.21 (m, 2H), 3.30–3.47 (m, 4H), 3.57 (m, 2H), 3.67 (m, 2H), 3.93 (s, 3H), 6.84 (m, 2H), 7.30 (t, J=7 Hz, 1H), 7.77 (m, 1H), 7.89 (m, 1H), 8.19 (m, 2H); HPLC-MS: 372 (MH$^+$).

Example 188

General Procedure (D)

1-(4-Chlorophenyl)-4-(4-cyclopentylpiperazin-1-yl)butane-1,4-dione hydrochloride

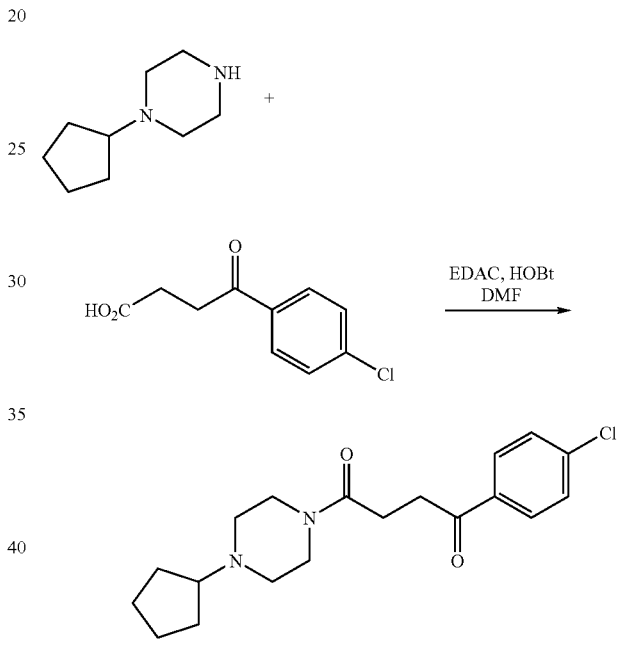

To a mixture of 3-(4-chlorobenzoyl)propionic acid (31.9 g, 150 mmol), DMF (200 ml), and N-hydroxybenzotriazole (40.6 g, 301 mmol) was added a solution of N-ethyl-N'-(3-dimethylaminopropyl)carbodiimide hydrochloride (28.8 g, 150 mmol) in DMF (100 ml). The mixture was stirred at room temperature for 1.5 hour, and a solution of 1-cyclopentylpiperazine (23.2 g, 150 mmol) in DCM (100 ml) was added. The mixture was stirred at room temperature for 4 hours, concentrated under reduced pressure, and the residue was distributed between ethyl acetate (1.0 l) and a saturated, aqueous NaHCO$_3$ solution (1.0 l). Phases were separated, the organic layer was dried (MgSO$_4$), and concentrated, and the residue was redissolved in 1 molar aqueous hydrochloric acid (150 ml). The solution was concentrated, and the residue was dried by coevaporation with ethanol. Recrystallization of the residue from ethanol yielded 31.1 g (54%) of the title compound. Concentration of the mother liquor gave additional 19.4 g (34%) of product.

Using one of the above general procedures, the following compounds were prepared:

| Example No | Structure | Name | Found MH+ |
|---|---|---|---|
| 1 | 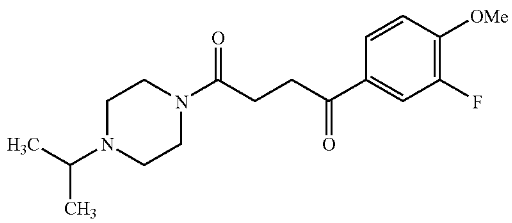 | 1-(3-Fluoro-4-methoxy-phenyl)-4-(4-isopropyl-piperazin-1-yl)butane-1,4-dione hydrochloride | 337 |
| 2 | 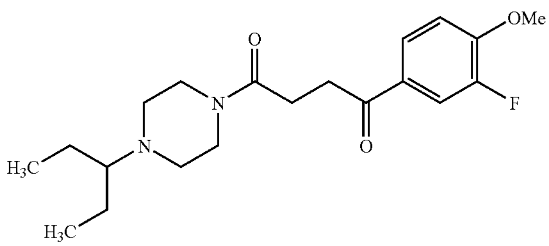 | 1-[4-(1-Ethylpropyl)-piperazin-1-yl]-4-(3-fluoro-4-methoxyphenyl)butane-1,4-dione hydrochloride | 365 |
| 3 | 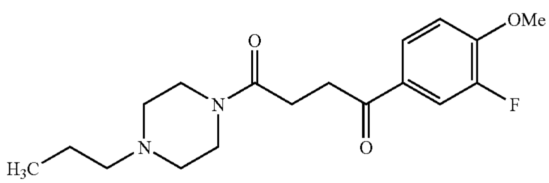 | 1-(3-Fluoro-4-methoxy-phenyl)-4-(4-propyl-piperazin-1-yl)butane-1,4-dione hydrochloride | 337 |
| 4 | 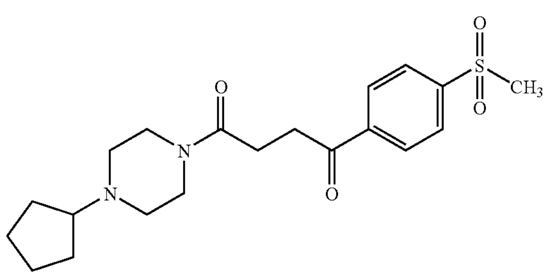 | 1-(4-Cyclopentylpiperazin-1-yl)-4-(4-methanesulfonyl-phenyl)butane-1,4-dione hydrochloride | 393 |
| 5 | 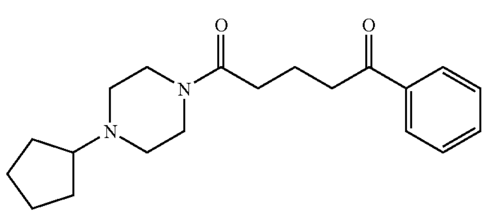 | 1-(4-Cyclopentylpiperazin-1-yl)-4-phenylpentane-1,5-dione hydrochloride | 329 |
| 6 | 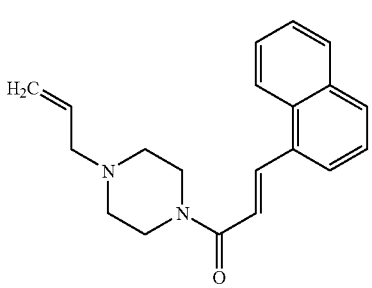 | 1-(4-Allylpiperazin-1-yl)-3-naphth-1-ylpropenone | 307 |

-continued

| Example No | Structure | Name | Found MH+ |
|---|---|---|---|
| 7 | 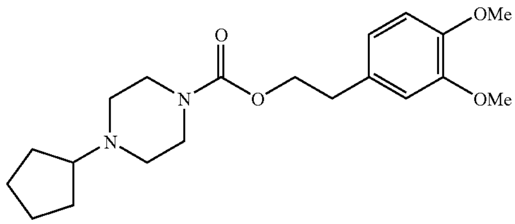 | 4-Cyclopentylpiperazine-1-carboxylic acid 2-(3,4-dimethoxyphenyl)ethyl ester hydrochloride | 363 |
| 8 | 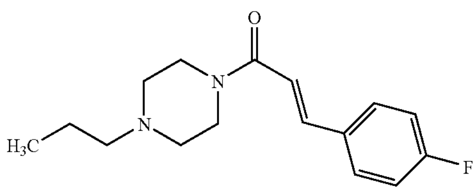 | 3-(4-Fluorophenyl)-1-(4-propylpiperazin-1-yl)-propenone | |
| 9 | 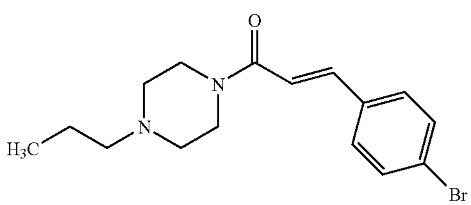 | 3-(4-Bromophenyl)-1-(4-propylpiperazin-1-yl)-propenone | |
| 10 | 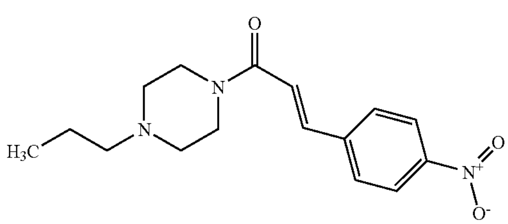 | 3-(4-Nitrophenyl)-1-(4-propylpiperazin-1-yl)-propenone | |
| 11 | 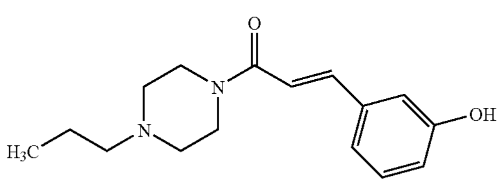 | 3-(3-Hydroxyphenyl)-1-(4-propylpiperazin-1-yl)-propenone | 275 |
| 12 | 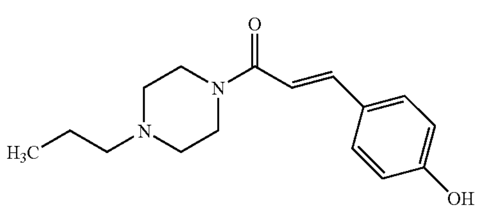 | 3-(4-Hydroxyphenyl)-1-(4-propylpiperazin-1-yl)-propenone | |
| 13 | 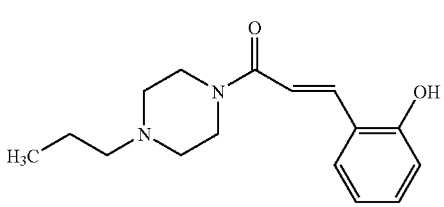 | 3-(2-Hydroxyphenyl)-1-(4-propylpiperazin-1-yl)-propenone | |

-continued

| Example No | Structure | Name | Found MH+ |
|---|---|---|---|
| 14 | 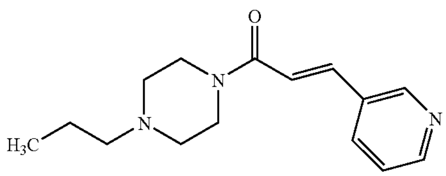 | 1-(4-Propylpiperazin-1-yl)-3-pyridin-3-ylpropenone | |
| 15 | 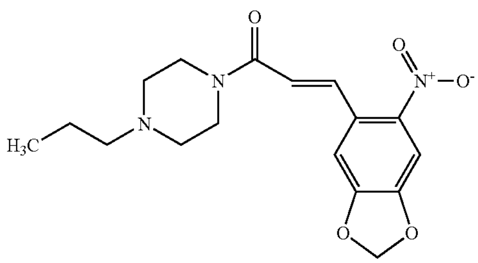 | 3-(6-Nitrobenzo[1,3]dioxol-5-yl)-1-(4-propylpiperazin-1-yl)propenone | |
| 16 | 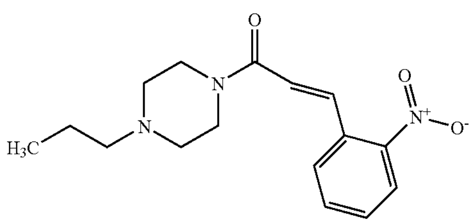 | 3-(2-Nitrophenyl)-1-(4-propylpiperazin-1-yl)-propenone | |
| 17 | 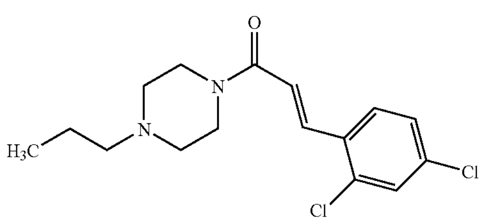 | 3-(2,4-Dichlorophenyl)-1-(4-propylpiperazin-1-yl)-propenone | |
| 18 | 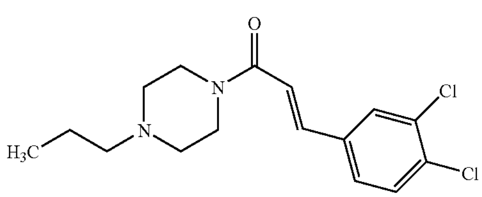 | 3-(3,4-Dichlorophenyl)-1-(4-propylpiperazin-1-yl)-propenone | |
| 19 | 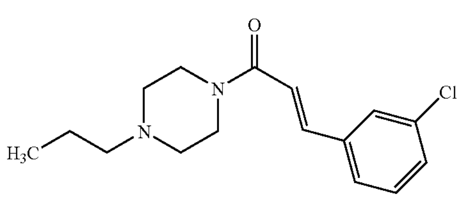 | 3-(3-Chlorophenyl)-1-(4-propylpiperazin-1-yl)-propenone | |
| 20 | 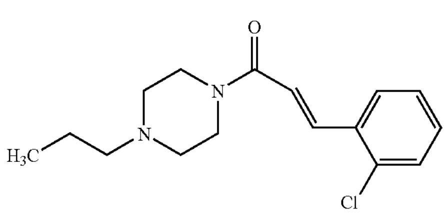 | 3-(2-Chlorophenyl)-1-(4-propylpiperazin-1-yl)-propenone | 293 |

-continued
| Example No | Structure | Name | Found MH+ |
|---|---|---|---|
| 21 | 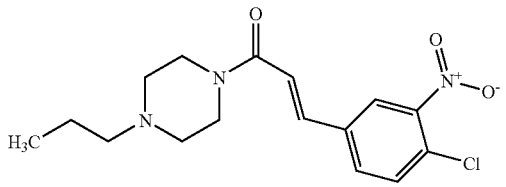 | 3-(4-Chloro-3-nitrophenyl)-1-(4-propylpiperazin-1-yl)-propenone | |
| 22 | 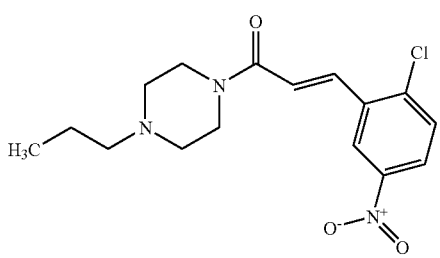 | 3-(2-Chloro-5-nitrophenyl)-1-(4-propylpiperazin-1-yl)-propenone | |
| 23 | 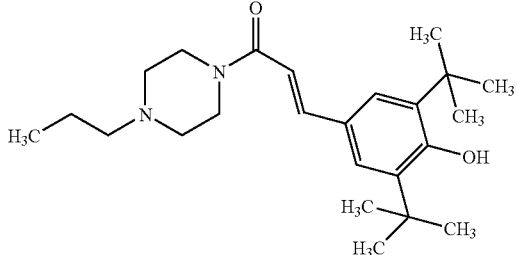 | 3-(3,5-Di-tert-butyl-4-hydroxyphenyl)-1-(4-propyl-piperazin-1-yl)propenone | 387 |
| 24 | 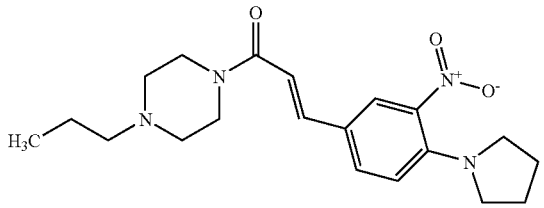 | 3-(3-Nitro-4-pyrrolidin-1-ylphenyl)-1-(4-propyl-piperazin-1-yl)propenone | |
| 25 | 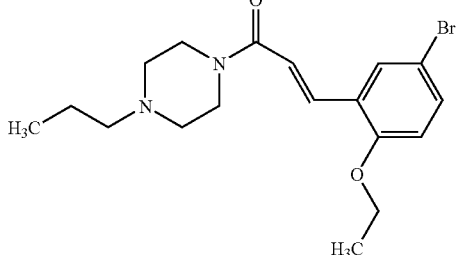 | 3-(5-Bromo-2-ethoxyphenyl)-1-(4-propylpiperazin-1-yl)-propenone | |
| 26 | 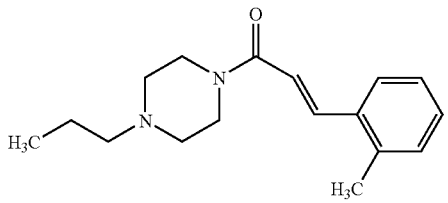 | 1-(4-Propylpiperazin-1-yl)-3-o-tolylpropenone | |

-continued

| Example No | Structure | Name | Found MH+ |
|---|---|---|---|
| 27 | 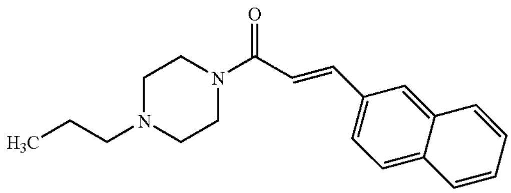 | 3-Naphth-2-yl-1-(4-propyl-piperazin-1-yl)propenone | |
| 28 | 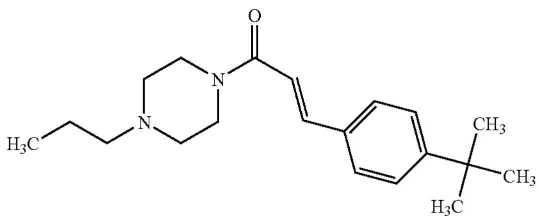 | 3-(4-tert-Butylphenyl)-1-(4-propylpiperazin-1-yl) propenone | |
| 29 | 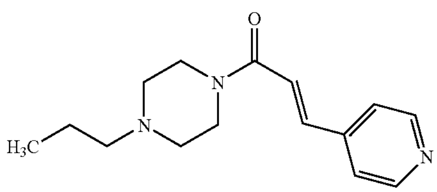 | 1-(4-Propylpiperazin-1-yl)-3-pyridin-4-ylpropenone | |
| 30 | 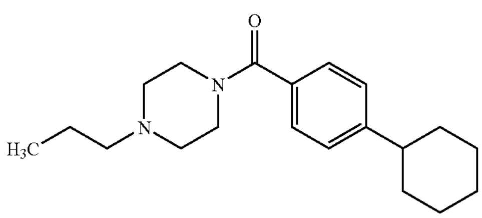 | (4-Cyclohexylphenyl)-(4-propylpiperazin-1-yl)-methanone | |
| 31 | 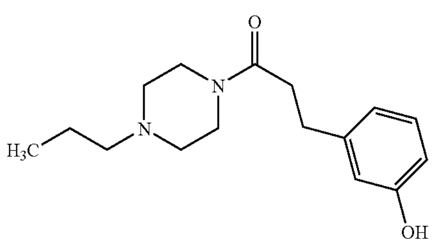 | 3-(3-Hydroxyphenyl)-1-(4-propylpiperazin-1-yl) propan-1-one | |
| 32 | 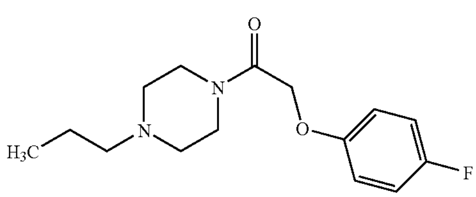 | 2-(4-Fluorophenoxy)-1-(4-propylpiperazin-1-yl)-ethanone | |
| 33 | 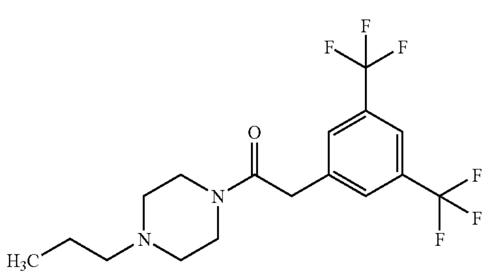 | 2-(3,5-Bis-trifluoromethyl-phenyl)-1-(4-propylpiperazin-1-yl)ethanone | |

-continued

| Example No | Structure | Name | Found MH+ |
|---|---|---|---|
| 34 | 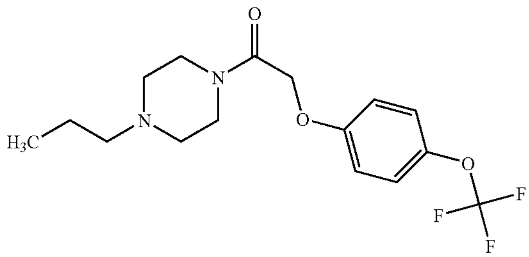 | 1-(4-Propylpiperazin-1-yl)-2-(4-trifluoromethoxyphenoxy)-ethanone | 347 |
| 35 | 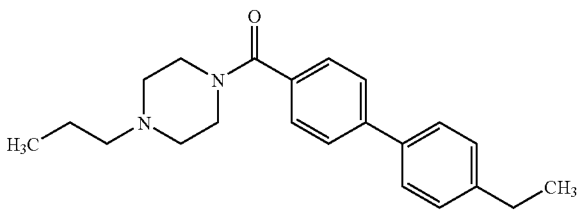 | (4'-Ethylbiphenyl-4-yl)-(4-propylpiperazin-1-yl)-methanone | |
| 36 | 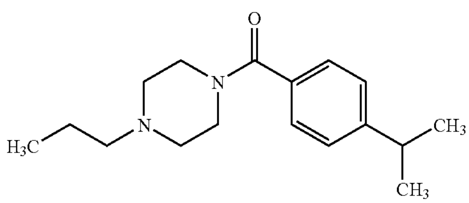 | (4-Isopropylphenyl)-(4-propylpiperazin-1-yl)-methanone | |
| 37 | 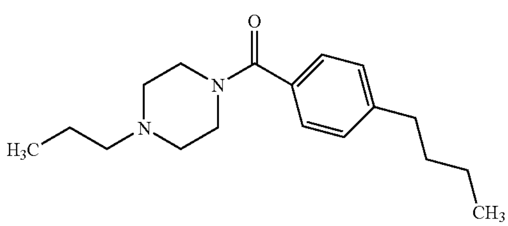 | (4-Butylphenyl)-(4-propyl-piperazin-1-yl)-methanone | |
| 38 | 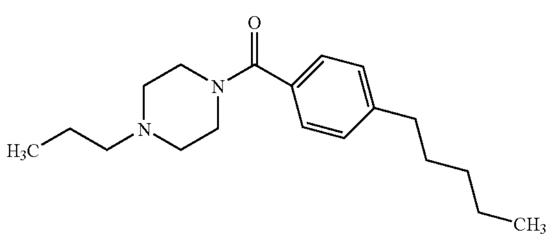 | (4-Pentylphenyl)-(4-propyl-piperazin-1-yl)methanone | |
| 39 | 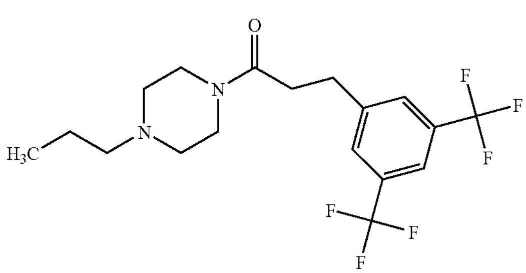 | 3-(3,5-Bis-trifluoromethyl-phenyl)-1-(4-propylpiperazin-1-yl)propan-1-one | |

-continued

| Example No | Structure | Name | Found MH+ |
|---|---|---|---|
| 40 | 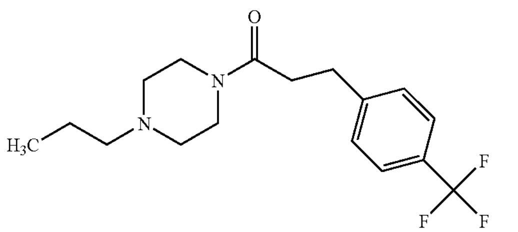 | 1-(4-Propylpiperazin-1-yl)-3-(4-trifluoromethylphenyl)-propan-1-one | |
| 41 | 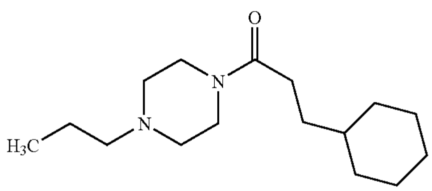 | 3-Cyclohexyl-1-(4-propyl-piperazin-1-yl)propan-1-one | |
| 42 | 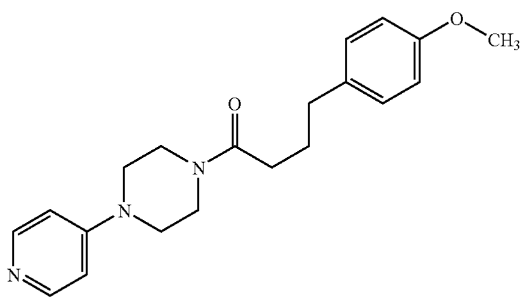 | 4-(4-Methoxyphenyl)-1-(4-pyridin-4-ylpiperazin-1-yl)-butan-1-one | 340 |
| 43 | 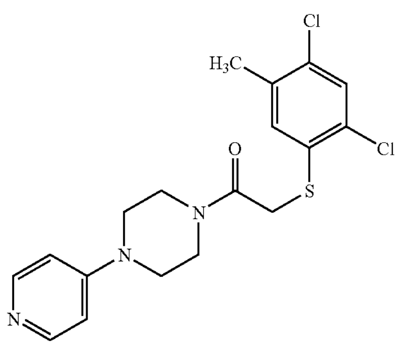 | 2-(2,4-Dichloro-5-methyl-phenylsulfanyl)-1-(4-pyridin-4-ylpiperazin-1-yl)ethanone | 397 |
| 44 | 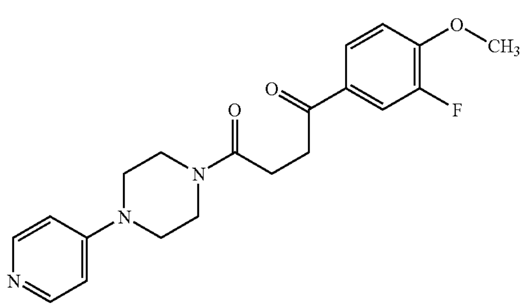 | 1-(3-Fluoro-4-methoxy-phenyl)-4-(4-pyridin-4-yl-piperazin-1-yl)butane-1,4-dione | 372 |

-continued

| Example No | Structure | Name | Found MH+ |
|---|---|---|---|
| 45 | 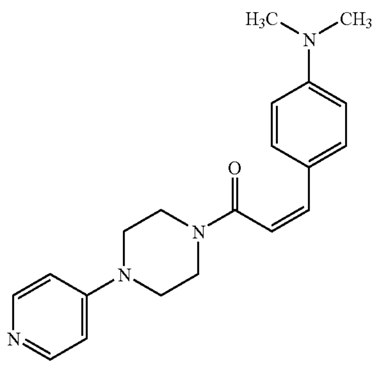 | 3-(4-Dimethylaminophenyl)-1-(4-pyridin-4-ylpiperazin-1-yl)propenone | 337 |
| 46 | 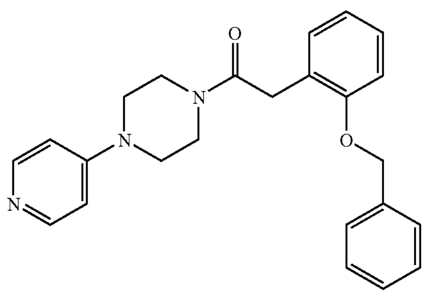 | 2-(2-Benzyloxyphenyl)-1-(4-pyridin-4-ylpiperazin-1-yl)ethanone | 388 |
| 47 | 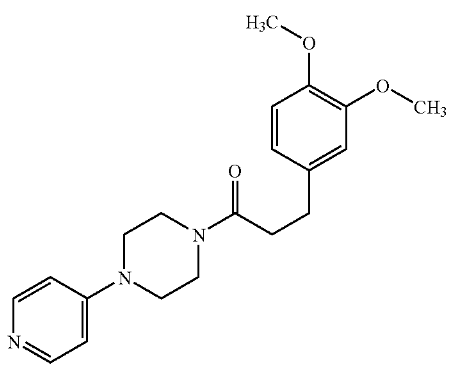 | 3-(3,4-Dimethoxyphenyl)-1-(4-pyridin-4-ylpiperazin-1-yl)propan-1-one | 356 |
| 48 | 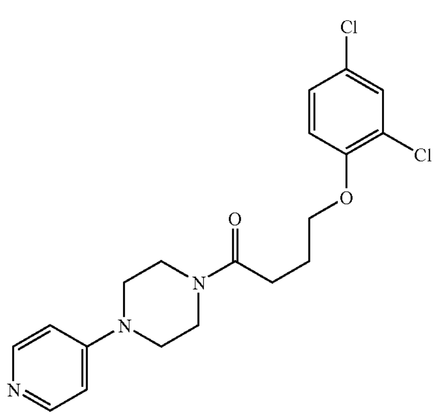 | 4-(2,4-Dichlorophenoxy)-1-(4-pyridin-4-ylpiperazin-1-yl)-butan-1-one | 395 |

-continued

| Example No | Structure | Name | Found MH+ |
|---|---|---|---|
| 49 | 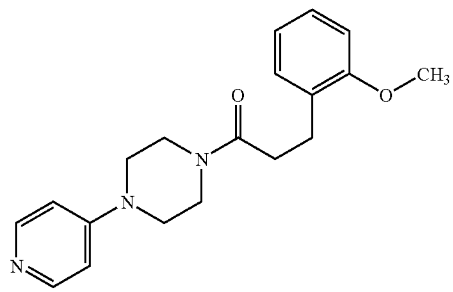 | 3-(2-Methoxyphenyl)-1-(4-pyridin-4-ylpiperazin-1-yl)-propan-1-one | 326 |
| 50 | 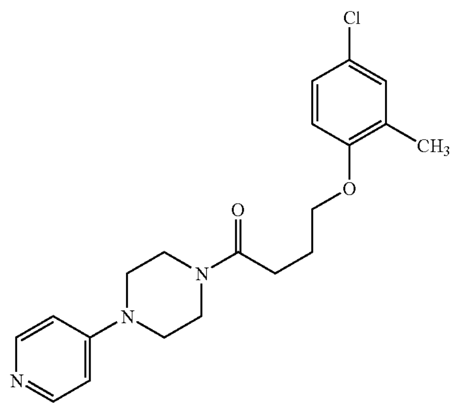 | 4-(4-Chloro-2-methyl-phenoxy)-1-(4-pyridin-4-ylpiperazin-1-yl)butan-1-one | 374 |
| 51 | 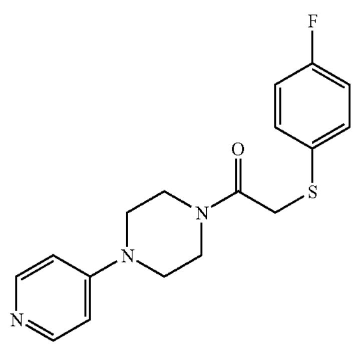 | 2-(4-Fluorophenylsulfanyl)-1-(4-pyridin-4-ylpiperazin-1-yl)-ethanone | 332 |
| 52 | 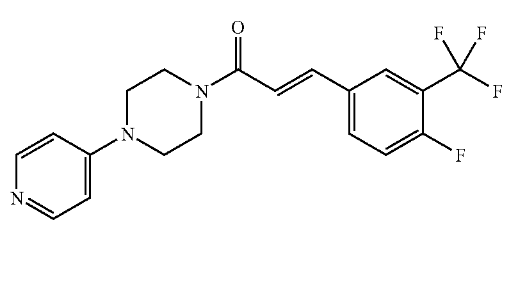 | 3-(4-Fluoro-3-trifluoro-methylphenyl)-1-(4-pyridin-4-ylpiperazin-1-yl)propenone | 380 |

-continued
| Example No | Structure | Name | Found MH+ |
|---|---|---|---|
| 53 | 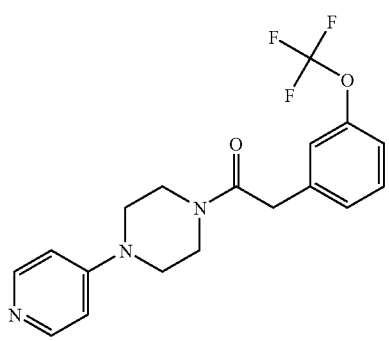 | 1-(4-Pyridin-4-ylpiperazin-1-yl)-2-(3-trifluoromethoxy-phenyl)ethanone | 366 |
| 54 | 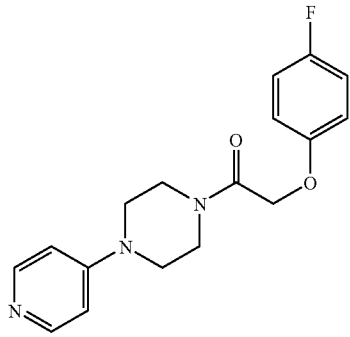 | 2-(4-Fluorophenoxy)-1-(4-pyridin-4-ylpiperazin-1-yl)-ethanone | 316 |
| 55 | 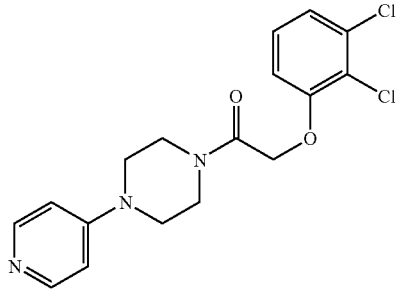 | 2-(2,3-Dichlorophenoxy)-1-(4-pyridin-4-ylpiperazin-1-yl)ethanone | 367 |
| 56 | 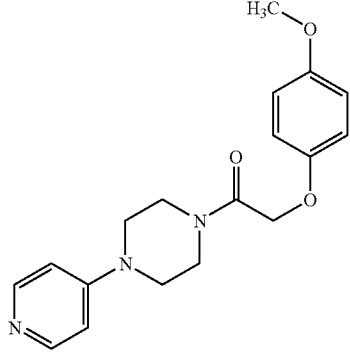 | 2-(4-Methoxyphenoxy)-1-(4-pyridin-4-ylpiperazin-1-yl)ethanone | 328 |

-continued

| Example No | Structure | Name | Found MH+ |
|---|---|---|---|
| 57 | 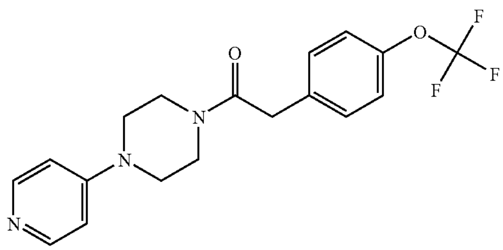 | 1-(4-Pyridin-4-ylpiperazin-1-yl)-2-(4-trifluoromethoxy-phenyl)ethanone | 366 |
| 58 | 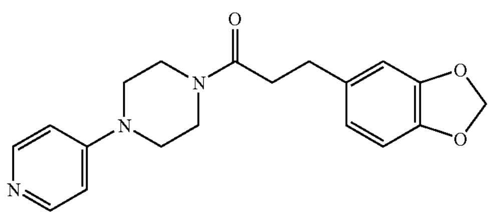 | 3-Benzo[1,3]dioxol-5-yl-1-(4-pyridin-4-ylpiperazin-1-yl)propan-1-one | 340 |
| 59 | 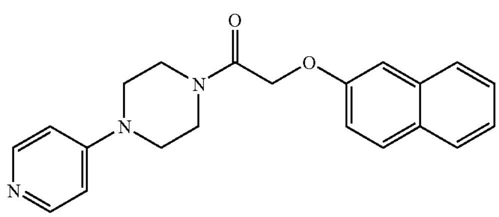 | 2-(Naphth-2-yloxy)-1-(4-pyridin-4-ylpiperazin-1-yl)-ethanone | 348 |
| 60 | 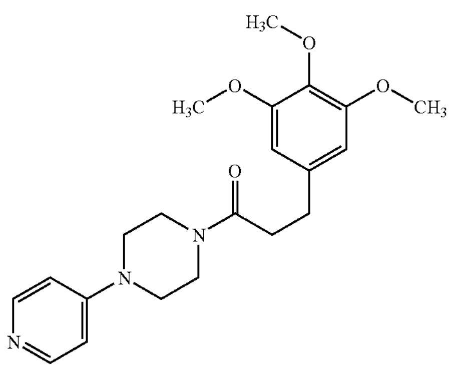 | 1-(4-Pyridin-4-ylpiperazin-1-yl)-3-(3,4,5-trimethoxy-phenyl)propan-1-one | 386 |
| 61 | 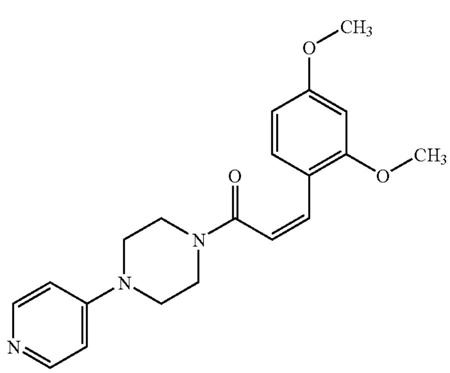 | 3-(2,4-Dimethoxyphenyl)-1-(4-pyridin-4-ylpiperazin-1-yl)propenone | 354 |

-continued

| Example No | Structure | Name | Found MH+ |
|---|---|---|---|
| 62 | 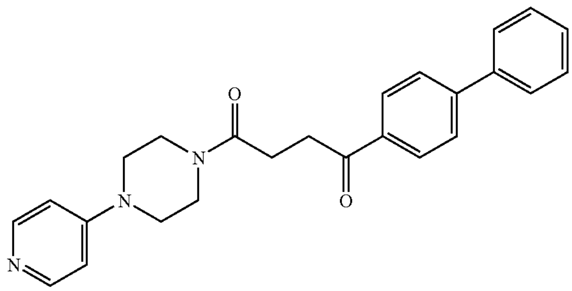 | 1-Biphenyl-4-yl-4-(4-pyridin-4-ylpiperazin-1-yl)butane-1,4-dione hydrochloride | 400 |
| 63 | 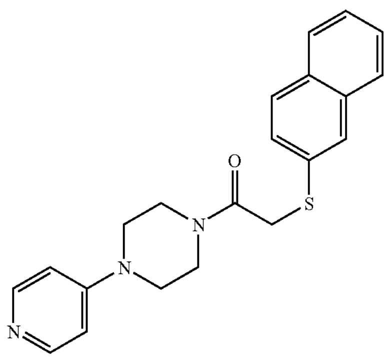 | 2-(Naphth-2-ylsulfanyl)-1-(4-pyridin-4-ylpiperazin-1-yl)-ethanone | 364 |
| 64 | 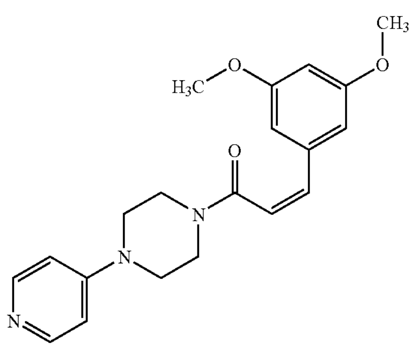 | 3-(3,5-Dimethoxyphenyl)-1-(4-pyridin-4-ylpiperazin-1-yl)propenone | 354 |
| 65 | 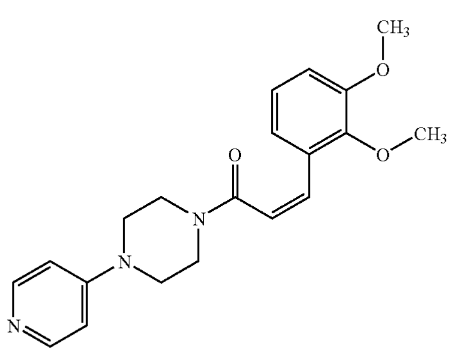 | 3-(2,3-Dimethoxyphenyl)-1-(4-pyridin-4-ylpiperazin-1-yl)propenone | 354 |

-continued

| Example No | Structure | Name | Found MH+ |
|---|---|---|---|
| 66 | 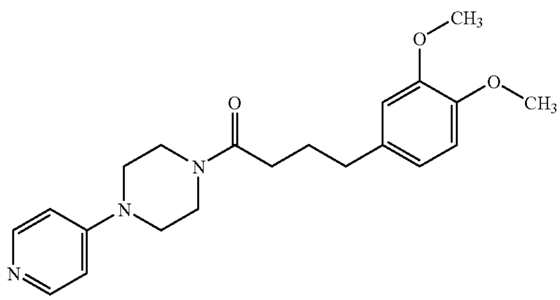 | 4-(3,4-Dimethoxyphenyl)-1-(4-pyridin-4-ylpiperazin-1-yl)-butan-1-one | 370 |
| 67 | 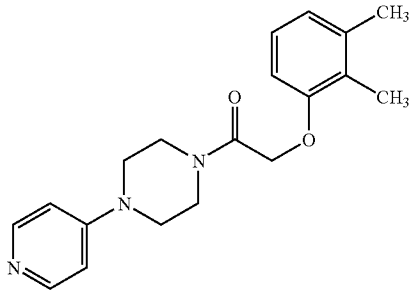 | 2-(2,3-Dimethylphenoxy)-1-(4-pyridin-4-ylpiperazin-1-yl)-ethanone | 326 |
| 68 | 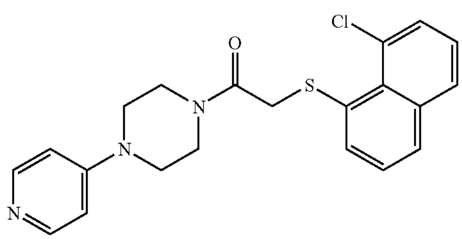 | 2-(8-Chloro-naphth-1-yl-sulfanyl)-1-(4-pyridin-4-yl-piperazin-1-yl)ethanone | 398 |
| 69 | 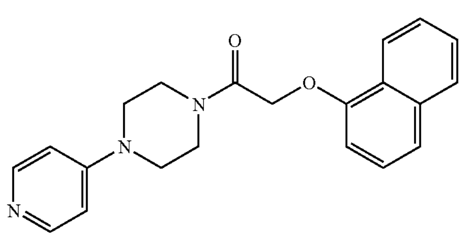 | 2-(Naphth-1-yloxy)-1-(4-pyridin-4-ylpiperazin-1-yl)-ethanone | 378 |
| 70 | 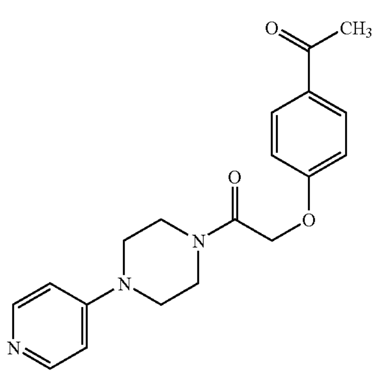 | 2-(4-Acetylphenoxy)-1-(4-pyridin-4-ylpiperazin-1-yl)-ethanone | 340 |

-continued
| Example No | Structure | Name | Found MH+ |
|---|---|---|---|
| 71 | 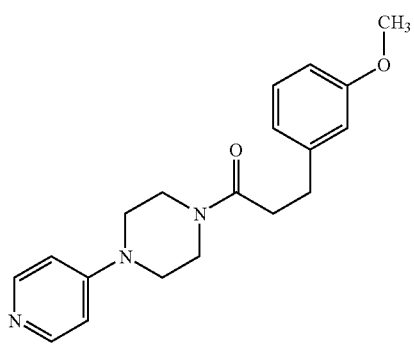 | 3-(3-Methoxyphenyl)-1-(4-pyridin-4-ylpiperazin-1-yl)-propan-1-one | 326 |
| 72 | 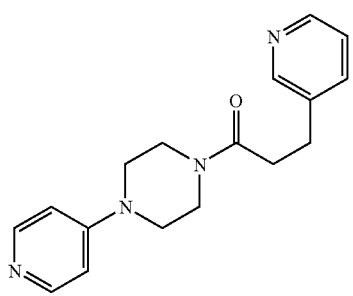 | 3-Pyridin-3-yl-1-(4-pyridin-4-ylpiperazin-1-yl)propan-1-one | 297 |
| 73 | 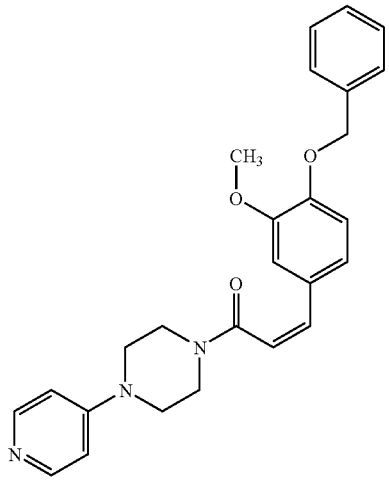 | 3-(4-Benzyloxy-3-methoxy-phenyl)-1-(4-pyridin-4-yl-piperazin-1-yl)propenone | 430 |
| 74 | 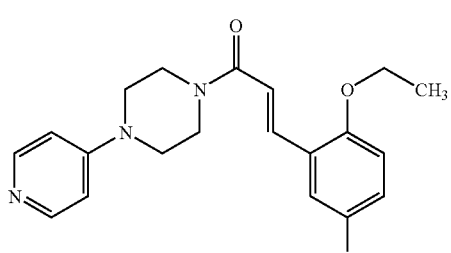 | 3-(5-Bromo-2-ethoxyphenyl)-1-(4-pyridin-4-ylpiperazin-1-yl)propenone | 417 |

-continued

| Example No | Structure | Name | Found MH+ |
|---|---|---|---|
| 75 | 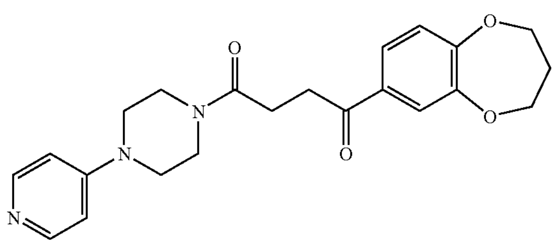 | 1-(3,4-Dihydro-2H-benzo[b]-[1,4]dioxepin-7-yl)-4-(4-pyridin-4-ylpiperazin-1-yl)-butane-1,4-dione | 396 |
| 76 | 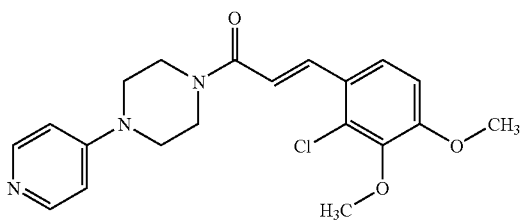 | 3-(2-Chloro-3,4-dimethoxy-phenyl)-1-(4-pyridin-4-yl-piperazin-1-yl)propenone | 388 |
| 77 | 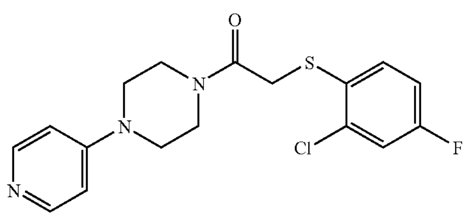 | 2-(2-Chloro-4-fluorophenyl-sulfanyl)-1-(4-pyridin-4-yl-piperazin-1-yl)-ethanone | 366 |
| 78 | 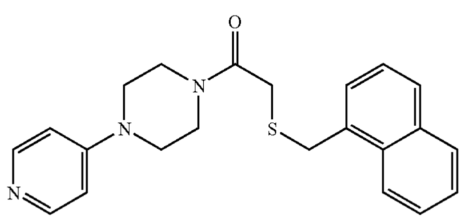 | 2-(Naphth-1-ylmethyl-sulfanyl)-1-(4-pyridin-4-yl-piperazin-1-yl)ethanone | 378 |
| 79 | 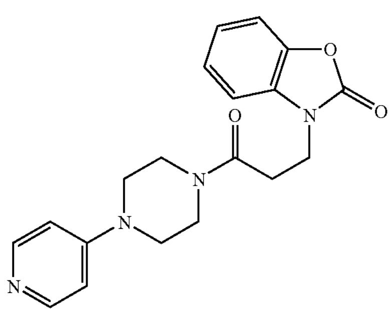 | 3-[3-Oxo-3-(4-pyridin-4-yl-piperazin-1-yl)propyl]-3H-benzoxazol-2-one hydrochloride | 353 |
| 80 | 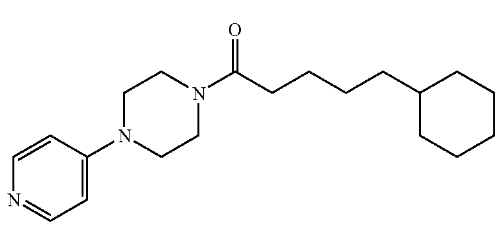 | 5-Cyclohexyl-1-(4-pyridin-4-ylpiperazin-1-yl)pentan-1-one | 330 |

-continued
| Example No | Structure | Name | Found MH+ |
|---|---|---|---|
| 81 | 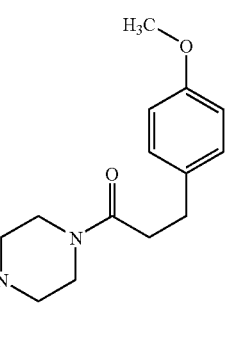 | 3-(4-Methoxyphenyl)-1-(4-pyridin-4-ylpiperazin-1-yl)-propan-1-one | 326 |
| 82 | 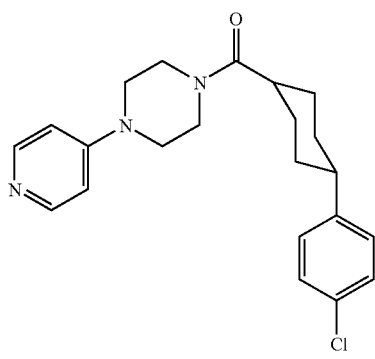 | [4-(4-Chlorophenyl)cyclohexyl]-(4-pyridin-4-yl-piperazin-1-yl)methanone | 384 |
| 83 | 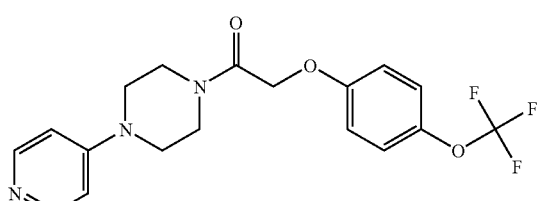 | 1-(4-Pyridin-4-ylpiperazin-1-yl)-2-(4-trifluoromethoxyphenoxy)ethanone | 382 |
| 84 | 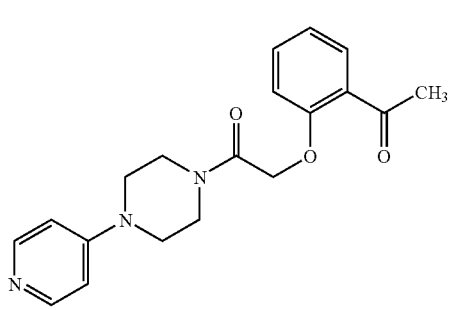 | 2-(2-Acetylphenoxy)-1-(4-pyridin-4-ylpiperazin-1-yl)-ethanone hydrochloride | 340 |
| 85 | 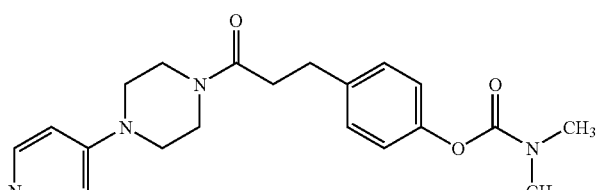 | Dimethyl-carbamic acid 4-[3-oxo-3-(4-pyridin-4-yl-piperazin-1-yl)propyl]phenyl ester | 383 |

-continued

| Example No | Structure | Name | Found MH+ |
|---|---|---|---|
| 86 | 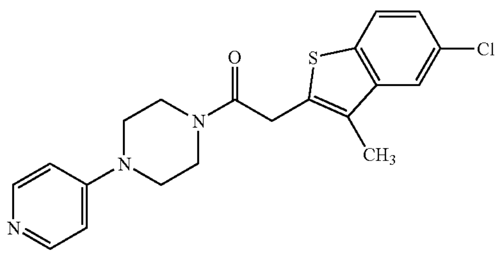 | 2-(5-Chloro-3-methyl-benzo[b]thiophen-2-yl)-1-(4-pyridin-4-ylpiperazin-1-yl)-ethanone | 386 |
| 87 | 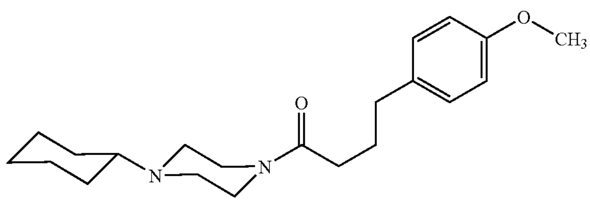 | 1-(4-Cyclohexylpiperazin-1-yl)-4-(4-methoxyphenyl)-butan-1-one | 345 |
| 88 | 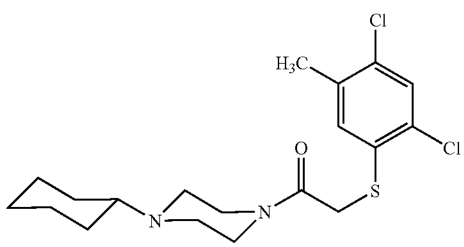 | 1-(4-Cyclohexylpiperazin-1-yl)-2-(2,4-dichloro-5-methyl-phenylsulfanyl)ethanone | 402 |
| 89 | 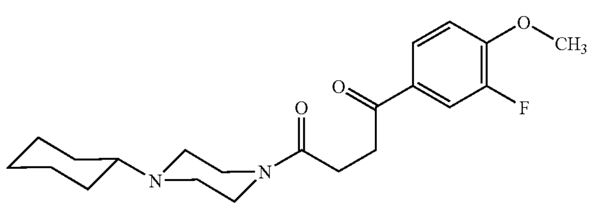 | 1-(4-Cyclohexylpiperazin-1-yl)-4-(3-fluoro-4-methoxy-phenyl)butane-1,4-dione hydrochloride | 377 |
| 90 | 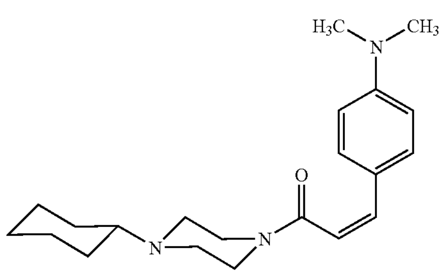 | 1-(4-Cyclohexylpiperazin-1-yl)-3-(4-dimethylamino-phenyl)propenone | 342 |
| 91 | 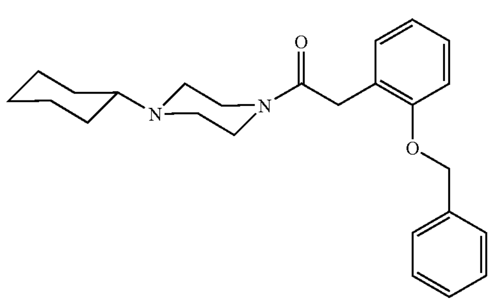 | 2-(2-Benzyloxyphenyl)-1-(4-cyclohexylpiperazin-1-yl)-ethanone | 393 |

-continued

| Example No | Structure | Name | Found MH+ |
|---|---|---|---|
| 92 | 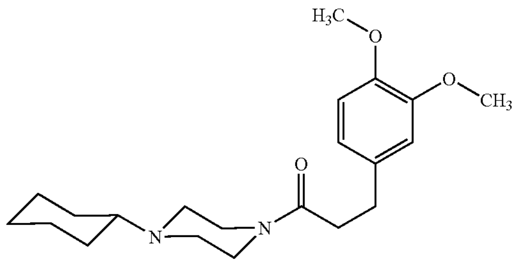 | 1-(4-Cyclohexylpiperazin-1-yl)-3-(3,4-dimethoxyphenyl)-propan-1-one | 361 |
| 93 | 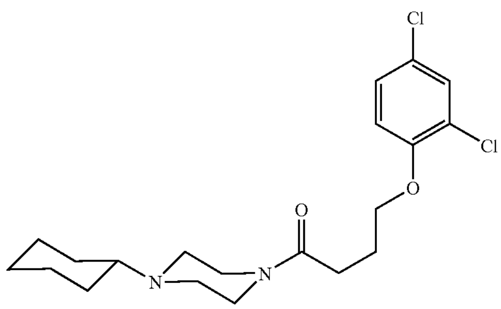 | 1-(4-Cyclohexylpiperazin-1-yl)-4-(2,4-dichlorophenoxy)-butan-1-one | 400 |
| 94 | 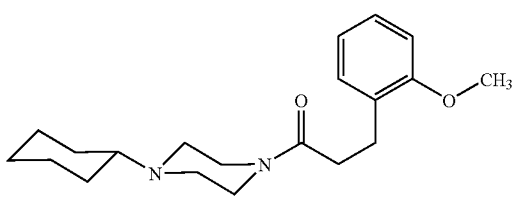 | 1-(4-Cyclohexylpiperazin-1-yl)-3-(2-methoxyphenyl)-propan-1-one | 331 |
| 95 | 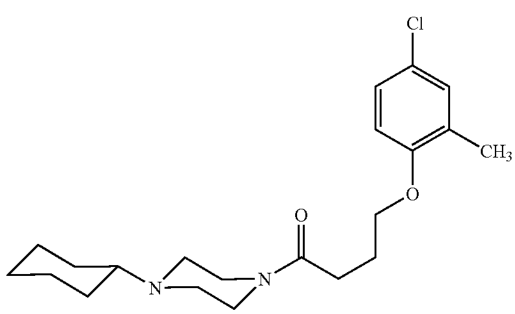 | 4-(4-Chloro-2-methyl-phenoxy)-1-(4-cyclohexyl-piperazin-1-yl)butan-1-one | 379 |
| 96 | 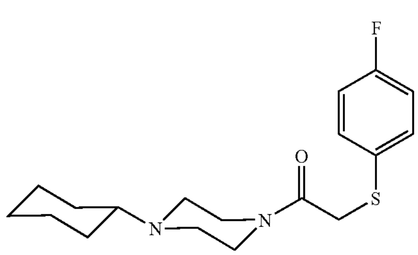 | 1-(4-Cyclohexylpiperazin-1-yl)-2-(4-fluorophenyl-sulfanyl)ethanone | 337 |
| 97 | 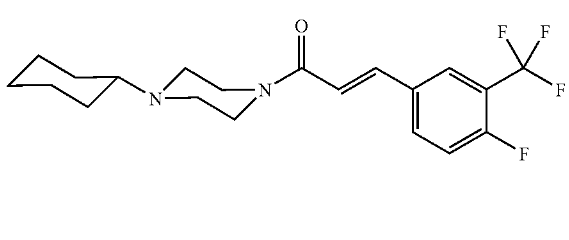 | 1-(4-Cyclohexylpiperazin-1-yl)-3-(4-fluoro-3-trifluoro-methylphenyl)propenone | 385 |

-continued

| Example No | Structure | Name | Found MH+ |
|---|---|---|---|
| 98 | 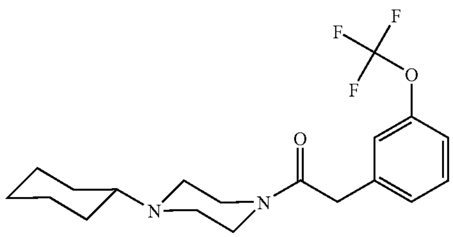 | 1-(4-Cyclohexylpiperazin-1-yl)-2-(3-trifluoromethoxy-phenyl)ethanone | 371 |
| 99 | 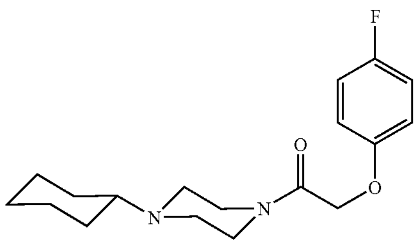 | 1-(4-Cyclohexylpiperazin-1-yl)-2-(4-fluorophenoxy)-ethanone | 321 |
| 100 | 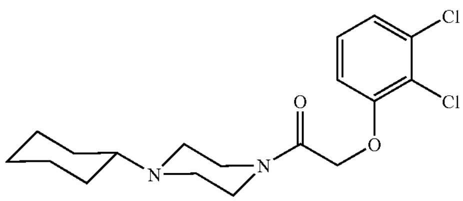 | 1-(4-Cyclohexylpiperazin-1-yl)-2-(2,3-dichlorophenoxy)-ethanone | 372 |
| 101 | 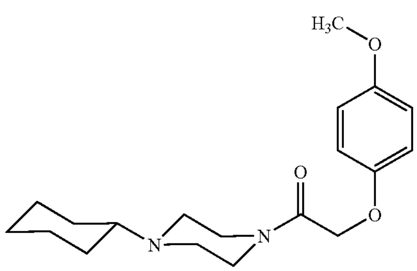 | 1-(4-Cyclohexylpiperazin-1-yl)-2-(4-methoxyphenoxy)-ethanone | 333 |
| 102 | 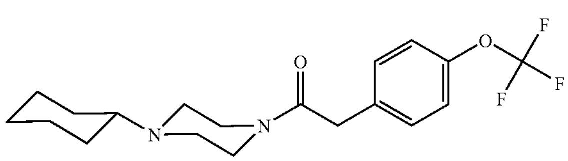 | 1-(4-Cyclohexylpiperazin-1-yl)-2-(4-trifluoromethoxy-phenyl)ethanone | 371 |
| 103 | 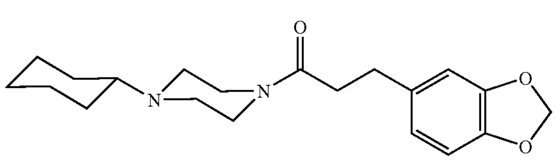 | 3-Benzo[1,3]dioxol-5-yl-1-(4-cyclohexylpiperazin-1-yl)-propan-1-one | 345 |
| 104 | 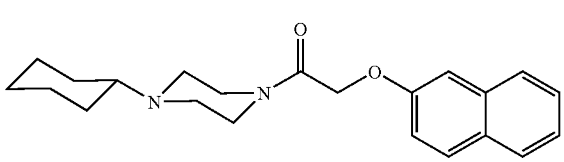 | 1-(4-Cyclohexylpiperazin-1-yl)-2-(naphth-2-yloxy)-ethanone | 353 |

-continued

| Example No | Structure | Name | Found MH+ |
|---|---|---|---|
| 105 | 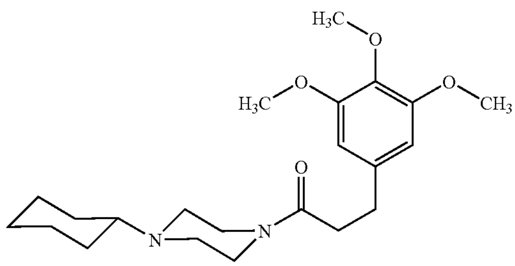 | 1-(4-Cyclohexylpiperazin-1-yl)-3-(3,4,5-trimethoxyphenyl)propan-1-one | 391 |
| 106 | 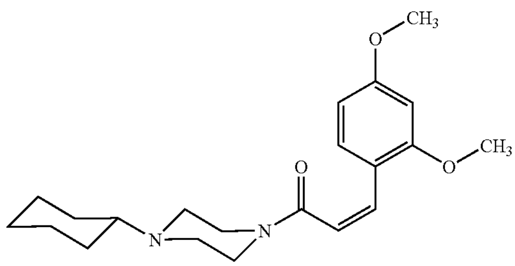 | 1-(4-Cyclohexylpiperazin-1-yl)-3-(2,4-dimethoxyphenyl)-propenone | 359 |
| 107 | 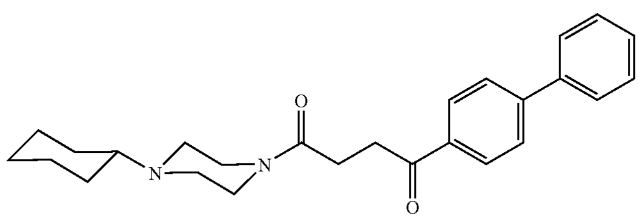 | 1-Biphenyl-4-yl-4-(4-cyclohexylpiperazin-1-yl)butane-1,4-dione | 405 |
| 108 | 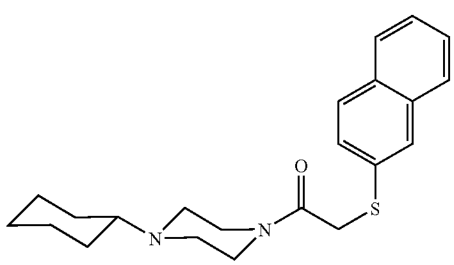 | 1-(4-Cyclohexylpiperazin-1-yl)-2-(naphth-2-ylsulfanyl)-ethanone | 369 |
| 109 | 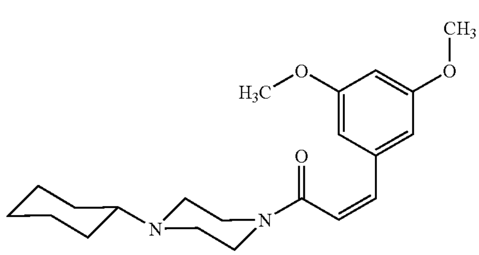 | 1-(4-Cyclohexylpiperazin-1-yl)-3-(3,5-dimethoxyphenyl)-propenone | 359 |
| 110 | 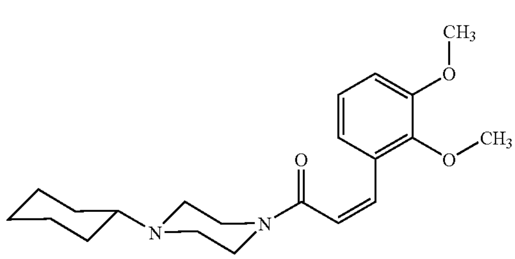 | 1-(4-Cyclohexylpiperazin-1-yl)-3-(2,3-dimethoxyphenyl)-propenone | 359 |

-continued

| Example No | Structure | Name | Found MH+ |
|---|---|---|---|
| 111 | 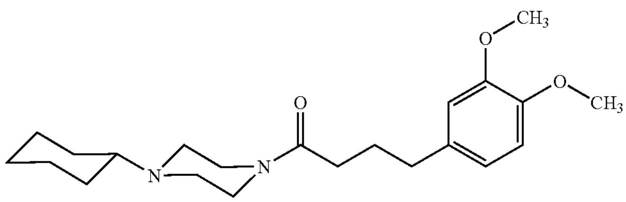 | 1-(4-Cyclohexylpiperazin-1-yl)-4-(3,4-dimethoxyphenyl)-butan-1-one | 375 |
| 112 | 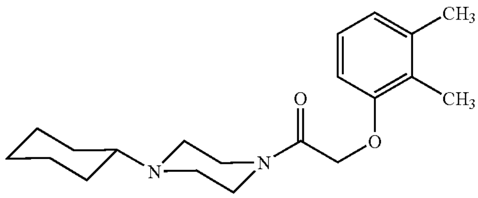 | 1-(4-Cyclohexylpiperazin-1-yl)-2-(2,3-dimethylphenoxy)-ethanone | 331 |
| 113 | 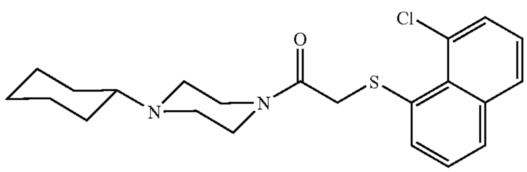 | 2-(8-Chloronaphth-1-yl-sulfanyl)-1-(4-cyclohexyl-piperazin-1-yl)ethanone | 404 |
| 114 | 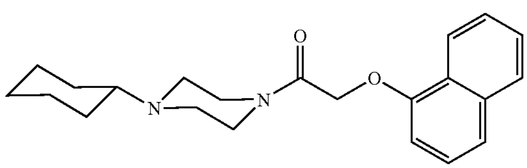 | 1-(4-Cyclohexylpiperazin-1-yl)-2-(naphth-1-yloxy)-ethanone | 353 |
| 115 | 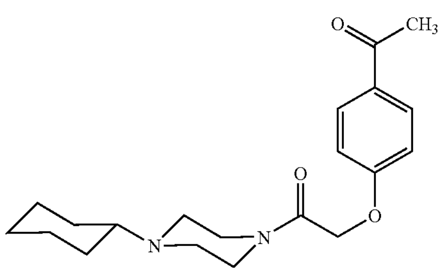 | 2-(4-Acetylphenoxy)-1-(4-cyclohexylpiperazin-1-yl)-ethanone | 345 |
| 116 | 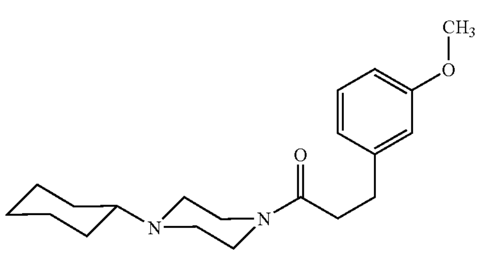 | 1-(4-Cyclohexylpiperazin-1-yl)-3-(3-methoxyphenyl)-propan-1-one | 331 |
| 117 | 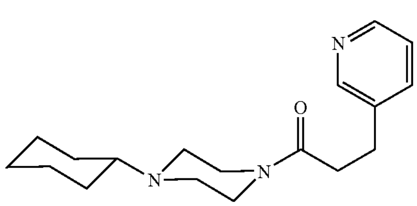 | 1-(4-Cyclohexylpiperazin-1-yl)-3-pyridin-3-ylpropan-1-one | 302 |

-continued

| Example No | Structure | Name | Found MH+ |
|---|---|---|---|
| 118 | 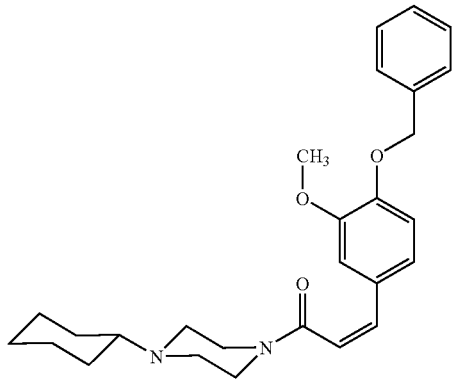 | 3-(4-Benzyloxy-3-methoxy-phenyl)-1-(4-cyclohexyl-piperazin-1-yl)propenone | 435 |
| 119 | 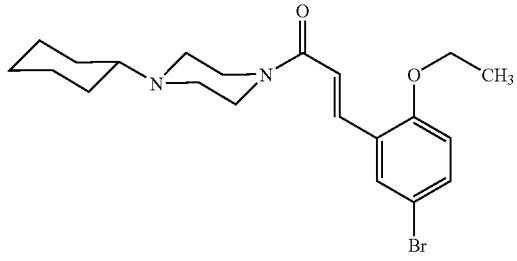 | 3-(5-Bromo-2-ethoxyphenyl)-1-(4-cyclohexylpiperazin-1-yl)propenone | 422 |
| 120 | 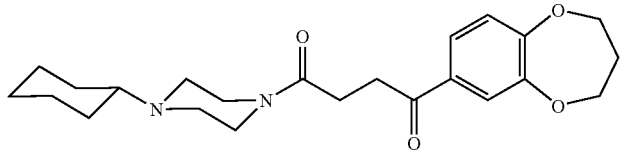 | 1-(4-Cyclohexylpiperazin-1-yl)-4-(3,4-dihydro-2H-benzo[b][1,4]dioxepin-7-yl)-butane-1,4-dione | 401 |
| 121 | 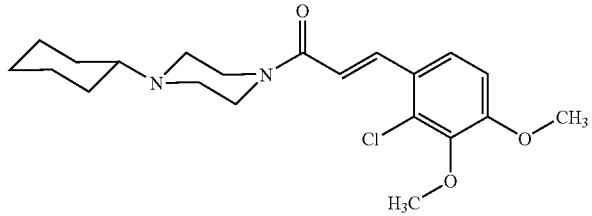 | 3-(2-Chloro-3,4-dimethoxy-phenyl)-1-(4-cyclohexyl-piperazin-1-yl)propenone | 393 |
| 122 | 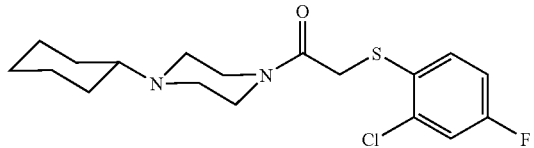 | 2-(2-Chloro-4-fluorophenyl-sulfanyl)-1-(4-cyclohexyl-piperazin-1-yl)ethanone | 371 |
| 123 | 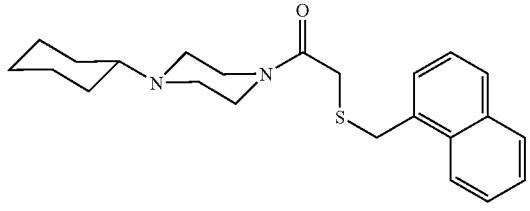 | 1-(4-Cyclohexylpiperazin-1-yl)-2-(naphth-1-ylmethyl-sulfanyl)ethanone | 383 |

-continued

| Example No | Structure | Name | Found MH+ |
|---|---|---|---|
| 124 | 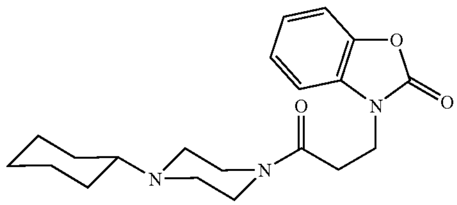 | 3-[3-(4-Cyclohexylpiperazin-1-yl)-3-oxopropyl]-3H-benzoxazol-2-one | 358 |
| 125 | 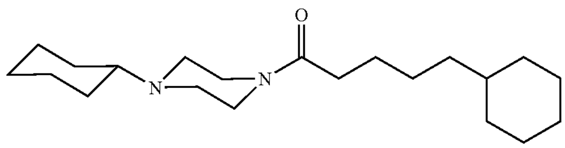 | 5-Cyclohexyl-1-(4-cyclohexylpiperazin-1-yl)pentan-1-one | 335 |
| 126 | 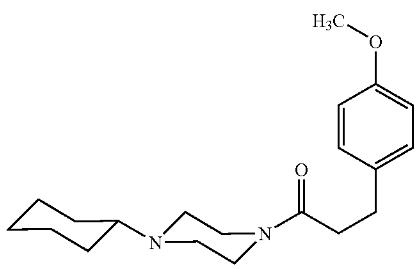 | 1-(4-Cyclohexylpiperazin-1-yl)-3-(4-methoxyphenyl)-propan-1-one | 331 |
| 127 | 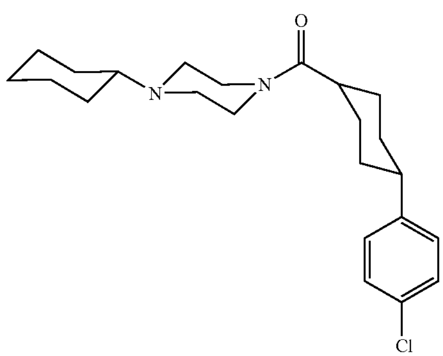 | [4-(4-Chlorophenyl)-cyclohexyl]-(4-cyclohexyl-piperazin-1-yl)methanone | 390 |
| 128 | 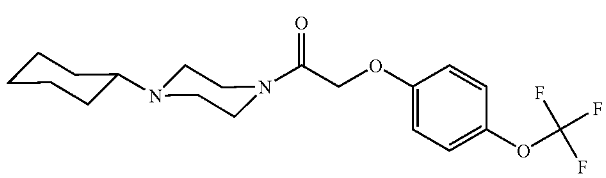 | 1-(4-Cyclohexylpiperazin-1-yl)-2-(4-trifluoromethoxy-phenoxy)ethanone | 387 |
| 129 | 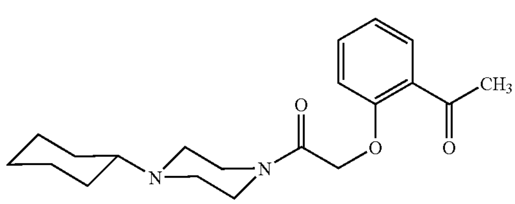 | 2-(2-Acetylphenoxy)-1-(4-cyclohexylpiperazin-1-yl)-ethanone | 345 |

-continued

| Example No | Structure | Name | Found MH+ |
|---|---|---|---|
| 130 | 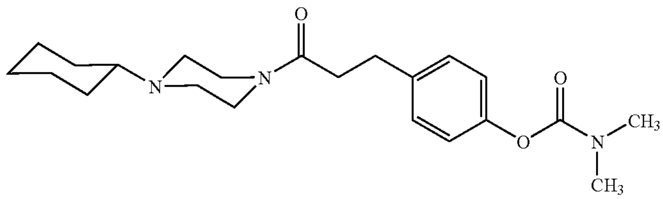 | Dimethylcarbamic acid 4-[3-(4-cyclohexylpiperazin-1-yl)-3-oxopropyl]phenyl ester | 388 |
| 131 | 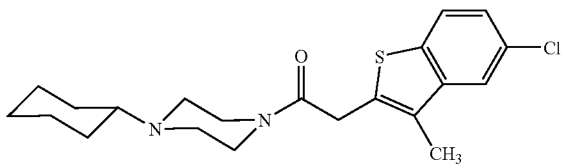 | 2-(5-Chloro-3-methyl-benzo[b]thiophen-2-yl)-1-(4-cyclohexylpiperazin-1-yl)-ethanone | 391 |
| 132 | 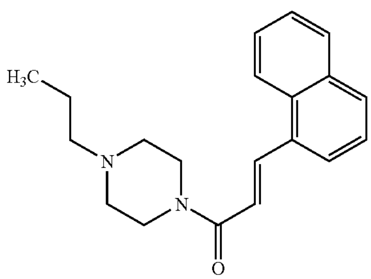 | 3-Naphth-1-yl-1-(4-propyl-piperazin-1-yl)propenone | 309 |
| 133 | 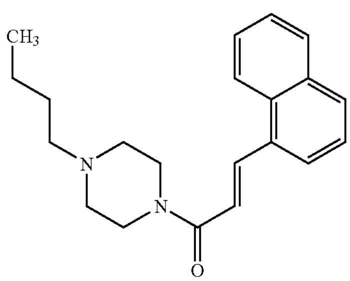 | 1-(4-Butylpiperazin-1-yl)-3-naphth-1-ylpropenone | 323 |
| 134 | 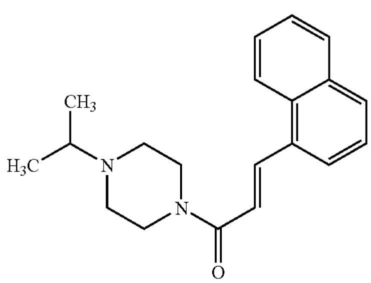 | 1-(4-Isopropylpiperazin-1-yl)-3-naphth-1-ylpropenone | 309 |
| 135 | 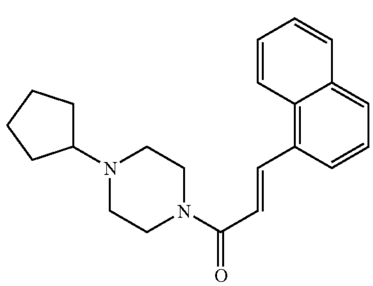 | 1-(4-Cyclopentylpiperazin-1-yl)-3-naphth-1-ylpropenone hydrochloride | 335 |

-continued

| Example No | Structure | Name | Found MH+ |
|---|---|---|---|
| 136 | 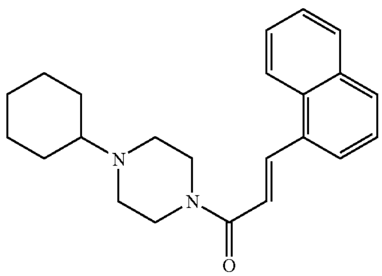 | 1-(4-Cyclohexylpiperazin-1-yl)-3-naphth-1-ylpropenone | 349 |
| 137 | 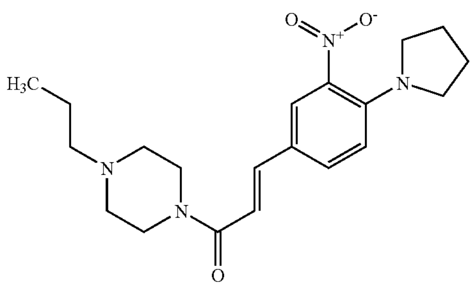 | 3-(3-Nitro-4-pyrrolidin-1-ylphenyl)-1-(4-propyl-piperazin-1-yl)propenone | 373 |
| 138 | 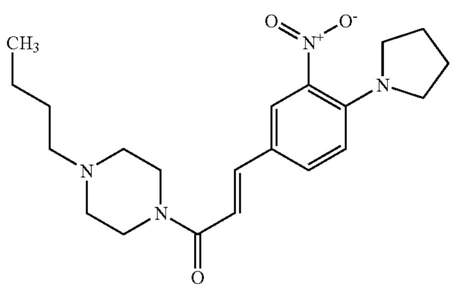 | 1-(4-Butylpiperazin-1-yl)-3-(3-nitro-4-pyrrolidin-1-yl-phenyl)propenone | 387 |
| 139 | 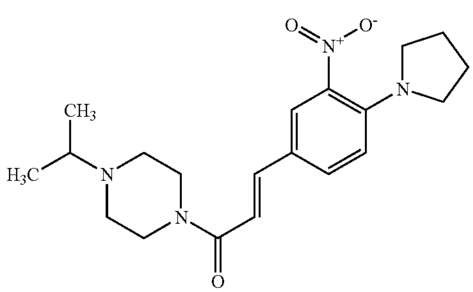 | 1-(4-Isopropylpiperazin-1-yl)-3-(3-nitro-4-pyrrolidin-1-ylphenyl)propenone | 374 |
| 140 | 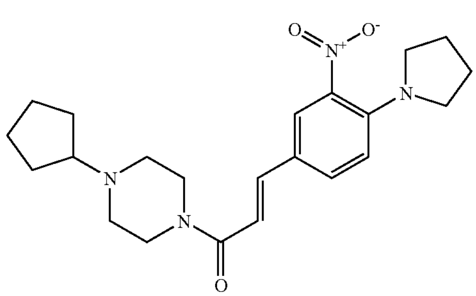 | 1-(4-Cyclopentylpiperazin-1-yl)-3-(3-nitro-4-pyrrolidin-1-ylphenyl)propenone | 399 |

-continued

| Example No | Structure | Name | Found MH+ |
|---|---|---|---|
| 141 | 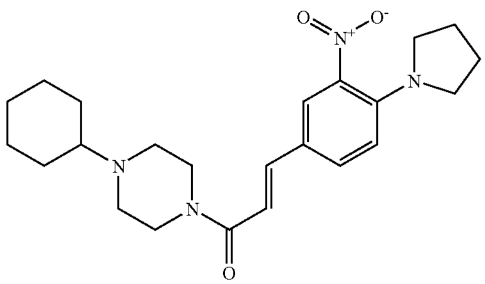 | 1-(4-Cyclohexylpiperazin-1-yl)-3-(3-nitro-4-pyrrolidin-1-ylphenyl)propenone | 413 |
| 142 | 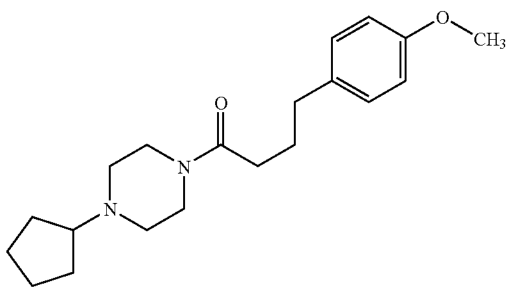 | 1-(4-Cyclopentylpiperazin-1-yl)-4-(4-methoxyphenyl)-butan-1-one hydrochloride | 331 |
| 143 | 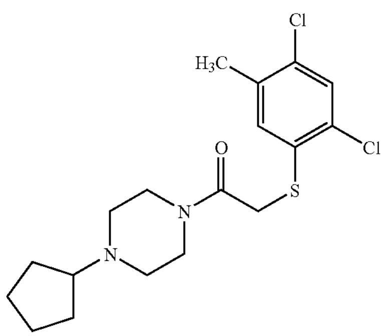 | 1-(4-Cyclopentylpiperazin-1-yl)-2-(2,4-dichloro-5-methyl-phenylsulfanyl)ethanone | |
| 144 | 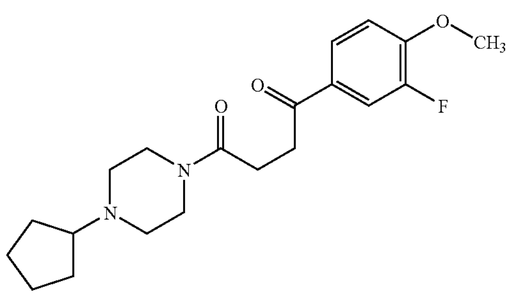 | 1-(4-Cyclopentylpiperazin-1-yl)-4-(3-fluoro-4-methoxy-phenyl)butane-1,4-dione | 363 |
| 145 | 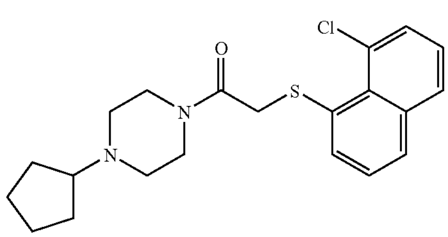 | 2-(8-Chloro-naphth-1-yl-sulfanyl)-1-(4-cyclopentyl-piperazin-1-yl)ethanone | |

-continued

| Example No | Structure | Name | Found MH+ |
|---|---|---|---|
| 146 | 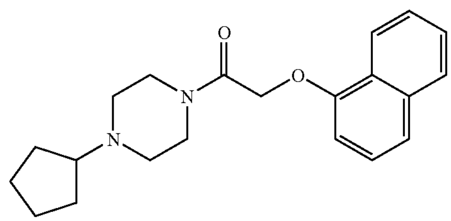 | 1-(4-Cyclopentylpiperazin-1-yl)-2-(naphth-1-yloxy)-ethanone | 339 |
| 147 | 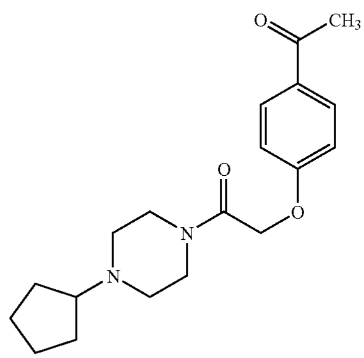 | 2-(4-Acetylphenoxy)-1-(4-cyclopentylpiperazin-1-yl)-ethanone hydrochloride | 331 |
| 148 | 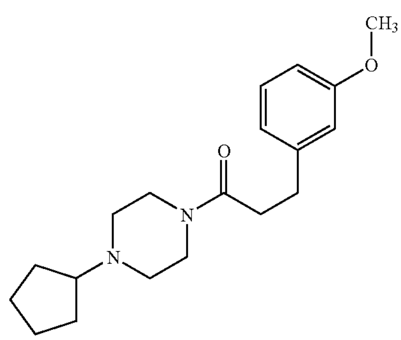 | 1-(4-Cyclopentylpiperazin-1-yl)-3-(3-methoxyphenyl)-propan-1-one | 317 |
| 149 | 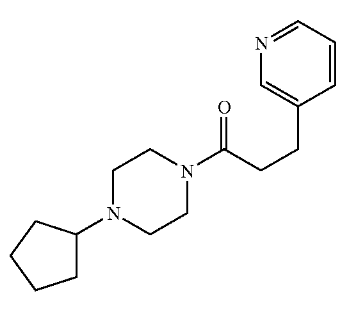 | 1-(4-Cyclopentylpiperazin-1-yl)-3-pyridin-3-ylpropan-1-one | |

-continued

| Example No | Structure | Name | Found MH+ |
|---|---|---|---|
| 150 | 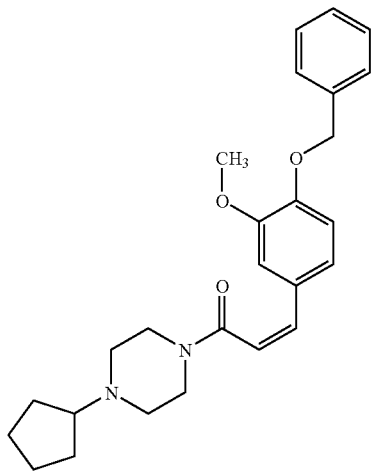 | 3-(4-Benzyloxy-3-methoxy-phenyl)-1-(4-cyclopentyl-piperazin-1-yl)propenone | 421 |
| 151 | 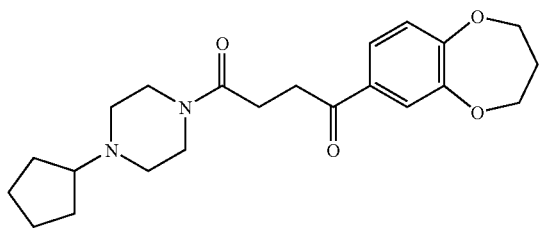 | 1-(4-Cyclopentylpiperazin-1-yl)-4-(3,4-dihydro-2H-benzo[b][1,4]dioxepin-7-yl)-butane-1,4-dione | 387 |
| 152 | 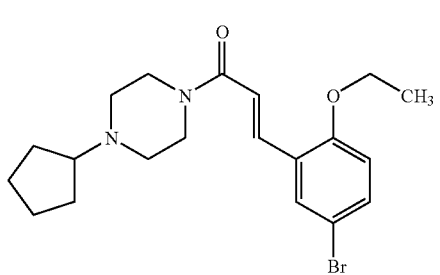 | 3-(5-Bromo-2-ethoxyphenyl)-1-(4-cyclopentylpiperazin-1-yl)propenone | 408 |
| 153 | 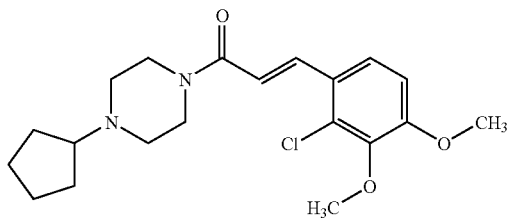 | 3-(2-Chloro-3,4-dimethoxy-phenyl)-1-(4-cyclopentyl-piperazin-1-yl)propenone | 379 |
| 154 | 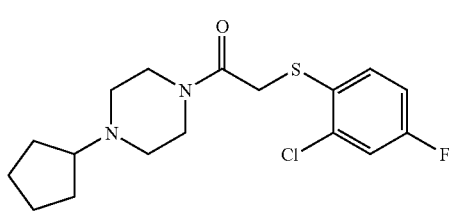 | 2-(2-Chloro-4-fluorophenyl-sulfanyl)-1-(4-cyclopentyl-piperazin-1-yl)ethanone | |

-continued
| Example No | Structure | Name | Found MH+ |
|---|---|---|---|
| 155 | 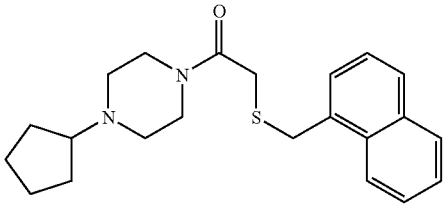 | 1-(4-Cyclopentylpiperazin-1-yl)-2-(naphth-1-ylmethyl-sulfanyl)ethanone | 369 |
| 156 | 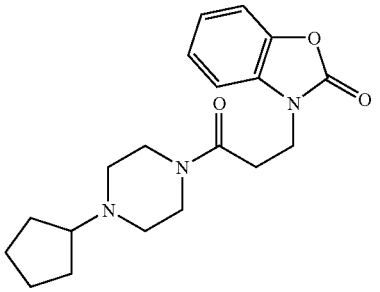 | 3-[3-(4-Cyclopentylpiperazin-1-yl)-3-oxopropyl]-3H-benz-oxazol-2-one | 344 |
| 157 | 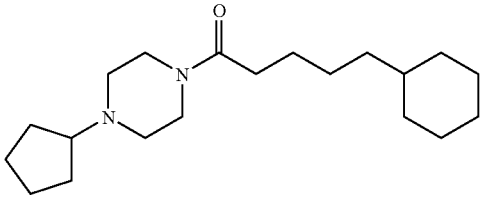 | 5-Cyclohexyl-1-(4-cyclo-pentylpiperazin-1-yl)pentan-1-one | 321 |
| 158 | 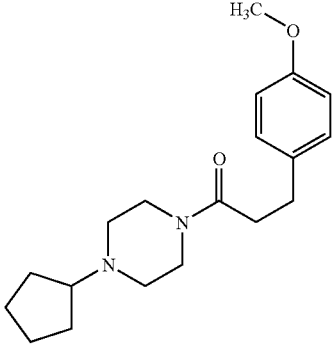 | 1-(4-Cyclopentylpiperazin-1-yl)-3-(4-methoxyphenyl)-propan-1-one | 317 |
| 159 | 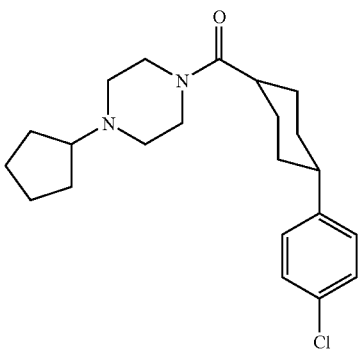 | [4-(4-Chlorophenyl)-cyclo-hexyl]-(4-cyclopentyl-piperazin-1-yl)methanone | 376 |

-continued

| Example No | Structure | Name | Found MH+ |
|---|---|---|---|
| 160 | 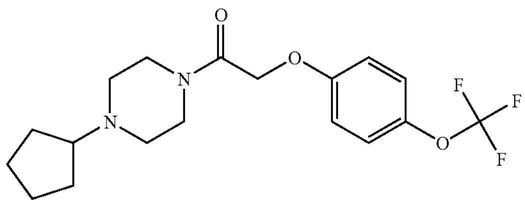 | 1-(4-Cyclopentylpiperazin-1-yl)-2-(4-trifluoromethoxy-phenoxy)ethanone | 373 |
| 161 | 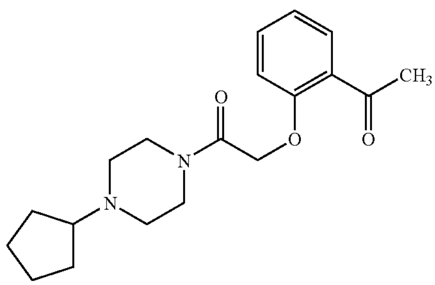 | 2-(2-Acetylphenoxy)-1-(4-cyclopentylpiperazin-1-yl)-ethanone | |
| 162 | 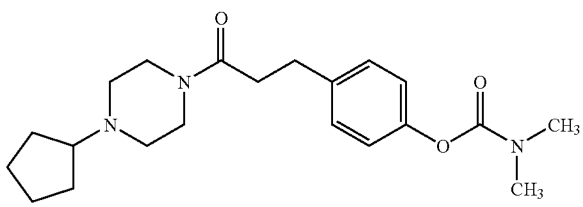 | Dimethylcarbamic acid 4-[3-(4-cyclopentylpiperazin-1-yl)-3-oxopropyl]phenyl ester | 374 |
| 163 | 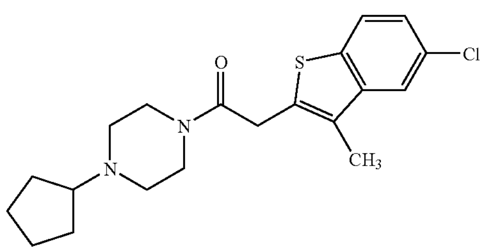 | 2-(5-Chloro-3-methyl-benzo[b]thiophen-2-yl)-1-(4-cyclopentylpiperazin-1-yl)-ethanone | 378 |
| 164 | 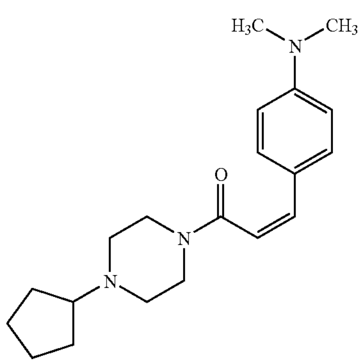 | 1-(4-Cyclopentylpiperazin-1-yl)-3-(4-dimethylamino-phenyl)propenone | 328 |

-continued

| Example No | Structure | Name | Found MH+ |
|---|---|---|---|
| 165 | 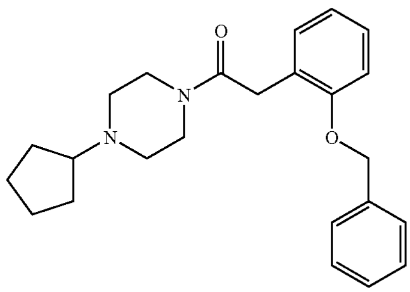 | 2-(2-Benzyloxyphenyl)-1-(4-cyclopentylpiperazin-1-yl)-ethanone | 379 |
| 166 | 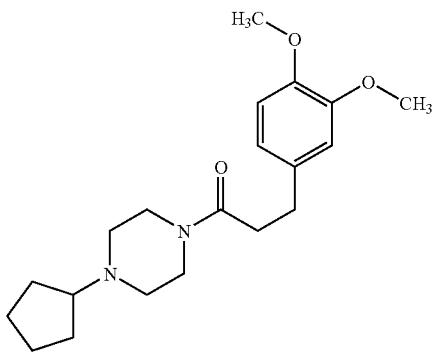 | 1-(4-Cyclopentylpiperazin-1-yl)-3-(3,4-dimethoxyphenyl)-propan-1-one | 347 |
| 167 | 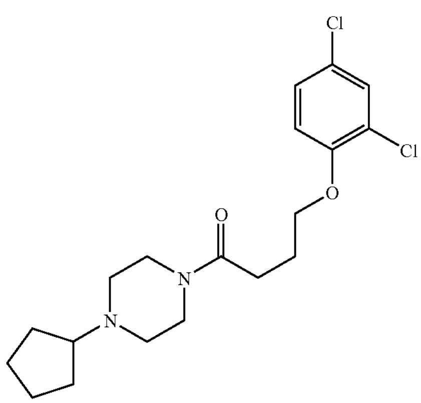 | 1-(4-Cyclopentylpiperazin-1-yl)-4-(2,4-dichlorophenoxy)-butan-1-one | 386 |
| 168 | 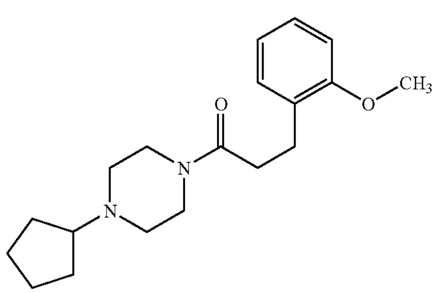 | 1-(4-Cyclopentylpiperazin-1-yl)-3-(2-methoxyphenyl)-propan-1-one | 317 |

| Example No | Structure | Name | Found MH+ |
|---|---|---|---|
| 169 | 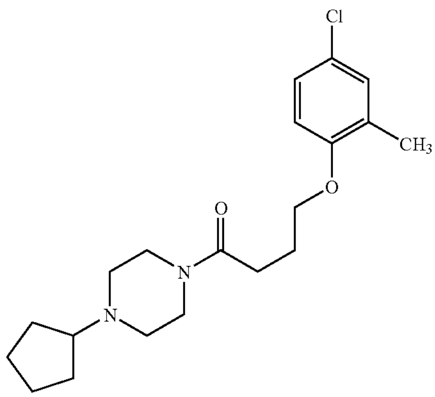 | 4-(4-Chloro-2-methyl-phenoxy)-1-(4-cyclopentyl-piperazin-1-yl)-butan-1-one | 365 |
| 170 | 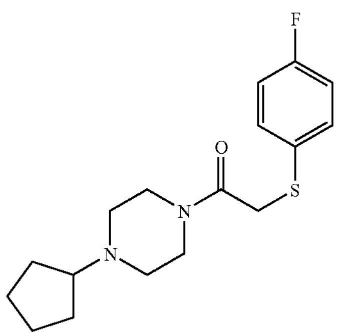 | 1-(4-Cyclopentylpiperazin-1-yl)-2-(4-fluorophenyl-sulfanyl)ethanone | |
| 171 | 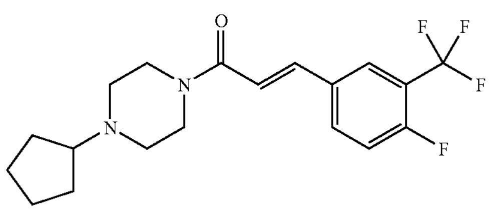 | 1-(4-Cyclopentylpiperazin-1-yl)-3-(4-fluoro-3-trifluoro-methylphenyl)propenone | 371 |
| 172 | 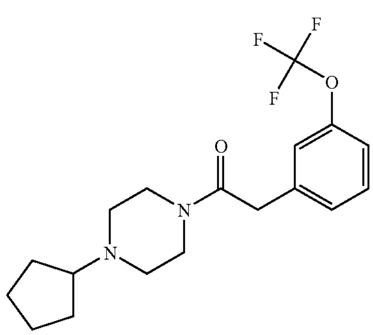 | 1-(4-Cyclopentylpiperazin-1-yl)-2-(3-trifluoromethoxy-phenyl)ethanone | 357 |

-continued
| Example No | Structure | Name | Found MH+ |
|---|---|---|---|
| 173 | 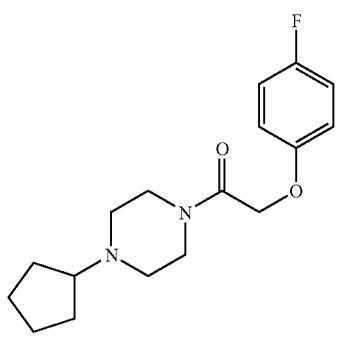 | 1-(4-Cyclopentylpiperazin-1-yl)-2-(4-fluorophenoxy)-ethanone | |
| 174 | 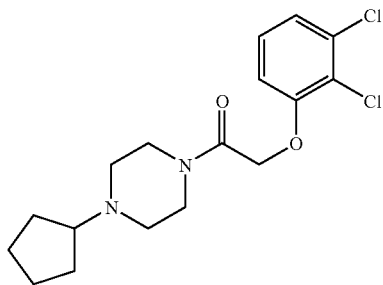 | 1-(4-Cyclopentylpiperazin-1-yl)-2-(2,3-dichlorophenoxy)-ethanone | |
| 175 | 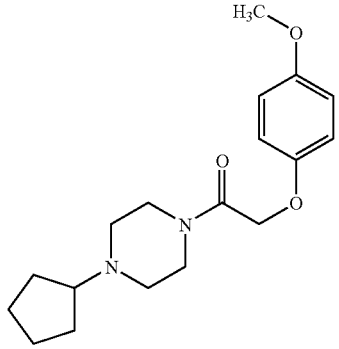 | 1-(4-Cyclopentylpiperazin-1-yl)-2-(4-methoxyphenoxy)-ethanone | |
| 176 | 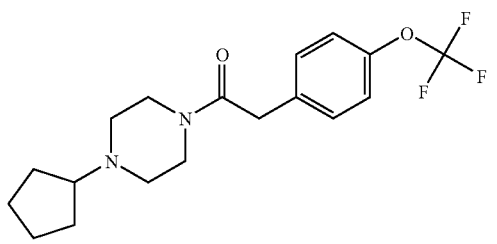 | 1-(4-Cyclopentylpiperazin-1-yl)-2-(4-trifluoromethoxy-phenyl)ethanone | 357 |
| 177 | 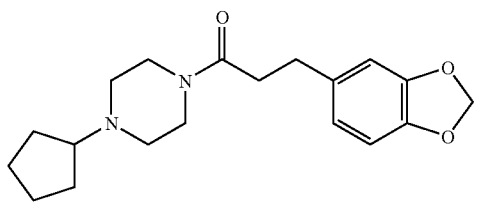 | 3-Benzo[1,3]dioxol-5-yl-1-(4-cyclopentylpiperazin-1-yl)propan-1-one | 331 |

-continued
| Example No | Structure | Name | Found MH+ |
|---|---|---|---|
| 178 | 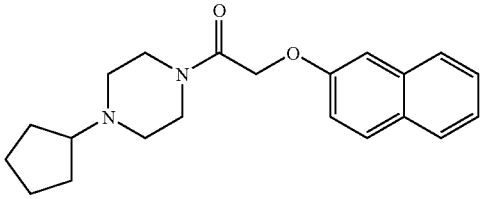 | 1-(4-Cyclopentylpiperazin-1-yl)-2-(naphth-2-yloxy)-ethanone | 339 |
| 179 | 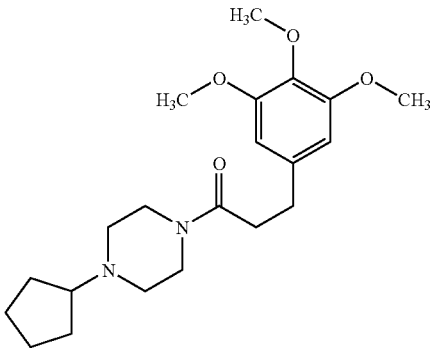 | 1-(4-Cyclopentylpiperazin-1-yl)-3-(3,4,5-trimethoxy-phenyl)propan-1-one | 377 |
| 180 | 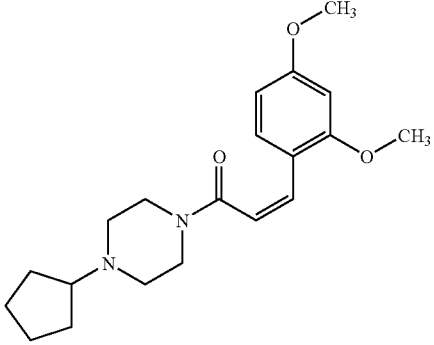 | 1-(4-Cyclopentylpiperazin-1-yl)-3-(2,4-dimethoxyphenyl)-propenone | 345 |
| 181 | 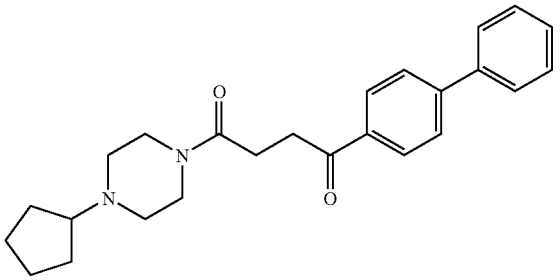 | 1-Biphenyl-4-yl-4-(4-cyclopentylpiperazin-1-yl)butane-1,4-dione | 391 |
| 182 | 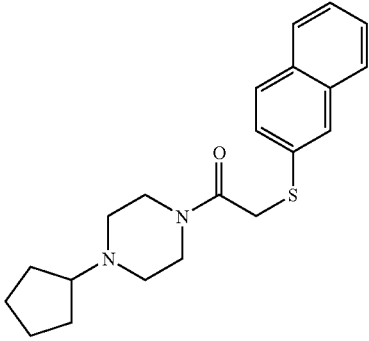 | 1-(4-Cyclopentylpiperazin-1-yl)-2-(naphth-2-ylsulfanyl)-ethanone | |

-continued

| Example No | Structure | Name | Found MH+ |
|---|---|---|---|
| 183 | 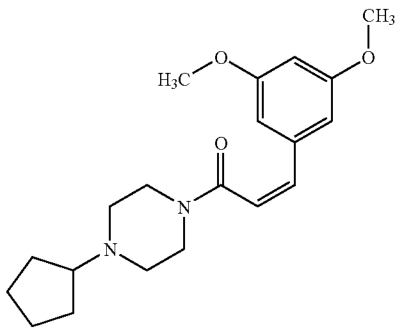 | 1-(4-Cyclopentylpiperazin-1-yl)-3-(3,5-dimethoxyphenyl)-propenone | 345 |
| 184 | 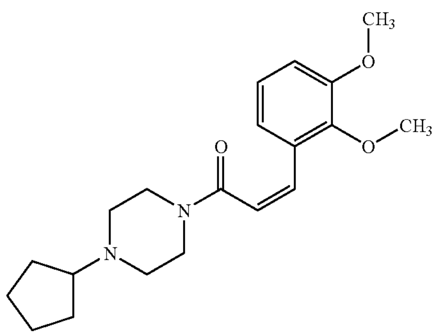 | 1-(4-Cyclopentylpiperazin-1-yl)-3-(2,3-dimethoxyphenyl)-propenone | 345 |
| 185 | 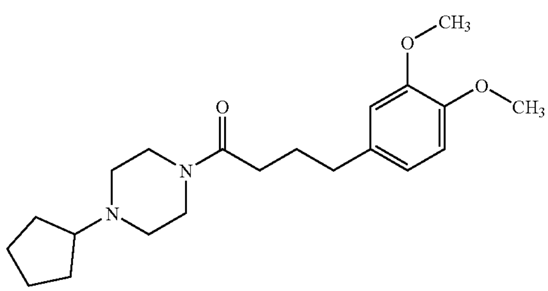 | 1-(4-Cyclopentylpiperazin-1-yl)-4-(3,4-dimethoxyphenyl)-butan-1-one hydrochloride | 361 |
| 186 | 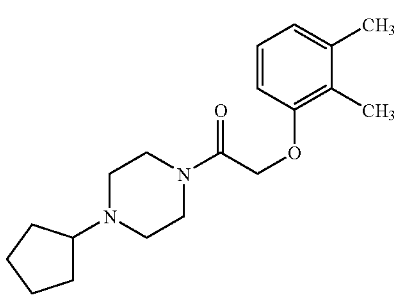 | 1-(4-Cyclopentylpiperazin-1-yl)-2-(2,3-dimethylphenoxy)-ethanone | |
| 187 | 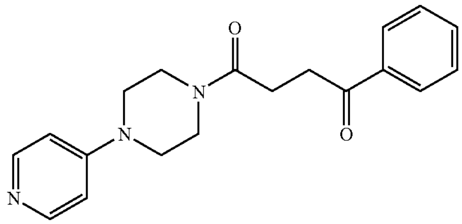 | 1-phenyl-4-(4-pyridin-4-yl-piperazin-1-yl)butane-1,4-dione | 324 |

-continued

| Example No | Structure | Name | Found MH+ |
|---|---|---|---|
| 188 | 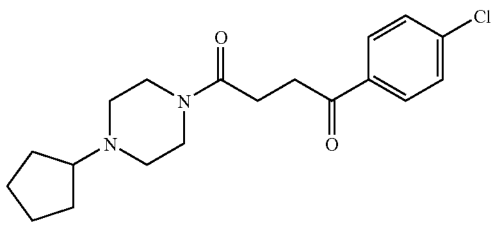 | 1-(4-Chlorophenyl)-4-(4-cyclopentylpiperazin-1-yl)-butane-1,4-dione hydrochloride | 349 |
| 189 | 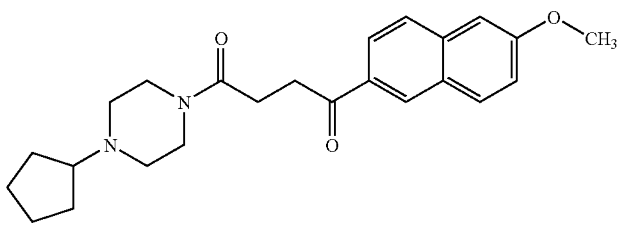 | 1-(4-Cyclopentylpiperazin-1-yl)-4-(6-methoxynaphth-2-yl)butane-1,4-dione hydrochloride | 395 |
| 190 | 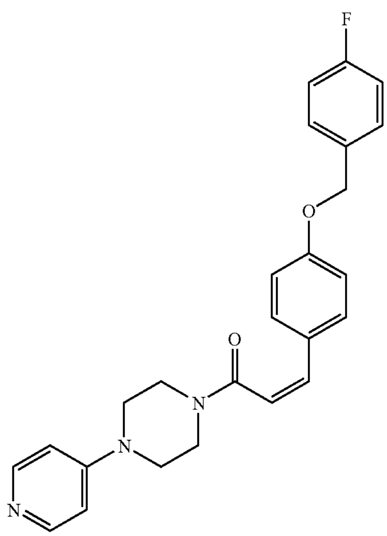 | 3-[4-(4-Fluorobenzyloxy)-phenyl]-1-(4-pyridin-4-yl-piperazin-1-yl)propenone | 418 |
| 191 | 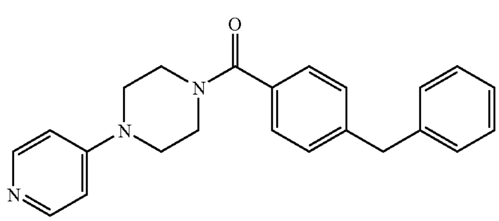 | (4-Benzylphenyl)-(4-pyridin-4-ylpiperazin-1-yl)methanone | 358 |
| 192 | 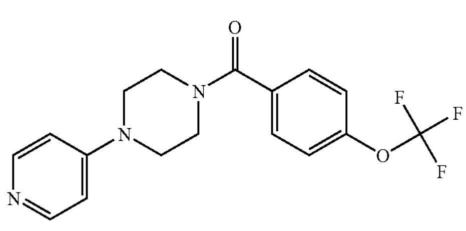 | (4-Pyridin-4-ylpiperazin-1-yl)-(4-trifluoromethoxy-phenyl)methanone | 352 |

-continued

| Example No | Structure | Name | Found MH+ |
|---|---|---|---|
| 193 | 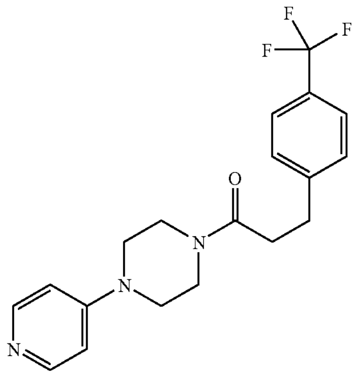 | 1-(4-Pyridin-4-ylpiperazin-1-yl)-3-(4-trifluoromethyl-phenyl)propan-1-one | 364 |
| 194 | 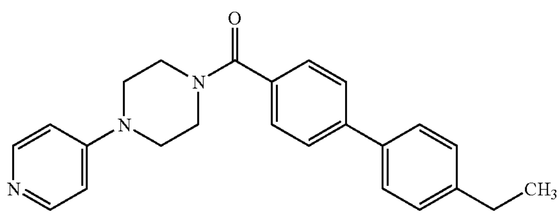 | (4'-Ethylbiphenyl-4-yl)-(4-pyridin-4-ylpiperazin-1-yl)-methanone | 372 |
| 195 | 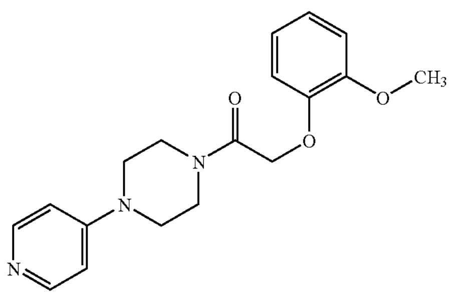 | 2-(2-Methoxyphenoxy)-1-(4-pyridin-4-ylpiperazin-1-yl)-ethanone | 328 |
| 196 | 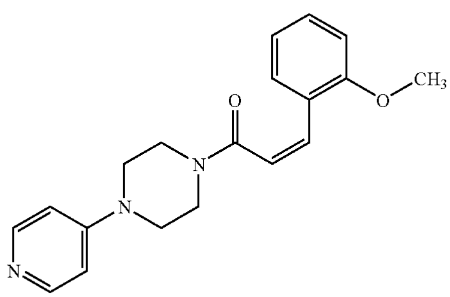 | 3-(2-Methoxyphenyl)-1-(4-pyridin-4-ylpiperazin-1-yl)-propenone | 324 |
| 197 | 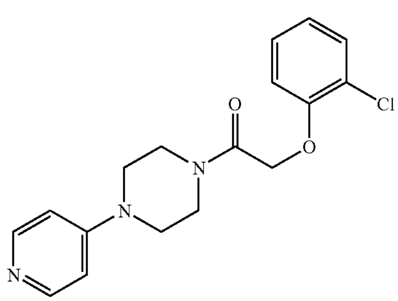 | 2-(2-Chlorophenoxy)-1-(4-pyridin-4-ylpiperazin-1-yl)-ethanone | 332 |

-continued

| Example No | Structure | Name | Found MH+ |
|---|---|---|---|
| 198 | 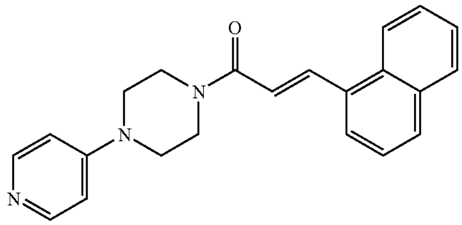 | 3-Naphth-1-yl-1-(4-pyridin-4-ylpiperazin-1-yl)propenone | 344 |
| 199 | 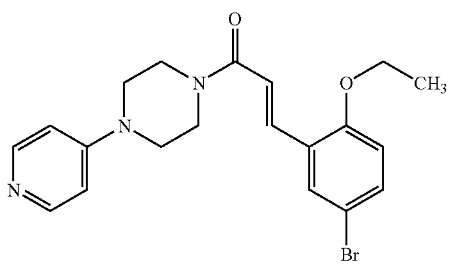 | 3-(5-Bromo-2-ethoxyphenyl)-1-(4-pyridin-4-ylpiperazin-1-yl)propenone | 416 |
| 200 | 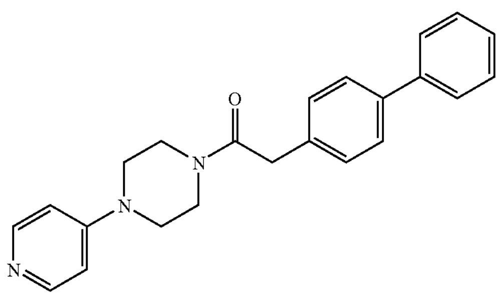 | 2-Biphenyl-4-yl-1-(4-pyridin-4-ylpiperazin-1-yl)ethanone | 358 |
| 201 | 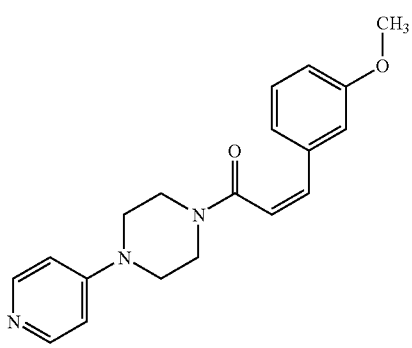 | 3-(3-Methoxyphenyl)-1-(4-pyridin-4-ylpiperazin-1-yl)-propenone | 324 |
| 202 | 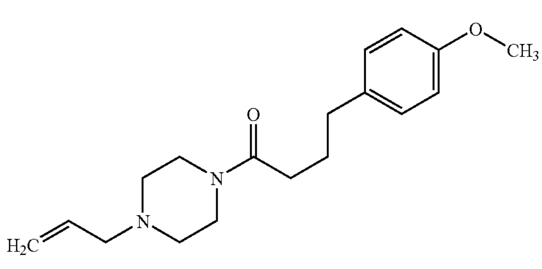 | 1-(4-Allylpiperazin-1-yl)-4-(4-methoxyphenyl)butan-1-one | 303 |

-continued
| Example No | Structure | Name | Found MH+ |
|---|---|---|---|
| 203 | 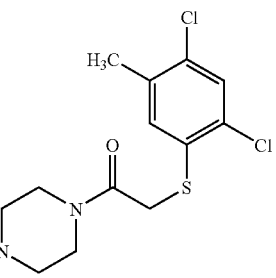 | 1-(4-Allylpiperazin-1-yl)-2-(2,4-dichloro-5-methyl-phenylsulfanyl)ethanone | 360 |
| 204 | 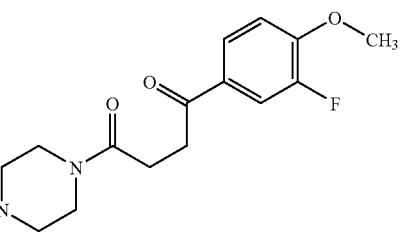 | 1-(4-Allylpiperazin-1-yl)-4-(3-fluoro-4-methoxyphenyl)-butane-1,4-dione | 335 |
| 205 | 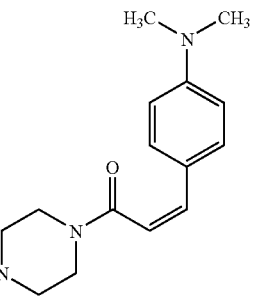 | 1-(4-Allylpiperazin-1-yl)-3-(4-dimethylaminophenyl)-propenone | 300 |
| 206 | 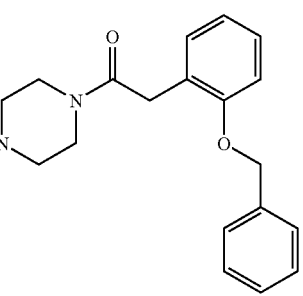 | 1-(4-Allylpiperazin-1-yl)-2-(2-benzyloxyphenyl)ethanone | 351 |
| 207 | 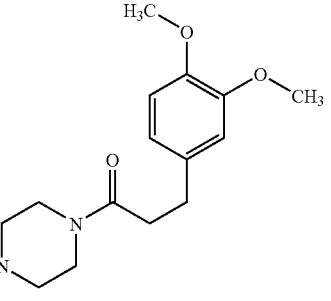 | 1-(4-Allylpiperazin-1-yl)-3-(3,4-dimethoxyphenyl)-propan-1-one | 319 |

-continued

| Example No | Structure | Name | Found MH+ |
|---|---|---|---|
| 208 | 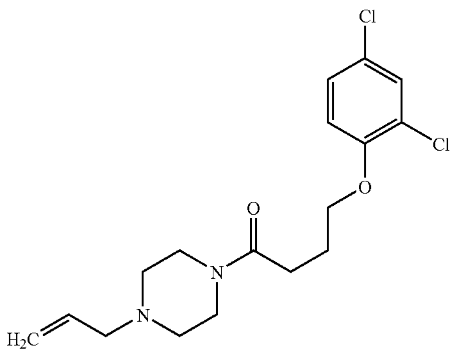 | 1-(4-Allylpiperazin-1-yl)-4-(2,4-dichlorophenoxy)butan-1-one | 358 |
| 209 | 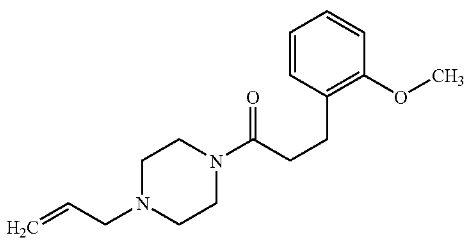 | 1-(4-Allylpiperazin-1-yl)-3-(2-methoxyphenyl)propan-1-one | 289 |
| 210 | 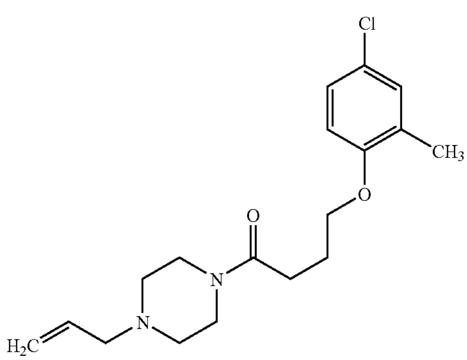 | 1-(4-Allylpiperazin-1-yl)-4-(4-chloro-2-methylphenoxy)-butan-1-one | 337 |
| 211 | 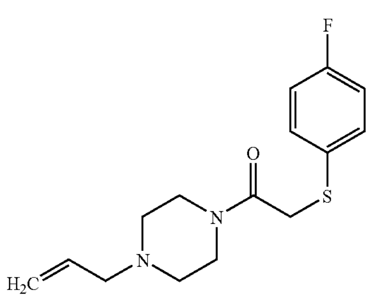 | 1-(4-Allylpiperazin-1-yl)-2-(4-fluorophenylsulfanyl)-ethanone | 295 |
| 212 | 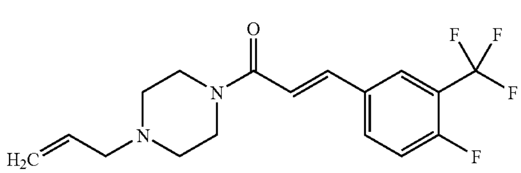 | 1-(4-Allylpiperazin-1-yl)-3-(4-fluoro-3-trifluoromethyl-phenyl)propenone | 343 |

-continued

| Example No | Structure | Name | Found MH+ |
|---|---|---|---|
| 213 | 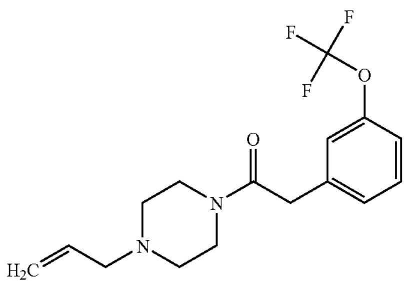 | 1-(4-Allylpiperazin-1-yl)-2-(3-trifluoromethoxyphenyl)-ethanone | 329 |
| 214 | 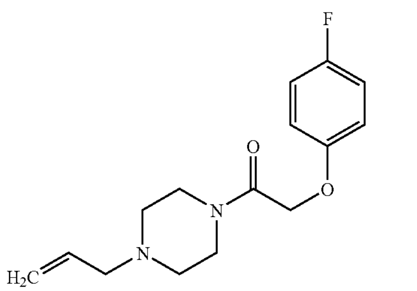 | 1-(4-Allylpiperazin-1-yl)-2-(4-fluorophenoxy)ethanone | 279 |
| 215 | 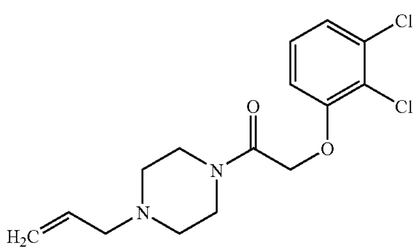 | 1-(4-Allylpiperazin-1-yl)-2-(2,3-dichlorophenoxy)-ethanone | 330 |
| 216 | 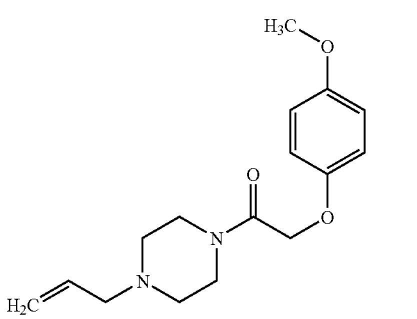 | 1-(4-Allylpiperazin-1-yl)-2-(4-methoxyphenoxy)-ethanone | 291 |
| 217 | 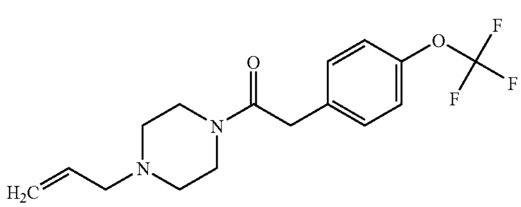 | 1-(4-Allylpiperazin-1-yl)-2-(4-trifluoromethoxyphenyl)-ethanone | 329 |
| 218 | 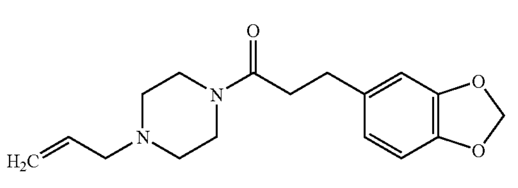 | 1-(4-Allylpiperazin-1-yl)-3-benzo[1,3]dioxol-5-ylpropan-1-one | 303 |

-continued

| Example No | Structure | Name | Found MH+ |
|---|---|---|---|
| 219 | 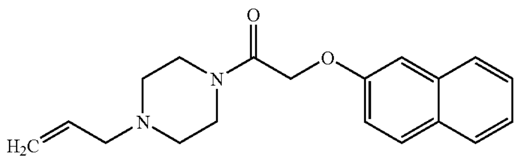 | 1-(4-Allylpiperazin-1-yl)-2-(naphth-2-yloxy)ethanone | 311 |
| 220 | 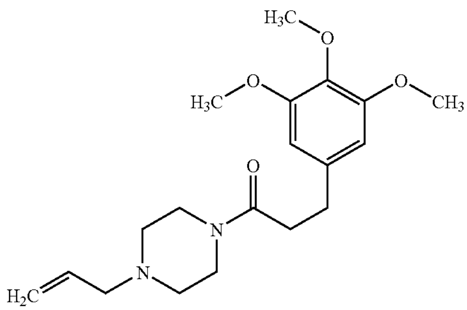 | 1-(4-Allylpiperazin-1-yl)-3-(3,4,5-trimethoxyphenyl)-propan-1-one | 349 |
| 221 | 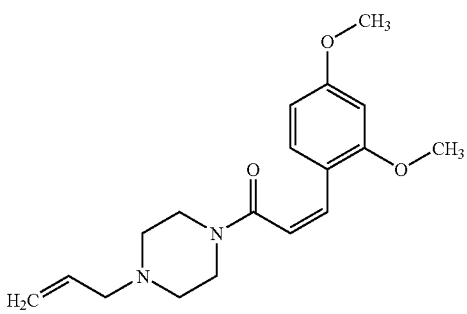 | 1-(4-Allylpiperazin-1-yl)-3-(2,4-dimethoxyphenyl)-propenone | 317 |
| 222 | 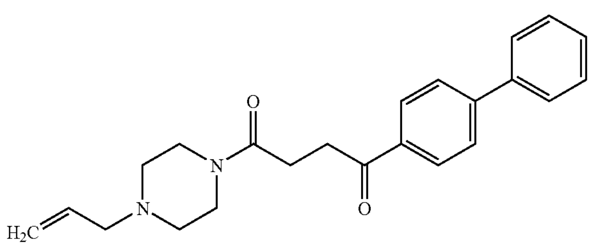 | 1-(4-Allylpiperazin-1-yl)-4-biphenyl-4-yl-butane-1,4-dione | 363 |
| 223 | 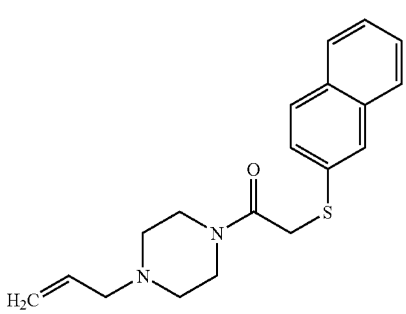 | 1-(4-Allylpiperazin-1-yl)-2-(naphth-2-ylsulfanyl)-ethanone | 327 |

-continued

| Example No | Structure | Name | Found MH+ |
|---|---|---|---|
| 224 | 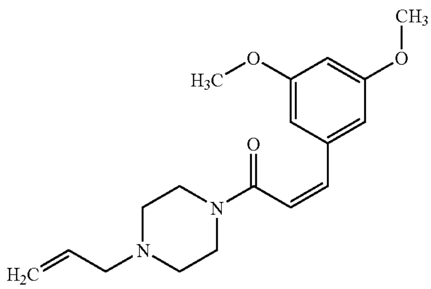 | 1-(4-Allylpiperazin-1-yl)-3-(3,5-dimethoxyphenyl)-propenone | 317 |
| 225 | 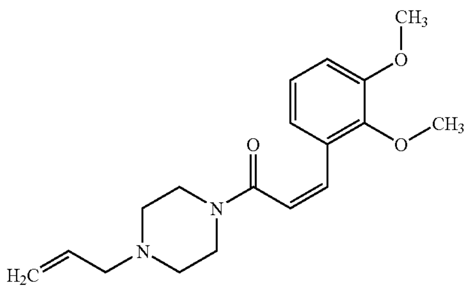 | 1-(4-Allylpiperazin-1-yl)-3-(2,3-dimethoxyphenyl)-propenone | 317 |
| 226 | 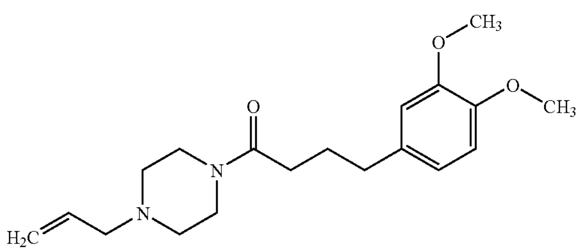 | 1-(4-Allylpiperazin-1-yl)-4-(3,4-dimethoxyphenyl)-butan-1-one | 333 |
| 227 | 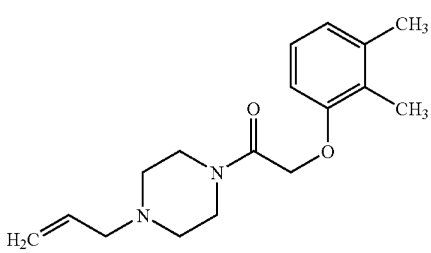 | 1-(4-Allylpiperazin-1-yl)-2-(2,3-dimethylphenoxy)-ethanone | 289 |
| 228 | 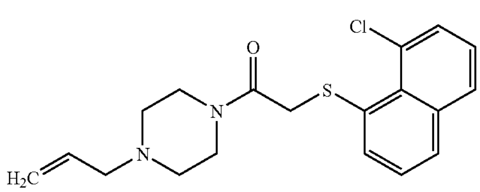 | 1-(4-Allylpiperazin-1-yl)-2-(8-chloronaphth-1-ylsulfanyl)ethanone | 361 |
| 229 | 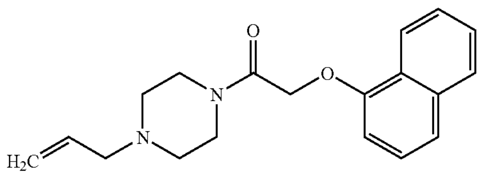 | 1-(4-Allylpiperazin-1-yl)-2-(naphth-1-yloxy)ethanone | 311 |

-continued

| Example No | Structure | Name | Found MH+ |
|---|---|---|---|
| 230 | 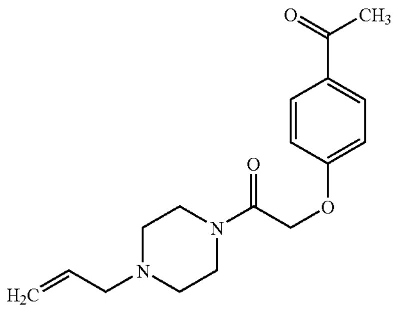 | 2-(4-Acetylphenoxy)-1-(4-allylpiperazin-1-yl)ethanone | 303 |
| 231 | 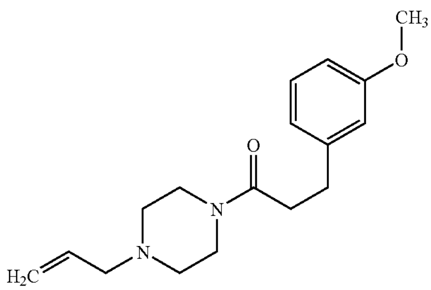 | 1-(4-Allylpiperazin-1-yl)-3-(3-methoxyphenyl)propan-1-one | 289 |
| 232 | 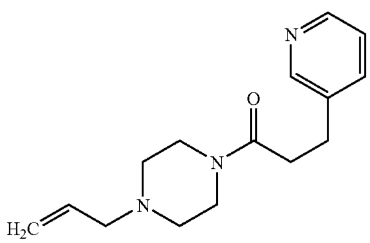 | 1-(4-Allylpiperazin-1-yl)-3-pyridin-3-ylpropan-1-one | 260 |
| 233 | 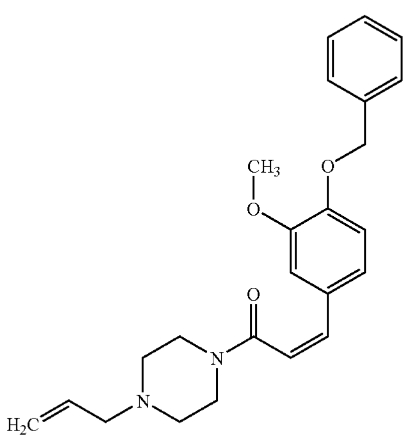 | 1-(4-Allylpiperazin-1-yl)-3-(4-benzyloxy-3-methoxyphenyl)propenone | 393 |
| 234 | 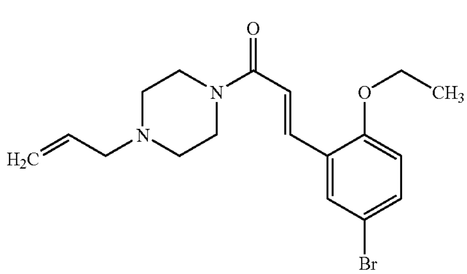 | 1-(4-Allylpiperazin-1-yl)-3-(5-bromo-2-ethoxyphenyl)-propenone | 380 |

-continued

| Example No | Structure | Name | Found MH+ |
|---|---|---|---|
| 235 | 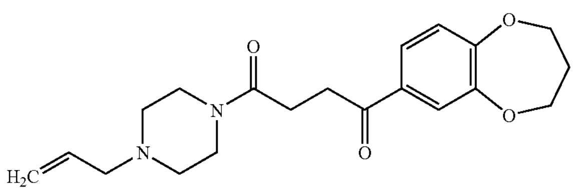 | 1-(4-Allylpiperazin-1-yl)-4-(3,4-dihydro-2H-benzo-[b][1,4]dioxepin-7-yl)-butane-1,4-dione | 359 |
| 236 | 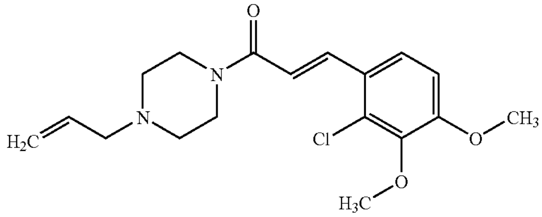 | 1-(4-Allylpiperazin-1-yl)-3-(2-chloro-3,4-dimethoxy-phenyl)propenone | 351 |
| 237 | 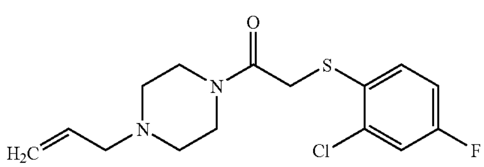 | 1-(4-Allylpiperazin-1-yl)-2-(2-chloro-4-fluorophenyl-sulfanyl)ethanone | 329 |
| 238 | 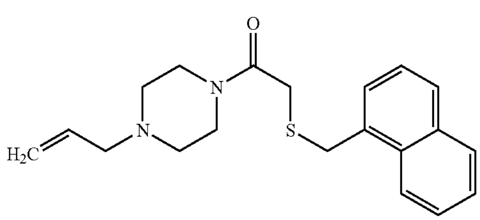 | 1-(4-Allylpiperazin-1-yl)-2-(naphth-1-ylmethylsulfanyl)-ethanone | 341 |
| 239 | 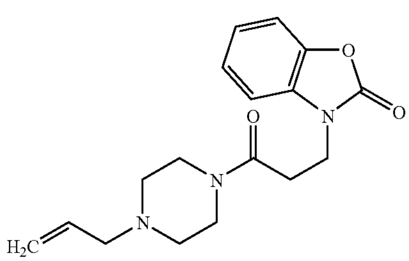 | 3-[3-(4-Allylpiperazin-1-yl)-3-oxopropyl]-3H-benzooxazol-2-one | 316 |
| 240 | 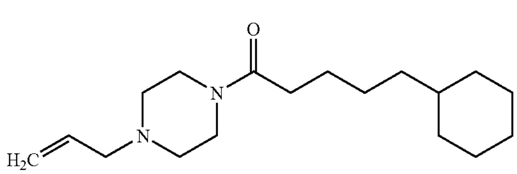 | 1-(4-Allylpiperazin-1-yl)-5-cyclohexylpentan-1-one | 293 |

| Example No | Structure | Name | Found MH+ |
|---|---|---|---|
| 241 | 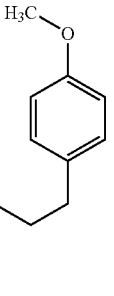 | 1-(4-Allylpiperazin-1-yl)-3-(4-methoxyphenyl)propan-1-one | 289 |
| 242 | 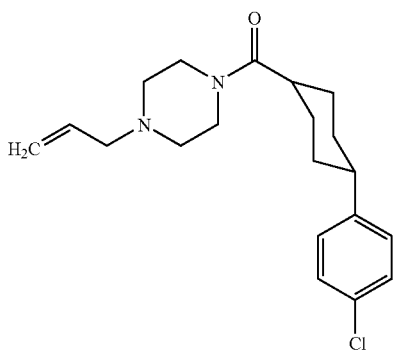 | (4-Allylpiperazin-1-yl)-[4-(4-chlorophenyl)cyclohexyl]-methanone | 347 |
| 243 | 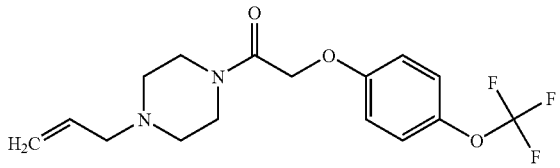 | 1-(4-Allylpiperazin-1-yl)-2-(4-trifluoromethoxyphenoxy)-ethanone | 345 |
| 244 | 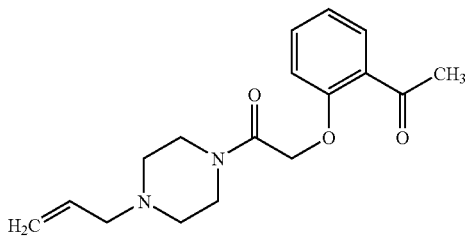 | 2-(2-Acetylphenoxy)-1-(4-allylpiperazin-1-yl)ethanone | 303 |
| 245 | 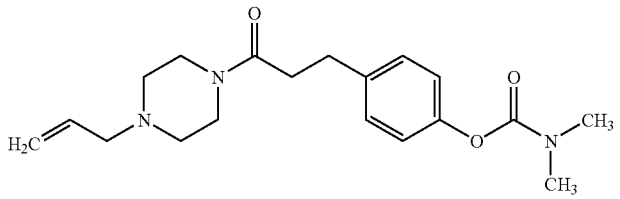 | Dimethyl-carbamic acid 4-[3-(4-allylpiperazin-1-yl)-3-oxopropyl]phenyl ester | 346 |
| 246 | 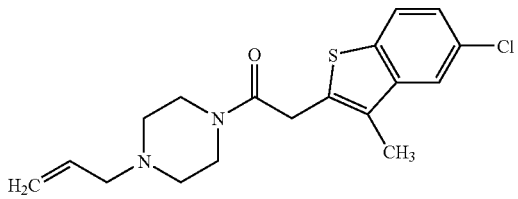 | 1-(4-Allylpiperazin-1-yl)-2-(5-chloro-3-methylbenzo[b]-thiophen-2-yl)ethanone | 349 |

-continued

| Example No | Structure | Name | Found MH+ |
|---|---|---|---|
| 247 | 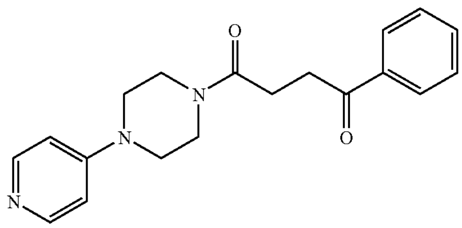 | 1-phenyl-4-(4-pyridin-4-yl-piperazin-1-yl)butane-1,4-dione hydrochloride | 324 |
| 248 | 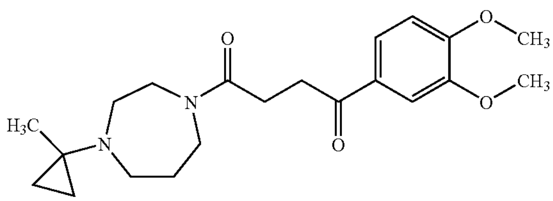 | 1-(3,4-Dimethoxyphenyl)-4-[4-(1-methylcyclopropyl)-[1,4]-diazepan-1-yl]butane-1,4-dione hydrochloride | 375 |
| 249 | 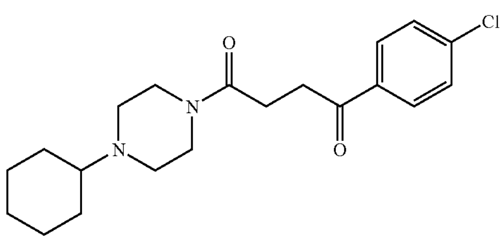 | 1-(4-Chlorophenyl)-4-(4-cyclohexylpiperazin-1-yl)-butane-1,4-dione hydrochloride | 363 |
| 250 | 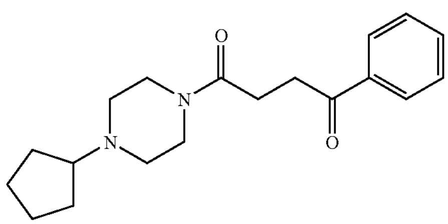 | 1-(4-Cyclopentylpiperazin-1-yl)-4-phenylbutane-1,4-dione hydrochloride | 315 |
| 251 | 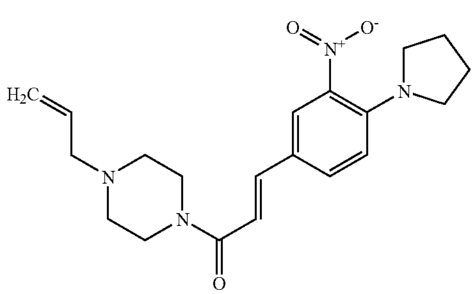 | 1-(4-Allylpiperazin-1-yl)-3-(3-nitro-4-pyrrolidin-1-yl-phenyl)propenone | 371 |
| 252 | 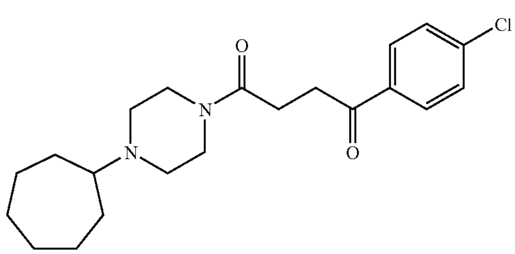 | 1-(4-Chlorophenyl)-4-(4-cycloheptylpiperazin-1-yl)-butane-1,4-dione hydrochloride | 377 |

-continued

| Example No | Structure | Name | Found MH+ |
|---|---|---|---|
| 253 | 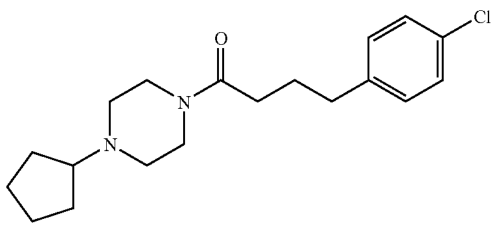 | 4-(4-Chlorophenyl)-1-(4-cyclopentylpiperazin-1-yl)-butan-1-one hydrochloride | 335 |
| 254 | 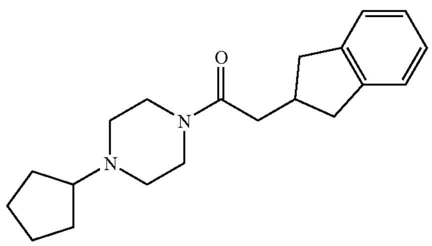 | 1-(4-Cyclopentylpiperazin-1-yl)-2-indan-2-ylethanone hydrochloride | 313 |
| 255 | 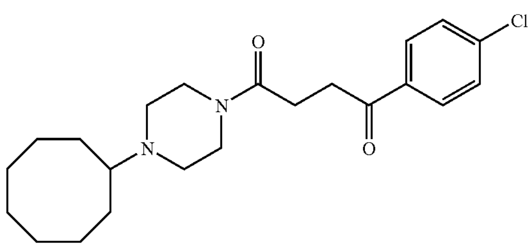 | 1-(4-Chlorophenyl)-4-(4-cyclooctylpiperazin-1-yl)-butane-1,4-dione hydrochloride | 392 |
| 256 | 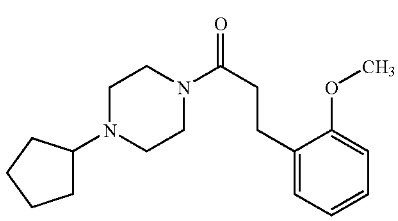 | 1-(4-Cyclopentylpiperazin-1-yl)-3-(4-methoxyphenoxy)-propan-1-one hydrochloride | 333 |
| 257 | 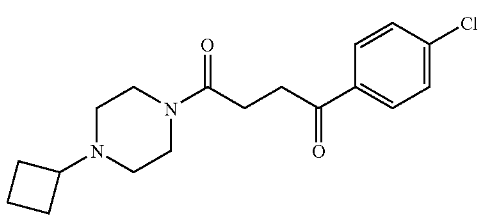 | 1-(4-Chlorophenyl)-4-(4-cyclobutylpiperazin-1-yl)-butane-1,4-dione hydrochloride | 335 |
| 258 | 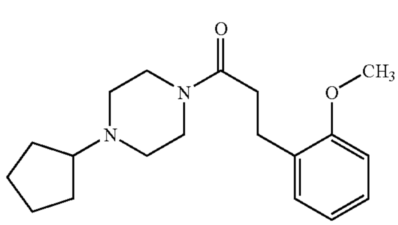 | 1-(4-Cyclopentylpiperazin-1-yl)-3-(2-methoxyphenyl)-propan-1-one hydrochloride | 317 |

-continued

| Example No | Structure | Name | Found MH+ |
|---|---|---|---|
| 259 | 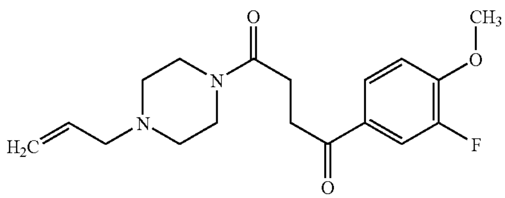 | 1-(4-Allylpiperazin-1-yl)-4-(3-fluoro-4-methoxyphenyl)-butane-1,4-dione hydrochloride | 335 |
| 260 | 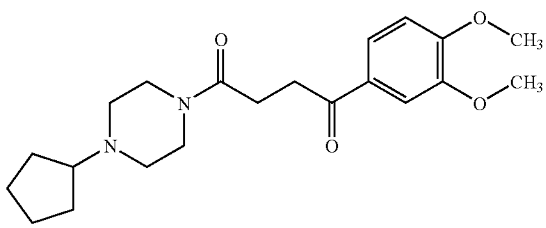 | 1-(4-Cyclopentylpiperazin-1-yl)-4-(3,4-dimethoxyphenyl)-butane-1,4-dione hydrochloride | 375 |
| 261 | 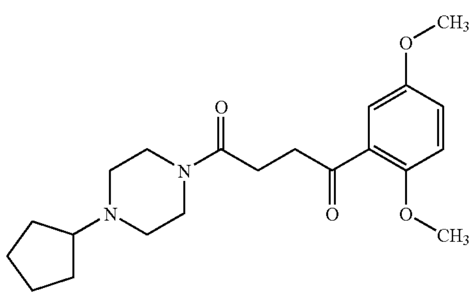 | 1-(4-Cyclopentylpiperazin-1-yl)-4-(2,5-dimethoxyphenyl)-butane-1,4-dione hydrochloride | 375 |
| 262 | 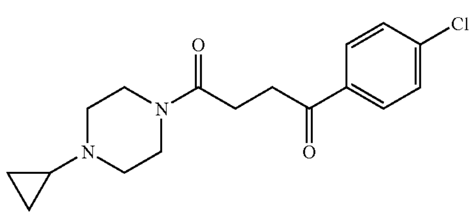 | 1-(4-Chlorophenyl)-4-(4-cyclopropylpiperazin-1-yl)-butane-1,4-dione hydrochloride | 321 |
| 263 | 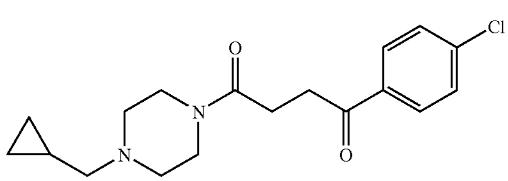 | 1-(4-Chlorophenyl)-4-(4-cyclopropylmethylpiperazin-1-yl)butane-1,4-dione hydrochloride | 335 |
| 264 | 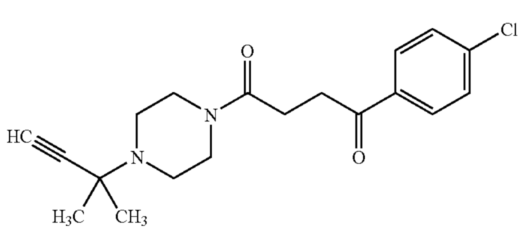 | 1-(4-Chlorophenyl)-4-[4-(1,1-dimethylprop-2-ynyl)-piperazin-1-yl]butane-1,4-dione hydrochloride | 347 |

-continued

| Example No | Structure | Name | Found MH+ |
|---|---|---|---|
| 265 | 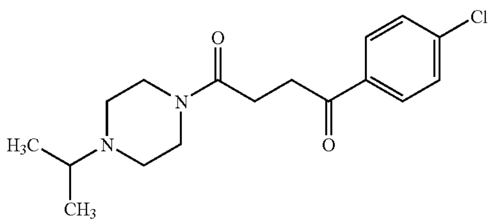 | 1-(4-Chlorophenyl)-4-(4-iso-propylpiperazin-1-yl)butane-1,4-dione hydrochloride | 323 |
| 266 | 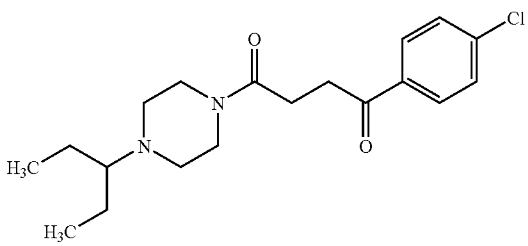 | 1-(4-Chlorophenyl)-4-[4-(1-ethylpropyl)piperazin-1-yl]butane-1,4-dione hydrochloride | 351 |
| 267 | 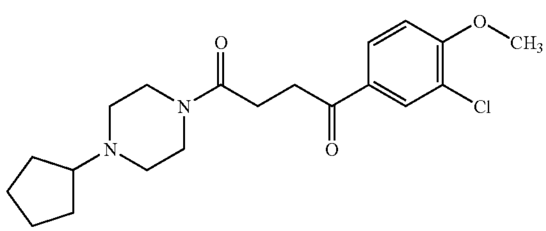 | 1-(3-Chloro-4-methoxy-phenyl)-4-(4-cyclopentyl-piperazin-1-yl)butane-1,4-dione hydrochloride | 379; Rf: 3.92 min. |
| 268 | 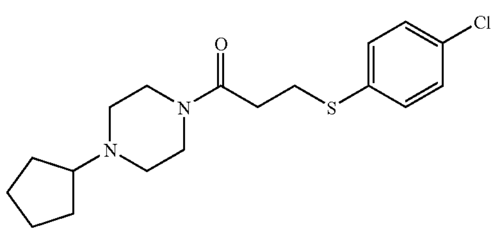 | 3-(4-Chlorophenylsulfanyl)-1-(4-cyclopentylpiperazin-1-yl)propan-1-one hydrochloride | 353; Rf: 4.50 min. |
| 269 | 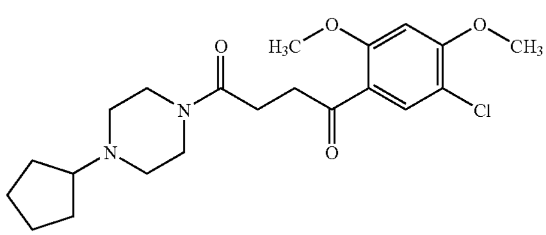 | 1-(5-Chloro-2,4-dimethoxy-phenyl)-4-(4-cyclopentyl-piperazin-1-yl)butane-1,4-dione hydrochloride | 409; Rf: 4.26 min. |
| 270 | 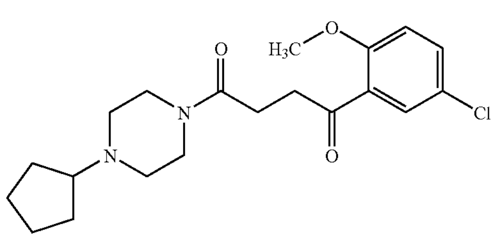 | 1-(5-Chloro-2-methoxy-phenyl)-4-(4-cyclopentyl-piperazin-1-yl)butane-1,4-dione hydrochloride | 379; Rf: 4.13 min. |

-continued

| Example No | Structure | Name | Found MH+ |
|---|---|---|---|
| 271 | 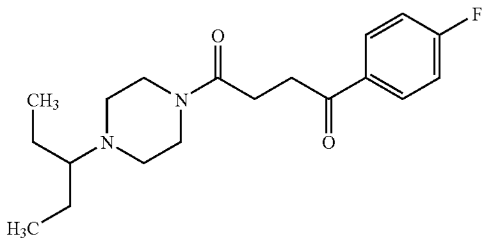 | 1-[4-(1-Ethylpropyl)-piperazin-1-yl]-4-(4-fluoro-phenyl)butane-1,4-dione hydrochloride | 335; Rf: 3.83 min. |
| 272 | 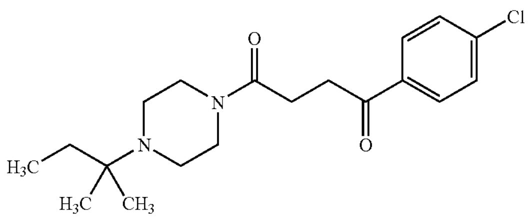 | 1-(4-Chlorophenyl)-4-[4-(1,1-dimethylpropyl)-piperazin-1-yl]butane-1,4-dione hydrochloride | 351; Rf: 4.13 min. |
| 273 | 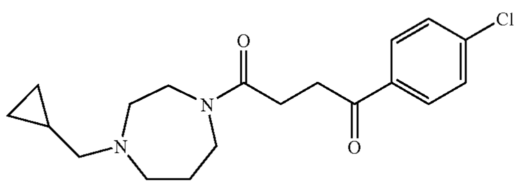 | 1-(4-Chlorophenyl)-4-(4-cyclopropylmethyl[1,4]di-azepan-1-yl)butane-1,4-dione hydrochloride | 349; Rf: 4.00 min. |
| 274 | 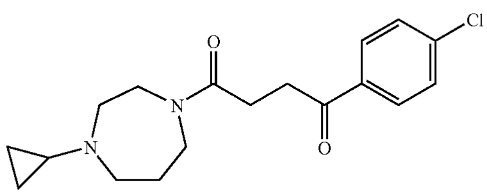 | 1-(4-Chlorophenyl)-4-(4-cyclopropyl[1,4]diazepan-1-yl)butane-1,4-dione hydrochloride | 335; Rf: 3.93 min. |
| 275 | 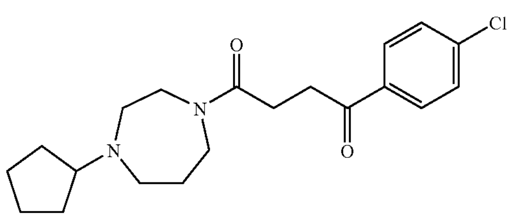 | 1-(4-Chlorophenyl)-4-(4-cyclopentyl[1,4]diazepan-1-yl)butane-1,4-dione hydrochloride | 363; Rf: 4.17 min. |
| 276 | 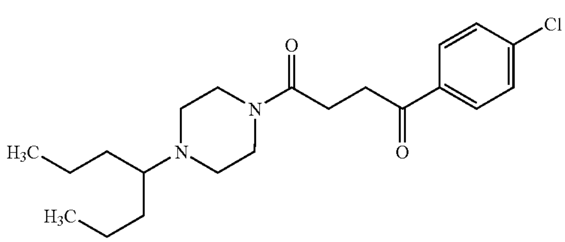 | 1-(4-Chlorophenyl)-4-[4-(1-propylbutyl)piperazin-1-yl]-butane-1,4-dione hydrochloride | 379; Rf: 4.63 min. |
| 277 | 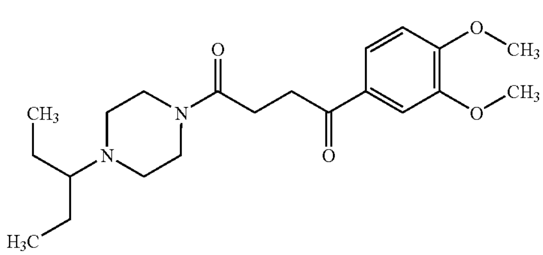 | 1-(3,4-Dimethoxyphenyl)-4-[4-(1-ethylpropyl)piperazin-1-yl]butane-1,4-dione hydrochloride | 377; Rf: 3.67 min. |

-continued

| Example No | Structure | Name | Found MH+ |
|---|---|---|---|
| 278 | 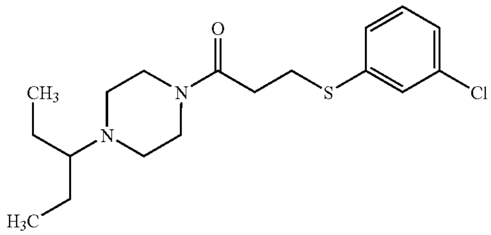 | 3-(3-Chlorophenylsulfanyl)-1-[4-(1-ethylpropyl)-piperazin-1-yl]propan-1-one hydrochloride | 355; Rf: 4.43 min. |
| 279 | 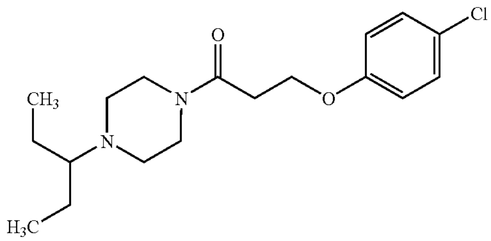 | 3-(4-Chlorophenoxy)-1-[4-(1-ethylpropyl)piperazin-1-yl]propan-1-one hydrochloride | 339; Rf: 4.27 min. |
| 280 | 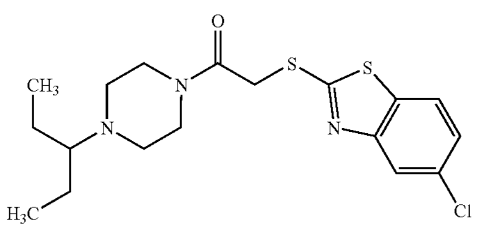 | 2-(5-Chlorobenzothiazol-2-ylsulfanyl)-1-[4-(1-ethyl-propyl)piperazin-1-yl]-ethanone hydrochloride | 398; Rf: 4.33 min. |
| 281 | 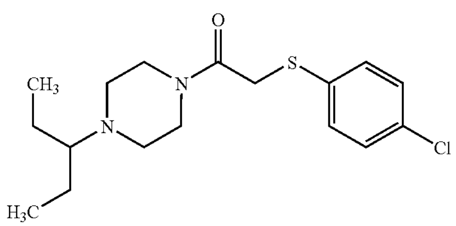 | 2-(4-Chlorophenylsulfanyl)-1-[4-(1-ethylpropyl)-piperazin-1-yl]ethanone | |
| 282 | 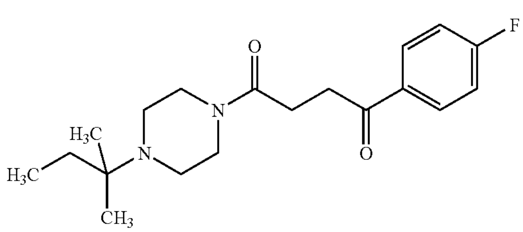 | 1-[4-(1,1-Dimethylpropyl)-piperazin-1-yl]-4-(4-fluoro-phenyl)butane-1,4-dione hydrochloride | 335; Rf: 3.67 min. |
| 283 | 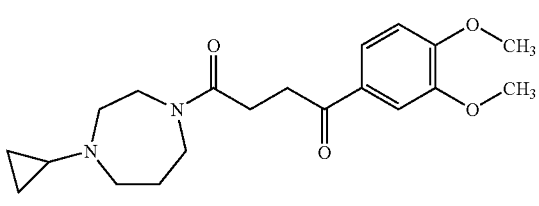 | 1-(4-Cyclopropyl[1,4]diaze-pan-1-yl)-4-(3,4-dimethoxy-phenyl)butane-1,4-dione hydrochloride | 361; Rf: 3.40 min. |

-continued

| Example No | Structure | Name | Found MH+ |
|---|---|---|---|
| 284 | 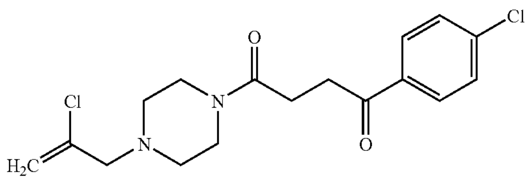 | 1-[4-(2-Chloroallyl)-piperazin-1-yl]-4-(4-chlorophenyl)butane-1,4-dione hydrochloride | 356; Rf: 3.93 min. |
| 285 | 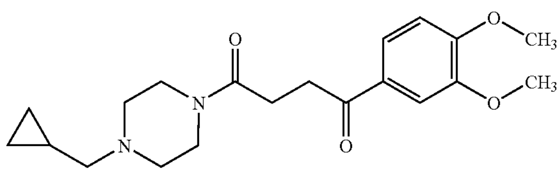 | 1-(4-Cyclopropylmethyl-piperazin-1-yl)-4-(3,4-dimethoxyphenyl)butane-1,4-dione hydrochloride | 361; Rf: 3.53 min. |
| 286 | 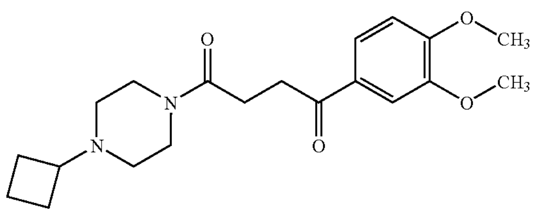 | 1-(4-Cyclobutylpiperazin-1-yl)-4-(3,4-dimethoxyphenyl)-butane-1,4-dione hydrochloride | 361; Rf: 3.40 min. |
| 287 | 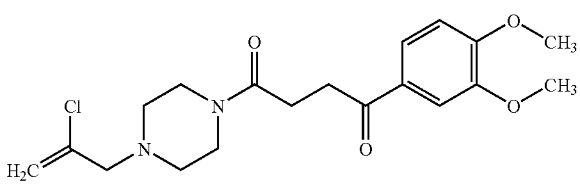 | 1-[4-(2-Chloroallyl)-piperazin-1-yl]-4-(3,4-dimethoxyphenyl)butane-1,4-dione hydrochloride | 381; Rf: 3.43 min. |
| 288 | 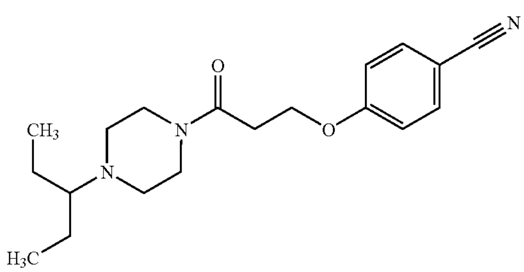 | 4-{3-[4-(1-Ethylpropyl)-piperazin-1-yl]-3-oxo-propoxy}benzonitrile hydrochloride | 330; Rf: 3.67 min. |
| 289 | 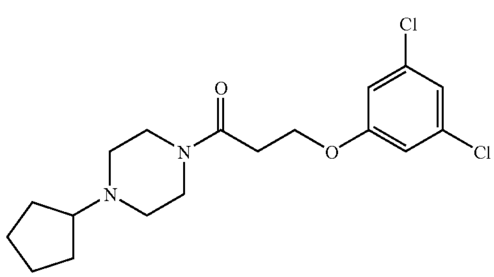 | 1-(4-Cyclopentylpiperazin-1-yl)-3-(3,5-dichlorophenoxy)-propan-1-one hydrochloride | 371; Rf: 4.53 min. |
| 290 | 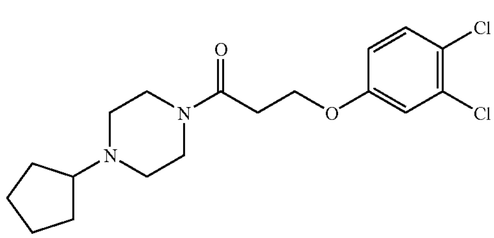 | 1-(4-Cyclopentylpiperazin-1-yl)-3-(3,4-dichlorophenoxy)-propan-1-one hydrochloride | 371 Rf: 4.47 min. |

-continued

| Example No | Structure | Name | Found MH+ |
|---|---|---|---|
| 291 | 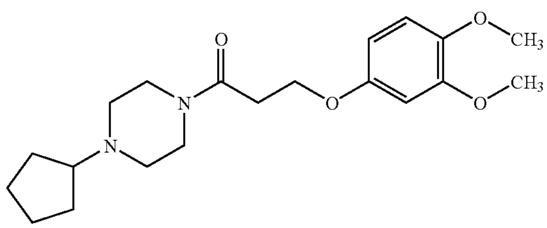 | 1-(4-Cyclopentylpiperazin-1-yl)-3-(3,4-dimethoxy-phenoxy)propan-1-one hydrochloride | 363; Rf: 3.50 min. |
| 292 | 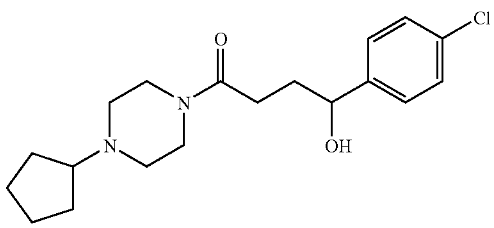 | 4-(4-Chlorophenyl)-1-(4-cyclopentylpiperazin-1-yl)-4-hydroxybutan-1-one hydrochloride | 351; Rf: 3.70 min. |
| 293 | 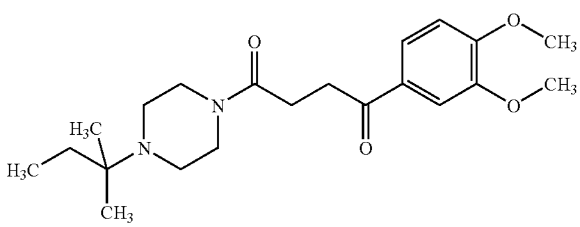 | 1-(3,4-Dimethoxyphenyl)-4-[4-(1,1-dimethylpropyl)-piperazin-1-yl]butane-1,4-dione hydrochloride | 377; Rf: 3.33 min. |
| 294 | 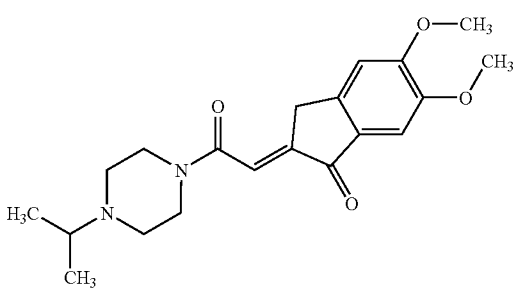 | 2-[2-(4-Isopropylpiperazin-1-yl)-2-oxoethylidene]-5,6-dimethoxyindan-1-one hydrochloride | 359; Rf: 3.20 min. |
| 295 | 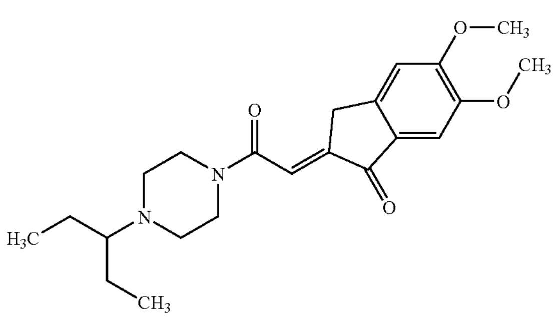 | 2-{2-[4-(1-Ethylpropyl)-piperazin-1-yl]-2-oxo-ethylidene}-5,6-dimethoxy-indan-1-one hydrochloride | 387; Rf: 3.50 min.387 |

-continued

| Example No | Structure | Name | Found MH+ |
|---|---|---|---|
| 296 | 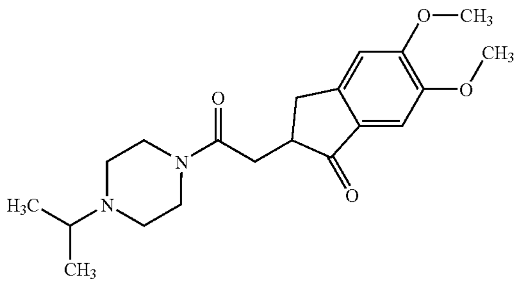 | 2-[2-(4-Isopropylpiperazin-1-yl)-2-oxoethyl]-5,6-dimethoxyindan-1-one hydrochloride | 361; Rf: 2.87 min. |
| 297 | 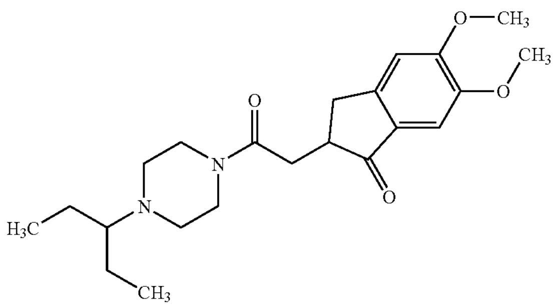 | 2-{2-[4-(1-Ethylpropyl)-piperazin-1-yl]-2-oxoethyl}-5,6-dimethoxyindan-1-one hydrochloride | 389; Rf: 3.33 min. |
| 298 | 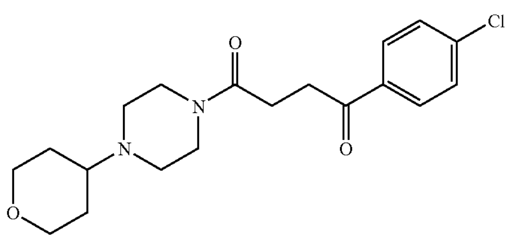 | 1-(4-Chlorophenyl)-4-[4-(tetrahydropyran-4-yl)-piperazin-1-yl]butane-1,4-dione hydrochloride | 365; Rf: 3.73 min. |
| 299 | 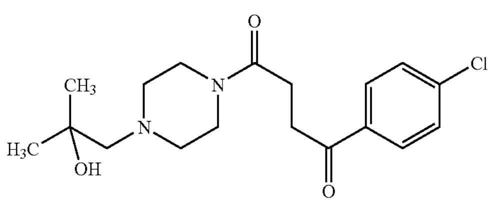 | 1-(4-Chlorophenyl)-4-[4-(2-hydroxy-2-methylpropyl)-piperazin-1-yl]butane-1,4-dione hydrochloride | 353; Rf: 1.91 min. |
| 300 | 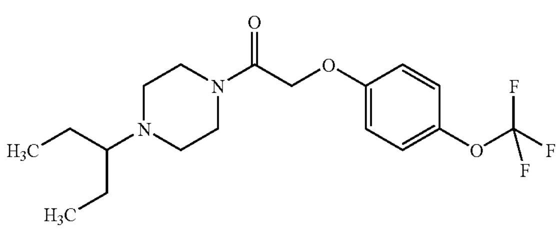 | 1-[4-(1-Ethylpropyl)-piperazin-1-yl]-2-(4-trifluoromethoxyphenoxy)ethanone hydrochloride | 375; Rf: 4.50 min. |
| 301 | 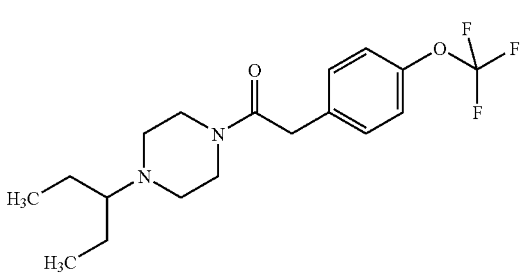 | 1-[4-(1-Ethylpropyl)-piperazin-1-yl]-2-(4-trifluoromethoxyphenyl)ethanone hydrochloride | 359; Rf: 4.33 min. |

-continued

| Example No | Structure | Name | Found MH+ |
|---|---|---|---|
| 302 | 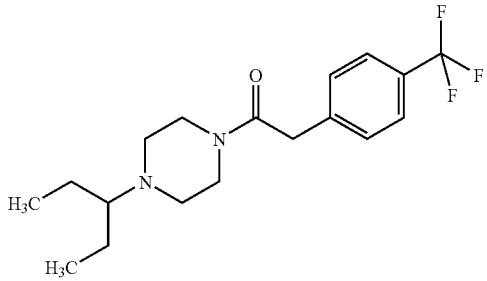 | 1-[4-(1-Ethylpropyl)-piperazin-1-yl]-2-(4-trifluoromethylphenyl)ethanone hydrochloride | 343; Rf: 4.37 min. |
| 303 | 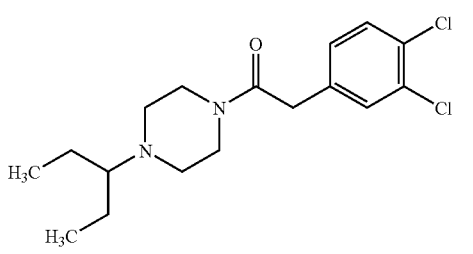 | 2-(3,4-Dichlorophenyl)-1-[4-(1-ethylpropyl)piperazin-1-yl]ethanone hydrochloride | 343; Rf: 4.33 min. |
| 304 | 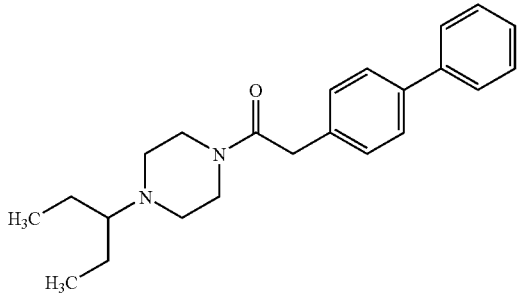 | 2-Biphenyl-4-yl-1-[4-(1-ethylpropyl)piperazin-1-yl]-ethanone hydrochloride | 351; Rf: 4.63 min. |
| 305 | 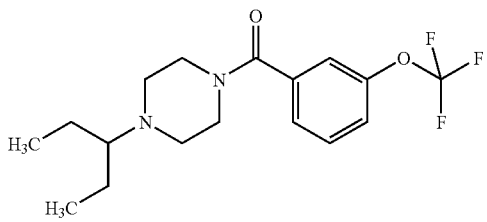 | [4-(1-Ethylpropyl)piperazin-1-yl]-(3-trifluoromethoxyphenyl)methanone hydrochloride | 345; Rf: 4.23 min. |
| 306 | 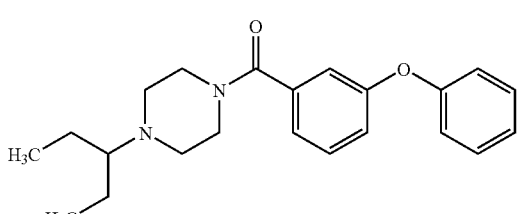 | [4-(1-Ethylpropyl)piperazin-1-yl](3-phenoxyphenyl)-methanone hydrochloride | 353; 4.50 min. |
| 307 | 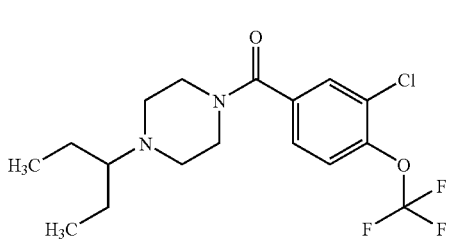 | (3-Chloro-4-trifluoromethoxyphenyl)-[4-(1-ethylpropyl)piperazin-1-yl]methanone hydrochloride | 379; Rf: 4.60 min. |

-continued

| Example No | Structure | Name | Found MH+ |
|---|---|---|---|
| 308 | 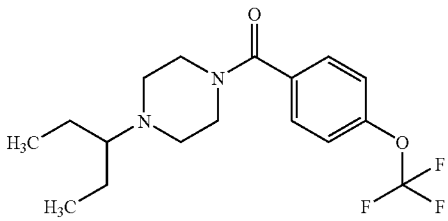 | [4-(1-Ethylpropyl)piperazin-1-yl](4-trifluoromethoxyphenyl)methanone hydrochloride | 345; Rf: 4.23 min. |
| 309 | 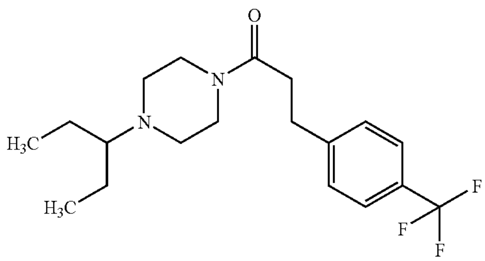 | 1-[4-(1-Ethylpropyl)-piperazin-1-yl]-3-(4-trifluoromethylphenyl)propan-1-one hydrochloride | 357; Rf: 4.53 min. |
| 310 | 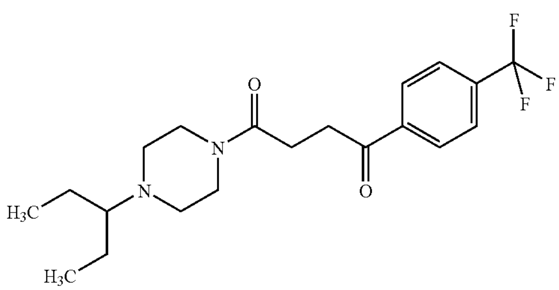 | 1-[4-(1-Ethylpropyl)-piperazin-1-yl]-4-(4-trifluoromethylphenyl)butane-1,4-dione hydrochloride | 385; Rf: 2.73 min. |
| 311 | 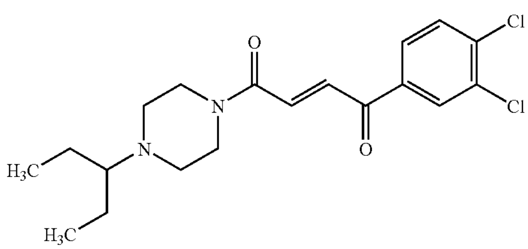 | 1-(3,4-Dichlorophenyl)-4-[4-(1-ethylpropyl)piperazin-1-yl]but-2-ene-1,4-dione hydrochloride | 383; Rf: 2.85 min. |
| 312 | 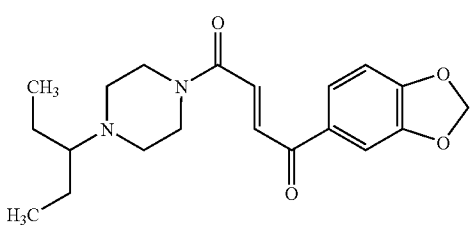 | 1-Benzo[1,3]dioxol-5-yl-4-[4-(1-ethylpropyl)piperazin-1-yl]but-2-ene-1,4-dione hydrochloride | 359; Rf: 2.08 min. |
| 313 | 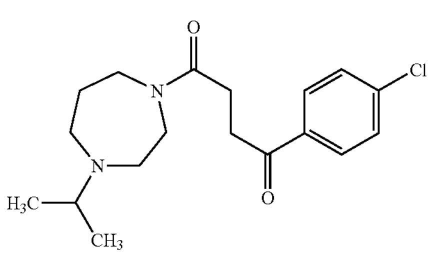 | 1-(4-Chlorophenyl)-4-(4-isopropyl[1,4]diazepan-1-yl)-butane-1,4-dione hydrochloride | 337; Rf: 3.93 min. |

-continued

| Example No | Structure | Name | Found MH+ |
|---|---|---|---|
| 314 | 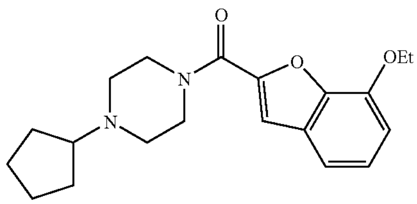 | (4-Cyclopentylpiperazin-1-yl)-(7-ethoxybenzofuran-2-yl)methanone hydrochloride | 343; Rf: 4.12 min. |
| 315 | 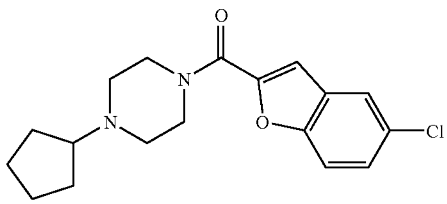 | (5-Chlorobenzofuran-2-yl)-(4-cyclopentylpiperazin-1-yl)methanone hydrochloride | 333; Rf: 4.15 min. |
| 316 | 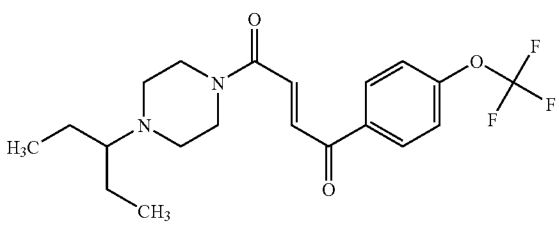 | 1-[4-(1-Ethylpropyl)-piperazin-1-yl]-4-(4-trifluoromethoxyphenyl)but-2-ene-1,4-dione hydrochloride | 399; Rf: 4.63 min. |
| 317 | 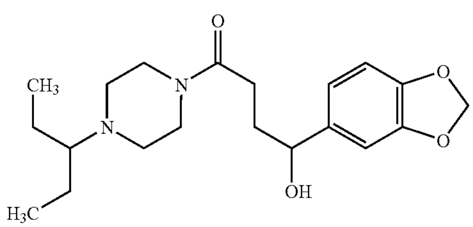 | 4-Benzo[1,3]dioxol-5-yl-1-[4-(1-ethylpropyl)piperazin-1-yl]-4-hydroxybutan-1-one hydrochloride | 363 (MH+), 345 (MH+ − H2O); Rf: 3.50 min. |
| 318 | 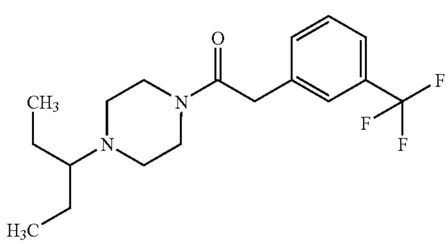 | 1-[4-(1-Ethylpropyl)piperazin-1-yl]-2-(3-trifluoromethylphenyl)ethanone hydrochloride | 343; Rf: 4.07 min. |
| 319 | 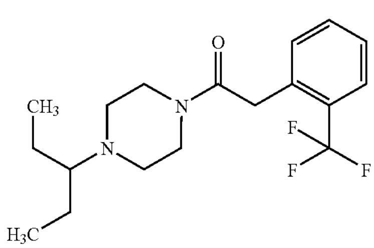 | 1-[4-(1-Ethylpropyl)-piperazin-1-yl]-2-(2-trifluoromethylphenyl)ethanone hydrochloride | 343; Rf: 3.90 min. |

| Example No | Structure | Name | Found MH+ |
|---|---|---|---|
| 320 | 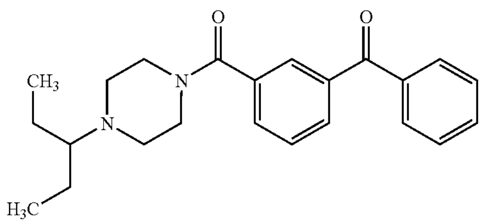 | (3-Benzoylphenyl)-[4-(1-ethylpropyl)piperazin-1-yl]-methanone hydrochloride | 365; Rf: 4.03 min. |
| 321 | 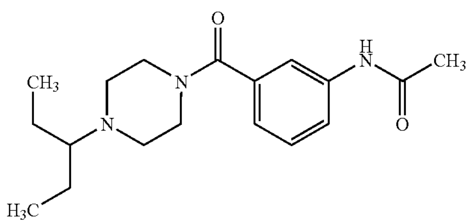 | N-{3-[4-(1-Ethylpropyl)-piperazine-1-carbonyl]-phenyl}acetamide hydrochloride | 318; Rf: 2.57 min. |
| 322 | 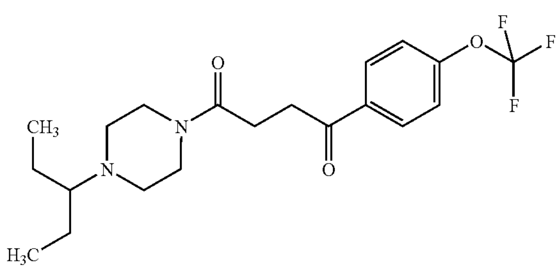 | 1-[4-(1-Ethylpropyl)-piperazin-1-yl]-4-(4-trifluoro-methoxyphenyl)butane-1,4-dione hydrochloride | 401; Rf: 4.40 min. |
| 323 | 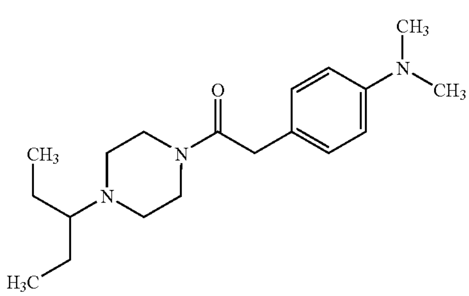 | 2-(4-Dimethylaminophenyl)-1-[4-(1-ethylpropyl)-piperazin-1-yl]ethanone dihydrochloride | 318; Rf: 0.43 min. |
| 324 | 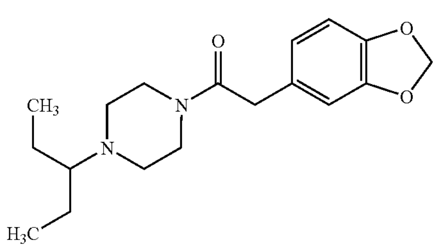 | 2-Benzo[1,3]dioxol-5-yl-1-[4-(1-ethylpropyl)piperazin-1-yl]ethanone hydrochloride | 319; Rf: 3.30 min. |
| 325 | 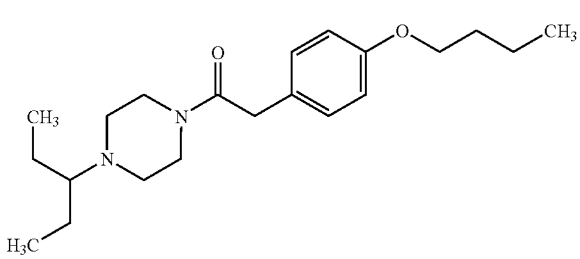 | 2-(4-Butoxyphenyl)-1-[4-(1-ethylpropyl)piperazin-1-yl]-ethanone hydrochloride | 347; Rf: 4.47 min. |

-continued

| Example No | Structure | Name | Found MH+ |
|---|---|---|---|
| 326 | 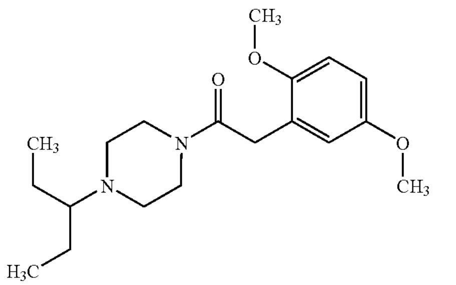 | 2-(2,5-Dimethoxyphenyl)-1-[4-(1-ethylpropyl)piperazin-1-yl]ethanone hydrochloride | 335; Rf: 3.57 min. |
| 327 | 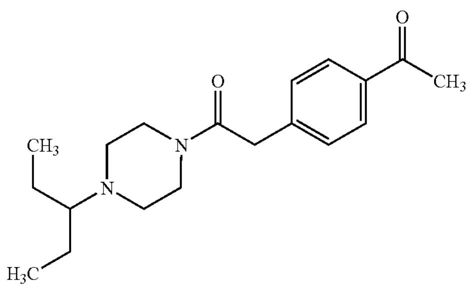 | 2-(4-Acetylphenyl)-1-[4-(1-ethylpropyl)piperazin-1-yl]-ethanone hydrochloride | 333; (reduced methyl enol ether); Rf: 3.27 min. |
| 328 | 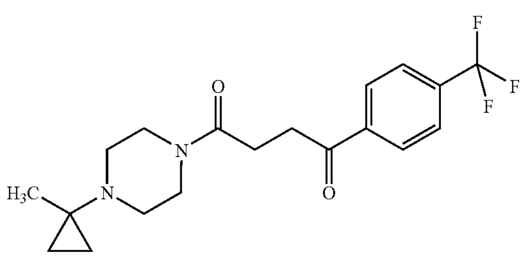 | 1-[4-(1-Methylcyclopropyl)-piperazin-1-yl]-4-(4-trifluoro-methylphenyl)butane-1,4-dione hydrochloride | 369 |
| 329 | 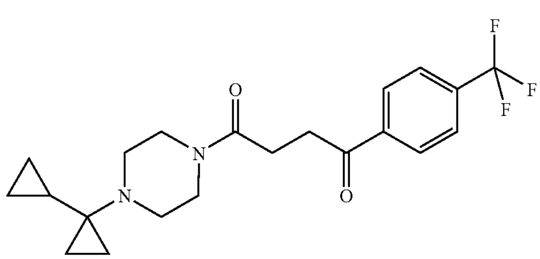 | 1-(4-Bicyclopropyl-1-yl-piperazin-1-yl)-4-(4-trifluoro-methylphenyl)butane-1,4-dione hydrochloride | 395 |

Spectral Data for Selected Examples:

Example 1

1-(3-Fluoro-4-methoxyphenyl)-4-(4-isopropylpiperazin-1-yl)butane-1,4-dione hydrochloride $^1$H NMR (DMSO-d$_6$), δ 1.29 (d, J=7 Hz, 6H), 2.70–2.92 (m, 3H), 3.00–3.23 (m, 4H), 3.32–3.71 (m, 4H), 3.92 (s, 3H), 4.18 (m, 1H), 4.43 (m, 1H), 7.29 (t, J=7 Hz, 1H), 7.76 (dd, J=14 Hz, 1 Hz, 1H), 7.84 (br d, J=7 Hz, 1H), 10.95 (br s, 1H).

Example 2

1-[4-(1-Ethylpropyl)piperazin-1-yl]-4-(3-fluoro-4-methoxyphenyl)butane-1,4-dione hydrochloride $^1$H NMR (DMSO-d$_6$) δ 0.98 (t, J=7 Hz, 6H), 1.61 (sept, J=7 Hz, 2H), 1.87 (m, 2H), 2.72 (m, 2H), 2.85–3.28 (m, 6H), 3.40 (m, 2H), 3.72 (m, 1H), 3.93 (s, 3H), 4.11 (m, 1H), 4.39 (m, 1H), 7.29 (t, J=7 Hz, 1H), 7.76 (br d, J=14 Hz, 1H), 7.84 (br d, J=7 Hz, 1H), 10.75 (br s, 1H).

Example 3

1-(3-Fluoro-4-methoxyphenyl)-4-(4-propylpiperazin-1-yl)butane-1,4-dione hydrochloride $^1$H NMR (DMSO-d$_6$) δ 0.91 (t, J=7 Hz, 3H), 1.69 (sext, J=7 Hz, 2H), 2.69–3.10 (m, 7H), 3.20 (t, J=7 Hz, 2H), 3.48 (m, 3H), 3.92 (s, 3H), 4.16 (m, 1H), 4.39 (m, 1H) 7.29 (t, J=7 Hz, 1H), 7.78 (dd, J=14 Hz, 1 Hz, 1H), 7.84 (br d, J=7 Hz, 1H), 10.15 (br s, 1H).

Example 4

1-(4-Cyclopentylpiperazin-1-yl)-4-(4-methanesulfonylphenyl)butane-1,4-dione hydrochloride $^1$H NMR (DMSO-d$_6$) δ 1.55 (m, 2H), 1.65–1.88 (m, 4H), 1.98 (m, 2H), 2.75–3.14 (m, 5H), 3.29 (s, 3H), 3.32 (m, 2H), 3.45–3.64 (m, 4H), 4.14 (m, 1H), 4.39 (m, 1H), 8.08 (d, J=8 Hz, 2H), 8.19 (d, J=8 Hz, 2H), 10.95 (br s, 1H).

Example 5

1-(4-Cyclopentylpiperazin-1-yl)-4-phenylpentane-1,5-dione hydrochloride $^1$H NMR (DMSO-d$_6$) δ 1.45–2.05 (m, 10H), 2.43 (m, 2H), 2.82–3.16 (m, 5H), 3.40–3.62 (m, 4H), 4.05 (m, 1H), 4.45 (m, 1H), 7.52 (t, J=8 Hz, 2H), 7.63 (t, J=8 Hz, 1H), 7.96 (d, J=8 Hz, 2H), 11.28 (br s, 1H).

Example 7

4-Cyclopentylpiperazine-1-carboxylic acid 2-(3,4-dimethoxyphenyl)ethyl ester hydrochloride This compound was prepared by treatment of a solution of 2-(3,4-dimethoxyphenyl)ethanol (1.82 g, 10 mmol) in DCM (30 ml) with pyridine (1.6 ml) and then with a solution of 4-nitrophenyl chloroformate (2.0 g, 10 mmol) in DCM (25 ml). The mixture was stirred at room temperature for 2 hours, and was then washed with dilute hydrochloric acid and with water. After drying with magnesium sulfate the solution of the crude carbonate was concentrated, to yield 3.8 g of a yellow oil. To a solution of 0.69 g (2 mmol) of this oil in acetonitrile (10 ml) was added 1-cyclopentylpiperazine (0.6 g, 4 mmol). The resulting mixture was stirred at room temperature for 2 days, concentrated under reduced pressure, and the residue was redissolved in DCM and extracted with dilute hydrochloric acid. The aqueous phase was made alkaline by addition of solid NaHCO$_3$, and extracted three times with DCM. The combined extracts were dried over magnesium sulphate, concentrated, and the residue was redissolved in 1 M hydrochloric acid (5 ml) and ethanol. The mixture was concentrated, and the residue recrystallized from ethanol, to yield 82 mg of the title compound as colorless solid.

$^1$H NMR (DMSO-d$_6$) δ 1.53 (m, 2H), 1.65–1.83 (m, 4H), 1.98 (m, 2H), 2.82 (t, J=7 Hz, 2H), 2.85–3.00 (m, 2H), 3.24–3.49 (m, 5H), 3.71 (s, 3H), 3.74 (s, 3H), 4.01 (m, 2H), 4.21 (t, J=7 Hz, 2H), 6.74 (m, 1H), 6.87 (m, 2H), 11.05 (br s, 1H).

Example 62

1-Biphenyl-4-yl-4-(4-pyridin-4-ylpiperazin-1-yl)butane-1,4-dione hydrochloride $^1$H NMR (DMSO-d$_6$) δ 2.78 (t, J=7 Hz, 2H), 3.29 (t, J=7 Hz, 2H), 3.61–3.86 (m, 8H), 7.19 (m, 2H), 7.42 (m, 1H), 7.52 (m, 2H), 7.73 (d, J=7 Hz, 2H), 7.83 (d, J=7 Hz, 2H), 8.07 (d, J=7 Hz, 2H), 8.29 (d, J=7 Hz, 2H), 13.80 (br s, 1H).

Example 79

3-[3-Oxo-3-(4-pyridin-4-ylpiperazin-1-yl)propyl]-3H-benzoxazol-2-one hydrochloride $^1$H NMR (DMSO-d$_6$) δ 2.89 (t, J=7 Hz, 2H), 3.59–3.78 (m, 8H), 4.06 (t, J=7 Hz, 2H), 7.10–7.40 (m, 6H), 8.28 (d, J=7 Hz, 2H), 13.95 (br s, 1H).

Example 84

2-(2-Acetylphenoxy)-1-(4-pyridin-4-ylpiperazin-1-yl)ethanone hydrochloride $^1$H NMR (DMSO-d$_6$) δ 2.63 (s, 3H), 3.62–3.86 (m, 8H), 5.11 (s, 2H), 7.02 (t, J=7 Hz, 1H), 7.15 (d, J=7 Hz, 1H), 7.20 (d, J=7 Hz, 2H), 7.49 (brt, J=7 Hz, 1H), 7.58 (brd, J=7 Hz, 1H), 8.29 (d, J=7 Hz, 2H), 13.90 (br s, 1H).

Example 89

1-(4-Cyclohexylpiperazin-1-yl)-4-(3-fluoro-4-methoxyphenyl)butane-1,4-dione hydrochloride $^1$H NMR (DMSO-d$_6$) δ 1.03–1.49 (m, 5H), 1.60 (m, 1H), 1.82 (m, 2H), 2.10 (m, 2H), 2.72 (m, 2H), 2.80–3.23 (m, 6H), 3.41 (m, 2H), 3.63 (m, 1H), 3.93 (s, 3H), 4.17 (m, 1H), 4.42 (m, 1H), 7.29 (t, J=8 Hz, 1H), 7.76 (dd, J=11 Hz, 1 Hz, 1H), 7.87 (br d, J=8 Hz, 1H), 10.80 (br s, 1H).

Example 135

1-(4-Cyclopentylpiperazin-1-yl)-3-naphth-1-ylpropenone hydrochloride $^1$H NMR (DMSO-d$_6$) δ 1.56 (m, 2H), 1.69–1.85 (m, 4H), 2.02 (m, 2H), 2.95–3.15 (m, 3H), 3.53 (m, 4H), 4.58 (m, 2H), 7.34 (d, J=14 Hz, 1H), 7.55–7.65 (m, 3H), 8.01 (m, 3H), 8.19 (d, J=7 Hz, 1H), 8.35 (d, J=14 Hz, 1H), 10.85 (br s, 1H).

Example 142

1-(4-Cyclopentylpiperazin-1-yl)-4-(4-methoxyphenyl)butan-1-one hydrochloride $^1$H NMR (DMSO-d$_6$) δ 1.53 (m, 2H), 1.65–1.87 (m, 6H), 1.96 (m, 2H), 2.33 (t, J=7 Hz, 2H), 2.53 (t, J=7 Hz, 2H), 2.80–3.13 (m, 3H), 3.38–3.58 (m, 4H), 3.71 (s, 3H), 3.97 (m, 1H), 4.42 (m, 1H), 6.84 (d, J=8 Hz, 2H), 7.11 (d, J=8 Hz, 2H), 11.30 (br s, 1H).

Example 144

1-(4-Cyclopentylpiperazin-1-yl)-4-(3-fluoro-4-methoxyphenyl)butane-1,4-dione $^1$H NMR (DMSO-d$_6$) δ 1.25–1.66 (m, 6H), 1.79 (m, 2H), 2.28–2.49 (m, 4H), 2.67 (m, 2H), 3.16 (m, 2H), 3.38–3.55

(m, 4H), 3.93 (s, 3H), 7.29 (t, J=8 Hz, 1H), 7.75 (d, J=13 Hz), 7.85 (d, J=8 Hz).

Example 147

2-(4-Acetylphenoxy)-1-(4-cyclopentylpiperazin-1-yl)ethanone hydrochloride $^1$H NMR (DMSO-d$_6$) δ 1.56 (m, 2H), 1.67–1.88 (m, 4H), 1.98 (m, 2H), 2.52 (s, 3H), 2.85–3.18 (m, 3H), 3.51 (m, 4H), 4.01 (m, 1H), 4.40 (m, 1H), 5.01 (d, J=2 Hz, 2H), 7.02 (d, J=8 Hz, 2H), 7.91 (d, J=8 Hz, 2H), 10.90 (br s, 1H).

Example 181

1-Biphenyl-4-yl-4-(4-cyclopentylpiperazin-1-yl)butane-1,4-dione $^1$H NMR (DMSO-d$_6$) δ 1.32 (m, 2H), 1.45–1.63 (m, 4H), 1.79 (m, 2H), 2.33 (m, 2H), 2.43 (m, 3H), 2.72 (t, J=7 Hz, 2H), 3.24 (t, J=7 Hz, 2H), 3.41 (m, 2H), 3.51 (m, 2H), 7.40–7.53 (m, 3H), 7.76 (d, J=7 Hz, 2H), 7.82 (d, J=8 Hz, 2H), 8.07 (d, J=8 Hz, 2H).

Example 185

1-(4-Cyclopentylpiperazin-1-yl)-4-(3,4-dimethoxyphenyl)butan-1-one hydrochloride $^1$H NMR (DMSO-d$_6$) δ 1.53 (m, 2H), 1.65–1.83 (m, 6H), 1.96 (m, 2H), 2.34 (t, J=7 Hz, 2H), 2.53 (m, 2H), 2.80–3.12 (m, 3H), 3.44 (m, 4H), 3.71 (s, 3H), 3.73 (s, 3H), 3.98 (m, 1H), 4.43 (m, 1H), 6.69 (br d, J=8 Hz, 1H), 6.78 (br s, 1H), 6.84 (d, J=8 Hz), 11.05 (brs, 1H).

Example 188

1-(4-Chlorophenyl)-4-(4-cyclopentylpiperazin-1-yl)butane-1,4-dione hydrochloride $^1$H NMR (DMSO-d$_6$) δ 1.53 (m, 2H), 1.64–1.90 (m, 4H), 1.98 (m, 2H), 2.71–3.18 (m, 5H), 3.23 (t, J=7 Hz, 2H), 3.42–3.67 (m, 4H), 4.15 (m, 1H), 4.39 (m, 1H), 7.60 (d, J=8 Hz, 2H), 7.99 (d, J=8 Hz, 2H), 11.20 (br s, 1H).

Example 189

1-(4-Cyclopentylpiperazin-1-yl)-4-(6-methoxynaphth-2-yl)butane-1,4-dione hydrochloride $^1$H NMR (DMSO-d$_6$) δ 1.56 (m, 2H), 1.63–1.90 (m, 4H), 1.99 (m, 2H), 2.21–3.17 (m, 5H), 3.30–3.68 (m, 6H), 3.91 (s, 3H), 4.18 (m, 1H), 4.41 (m, 1H), 7.28 (m, 1H), 7.40 (brs, 1H), 7.89 (d, J=7 Hz, 1H), 7.97 (br d, J=7 Hz, 1H), 8.05 (d, J=7 Hz, 1H), 8.61 (brs, 1H), 11.10 (br s, 1H).

Example 190

3-[4-(4-Fluorobenzyloxy)phenyl]-1-(4-pyridin-4-ylpiperazin-1-yl)propenone $^1$H NMR (DMSO-d$_6$) δ 3.32–3.50 (m, 4H), 3.65–3.88 (m, 4H), 5.12 (s, 2H), 6.84 (d, J=7 Hz, 2H), 7.03 (d, J=9 Hz, 2H), 7.13–7.24 (m, 3H), 7.46–7.53 (m, 3H), 7.69 (d, J=9 Hz, 2H), 8.18 (d, J=7 Hz, 2H).

Example 247

1-Phenyl-4-(4-pyridin-4-ylpiperazin-1-yl)butane-1,4-dione hydrochloride $^1$H NMR (DMSO-d$_6$) δ 2.78 (t, J=7 Hz, 2H), 3.28 (t, J=7 Hz, 2H), 3.59–3.84 (m, 8H), 7.19 (d, J=7 Hz, 2H), 7.53 (t, J=7 Hz, 2H), 7.63 (m, 1H), 7.99 (d, J=7 Hz, 2H), 8.29 (d, J=7 Hz, 2H), 13.95 (br s, 1H).

Example 248

1-(3,4-Dimethoxyphenyl)-4-[4-(1-methylcyclopropyl)-[1,4]-diazepan-1-yl]butane-1,4-dione hydrochloride $^1$H NMR (DMSO-d$_6$) δ 0.74 (m, 2H), 1.31 (s, 2H), 1.38 (m, 3H), 1.95–2.20 (m, 2H), 2.25–2.80 (m, 4H), 3.10–3.75 (m, 6H), 3.81 (s, 3H), 3.85 (s, 3H), 4.00–4.22 (m, 2H), 7.08 (d, J=8 Hz, 1H), 7.45 (s, 1H), 7.68 (d, J=8 Hz, 1H), 10 28 (br s, 1H); HPLC-MS: m/z 375 (MH$^+$); Rf: 2.20 min.

Example 249

1-(4-Chlorophenyl)-4-(4-cyclohexylpiperazin-1-yl)butane-1,4-dione hydrochloride $^1$H NMR (DMSO-d$_6$) δ 1.05–1.65 (m, 6H), 1.82 (m, 2H), 2.11 (m, 2H), 2.72–2.98 (m, 3H), 3.04–3.28 (m, 5H), 3.42 (m, 2H), 3.63 (m, 1H), 4.14 (m, 1H), 4.41 (m, 1H), 7.61 (d, J=8 Hz, 2H), 7.99 (d, J=8 Hz, 2H), 10.80 (br s, 11H).

Example 250

1-(4-Cyclopentylpiperazin-1-yl)-4-phenylbutane-1,4-dione hydrochloride $^1$H NMR (DMSO-d$_6$) δ 1.54 (m, 2H), 1.65–1.90 (m, 4H), 1.98 (m, 2H), 2.73–3.15 (m, 5H), 3.26 (t, J=7 Hz, 2H), 3.42–3.67 (m, 4H), 4.15 (m, 1H), 4.39 (m, 1H), 7.52 (t, J=7 Hz, 2H), 7.63 (t, J=7 Hz, 1H), 7.99 (d, J=7 Hz, 2H), 11.15 (br s, 1H).

Example 251

1-(4-Allylpiperazin-1-yl)-3-(3-nitro-4-pyrrolidin-1-ylphenyl)propenone $^1$H NMR (CDCl$_3$) δ 2.01 (m, 4H), 2.51 (br s, 4H), 3.03 (d, J=7 Hz, 2H), 3.28 (m, 4H), 3.65–3.80 (m, 4H), 5.19–5.25 (m, 2H), 5.80–5.92 (m, 1H), 6.73 (d, J=14 Hz, 1H), 6.89 (d, J=8 Hz, 1H), 7.49 (d, J=8 Hz, 1H), 7.58 (d, J=14 Hz, 1H), 7.92 (br s, 1H).

Example 252

1-(4-Chlorophenyl)-4-(4-cycloheptylpiperazin-1-yl)butane-1,4-dione hydrochloride $^1$H NMR (DMSO-d$_6$) δ 1.35–1.78 (m, 10H), 2.12 (m, 2H), 2.73 (m, 2H), 2.90 (m, 1H), 3.08–3.36 (m, 7H), 3.68 (m, 1H), 4.13 (m, 1H), 4.42 (m, 1H), 7.59 (d, J=8 Hz, 2H), 7.98 (d, J=8 Hz, 2H), 10.85 (br s, 1H).

Example 253

4-(4-Chlorophenyl)-1-(4-cyclopentylpiperazin-1-yl)butan-1-one hydrochloride $^1$H NMR (DMSO-d$_6$) δ 1.54 (m, 2H), 1.65–1.80 (m, 6H), 1.97 (m, 2H), 2.35 (m, 2H), 2.60 (m, 2H), 2.85–3.05 (m, 3H), 3.27–3.55 (m, 4H), 3.99 (m, 1H), 4.44 (m, 1H), 7.23 (d, J=8 Hz, 2H), 7.34 (d, J=8 Hz, 2H), 10.39 (br s, 1H).

Example 254

1-(4-Cyclopentylpiperazin-1-yl)-2-indan-2-yletha-none hydrochloride $^1$H NMR (DMSO-d$_6$) δ 1.52 (m, 2H), 1.62–1.89 (m, 4H), 1.98 (m, 2H), 2.55 (m, 2H), 2.72 (sept, J=7 Hz, 1H), 2.90 (m, 3H), 3.06 (dd, J=15 Hz, 7 Hz, 2H), 3.46 (m, 6H), 4.04 (br d, J=7 Hz, 1H), 4.47 (br d, J=7 Hz, 1H), 7.09 (m, 2H), 7.18 (m, 2H), 11.29 (brs, 1H).

Example 255

1-(4-Chlorophenyl)-4-(4-cyclooctylpiperazin-1-yl)butane-1,4-dione hydrochloride $^1$H NMR (DMSO-d$_6$) δ 1.41–1.76 (m, 12H), 2.02 (m, 2H), 2.75 (m, 2H), 2.92 (m, 1H), 3.06–3.45 (m, 7H), 3.64 (m, 1H), 4.13 (m, 1H), 4.41 (m, 1H), 7.61 (d, J=8 Hz, 2H), 7.99 (d, J=8 Hz, 2H), 10.85 (br s, 1H).

Example 256

1-(4-Cyclopentylpiperazin-1-yl)-3-(4-methoxyphe-noxy)propan-1-one hydrochloride $^1$H NMR (DMSO-d$_6$) δ 1.53 (m, 2H), 1.65–1.88 (m, 4H), 1.98 (m, 2H), 2.83 (t, J=7 Hz, 2H), 2.88–3.15 (m, 3H), 3.48 (m, 4H), 3.69 (s, 3H), 4.10 (br d, J=7 Hz, 1H), 4.13 (t, J=7 Hz, 2H), 4.46 (br d, J=7 Hz, 1H), 6.85 (s, 4H), 11.07 (br s, 1H).

Example 257

1-(4-Chlorophenyl)-4-(4-cyclobutylpiperazin-1-yl)butane-1,4-dione hydrochloride $^1$H NMR (DMSO-d$_6$) δ 1.65–1.83 (m, 2H), 2.18 (m, 2H), 2.38 (m, 2H), 2.61–2.93 (m, 4H), 3.07 (m, 1H), 3.23 (t, J=7 Hz, 2H), 3.32 (m, 2H), 3.50–3.71 (m, 2H), 4.15 (m, 1H), 4.40 (m, 1H), 7.60 (d, J=8 Hz, 2H), 7.99 (d, J=8 Hz, 2H), 11.43 (br s, 1H).

Example 258

1-(4-Cyclopentylpiperazin-1-yl)-3-(2-methoxyphe-nyl)propan-1-one hydrochloride $^1$H NMR (DMSO-d$_6$) δ 1.53 (m, 2H), 1.63–1.85 (m, 4H), 1.97 (m, 2H), 2.58 (m, 2H), 2.78 (t, J=7 Hz, 2H), 2.82–3.11 (m, 3H), 3.37–3.56 (m, 4H), 3.79 (s, 3H), 4.01 (m, 1H), 4.43 (m, 1H), 6.86 (brt, J=7 Hz, 1H), 6.93 (d, J=7 Hz, 1H), 7.18 (m, 2H), 11.05 (br s, 1H).

Example 259

1-(4-Allylpiperazin-1-yl)-4-(3-fluoro-4-methoxyphe-nyl)butane-1,4-dione hydrochloride $^1$H NMR (DMSO-d$_6$) δ 2.70–3.13 (m, 5H), 3.19 (t, J=7 Hz, 2H), 3.35–3.62 (m, 3H), 3.76 (m, 2H), 3.93 (s, 3H), 4.18 (m, 1H), 4.40 (m, 1H), 5.51 (m, 2H), 5.99 (m, 1H), 7.29 (t, J=7 Hz, 1H), 7.76 (br d, J=14 Hz, 1H), 7.85 (br d, J=7 Hz, 1H), 11.31 (br s, 1H).

Example 260

1-(4-Cyclopentylpiperazin-1-yl)-4-(3,4-dimethox-yphenyl)butane-1,4-dione hydrochloride $^1$H NMR (DMSO-d$_6$) δ 1.50–2.08 (m, 8H), 2.72 (m, 2H), 2.79–3.16 (m, 3H), 3.21 (t, J=7 Hz, 2H), 3.42–3.66 (m, 4H), 3.81 (s, 3H), 3.85 (s, 3H), 4.16 (m, 1H), 4.40 (m, 1H), 7.08 (d, J=8 Hz, 1H), 7.46 (d, J=1 Hz, 1H), 7.68 (dd, J=8 Hz, 1 Hz, 1H), 11.18 (br s, 1H).

Example 261

1-(4-Cyclopentylpiperazin-1-yl)-4-(2,5-dimethox-yphenyl)butane-1,4-dione hydrochloride $^1$H NMR (DMSO-d$_6$) δ 1.54 (m, 2H), 1.65–1.88 (m, 4H), 1.99 (m, 2H), 2.69 (m, 2H), 2.80–3.20 (m, 5H), 3.50 (m, 4H), 3.72 (s, 3H), 3.83 (s, 3H), 4.12 (m, 1H), 4.40 (m, 1H), 7.09 (m, 1H), 7.13 (m, 2H), 10.90 (br s, 1H).

Example 262

1-(4-Chlorophenyl)-4-(4-cyclopropylpiperazin-1-yl)butane-1,4-dione hydrochloride $^1$H NMR (DMSO-d$_6$) δ 0.80 (br d, J=7 Hz, 2H), 1.12 (m, 2H), 2.71–2.89 (m, 3H), 3.08 (m, 2H), 3.23 (t, J=7 Hz, 2H), 3.44–3.62 (m, 4H), 4.15 (m, 1H), 4.40 (m, 1H), 7.60 (d, J=8 Hz, 2H), 7.98 (d, J=8 Hz, 2H), 11.00 (br s, 1H).

Example 263

1-(4-Chlorophenyl)-4-(4-cyclopropylmethylpiper-azin-1-yl)butane-1,4-dione hydrochloride $^1$H NMR (DMSO-d$_6$) δ 0.39 (m, 2H), 0.64 (m, 2H), 1.11 (m, 1H), 2.77 (quart, J=7 Hz, 2H), 2.80–3.18 (m, 5H), 3.22 (t, J=7 Hz, 2H), 3.46–3.62 (m, 3H), 4.18 (m, 1H), 4.40 (m, 1H), 7.58 (d, J=8 Hz, 2H), 7.98 (d, J=8 Hz, 2H), 10.82 (br s, 1H).

Example 264

1-(4-Chlorophenyl)-4-[4-(1,1-dimethylprop-2-ynyl)piperazin-1-yl]butane-1,4-dione hydrochloride $^1$H NMR (DMSO-d$_6$) δ 1.69 (br s, 6H), 2.70–2.93 (m, 3H), 3.02–3.29 (m, 3H), 3.64 (m, 4H), 4.03 (br s, 1H), 4.19 (m, 1H), 4.48 (m, 1H), 7.60 (d, J=8 Hz, 2H), 7.99 (d, J=8 Hz, 2H), 12.05 (br s, 1H).

Example 265

1-(4-Chlorophenyl)-4-(4-isopropylpiperazin-1-yl)butane-1,4-dione hydrochloride

¹H NMR (DMSO-d$_6$) δ 1.28 (d, J=7 Hz, 6H), 2.73 (m, 2H), 2.85 (m, 1H), 3.09 (m, 2H), 3.22 (m, 2H), 3.33–3.67 (m, 4H), 4.16 (m, 1H), 4.42 (m, 1H), 7.60 (d, J=8 Hz, 2H), 7.99 (d, J=8 Hz, 2H), 10.75 (br s, 1H).

Example 266

1-(4-Chlorophenyl)-4-[4-(1-ethylpropyl)piperazin-1-yl]butane-1,4-dione hydrochloride ¹H NMR (DMSO-d$_6$) δ 50.98 (t, J=7 Hz, 6H), 1.62 (m, 2H), 1.85 (m, 2H), 2.74 (m, 2H), 2.88–3.26 (m, 6H), 3.39 (m, 2H), 3.68 (m, 1H), 4.12 (m, 1H), 4.39 (m, 1H), 7.59 (d, J=8 Hz, 2H), 7.98 (d, J=8 Hz, 2H), 10.45 (br s, 1H).

Example 267

1-(3-Chloro-4-methoxyphenyl)-4-(4-cyclopentylpiperazin-1-yl)butane-1,4-dione hydrochloride ¹H NMR (DMSO-d$_6$) δ 1.55 (m, 2H), 1.65–1.88 (m, 4H), 2.00 (m, 2H), 2.73 (q, J=7 Hz, 2H), 2.80–3.15 (m, 3H), 3.22 (t, J=7 Hz, 2H), 3.44–3.65 (m, 4H), 3.96 (s, 3H), 4.15 (m, 1H), 4.39 (m, 1H), 7.28 (d, J=8 Hz, 1H), 7.98 (m, 2H), 11.15 (br s, 1H).

Example 268

3-(4-Chlorophenylsulfanyl)-1-(4-cyclopentylpiperazin-1-yl)propan-1-one hydrochloride ¹H NMR (DMSO-d$_6$) δ 1.53 (m, 2H), 1.62–1.88 (m, 4H), 1.96 (m, 2H), 2.71 (t, J=7 Hz, 2H), 2.80–3.12 (m, 3H), 3.17 (t, J=7 Hz, 2H), 3.35–3.59 (m, 4H), 3.97 (m, 1H), 4.43 (m, 1H), 7.36 (m, 4H), 11.21 (br s, 1H).

Example 269

1-(5-Chloro-2,4-dimethoxyphenyl)-4-(4-cyclopentylpiperazin-1-yl)butane-1,4-dione hydrochloride ¹H NMR (DMSO-d$_6$) δ 1.55 (m, 2H), 1.65–1.90 (m, 4H), 1.98 (m, 2H), 2.69 (q, J=7 Hz, 2H), 2.88 (m, 1H), 3.00–3.10 (m, 2H), 3.14 (t, J=7 Hz, 2H), 3.40–3.63 (m, 4H), 3.98 (s, 6H), 4.13 (m, 1H), 4.39 (m, 1H), 6.87 (s, 1H), 7.65 (s, 1H), 11.07 (br s, 1H).

Example 270

1-(5-Chloro-2-methoxyphenyl)-4-(4-cyclopentylpiperazin-1-yl)butane-1,4-dione hydrochloride ¹H NMR (DMSO-d$_6$) δ 1.54 (m, 2H), 1.64–1.94 (m, 4H), 1.85 (m, 2H), 2.70 (q, J=7 Hz, 2H), 2.85 (m, 1H), 3.06 (m, 2H), 3.14 (t, J=7 Hz, 2H), 3.40–3.66 (m, 4H), 3.90 (s, 3H), 4.12 (m, 1H), 4.39 (m, 1H), 7.24 (d, J=8 Hz, 1H), 7.51 (s, 1H), 7.59 (d, J=8 Hz, 1H), 11.31 (br s, 1H).

Example 271

1-[4-(1-Ethylpropyl)piperazin-1-yl]-4-(4-fluorophenyl)butane-1,4-dione hydrochloride ¹H NMR (DMSO-d$_6$) δ 0.97 (t, J=7 Hz, 6H), 1.62 (m, 2H), 1.88 (m, 2H), 2.75 (m, 2H), 2.85–3.30 (m, 5H), 3.38 (m, 2H), 3.73 (m, 1H), 4.14 (m, 1H), 4.40 (m, 1H), 7.36 (t, J=8 Hz, 2H), 8.07 (t, J=8 Hz, 2H), 10.76 (br s, 1H).

Example 272

1-(4-Chlorophenyl)-4-[4-(1,1-dimethylpropyl)piperazin-1-yl]butane-1,4-dione hydrochloride ¹H NMR (DMSO-d$_6$) δ 0.92 (t, J=7 Hz, 3H), 1.31 (s, 6H), 1.72 (q, J=7 Hz, 2H), 2.76 (t, J=7 Hz, 2H), 2.88 (m, 1H), 3.15 (m, 2H), 3.24 (q, J=7 Hz, 2H), 3.47 (m, 2H), 3.68 (m, 1H), 4.14 (m, 1H), 4.43 (m, 1H), 7.61 (d, J=8 Hz, 2H), 7.99 (d, J=8 Hz, 2H), 10.22 (br s, 1H).

Example 273

1-(4-Chlorophenyl)-4-(4-cyclopropylmethyl[1,4]diazepan-1-yl)butane-1,4-dione hydrochloride ¹H NMR (DMSO-d$_6$) δ 0.39 (m, 2H), 0.64 (m, 2H), 1.13 (m, 1H), 1.95–2.45 (m, 3H), 2.74 (m, 2H), 3.01 (m, 3H), 3.35–3.90 (m, 7H), 4.08 (m, 1H), 7.60 (d, J=8 Hz, 2H), 7.99 (d, J=8 Hz, 2H), 10.55 (br s, 1H).

Example 274

1-(4-Chlorophenyl)-4-(4-cyclopropyl[1,4]diazepan-1-yl)butane-1,4-dione Hydrochloride ¹H NMR (DMSO-d$_6$) δ 0.82 (m, 2H), 1.15 (m, 2H), 1.95–2.45 (m, 2H), 2.74 (m, 2H), 2.90 (m, 1H), 3.15 (m, 1H), 3.25 (m, 2H), 3.35–3.80 (m, 6H), 3.95–4.15 (m, 1H), 7.61 (d, J=8 Hz, 2H), 8.00 (d, J=8 Hz, 2H), 10.75 (m, 1H).

Example 275

1-(4-Chlorophenyl)-4-(4-cyclopentyl[1,4]diazepan-1-yl)butane-1,4-dione hydrochloride ¹H NMR (DMSO-d$_6$) δ 1.54 (m, 2H), 1.72 (m, 4H), 1.90–2.30 (m, 4H), 2.74 (m, 2H), 2.85–3.25 (m, 4H), 3.35–3.69 (m, 4H), 3.80 (m, 1H), 4.02 (m, 2H), 7.61 (d, J=8 Hz, 2H), 8.00 (d, J=8 Hz, 2H), 10.55 (m, 1H).

Example 276

1-(4-Chlorophenyl)-4-[4-(1-propylbutyl)piperazin-1-yl]butane-1,4-dione hydrochloride ¹H NMR (DMSO-d$_6$) δ 0.92 (t, J=7 Hz, 6H), 1.28–1.60 (m, 6H), 1.80 (m, 2H), 2.76 (m, 2H), 2.93 (m, 1H), 3.05–3.55 (m, 7H), 3.64 (m, 1H), 4.15 (m, 1H), 4.42 (m, 1H), 7.61 (d, J=8 Hz, 2H), 8.00 (d, J=8 Hz, 2H), 10.24 (m, 1H).

Example 277

1-(3,4-Dimethoxyphenyl)-4-[4-(1-ethylpropyl)piperazin-1-yl]butane-1,4-dione hydrochloride ¹H NMR (DMSO-d$_6$) δ 0.97 (t, J=7 Hz, 6H), 1.63 (m, 2H), 1.84 (m, 2H), 2.72 (m, 2H), 2.95 (m, 1H), 3.00–3.25 (m, 5H), 3.39 (m, 2H), 3.63 (m, 1H), 3.81 (s, 3H), 3.85 (s, 3H), 4.14 (m, 1H), 4.42 (m, 1H), 7.08 (d, J=8 Hz, 1H), 7.45 (s, 1H), 7.66 (d, J=8 Hz, 1H), 10.12 (br s, 1H).

Example 278

3-(3-Chlorophenylsulfanyl)-1-[4-(1-ethylpropyl) piperazin-1-yl]propan-1-one hydrochloride $^1$H NMR (DMSO-$d_6$) δ 0.95 (t, J=7 Hz, 6H), 1.61 (m, 2H), 1.82 (m, 2H), 2.73 (m, 2H), 2.85–3.15 (m, 3H), 3.20 (t, J=7 Hz, 2H), 3.28–3.60 (m, 4H), 3.96 (m, 1H), 4.45 (m, 1H), 7.22–7.40 (m, 4H), 10.07 (br s, 1H).

Example 279

3-(4-Chlorophenoxy)-1-[4-(1-ethylpropyl)piperazin-1-yl]propan-1-one hydrochloride $^1$H NMR (DMSO-$d_6$) δ 0.96 (t, J=7 Hz, 6H), 1.62 (m, 2H), 1.85 (m, 2H), 2.87 (t, J=7 Hz, 2H), 2.90–3.28 (m, 4H), 3.41 (m, 2H), 3.65 (m, 1H), 4.08 (m, 1H), 4.20 (t, J=7 Hz, 2H), 4.47 (m, 1H), 6.96 (d, J=8 Hz, 2H), 7.33 (d, J=8 Hz, 2H), 10.45 (br s, 1H).

Example 280

2-(5-Chlorobenzothiazol-2-ylsulfanyl)-1-[4-(1-ethylpropyl)piperazin-1-yl]ethanone hydrochloride $^1$H NMR (DMSO-$d_6$) δ 0.98 (t, J=7 Hz, 6H), 1.63 (m, 2H), 1.87 (m, 2H), 3.08 (m, 2H), 3.15–3.50 (m, 4H), 3.83 (m, 1H), 4.16 (m, 1H), 4.43 (m, 1H), 4.60 (s, 2H), 7.44 (d, J=8 Hz, 1H), 7.93 (s, 1H), 8.06 (d, J=8 Hz, 1H), 10.84 (br s, 1H).

Example 282

1-[4-(1,1-Dimethylpropyl)piperazin-1-yl]-4-(4-fluorophenyl)butane-1,4-dione hydrochloride $^1$H NMR (DMSO-$d_6$) δ 0.92 (t, J=7 Hz, 3H), 1.31 (s, 6H), 1.72 (quart, J=7 Hz, 2H), 2.75 (t, J=7 Hz, 2H), 2.86 (m, 1H), 3.00–3.31 (m, 4H), 3.50 (m, 2H), 3.71 (m, 1H), 4.14 (m, 1H), 4.43 (m, 1H), 7.36 (t, J=9 Hz, 2H), 8.06 (dd, J=8 Hz, 9 Hz, 2H), 10.37 (brs, 1H).

Example 283

1-(4-Cyclopropyl[1,4]diazepan-1-yl)-4-(3,4-dimethoxyphenyl)butane-1,4-dione hydrochloride $^1$H NMR (DMSO-$d_6$) δ 0.82 (m, 2H), 1.15 (m, 2H), 2.00–2.45 (m, 3H), 2.71 (m, 2H), 2.91 (m, 1H), 3.13 (m, 1H), 3.24 (m, 2H), 3.35–3.75 (m, 5H), 3.82 (s, 3H), 3.85 (s, 3H), 4.11 (m, 1H), 7.07 (d, J=8 Hz, 1H), 7.46 (s, 1H), 7.67 (d, J=8 Hz, 1H), 10.7 (br s, 1H).

Example 284

1-[4-(2-Chloroallyl)piperazin-1-yl]-4-(4-chlorophenyl)butane-1,4-dione hydrochloride $^1$H NMR (DMSO-$d_6$) δ 2.75 (m, 2H), 2.80–3.15 (m, 2H), 3.24 (t, J=7 Hz, 2H), 3.30–3.80 (m, 6H), 4.11 (m, 2H), 5.81 (br s, 1H), 5.94 (br s, 1H), 7.61 (d, J=8 Hz, 2H), 8.00 (d, J=8 Hz, 2H), 11.14 (brs, 1H).

Example 285

1-(4-Cyclopropylmethylpiperazin-1-yl)-4-(3,4-dimethoxyphenyl)butane-1,4-dione hydrochloride $^1$H NMR (DMSO-$d_6$) δ 0.40 (m, 2H), 0.64 (m, 2H), 1.09 (m, 1H), 2.73 (m, 2H), 2.80–3.15 (m, 5H), 3.22 (m, 2H), 3.54 (m, 3H), 3.81 (s, 3H), 3.85 (s, 3H), 4.19 (m, 1H), 4.40 (m, 1H), 7.07 (d, J=8 Hz, 1H), 7.45 (s, 1H), 7.66 (d, J=8 Hz, 1H), 10.73 (brs, 1H).

Example 286

1-(4-Cyclobutylpiperazin-1-yl)-4-(3,4-dimethoxyphenyl)butane-1,4-dione hydrochloride $^1$H NMR (DMSO-$d_6$) δ 1.75 (m, 2H), 2.17 (m, 2H), 2.39 (m, 2H), 2.60–2.95 (m, 4H), 3.00–3.35 (m, 5H), 3.63 (m, 2H), 3.81 (s, 3H), 3.85 (s, 3H), 4.17 (m, 1H), 4.41 (m, 1H), 7.07 (d, J=8 Hz, 1H), 7.45 (s, 1H), 7.66 (d, J=8 Hz, 1H), 10.53 (br s, 1H).

Example 287

1-[4-(2-Chloroallyl)piperazin-1-yl]-4-(3,4-dimethoxyphenyl)butane-1,4-dione hydrochloride $^1$H NMR (DMSO-$d_6$) δ 2.72 (br s, 2H), 2.86–3.57 (m, 10H), 3.81 (s, 3H), 3.85 (s, 3H), 4.09 (m, 2H), 5.80 (br s, 1H), 5.94 (br s, 1H), 7.07 (d, J=8 Hz, 1H), 7.45 (s, 1H), 7.67 (d, J=8 Hz, 1H), 11.15 (brs, 1H).

Example 288

4-{3-[4-(1-Ethylpropyl)piperazin-1-yl]-3-oxopropoxy}benzonitrile hydrochloride $^1$H NMR (DMSO-$d_6$) δ 0.96 (t, J=7 Hz, 6H), 1.61 (m, 2H), 1.83 (m, 2H), 2.91 (t, J=7 Hz, 2H), 2.92–3.45 (m, 6H), 3.71 (m, 1H), 4.07 (m, 1H), 4.30 (t, J=7 Hz, 2H), 4.46 (m, 1H), 7.10 (d, J=8 Hz, 2H), 7.77 (d, J=8 Hz, 2H), 10.76 (br s, 1H).

Example 289

1-(4-Cyclopentylpiperazin-1-yl)-3-(3,5-dichlorophenoxy)propan-1-one hydrochloride $^1$H NMR (DMSO-$d_6$), δ 1.55 (m, 2H), 1.75 (m, 4H), 1.98 (m, 2H), 2.87 (t, J=7 Hz, 2H), 2.95–3.20 (m, 3H), 3.35–3.60 (m, 4H), 4.08 (m, 1H), 4.26 (t, J=7 Hz, 2H), 4.45 (m, 1H), 7.04 (s, 2H), 7.16 (s, 1H), 11.07 (br s, 1H).

Example 290

1-(4-Cyclopentylpiperazin-1-yl)-3-(3,4-dichlorophenoxy)propan-1-one hydrochloride $^1$H NMR (DMSO-$d_6$) δ 1.54 (m, 2H), 1.75 (m, 4H), 1.98 (m, 2H), 2.88 (t, J=7 Hz, 2H), 2.90–3.15 (m, 2H), 3.39–3.65 (m, 5H), 4.09 (m, 1H), 4.24 (t, J=7 Hz, 2H), 4.45 (m, 1H), 6.97 (m, 1H), 7.23 (s, 1H), 7.51 (d, J=8 Hz, 1H), 11.15 (brs, 1H).

Example 291

1-(4-Cyclopentylpiperazin-1-yl)-3-(3,4-dimethoxyphenoxy)propan-1-one hydrochloride $^1$H NMR (DMSO-d$_6$) δ 1.54 (m, 2H), 1.75 (m, 4H), 1.97 (m, 2H), 2.84 (t, J=7 Hz, 2H), 2.87–3.18 (m, 2H), 3.35–3.60 (m, 5H), 3.68 (s, 3H), 3.73 (s, 3H), 4.09 (m, 1H), 4.15 (t, J=7 Hz, 2H), 4.45 (m, 1H), 6.44 (d, J=8 Hz, 1H), 6.52 (s, 1H), 6.84 (d, J=8 Hz, 1H), 11.23 (br s, 1H).

Example 292

4-(4-Chlorophenyl)-1-(4-cyclopentylpiperazin-1-yl)-4-hydroxybutan-1-one hydrochloride $^1$H NMR (DMSO-d$_6$) δ 1.55 (m, 2H), 1.75 (m, 4H), 1.95 (m, 2H), 2.40 (m, 2H), 2.80–3.10 (m, 3H), 3.45 (m, 5H), 3.97 (m, 1H), 4.42 (m, 1H), 4.57 (m, 1H), 5.36 (br s, 1H), 7.36 (m, 4H), 10.64 (brs, 1H).

Example 293

1-(3,4-Dimethoxyphenyl)-4-[4-(1,1-dimethylpropyl)piperazin-1-yl]butane-1,4-dione hydrochloride $^1$H NMR (DMSO-d$_6$) δ 0.92 (t, J=7 Hz, 3H), 1.32 (s, 6H), 1.73 (quart, J=7 Hz, 2H), 2.72 (t, J=7 Hz, 2H), 2.85 (m, 1H), 3.05–3.30 (m, 4H), 3.50 (m, 2H), 3.72 (m, 1H), 3.81 (s, 3H), 3.85 (s, 3H), 4.15 (m, 1H), 4.44 (m, 1H), 7.07 (d, J=8 Hz, 1H), 7.45 (s, 1H), 7.67 (d, J=8 Hz, 1H), 10.47 (br s, 1H).

Example 294

2-[2-(4-Isopropylpiperazin-1-yl)-2-oxoethylidene]-5,6-dimethoxyindan-1-one hydrochloride $^1$H NMR (DMSO-d$_6$) δ 1.28 (d, J=7 Hz, 6H), 2.90–3.55 (m, 5H), 3.71 (m, 1H), 3.83 (s, 3H), 3.91 (brs, 4H), 4.23 (m, 1H), 4.58 (m, 1H), 7.12 (s, 1H), 7.21 (s, 2H), 11.11 (br s, 1H).

Example 295

2-{2-[4-(1-Ethylpropyl)piperazin-1-yl]-2-oxoethylidene}-5,6-dimethoxyindan-1-one hydrochloride $^1$H NMR (DMSO-d$_6$) δ 0.97 (t, J=7 Hz, 6H), 1.62 (m, 2H), 1.86 (m, 2H), 3.05 (m, 2H), 3.10–3.50 (m, 3H), 3.76 (m, 1H), 3.83 (s, 3H), 3.91 (br s, 4H), 4.19 (m, 1H), 4.55 (m, 1H), 7.12 (s, 1H), 7.21 (s, 2H), 10.66 (brs, 1H).

Example 296

2-[2-(4-Isopropylpiperazin-1-yl)-2-oxoethyl]-5,6-dimethoxyindan-1-one hydrochloride $^1$H NMR (DMSO-d$_6$) δ 1.27 (d, J=7 Hz, 6H), 2.60–3.65 (m, 12H), 3.80 (s, 3H), 4.06 (m, 1H), 4.44 (m, 1H), 7.07 (s, 1H), 7.09 (s, 1H), 10.88 (br s, 1H).

Example 297

2-{2-[4-(1-Ethylpropyl)piperazin-1-yl]-2-oxoethyl}-5,6-dimethoxyindan-1-one hydrochloride $^1$H NMR (DMSO-d$_6$) δ 0.96 (t, J=7 Hz, 6H), 1.62 (m, 2H), 1.86 (m, 2H), 2.60–3.50 (m, 11H), 3.65 (m, 1H), 3.80 (s, 3H), 3.86 (s, 3H), 4.03 (m, 1H), 4.40 (m, 1H), 7.07 (s, 1H), 7.09 (s, 1H), 10.53 (br s, 1H).

Example 298

1-(4-Chlorophenyl)-4-[4-(tetrahydro-pyran-4-yl)piperazin-1-yl]butane-1,4-dione hydrochloride $^1$H NMR (DMSO-d$_6$) δ 1.72 (m, 2H), 1.99 (m, 2H), 2.76 (m, 2H), 2.85 (m, 1H), 3.10 (m, 2H), 3.21–3.68 (m, 8H), 3.97 (m, 2H), 4.16 (m, 1H), 4.41 (m, 1H), 7.60 (d, J=8 Hz, 2H), 7.99 (d, J=8 Hz, 2H), 11.15 (brs, 1H).

Example 299

1-(4-Chlorophenyl)-4-[4-(2-hydroxy-2-methylpropyl)piperazin-1-yl]butane-1,4-dione hydrochloride $^1$H NMR (DMSO-d$_6$) δ 1.28 (s, 6H), 2.76 (m, 2H), 3.05 (m, 1H), 3.24 (t, J=7 Hz, 2H), 3.36 (m, 4H), 3.57 (m, 2H), 3.78 (m, 1H), 4.05 (m, 1H), 4.19 (m, 1H), 5.31 (brs, 1H), 7.60 (d, J=8 Hz, 2H), 8.00 (d, J=8 Hz, 2H), 9.97 (br s, 1H).

Example 300

1-[4-(1-Ethylpropyl)piperazin-1-yl]-2-(4-trifluoromethoxyphenoxy)ethanone hydrochloride $^1$H NMR (DMSO-d$_6$) δ 0.97 (t, J=7 Hz, 6H), 1.61 (m, 2H), 1.86 (m, 2H), 2.90–3.10 (m, 2H), 3.22 (m, 2H), 3.39 (m, 2H), 3.69 (m, 1H), 3.98 (m, 1H), 4.40 (m, 1H), 4.94 (s, 2H), 7.04 (m, 2H), 7.29 (m, 2H), 10.61 (br s, 1H).

Example 301

1-[4-(1-Ethylpropyl)piperazin-1-yl]-2-(4-trifluoromethoxyphenyl)ethanone hydrochloride $^1$H NMR (DMSO-d$_6$) δ 0.96 (t, J=7 Hz, 6H), 1.62 (m, 2H), 1.84 (m, 2H), 2.85–3.46 (m, 6H), 3.65 (m, 1H), 3.82 (m, 2H), 4.14 (m, 1H), 4.43 (m, 1H), 7.32 (m, 4H), 10.53 (br s, 1H).

Example 302

1-[4-(1-Ethylpropyl)piperazin-1-yl]-2-(4-trifluoromethylphenyl)ethanone hydrochloride $^1$H NMR (DMSO-d$_6$) δ 0.96 (t, J=7 Hz, 6H), 1.61 (m, 2H), 1.85 (m, 2H), 2.90–3.50 (m, 6H), 3.69 (m, 1H), 3.90 (m, 2H), 4.15 (m, 1H), 4.45 (m, 1H), 7.45 (d, J=8 Hz, 2H), 7.68 (d, J=8 Hz, 2H), 10.71 (brs, 1H).

Example 303

2-(3,4-Dichlorophenyl)-1-[4-(1-ethylpropyl)piperazin-1-yl]ethanone hydrochloride $^1$H NMR (DMSO-d$_6$) δ 0.96 (t, J=7 Hz, 6H), 1.61 (m, 2H), 1.88 (m, 2H), 2.90–3.50 (m, 6H), 3.74 (m, 1H), 3.81 (s, 2H), 4.14 (m, 1H), 4.43 (m, 1H), 7.21 (m, 1H), 7.49 (s, 1H), 7.57 (d, J=8 Hz, 1H), 10.96 (brs, 1H).

Example 304

2-Biphenyl-4-yl-1-[4-(1-ethylpropyl)piperazin-1-yl]ethanone hydrochloride $^1$H NMR (DMSO-d$_6$) δ 0.95 (t, J=7 Hz, 6H), 1.62 (m, 2H), 1.82 (m, 2H), 2.80–3.50 (m, 6H), 3.60 (m, 1H), 3.82 (m, 2H), 4.17 (m, 1H), 4.45 (m, 1H), 7.25–7.55 (m, 5H), 7.64 (m, 4H), 10.29 (brs, 1H).

Example 305

[4-(1-Ethylpropyl)piperazin-1-yl]-(3-trifluoromethoxyphenyl)methanone hydrochloride $^1$H NMR (DMSO-d$_6$) δ 0.97 (t, J=7 Hz, 6H), 1.62 (m, 2H), 1.90 (m, 2H), 3.05 (m, 1H). (m, 2H), 3.25–3.60 (m, 5H), 4.54 (br s, 1H), 7.51 (m, 3H), 7.63 (m, 1H), 10.69 (br s, 1H).

Example 306

[4-(1-Ethylpropyl)piperazin-1-yl]-(3-phenoxyphenyl)methanone hydrochloride $^1$H NMR (DMSO-d$_6$) δ 0.96 (t, J=7 Hz, 6H), 1.62 (m, 2H), 1.87 (m, 2H), 3.04 (m, 1H), 3.14 (m, 2H), 3.30–3.80 (m, 5H), 4.50 (brs, 1H), 7.05–7.15 (m, 4H), 7.16–7.25 (m, 2), 7.40–7.51 (m, 3H), 10.51 (brs, 1H).

Example 307

(3-Chloro-4-trifluoromethoxyphenyl)-[4-(1-ethylpropyl)piperazin-1-yl]methanone hydrochloride $^1$H NMR (DMSO-d$_6$) δ 0.97 (t, J=7 Hz, 6H), 1.61 (m, 2H), 1.87 (m, 2H), 3.06 (m, 1H), 3.10–3.80 (m, 7H), 4.52 (br s, 1H), 7.50 (m, 1H), 7.68 (m, 1H), 7.86 (s, 1H), 10.59 (br s, 1H).

Example 308

[4-(1-Ethylpropyl)piperazin-1-yl]-(4-trifluoromethoxyphenyl)methanone hydrochloride $^1$H NMR (DMSO-d$_6$) δ 0.97 (t, J=7 Hz, 6H), 1.61 (m, 2H), 1.88 (m, 2H), 3.06 (m, 1H), 3.17 (m, 2H), 3.40–3.90 (m, 5H), 4.53 (br s, 1H), 7.47 (d, J=8 Hz, 2H), 7.65 (d, J=8 Hz, 2H), 10.63 (brs, 1H).

Example 309

1-[4-(1-Ethylpropyl)piperazin-1-yl]-3-(4-trifluoromethylphenyl)propan-1-one hydrochloride $^1$H NMR (DMSO-d$_6$) δ 0.95 (t, J=7 Hz, 6H), 1.62 (m, 2H), 1.84 (m, 2H), 3.04 (m, 1H), 2.75 (m, 2H), 2.80–3.50 (m, 7H), 3.64 (m, 1H), 4.05 (m, 1H), 4.43 (m, 1H), 7.48 (d, J=8 Hz, 2H), 7.64 (d, J=8 Hz, 2H), 10.71 (br s, 1H).

Example 310

1-[4-(1-Ethylpropyl)piperazin-1-yl]-4-(4-trifluoromethylphenyl)butane-1,4-dione hydrochloride $^1$H NMR (DMSO-d$_6$) δ 0.97 (t, J=7 Hz, 6H), 1.62 (m, 2H), 1.85 (m, 2H), 2.79 (m, 2H), 2.95 (m, 1H), 3.00–3.50 (m, 7H), 3.68 (m, 1H), 4.14 (m, 1H), 4.41 (m, 1H), 7.91 (d, J=8 Hz, 2H), 8.18 (d, J=8 Hz, 2H), 10.42 (br s, 1H).

Example 311

1-(3,4-Dichlorophenyl)-4-[4-(1-ethylpropyl)piperazin-1-yl]but-2-ene-1,4-dione Hydrochlo $^1$H NMR (DMSO-d$_6$) δ 0.97 (t, J=7 Hz, 6H), 1.62 (m, 2H), 1.85 (m, 2H), 3.06 (m, 2H), 3.20 (m, 1H), 3.39–3.55 (m, 3H), 3.75 (m, 1H), 4.21 (m, 1H), 4.54 (m, 1H), 7.45 (d, J=15 Hz, 1H), 7.76 (d, J=15 Hz, 1H), 7.86 (d, J=8 Hz, 1H), 8.01 (brd, J=8 Hz, 1H), 8.22 (s, 1H), 10.65 (brs, 1H).

Example 312

1-Benzo[1,3]dioxol-5-yl-4-[4-(1-ethylpropyl)piperazin-1-yl]but-2-ene-1,4-dion $^1$H NMR (DMSO-d$_6$) δ 0.97 (t, J=7 Hz, 6H), 1.62 (m, 2H), 1.85 (m, 2H), 3.06 (m, 2H), 3.20 (m, 1H), 3.39–3.55 (m, 3H), 3.78 (m, 1H), 4.20 (m, 1H), 4.54 (m, 1H), 6.18 (s, 2H), d, J=8 Hz, 1H), 7.40 (d, J=15 Hz, 1H), 7.51 (d, J=1 Hz, 1H), 7.72 (dd, J=1 Hz, 8 Hz, 1H), 7.77 (d, J=15 Hz, 1H), 10.83 (br s, 1H).

Example 313

1-(4-Chlorophenyl)-4-(4-isopropyl[1,4]diazepan-1-yl)butane-1,4-dione hydrochloride $^1$H NMR (DMSO-d$_6$) δ 1.26 (m, 6H), 1.95–2.45 (m, 3H), 2.60–3.30 (m, 6H), 3.40–3.85 (m, 5), 4.03 (m, 1H), 7.61 (d, J=8 Hz, 2H), 8.00 (d, J=8 Hz, 2H), 10.05 (br s, 1H).

Example 314

(4-Cyclopentylpiperazin-1-yl)-(7-ethoxybenzofuran-2-yl)methanone hydrochloride $^1$H NMR (DMSO-d$_6$) δ 1.41 (t, J=7 Hz, 3H), 1.55 (m, 2H), 1.65–1.92 (m, 4H), 2.01 (m, 2H), 3.13 (m, 2H), 3.54 (m, 5H), 4.26 (quart, J=7 Hz, 2H), 4.51 (m, 2H), 7.06 (br d, J=8 Hz, 1H), 7.21–7.32 (m, 2H), 7.48 (s, 1H), 11.25 (br s, 1H).

Example 315

(5-Chlorobenzofuran-2-yl)-(4-cyclopentylpiperazin-1-yl)methanone hydrochloride $^1$H NMR (DMSO-d$_6$) δ 1.55 (m, 2H), 1.65–1.92 (m, 4H), 2.01 (m, 2H), 3.13 (m, 2H), 3.53 (m, 5H), 4.51 (m, 2H), 7.51 (m, 2H), 7.74 (d, J=8 Hz, 1H), 7.86 (d, J=1 Hz, 1H), 11.45 (br s, 1H).

Example 316

1-[4-(1-Ethylpropyl)piperazin-1-yl]-4-(4-trifluoromethoxyphenyl)but-2-ene-1,4-dione hydrochloride ¹H NMR (CDCl₃) δ 0.91 (t, J=7 Hz, 6H), 1.31 (m, 2H), 1.44 (m, 2H), 2.21 (m, 1H), 2.56 (m, 4H), 3.59 (m, 2H), 3.71 (m, 2H), 7.32 (d, J=8 Hz, 2H), 7.53 (d, J=14 Hz, 1H), 7.90 (d, J=14 Hz, 1H), 8.10 (d, J=8 Hz, 2H).

Example 317

4-Benzo[1,3]dioxol-5-yl-1-[4-(1-ethylpropyl)piperazin-1-yl]-4-hydroxybutan-1-one hydrochloride ¹H NMR (DMSO-d₆) δ 0.91 (t, J=7 Hz, 6H), 1.58 (m, 2H), 1.80 (m, 4H), 2.35 (m, 2H), 2.90–3.20 (m, 6H), 3.50 (m, 1H), 3.98 (m, 1H), 4.46 (m, 2H), 5.20 (br s, 1H), 5.97 (s, 2H), 6.75–6.88 (m, 3H), 9.90 (br s, 1H).

Example 318

1-[4-(1-Ethylpropyl)piperazin-1-yl]-2-(3-trifluoromethylphenyl)ethanone hydrochloride ¹H NMR (DMSO-d₆) δ 0.97 (t, J=7 Hz, 6H), 1.61 (m, 2H), 1.86 (m, 2H), 2.90–3.33 (m, 4H), 3.41 (m, 2H), 3.70 (m, 1H), 3.90 (m, 2H), 4.18 (m, 1H), 4.45 (m, 1H), 7.48–7.64 (m, 4H), 10.69 (br s, 1H).

Example 319

1-[4-(1-Ethylpropyl)piperazin-1-yl]-2-(2-trifluoromethylphenyl)ethanone hydrochloride ¹H NMR (DMSO-d₆) δ 0.97 (t, J=7 Hz, 6H), 1.64 (m, 2H), 1.86 (m, 2H), 2.90–3.28 (d, J=8 Hz, 1H), 3.43 (m, 2H), 3.69 (m, 1H), 3.93 (s, 2H), 4.18 (m, 1H), 4.45 (m, 1H), 7.38 (d, J=8 Hz, 1H), 7.48 (t, J=8 Hz, 1H), 7.62 (t, J=8 Hz, 1H), 7.70 (d, J=8 Hz, 1H), 10.38 (br s, 1H).

Example 320

(3-Benzoylphenyl)-[4-(1-ethylpropyl)piperazin-1-yl]methanone hydrochloride

¹H NMR (DMSO-d₆) δ 0.96 (t, J=7 Hz, 6H), 1.61 (m, 2H), 1.87 (m, 2H), 3.00–3.25 (m, 3H), 3.30–3.85 (m, 5H), 4.54 (br s, 1H), 7.55–7.87 (m, 9H), 10.62 (br s, 1H).

Example 321

N-{3-[4-(1-Ethylpropyl)piperazine-1-carbonyl]phenyl}acetamide hydrochloride

¹H NMR (DMSO-d₆) δ 0.96 (t, J=7 Hz, 6H), 1.61 (m, 2H), 1.87 (m, 2H), 3.00–3.21 (m, 3H), 3.30–3.85 (m, 5H), 4.53 (br s, 1H), 7.14 (d, J=8 Hz, 1H), 7.38 (t, J=8 Hz, 1H), 7.61 (d, J=8 Hz, 1H), 7.78 (br s, 1H), 10.20 (s, 1H), 10.58 (br s, 1H).

Example 322

1-[4-(1-Ethylpropyl)piperazin-1-yl]-4-(4-trifluoromethoxyphenyl)butane-1,4-dione hydrochloride ¹H NMR (DMSO-d₆) δ 0.97 (t, J=7 Hz, 6H), 1.63 (m, 2H), 1.85 (m, 2H), 2.77 (m, 2H), 2.95 (m, 1H), 3.00–3.31 (m, 5H), 3.35–3.55 (m, 2H), 3.68 (m, 1H), 4.14 (m, 1H), 7.52 (d, J=8 Hz, 2H), 8.12 (d, J=8 Hz, 2H), 10.47 (br s, 1H).

Example 323

2-(4-Dimethylaminophenyl)-1-[4-(1-ethylpropyl)piperazin-1-yl]ethanone dihydrochloride ¹H NMR (DMSO-d₆) δ 0.96 (t, J=7 Hz, 6H), 1.61 (m, 2H), 1.85 (m, 2H), 2.90–3.15 (m, 7H), 3.24 (m, 1H), 3.38 (m, 2H), 3.62–4.30 (m, 6H), 4.43 (m, 1H), 7.25–7.55 (m, 4H), 10.87 (br s, 1H).

Example 324

2-Benzo[1,3]dioxol-5-yl-1-[4-(1-ethylpropyl)piperazin-1-yl]ethanone hydrochloride ¹H NMR (DMSO-d₆) δ 0.95 (t, J=7 Hz, 6H), 1.60 (m, 2H), 1.84 (m, 2H), 2.85–3.10 (m, 3H), 3.21 (m, 1H), 3.38 (m, 2H), 3.55–3.78 (m, 3H), 4.13 (m, 1H), 4.43 (m, 1H), 5.98 (s, 2H), 6.68 (d, J=8 Hz, 1H), 6.78 (s, 1H), 6.85 (d, J=8 Hz, 1H), 10.77 (brs, 1H).

Example 325

2-(4-Butoxyphenyl)-1-[4-(1-ethylpropyl)piperazin-1-yl]ethanone hydrochloride

¹H NMR (DMSO-d₆) δ 0.89 (m, 9H), 1.42 (sext, J=7 Hz, 2H), 1.50–1.74 (m, 4H), 1.85 (m, 2H), 2.85–3.07 (m, 3H), 3.18 (m, 1H), 3.30–3.46 (m, 2H), 3.55–3.78 (m, 3H), 3.93 (t, J=7 Hz, 2H), 4.11 (m, 1H), 4.44 (m, 1H), 6.86 (d, J=8 Hz, 2H), 7.12 (d, J=8 Hz, 2H0, 10.68 (br s, 1H).

Example 326

2-(2,5-Dimethoxyphenyl)-1-[4-(1-ethylpropyl)piperazin-1-yl]ethanone hydrochloride ¹H NMR (DMSO-d₆) δ 0.96 (t, J=7 Hz, 6H), 1.62 (m, 2H), 1.85 (m, 2H), 2.90–3.10 (m, 3H), 3.24 (m, 1H), 3.40 (m, 2H), 3.53–3.80 (m, 9H), 4.11 (m, 1H), 4.43 (m, 1H), 6.71 (s, 1H), 6.79 (d, J=8 Hz, 1H), 6.90 (d, J=8 Hz, 1H), 10.85 (brs, 1H).

Example 327

2-(4-Acetylphenyl)-1-[4-(1-ethylpropyl)piperazin-1-yl]ethanone hydrochloride

¹H NMR (DMSO-d₆) δ 0.97 (t, J=7 Hz, 6H), 1.62 (m, 2H), 1.86 (m, 2H), 2.52 (s, 3H), 2.90–3.10 (m, 3H), 3.15–3.50 (m, 3H), 3.71 (m, 1H), 3.99 (m, 1H), 4.41 (m, 1H), 5.02 (s, 2H), 7.05 (d, J=8 Hz, 2H), 7.92 (d, J=8 Hz, 2H), 10.64 (br s, 1H).

Example 328

1-[4-(1-Methylcyclopropyl)piperazin-1-yl]-4-(4-trifluoromethylphenyl)butane-1,4-dione hydrochloride This compound was prepared from 1-acetyl-4-(tert-butyloxycarbonyl)piperazine according to the procedure reported by H. Winsel et al. (*Synlett*, 1999, 1999–2003).

$^1$H NMR (DMSO-$d_6$) δ 0.74 (br s, 2H), 1.32 (s, 3H), 1.38 (br s, 2H), 2.81 (brs, 2H), 3.10–3.45 (m, 7H), 3.71 (m, 1H), 4.15 (m, 1H), 4.46 (m, 1H), 7.92 (d, J=8 Hz, 2H), 8.18 (d, J=8 Hz, 2H), 10.90 (br s, 1H); HPLC-MS: m/z 369 (MH$^+$); Rf: 4.07 min.

Example 329

1-(4-Bicyclopropyl-1-ylpiperazin-1-yl)-4-(4-trifluoromethylphenyl)butane-1,4-dione hydrochloride This compound was prepared from 1-cyclopropanoyl-4-(tert-butyloxycarbonyl)piperazine according to the procedure reported by H. Winsel et al. (*Synlett*, 1999, 1999–2003).

$^1$H NMR (DMSO-$d_6$) δ 0.19 (brs, 2H), 0.55 (m, 2H), 0.64 (brs, 2H), 1.27 (br s, 2H), 1.47 (m, 1H), 2.81 (m, 2H), 3.15–3.80 (m, 8H), 4.17 (m, 1H), 4.47 (m, 1H), 7.92 (d, J=8 Hz, 2H), 8.18 (d, J=8 Hz, 2H), 10.78 (br s, 1H); HPLC-MS: m/z 395 (MH$^+$); Rf: 4.37 min.

Example 330

4-(1-Ethylpropyl)piperazine-1-carboxylic Acid 4-nitrophenyl ester hydrochloride

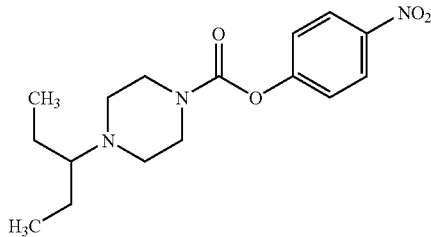

To a stirred mixture of 1-(1-ethylpropyl)piperazine (156 mg, 1.0 mmol) and dry DCM (10 ml) was added 4-nitrophenyl chloroformate (201 mg, 1.0 mmol). The mixture was stirred overnight at room temperature and then diluted with DCM (50 ml). The reaction mixture was washed with 1 N NaOH (3×20 ml) and water (3×20 ml) and dried (MgSO$_4$). The organic solution was concentrated to yield an oil that was dissolved in a 0.5 N HCl solution (15 ml). The acidic solution was concentrated and re-evaporated twice with acetonitrile to give 290 mg (81%) of the title compound as a solid. M.p. 251–253° C.

$^1$H NMR (400 MHz, DMSO-$d_6$): δ 1.08 (t, 6H), 1.65–1.80 (m, 2H), 1.93–2.06 (m, 2H), 3.12–3.21 (m, 1H), 3.22–3.41 (m, 2H), 3.50–3.59 (m, 2H), 3.62–3.90 (m, 2H), 4.15–4.35 (m, 2H), 7.58 (d, 2H), 8.40 (d, 2H), 10.9 (brs, 1H).

Example 331

4-(1-Ethylpropyl)piperazine-1-carboxylic acid 4-methoxyphenyl ester

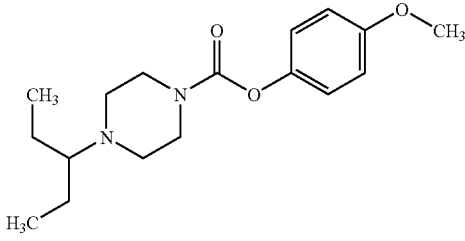

To a stirred mixture of 1-(1-ethylpropyl)piperazine (156 mg, 1.0 mmol) and dry DCM (10 ml) was added 4-methoxyphenyl chloroformate (190 mg, 1.0 mmol). The mixture was stirred overnight at room temperature and then diluted with DCM (50 ml). The reaction mixture was washed with 1 N NaOH (3×20 ml) and water (3×20 ml) and dried (MgSO$_4$). The organic solution was concentrated to yield an oil that was dissolved in a 0.5 N HCl solution (30 ml). The acidic solution was washed with diethyl ether (2×20 ml) and 4 N NaOH was added until pH 11. The resulting mixture was extracted with ethyl acetate (2×20 ml) and the combined organic extracts were dried (MgSO$_4$). The solvent was evaporated to give an oil that crystallized on standing. This afforded 185 mg (60%) of the title compound as a solid. M.p. 52–54° C.

$^1$H NMR (400 MHz, CDCl$_3$): δ 0.92 (t, 6H), 1.25–1.40 (m, 2H), 1.40–1.55 (m, 2H), 2.15–2.26 (m, 1H), 2.50–2.60 (m, 4H), 3.45–3.65 (m, 4H), 3.78 (s, 3H), 6.86 (d, 2H), 7.00 (d, 2H).

Example 332

4-(1-Ethylpropyl)piperazine-1-carboxylic acid benzyl ester hydrochloride

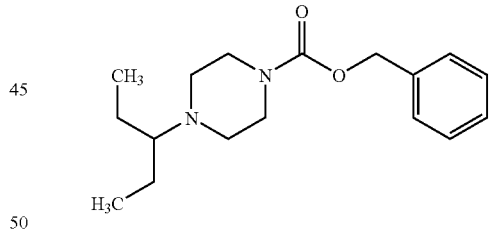

To a stirred mixture of 1-(1-ethylpropyl)piperazine (156 mg, 1.0 mmol) and dry DCM (10 ml) was added benzyl 4-nitrophenylcarbonate (273 mg, 1.0 mmol). The mixture was stirred overnight at room temperature and then diluted with DCM (50 ml). The reaction mixture was washed with 1 N NaOH (3×20 ml) and water (3×20 ml). The organic phase was concentrated and the oily residue was dissolved in a 0.5 N HCl solution (50 ml). The acidic solution was washed with diethyl ether (2×20 ml) and 4 N NaOH was added until pH 11. The resulting mixture was extracted with ethyl acetate (2×20 ml) and the combined organic extracts were dried (MgSO$_4$). The solvent was evaporated to give an oil that was dissolved in 0.5 N HCl (10 ml). The acidic solution was concentrated and re-evaporated twice with acetonitrile to give 200 mg (61%) of the title compound as a solid. M.p. 168–170° C.

¹H NMR (400 MHz, DMSO-d₆): δ 0.97 (t, 6H), 1.52–1.68 (m, 2H), 1.80–1.92 (m, 2H), 2.96–3.13 (m, 3H), 3.3–3.65 (m, 4H), 4.01–4.11 (m, 2H), 5.10 (s, 2H), 7.3–7.4 (m, 5H), 10.8 (brs, 1H).

Example 333

4-(1-Ethylpropyl)piperazine-1-carboxylic acid 2-(4-methoxyphenyl)ethyl ester hydrochloride

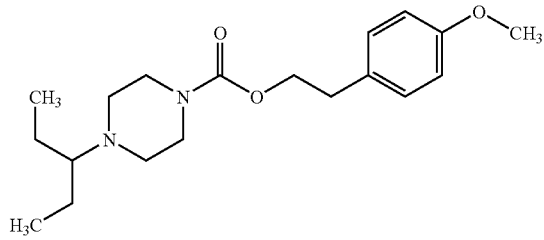

Step 1: 2-(4-Methoxyphenyl)ethyl 4-nitrophenylcarbonate

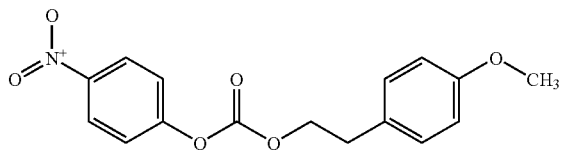

A stirred mixture of 2-(4-methoxyphenyl)ethanol (1.52 g, 10 mmol) and dry DCM (20 ml) was placed on an ice-bath under an atmosphere of nitrogen. A solution of 4-nitrophenyl chloroformate (2.0 g, 10 mmol) in DCM (10 ml) was added dropwise. The mixture was stirred for 15 min and then a solution of pyridine (0.85 ml) in DCM (6 ml) was added dropwise keeping the temperature at 0–5° C. Stirring was continued at this temperature for another 3 hours. The reaction mixture was washed with cold water (2×25 ml) and then dried (MgSO₄). The solvent was evaporated and the residue crystallized on standing to give 3.0 g (95%) of 2-(4-methoxyphenyl)ethyl 4-nitrophenylcarbonate as a solid. M.p. 53–55° C.

¹H NMR (400 MHz, CDCl₃): δ 3.00 (t, 2H), 3.78 (s, 3H), 4.45 (t, 2H), 6.88 (d, 2H), 7.16 (d, 2H), 7.33 (d, 2H), 8.25 (d, 2H).

Step 2:

To a stirred mixture of 1-(1-ethylpropyl)piperazine (156 mg, 1.0 mmol) and dry DCM (10 ml) was added 2-(4-methoxyphenyl)ethyl 4-nitrophenylcarbonate (310 mg, 1.0 mmol). The mixture was stirred overnight at room temperature and then diluted with DCM (50 ml). The reaction mixture was washed with 1 N NaOH (3×20 ml) and water (3×20 ml). The organic phase was concentrated and the oily residue was dissolved in a 0.5 N HCl solution (50 ml). The acidic solution was washed with diethyl ether (2×20 ml), concentrated and re-evaporated twice with acetone to give 200 mg (55%) of the title compound as a solid. M.p. 160–162° C.

¹H NMR (400 MHz, DMSO-d₆): δ 0.95 (t, 6H), 1.52–1.67 (m, 2H), 1.78–1.92 (m, 2H), 2.81 (t, 2H), 2.90–3.06 (m, 3H), 3.3–3.5 (m, 4H), 3.71 (s, 3H), 3.9–4.1 (m, 2H), 4.17 (t, 2H), 6.86 (d, 2H), 7.17 (d, 2H), 10.7 (brs, 1H).

Example 334

4-(2-Propyl)piperazine-1-carboxylic acid 2-(4-chlorophenoxy)ethyl ester hydrochloride

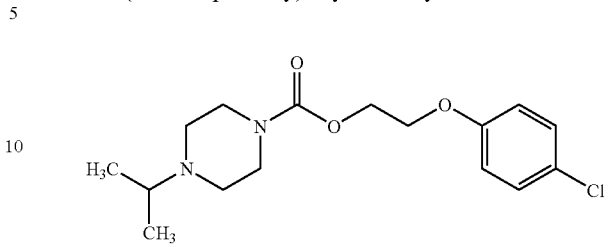

Step 1: 2-(4-Chlorophenoxy)ethyl 4-nitrophenylcarbonate

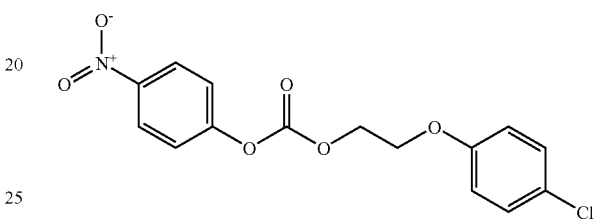

A stirred mixture of dry THF (20 ml) and 1.0 M lithiumaluminiumhydride (9.0 ml, 9.0 mmol) was placed under an atmosphere of nitrogen. A solution of 4-chlorophenoxyacetic acid (1.9 g, 10 mmol) in dry THF (10 ml) is slowly added dropwise. When addition was complete the reaction mixture was stirred for 30 min and then heated at reflux temperature for 10 min. The cooled reaction mixture was quenched with small amounts of water and 4 N NaOH and ethyl acetate was added. The mixture was dried (MgSO₄) and then concentrated. The residue was re-evaporated with DCM to give crude 2-(4-chlorophenoxy)ethanol as an oil.

A stirred mixture of the crude 2-(4-chlorophenoxy)ethanol and dry DCM (20 ml) was placed on an ice-bath under an atmosphere of nitrogen. A solution of 4-nitrophenyl chloroformate (2.2 g, 11 mmol) in DCM (10 ml) was added dropwise. The mixture was stirred for 15 min and then a solution of pyridine (0.90 ml) in DCM (6 ml) was added dropwise keeping the temperature at 0–5° C. Stirring was continued at this temperature for another 3 hours. The reaction mixture was washed with cold water (2×25 ml) and then dried (MgSO₄). The solvent was evaporated and the residue crystallized on standing to give 3.15 g (93%) of 2-(4-chlorophenoxy)ethyl 4-nitrophenylcarbonate as a solid. M.p. 58–60° C.

¹H NMR (400 MHz, CDCl₃): δ 4.26 (t, 2H), 4.63 (t, 2H), 6.85 (d, 2H), 7.26 (d, 2H), 7.37 (d, 2H), 8.27 (d, 2H).

Step 2:

To a stirred mixture of 1-(2-propyl)piperazine (130 mg, 1.0 mmol) and dry DCM (10 ml) was added 2-(4-chlorophenoxy)ethyl 4-nitrophenylcarbonate (330 mg, 1.0 mmol). The mixture was stirred overnight at room temperature and then diluted with DCM (30 ml). The reaction mixture was washed with 0.5 N NaOH (3×20 ml) and water (3×20 ml). The organic phase was concentrated and the oily residue was dissolved in a 0.5 N HCl solution (15 ml). The acidic solution was washed with diethyl ether (10 ml), concentrated and re-evaporated twice with acetonitrile to give 300 mg (82%) of the title compound as a solid. M.p. 174–176

$^1$H NMR (400 MHz, DMSO-d$_6$): δ 1.25 (d, 6H), 2.88–3.02 (m, 2H), 3.3–3.5 (m, 5H), 3.95–4.10 (m, 2H), 4.20 (t, 2H), 4.35 (t, 2H), 7.00 (d, 2H), 7.34 (d, 2H), 11.0 (brs, 1H).

Example 335

4-(1-Ethylpropyl)piperazine-1-carboxylic acid 2-(4-chlorophenoxy)ethyl ester hydrochloride

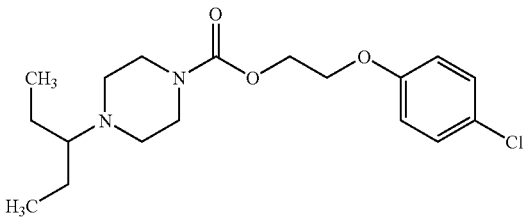

By a similar procedure as described in Example 334 and starting from 1-(1-ethylpropyl)piperazine (160 mg, 1.0 mmol) and 2-(4-chlorophenoxy)ethyl 4-nitrophenylcarbonate (330 mg, 1.0 mmol), 330 mg (84%) of the title compound was isolated as a solid. M.p. 144–146° C.

$^1$H NMR (400 MHz, DMSO-d$_6$): δ 0.92 (t, 6H), 1.52–1.68 (m, 2H), 1.78–1.93 (m, 2H), 2.95–3.10 (m, 3H), 3.3–3.5 (m, 4H), 3.9–4.1 (m, 2H), 4.20 (t, 2H), 4.35 (t, 2H), 7.00 (d, 2H), 7.33 (d, 2H), 10.7 (brs, 1H).

Example 336

4-(2-Propyl)piperazine-1-carboxylic acid 3-(4-chlorophenoxy)-1-propyl ester hydrochloride

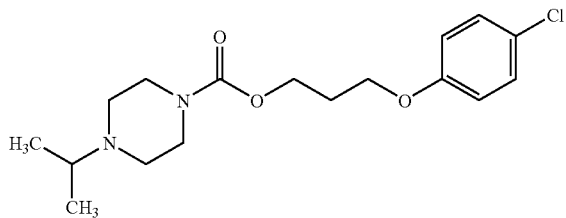

Step 1: 3-(4-Chlorophenoxy)-1-propyl 4-nitrophenylcarbonate

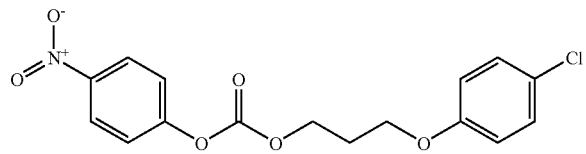

A mixture of 4-chlorophenol (13 g, 100 mmol) and crushed NaOH (5 g, 125 mmol) in DMF (60 ml) was stirred for 1 hour under an atmosphere of nitrogen. 3-Bromo-1-propanol (14 g, 100 mmol) was added dropwise. The reaction mixture was stirred overnight at room temperature and then the mixture was poured into cold water (600 ml). The mixture was extracted with diethyl ether (2×250 ml) and the combined organic extracts were washed with 1 N NaOH (2×100 ml). The organic phase was concentrated to give 14 g of an oily residue that was purified on silica gel (200 g) eluting with a mixture of heptane and ethyl acetate (1:1). This afforded 9.0 g (48%) of 3-(4-chlorophenoxy)-1-propanol.

A stirred mixture of 3-(4-chlorophenoxy)-1-propanol (1.87 g, 10 mmol) and dry DCM (25 ml) was placed on an ice-bath under an atmosphere of nitrogen. A solution of 4-nitrophenyl chloroformate (2.2 g, 11 mmol) in DCM (10 ml) was added dropwise. The mixture was stirred for 15 min and then a solution of pyridine (0.90 ml) in DCM (6 ml) was added dropwise keeping the temperature at 0–5° C. Stirring was continued at this temperature for another 3 hours. The reaction mixture was washed with cold water (2×25 ml) and then dried (MgSO$_4$). The solvent was evaporated and the residue crystallized on standing to give 3.48 g (98%) of 3-(4-chlorophenoxy)-1-propyl 4-nitrophenylcarbonate as a solid. M.p. 56–57° C.

$^1$H NMR (400 MHz, CDCl$_3$): δ 2.23 (pent. 2H), 4.09 (t, 2H), 4.50 (t, 2H), 6.85 (d, 2H), 7.25 (d, 2H), 7.38 (d, 2H), 8.27 (d, 2H).

Step 2:

By a similar procedure as described in Example 334 and starting from 1-(2-propyl)piperazine (0.2 ml, 1.0 mmol) and 3-(4-chlorophenoxy)-1-propyl 4-nitrophenylcarbonate (350 mg, 1.0 mmol), 330 mg (91%) of the title compound was isolated as a solid. M.p. 184–185° C.

$^1$H NMR (400 MHz, DMSO-d$_6$): δ 1.26 (d, 6H), 2.03 (pent. 2H), 2.88–3.02 (m, 2H), 3.3–3.5 (m, 5H), 4.02–4.10 (m, 4H), 4.16 (t, 2H), 6.96 (d, 2H), 7.32 (d, 2H), 11.0 (brs, 1H).

Example 337

4-(1-Ethylpropyl)piperazine-1-carboxylic acid 3-(4-chlorophenoxy)-1-propyl ester hydrochloride

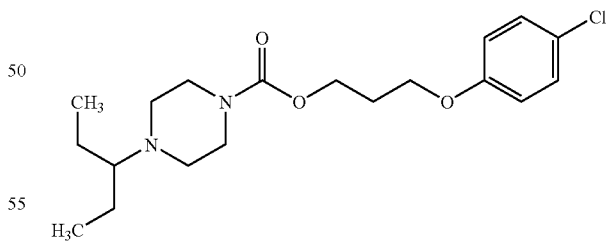

By a similar procedure as described in Example 334 and starting from 1-(1-ethylpropyl)piperazine (160 mg, 1.0 mmol) and 3-(4-chlorophenoxy)-1-propyl 4-nitrophenylcarbonate (350 mg, 1.0 mmol), 260 mg (64%) of the title compound was isolated as a solid. M.p. 136–138° C.

$^1$H NMR (400 MHz, DMSO-d$_6$): δ 0.96 (t, 6H), 1.52–1.68 (m, 2H), 1.78–1.92 (m, 2H), 2.04 (pent., 2H), 2.95–3.08 (m, 3H), 3.3–3.65 (m, 4H), 4.00–4.10 (m, 4H), 4.17 (t, 2H), 6.98 (d, 2H), 7.32 (d, 2H), 10.7 (brs, 1H).

Example 338

4-(1-Ethylpropyl)piperazine-1-carboxylic acid 2-(3,4-dimethoxyphenoxy)ethyl ester hydrochloride

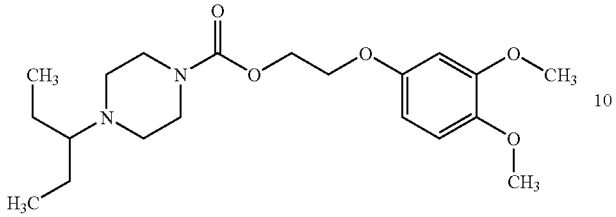

Step 1: 2-(3,4-Dimethoxyphenoxy)ethanol

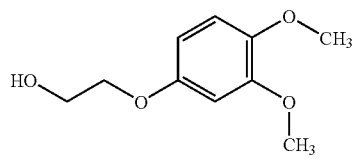

A mixture of 3,4-dimethoxyphenol (155 mg, 1.0 mmol) and 60% sodium hydride (50 mg, 1.25 mmol) in DMA (6 ml) was stirred for 20 min under an atmosphere of nitrogen. 2-(2-Pyranyloxy)ethylbromide (220 mg, 1.0 mmol) was added dropwise. The reaction mixture was stirred for 6 hours at room temperature and then the mixture was poured into water (100 ml). The mixture was extracted with ethyl acetate (2×30 ml) and the combined organic extracts were dried (MgSO$_4$). The organic phase was concentrated and the residue was dissolved in 2-propanol (30 ml) and 4 N HCl (20 ml) was added. The mixture was heated at reflux temperature for 30 min and then stirred at room temperature for 2 hours. The reaction mixture was concentrated and the residue was dissolved in ethyl acetate (50 ml). The organic solution was dried (MgSO$_4$) and the solvent was evaporated. The oily residue was purified on silica gel (50 g) eluting with a mixture of heptane and ethyl acetate (3:2). This afforded 100 mg (50%) of 2-(3,4-dimethoxyphenoxy)ethanol.

Step 2:

By a similar procedure as described in Example 333 and starting from 1-(1-ethylpropyl)piperazine (80 mg, 0.5 mmol) and 2-(3,4-dimethoxyphenoxy)ethanol (100 mg, 0.5 mmol), 80 mg (38%) of the title compound. contaminated with 4-(1-ethylpropyl)piperazine-1-carboxylic acid 4-nitrophenyl ester hydrochloride, was isolated as a solid.

$^1$H NMR (400 MHz, DMSO-d$_6$) δ 1.05 (t, 6H), 1.51–1.70 (m, 2H), 1.77–1.94 (m, 2H), 2.95–3.10 (m, 3H), 3.3–3.5 (m, 4H), 3.68 (s, 3H), 3.74 (s, 3H), 3.9–4.1 (m, 2H), 4.15 (t, 2H), 4.34 (t, 2H), 6.40–6.47 (m, 1H), 6.58 (s, 1H), 6.84 (d, 1H), 10.9 (brs, 1H).

Example 339

4-(1-Ethylpropyl)piperazine-1-carboxylic acid 3-(3,4-dimethoxyphenoxy)-1-propyl ester hydrochloride

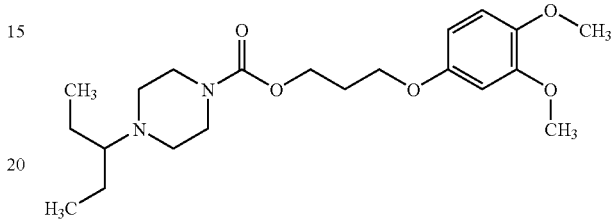

By a similar procedure as described in Example 338 and starting from 1-(1-ethylpropyl)piperazine (310 mg, 2.0 mmol) and 3-(3,4-dimethoxyphenoxy)-1-propanol (2.0 mmol, prepared similarly as described in Example 338), 650 mg (75%) of the title compound was isolated as a solid. M.p. 145–147° C.

$^1$H NMR (400 MHz, DMSO-d$_6$): δ 0.93 (t, 6H), 1.50–1.68 (m, 2H), 1.78–1.91 (m, 2H), 2.01 (pent., 2H), 2.93–3.08 (m, 3H), 3.3–3.6 (m, 4H), 3.66 (s, 3H), 3.71 (s, 3H), 3.93–4.08 (m, 4H), 4.16 (t, 2H), 6.38–6.43 (m, 1H), 6.55 (s, 1H), 6.81 (d, 1H), 10.7 (brs, 1H).

The following examples were prepared according to one of the above general procedures.

Example 340

1-(3,4-Dimethoxyphenyl)-4-[4-(1-ethylcyclopropyl)piperazin-1-yl]butane-1,4-dione hydrochloride

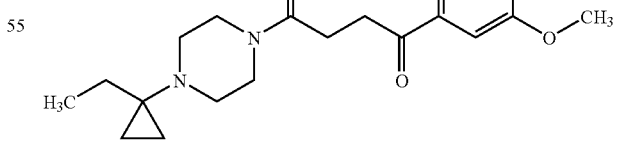

$^1$H NMR (DMSO-d$_6$) δ 0.79 (t, J=7 Hz, 3H), 0.87 (brs, 2H), 1.31 (brs, 2H), 1.85 (quart, J=7 Hz, 2H), 2.72 (m, 2H), 3.15–3.78 (m, 8H), 3.81 (s, 3H), 3.85 (s, 3H), 4.15 (m, 1H), 4.46 (m, 1H), 7.07 (d, J=8 Hz, 1H), 7.45 (d, J=1 Hz, 1H), 7.67 (dd, J=1 Hz, 8 Hz, 1H), 10.57 (brs, 1H); HPLC-MS: m/z 375 (MH$^+$); Rf: 2.50 min.

Example 341

1-[4-(1-Ethylpropyl)piperazin-1-yl]-2-(3-fluoro-4-hydroxyphenyl)ethanone hydrochloride

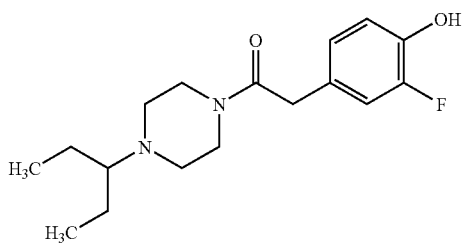

$^1$H NMR (DMSO-$d_6$) δ 0.95 (t, J=7 Hz, 6H), 1.59 (m, 2H), 1.82 (m, 2H), 2.88–3.25 (m, 9H), 4.08 (m, 1H), 4.42 (m, 1H), 6.80–7.00 (m, 3H), 9.82 (s, 1H), 10.45 (brs, 1H); HPLC-MS: m/z 309 (MH$^+$); Rf: 1.28 min.

Example 342

1-(4-Cyclopropylmethylpiperazin-1-yl)-4-(3,4-dimethoxyphenyl)butane-1,4-dione hydrochloride

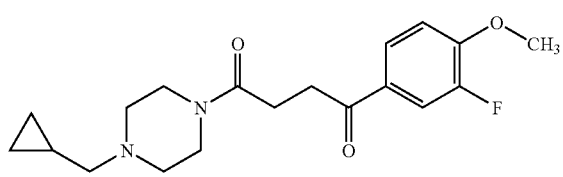

$^1$H NMR (DMSO-$d_6$) δ 0.40 (brs, 2H), 0.65 (m, 2H), 1.12 (m, 1H), 2.65–3.15 (m, 7H), 3.20 (t, J=7 Hz, 2H), 3.50–3.65 (m, 3H), 3.93 (s, 3H), 4.17 (m, 1H), 4.40 (m, 1H), 7.30 (t, J=8 Hz, 1H), 7.77 (d, J=8 Hz, 1H), 7.86 (d, J=7 Hz, 1H), 10.84 (brs, 1H); HPLC-MS: m/z 349 (MH$^+$); Rf: 1.98 min.

Example 343

1-[4-(1-Cyclopropyl-1-methylethyl)piperazin-1-yl]-4-(3,4-dimethoxyphenyl)butane-1,4-dione hydrochloride

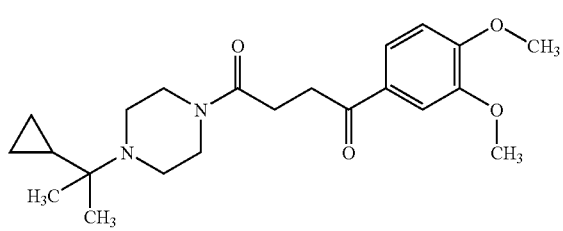

$^1$H NMR (DMSO-$d_6$) δ 0.50 (m, 2H), 0.58 (m, 2H), 1.22 (m, 7H), 2.72 (m, 2H), 2.92 (m, 1H), 3.07–3.26 (m, 4H), 3.58–3.76 (m, 3H), 3.81 (s, 3H), 3.85 (s, 3H), 4.18 (m, 1H), 4.47 (m, 1H), 7.07 (d, J=8 Hz, 1H), 7.46 (brs, 1H), 7.67 (brd, J=8 Hz, 1H), 10.69 (brs, 1H); HPLC-MS: m/z 389 (MH$^+$); Rf: 1.93 min.

Example 344

4-[3-(4-Cyclopropylmethyl-piperazin-1-yl)-3-oxo-propoxy]-benzonitrile hydrochloride

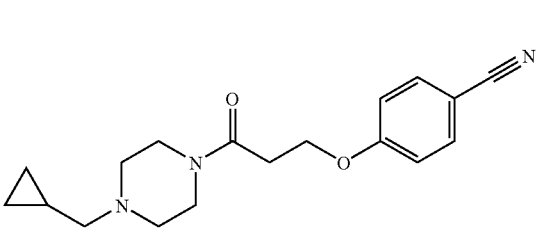

The acid required for the synthesis of this amide was prepared as described in the literature: R. Sarges, R. C. Schnur, J. L. Belleitre, M. J. Peterson, *J. Med. Chem.* 1988, 31, 230–243.

$^1$H NMR (DMSO-$d_6$) δ 0.39 (m, 2H), 0.63 (m, 2H), 1.10 (m, 1H), 2.84–3.20 (m, 7H), 3.52 (m, 3H), 4.11 (m, 1H), 4.29 (t, J=7 Hz, 2H), 4.46 (m, 1H), 7.09 (d, J=8 Hz, 2H), 7.77 (d, J=8 Hz, 2H), 10.86 (brs, 1H); HPLC-MS: m/z 314 (MH$^+$); Rf: 1.90 min.

Example 345

1-[4-(1-Cyclopropyl-1-methylethyl)piperazin-1-yl]-4-(3,4-dihydro-2H-benzo[b][1,4]dioxepin-7-yl)butane-1,4-dione hydrochloride

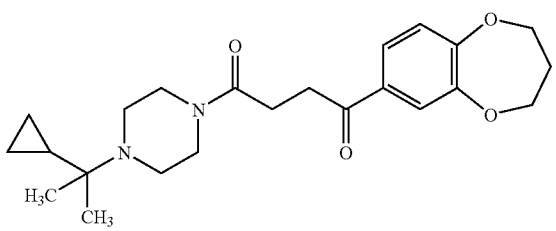

$^1$H NMR (DMSO-$d_6$) δ 0.48 (m, 2H), 0.58 (m, 2H), 1.20 (m, 7H), 2.16 (m, 2H), 2.72 (m, 2H), 2.91 (m, 1H), 3.08–3.22 (m, 3H), 3.58–3.70 (m, 3H), 4.12–4.26 (m, 5H), 4.46 (m, 1H), 7.06 (d, J=8 Hz, 1H), 7.52 (d, J=1 Hz, 1H), 7.59 (dd, J=8 Hz, 1 Hz, 1H), 10.44 (brs, 1H); HPLC-MS: m/z 401 (MH$^+$); Rf: 2.43 min.

Example 346

4-{3-[4-(1-Cyclopropyl-1-methylethyl)piperazin-1-yl]-3-oxo-propoxy}benzonitrile hydrochloride

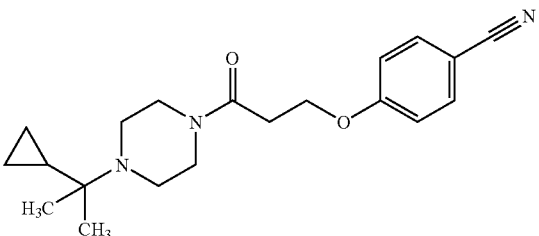

$^1$H NMR (DMSO-$d_6$) δ 0.49 (m, 2H), 0.56 (m, 2H), 1.20 (m, 7H), 2.86–3.31 (m, 3H), 3.52–3.83 (m, 5H), 4.11 (m,

1H), 4.31 (t, J=7 Hz, 2H), 4.50 (m, 1H), 7.11 (d, J=8 Hz, 2H), 7.77 (d, J=8 Hz, 2H), 10.99 (br s, 1H); HPLC-MS: m/z 342 (MH⁺); Rf: 2.20 min.

Example 347

1-[4-(1-Cyclopropyl-1-methylethyl)piperazin-1-yl]-4-(3-fluoro-4-methoxyphenyl)butane-1,4-dione hydrochloride

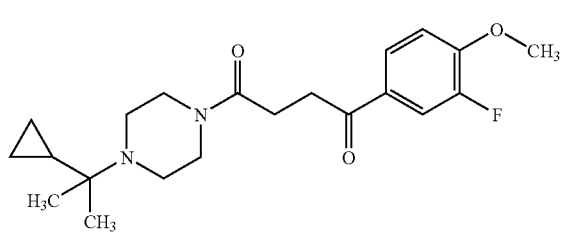

¹H NMR (DMSO-d₆) δ 0.45–0.62 (m, 4H), 1.22 (m, 7H), 2.72 (m, 2H), 2.93 (m, 1H), 3.05–3.25 (m, 4H), 3.57–3.77 (m, 3H), 3.93 (s, 3H), 4.16 (m, 1H), 4.45 (m, 1H), 7.29 (t, J=8 Hz, 1H), 7.75 (dd, J=8 Hz, 1 Hz, 1H), 7.87 (br d, J=7 Hz, 1H), 10.70 (br s, 1H); HPLC-MS: m/z 377 (MH⁺); Rf: 2.40 min.

Example 348

3-(5-Chlorobenzofuran-3-yl)-1-[4-(1-cyclopropyl-1-methylethyl)piperazin-1-yl]propan-1-one hydrochloride

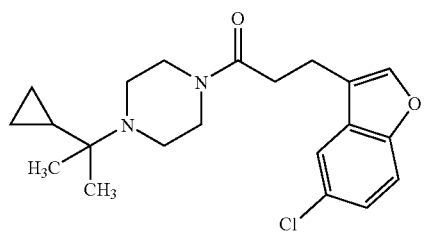

The acid required for the synthesis of this amide was prepared as described in the literature: Hallmann, Hägele, *Liebigs Ann. Chem.* 1963, 662, 147.

¹H NMR (DMSO-d₆) δ 0.42–0.61 (m, 4H), 1.20 (m, 7H), 2.71–3.25 (m, 7H), 3.51–3.71 (m, 3H), 4.08 (m, 1H), 4.52 (m, 1H), 7.32 (dd, J=8 Hz, 1 Hz, 1H), 7.58 (d, J=8 Hz, 1H), 7.76 (d, J=1 Hz, 1H), 7.88 (s, 1H), 10.72 (br s, 1H); HPLC-MS: m/z 375 (MH⁺); Rf: 3.10 min.

Example 349

1-[4-(1-Cyclopropyl-1-methylethyl)piperazin-1-yl]-4-(2,3-dihydrobenzo[1,4]dioxin-6-yl)butane-1,4-dione hydrochloride

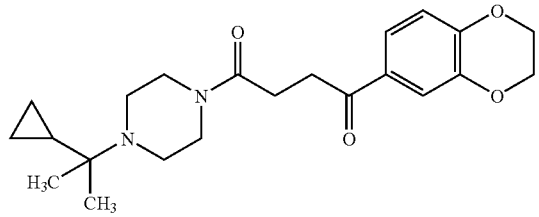

¹H NMR (DMSO-d₆) δ 0.45–0.62 (m, 4H), 1.21 (m, 7H), 2.71 (m, 2H), 2.93 (m, 1H), 3.05–3.28 (m, 4H), 3.56–3.76 (m, 3H), 4.16 (m, 1H), 4.31 (m, 4H), 4.46 (m, 1H), 6.98 (d, J=8 Hz, 1H), 7.45 (d, J=1 Hz, 1H), 7.52 (dd, J=8 Hz, 1 Hz, 1H), 10.80 (br s, 1H); HPLC-MS: m/z 387 (MH⁺); Rf: 2.30 min.

Example 350

4-{3-[4-(1-Cyclopropyl-1-methylethyl)piperazin-1-yl]-3-oxopropenyl}benzonitrile hydrochloride

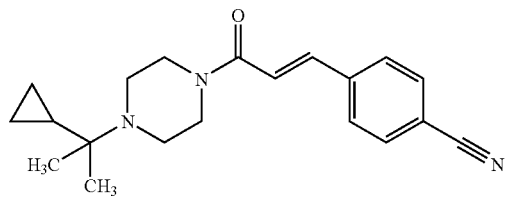

¹H NMR (DMSO-d₆) δ 0.45–0.62 (m, 4H), 1.23 (m, 7H), 2.93–3.20 (m, 2H), 3.40 (m, 1H), 3.55–3.87 (m, 3H), 4.58 (m, 2H), 7.47 (d, J=15 Hz, 1H), 7.59 (d, J=15 Hz, 1H), 7.39 (d, J=8 Hz, 2H), 7.95 (d, J=8 Hz, 2H), 11.10 (br s, 1H); HPLC-MS: m/z 324 (MH⁺); Rf: 2.23 min.

Example 351

1-[4-(1-Cyclopropyl-1-methylethyl)piperazin-1-yl]-3-(3,4-dimethoxyphenoxy)propan-1-one hydrochloride

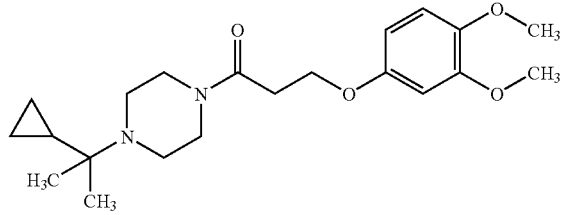

The acid required for the synthesis of this amide was prepared as described in the literature: R. Sarges, R. C. Schnur, J. L. Belletire, M. J. Peterson, *J. Med. Chem.* 1988, 31, 230–243.

¹H NMR (DMSO-d₆) δ 0.45–0.60 (m, 4H), 1.22 (m, 7H), 2.82 (t, J=7 Hz, 2H), 2.89–3.32 (m, 3H), 3.56–3.80 (m, 3H), 3.68 (s, 3H), 3.72 (s, 3H), 4.12 (m, 1H), 4.14 (t, J=7 Hz, 2H), 4.52 (m, 1H), 6.42 (dd, J=8 Hz, 1 Hz, 1H), 6.53 (d, J=1 Hz, 1H), 6.83 (d, J=8 Hz, 1H), 11.00 (br s, 1H); HPLC-MS: m/z 377 (MH⁺); Rf: 2.07 min.

Example 352

2-Biphenyl-4-yl-1-[4-(1-cyclopropyl-1-methylethyl)piperazin-1-yl]ethanone hydrochloride

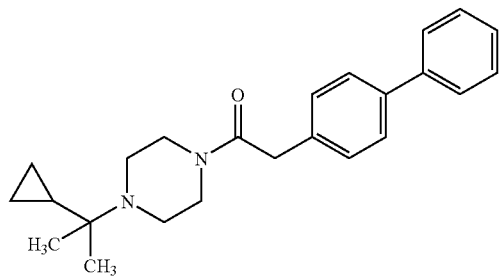

¹H NMR (DMSO-d₆) δ 0.43–0.59 (m, 4H), 1.20 (m, 7H), 2.96 (m, 2H), 3.21 (m, 1H), 3.52–3.88 (m, 5H), 4.20 (m, 1H), 4.52 (m, 1H), 7.32 (m, 3H), 7.45 (t, J=8 Hz, 2H), 7.63 (m, 4H), 10.68 (br s, 1H); HPLC-MS: m/z 363 (MH⁺); Rf: 3.40 min.

Example 353

1-[4-(1-Cyclopropyl-1-methylethyl)piperazin-1-yl]-2-(3-phenoxyphenyl)ethanone hydrochloride

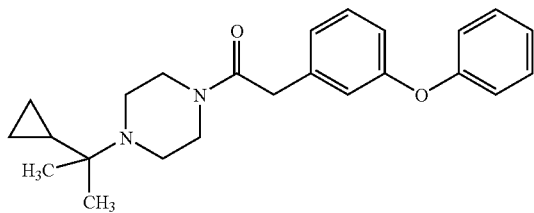

¹H NMR (DMSO-d₆) δ 0.43–0.59 (m, 4H), 1.20 (m, 7H), 2.98 (m, 2H), 3.19 (m, 1H), 3.52–3.85 (m, 5H), 4.14 (m, 1H), 4.48 (m, 1H), 6.89 (m, 2H), 7.01 (m, 3H), 7.14 (t, J=8 Hz, 1H), 7.29–7.43 (m, 3H), 10.72 (br s, 1H); HPLC-MS: m/z 379 (MH⁺); Rf: 3.43 min.

Example 354

1-[4-(1-Cyclopropyl-1-methylethyl)piperazin-1-yl]-2-(4-phenoxyphenyl)ethanone hydrochloride

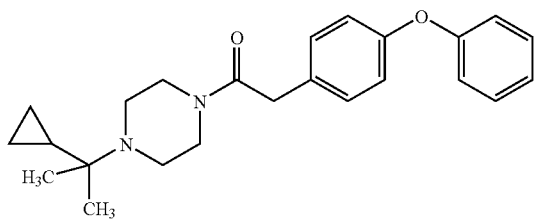

¹H NMR (DMSO-d₆) δ 0.43–0.60 (m, 4H), 1.20 (m, 7H), 2.96 (m, 2H), 3.18 (m, 1H), 3.53–3.84 (m, 5H), 4.18 (m, 1H), 4.51 (m, 1H), 6.98 (m, 4H), 7.13 (t, J=8 Hz, 1H), 7.22 (d, J=8 Hz, 2H), 7.39 (t, J=8 Hz, 2H), 10.62 (br s, 1H); HPLC-MS: m/z 379 (MH⁺); Rf: 3.43 min.

Example 355

1-[4-(1-Cyclopropyl-1-methylethyl)piperazin-1-yl]-4-(4-trifluoromethylphenyl)butane-1,4dione hydrochloride

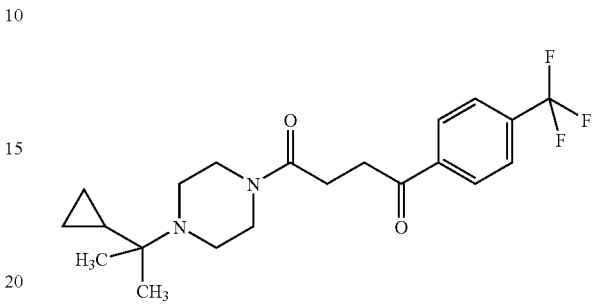

¹H NMR (DMSO-d₆) δ 0.46–0.62 (m, 4H), 1.22 (m, 7H), 2.80 (m, 2H), 2.94 (m, 1H), 3.07–3.40 (m, 4H), 3.56–3.80 (m, 3H), 4.17 (m, 1H), 4.43 (m, 1H), 7.90 (d, J=8 Hz, 2H), 8.17 (d, J=8 Hz, 2H), 10.75 (br s, 1H); HPLC-MS: m/z 397 (MH⁺); Rf: 3.27 min.

Example 356

3-Benzo[1,3]dioxol-5-yl-1-[4-(1-cyclopropyl-1-methylethyl)piperazin-1-yl]propenone

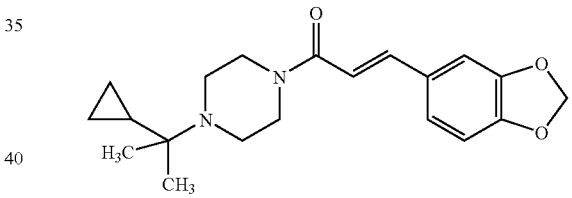

¹H NMR (DMSO-d₆) δ 0.44–0.62 (m, 4H), 1.22 (m, 7H), 3.05 (m, 2H), 3.28 (m, 1H), 3.65 (m, 3H), 4.58 (m, 2H), 6.07 (s, 2H), 6.95 (d, J=8 Hz, 1H), 7.12–7.20 (m, 2H), 7.44–7.51 (m, 2H), 10.80 (br s, 1H); HPLC-MS: m/z 343 (MH⁺); Rf: 2.67 min.

Example 357

1-(3-Chloro-4-methoxyphenyl)-4-[4-(1-cyclopropyl-1-methylethyl)piperazin-1-yl]butane-1,4-dione hydrochloride

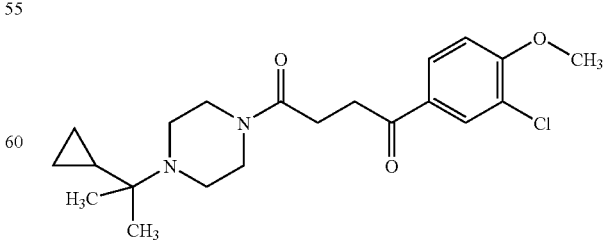

¹H NMR (DMSO-d₆) δ 0.45–0.62 (m, 4H), 1.22 (m, 7H), 2.74 (m, 2H), 2.93 (m, 1H), 3.09–3.25 (m, 4H), 3.56–3.78

(m, 3H), 3.95 (s, 3H), 4.16 (m, 1H), 4.44 (m, 1H), 7.28 (m, 1H), 7.99 (m, 2H), 10.70 (br s, 1H); HPLC-MS: m/z 393 (MH+); Rf: 3.00 min.

Example 358

4-(3,4-Dichlorophenyl)-1-[4-(1-ethylpropyl)piperazin-1-yl]-2-hydroxybutane-1,4-dione hydrochloride

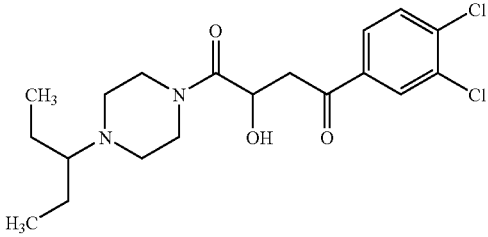

The acid required for the synthesis of this amide was prepared in the following way:

A mixture of 3,4-dichloroacetophenone (3.84 g, 20.3 mmol), glacial acetic acid (20.0 ml), and glyoxylic acid hydrate (1.85 g, 20.1 mmol) was stirred at 90° C. for 23 hours. More glyoxylic acid hydrate (0.93 g) was added, and heating was continued for 41 hours. Water (200 ml) was added, and the mixture was extracted twice with ethyl acetate. The combined extracts were washed with brine, dried (MgSO4), and concentrated under reduced pressure. Recrystallization of the residue from ethyl acetate/heptane yielded 2.01 g (38%) of 4-(3,4-dichlorophenyl)-4-oxo-2-hydroxybutyric acid. This acid was used to prepare the title amide using General Procedure (D).

¹H NMR (DMSO-d₆) δ 0.97 (t, J=7 Hz, 6H), 1.61 (m, 2H), 1.85 (m, 2H), 2.87–3.72 (m, 9H), 4.23–4.45 (m, 2H), 4.89 (m, 1H), 7.82 (d, J=8 Hz, 1H), 7.91 (dd, J=8 Hz, 1 Hz, 1H), 8.12 (d, J=1 Hz, 1H), 10.28 (br s, 1H); HPLC-MS: m/z 401 (MH+); Rf: 3.10 min.

Example 359

1-(3,4-Dimethoxyphenyl)-4-[4-(tetrahydropyran-4-yl)piperazin-1-yl]butane-1,4-dione hydrochloride

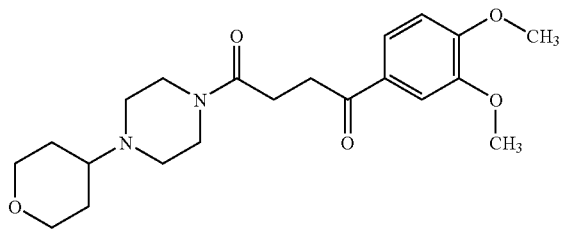

¹H NMR (DMSO-d₆) δ 1.71 (m, 2H), 2.02 (m, 2H), 2.68–3.65 (m, 13H), 3.81 (s, 3H), 3.85 (s, 3H), 3.98 (m, 2H), 4.19 (m, 1H), 4.42 (m, 1H), 7.08 (d, J=8 Hz, 1H), 7.43 (d, J=1 Hz, 1H), 7.68 (dd, J=8 Hz, 1 Hz, 1H), 10.90 (br s, 1H); HPLC-MS: m/z 391 (MH+); Rf: 2.07 min.

Example 360

1-(4-Cyclopentyl[1,4]diazepan-1-yl)-4-(3,4-dimethoxyphenyl)butane-1,4-dione hydrochloride

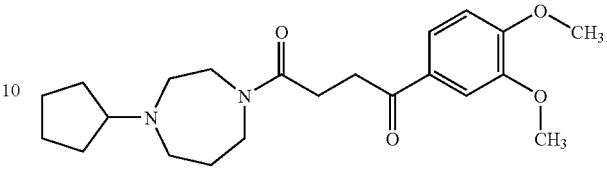

¹H NMR (DMSO-d₆) δ 1.42–2.45 (m, 10H), 2.69 (m, 2H), 2.90–3.67 (m, 9H), 3.81 (s, 3H), 3.84 (s, 3H), 3.93–4.13 (m, 2H), 7.08 (d, J=8 Hz, 1H), 7.44 (d, J=1 Hz, 1H), 7.68 (dd, J=8 Hz, 1 Hz, 1H), 10.75 (br s, 1H); HPLC-MS: m/z 389 (MH+); Rf: 2.43 min.

Example 361

[4-(1-Cyclopropyl-1-methylethyl)piperazin-1-yl]-[5-(3-fluoro-4-methoxy-phenyl)-2H-pyrazol-3-yl]methanone hydrochloride

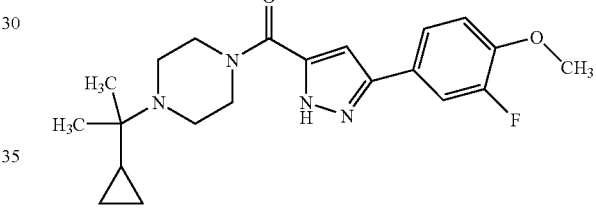

The acid required for the synthesis of this amide was prepared in the following way:

To a solution of 3-fluoro-4-methoxyacetophenone (2.59 g, 15.4 mmol) and dimethyl oxalate (2.0 g, 16.9 mmol) in THF (25 ml) was portionwise added a 1.7 M solution of potassium tert-amylate in toluene (25 ml, 42.5 mmol). The mixture was stirred at room temperature for 14 hours. Water (1.0 ml) and more THF (25 ml) were added, and stirring at room temperature was continued for 30 hours. Water (250 ml) was added, and the mixture was washed with a mixture of heptane and toluene. The aqueous phase was filtered, acidified with concentrated hydrochloric acid (6.0 ml), and filtered. After drying, 3.09 g (84%) of 4-(3-fluoro-4-methoxyphenyl)-4,2-dioxobutyric acid was obtained. A mixture of this acid (1.99 g, 8.29 mmol), ethanol (75 ml), and hydrazine hydrate (0.80 ml, 2 equiv.) was refluxed for 18 hours. Water (250 ml) and concentrated hydrochloric acid (4.0 ml) were added, and the mixture was filtered. After drying under reduced pressure 1.76 g (90%) of 5-(3-fluoro-4-methoxyphenyl)-2H-pyrazole-3-carboxylic acid acid was obtained as a solid. This acid was used to prepare the title amide using General Procedure (D).

¹H NMR (DMSO-d₆) δ 0.45–0.65 (m, 4H), 1.22 (m, 7H), 3.11 (m, 2H), 3.60 (m, 2H), 3.70 (m, 2H), 3.87 (s, 3H), 4.64 (m, 1H), 5.16 (m, 1H), 7.07 (br s, 1H), 7.26 (m, 1H), 7.60–7.80 (m, 2H), 10.62 (br s, 1H), 13.69 (br s, 1H); HPLC-MS: m/z 387 (MH+); Rf: 2.90 min.

Example 362

1-[4-(1-Cyclopropyl-1-methylethyl)piperazin-1-yl]-2-(4'-fluorobiphenyl-4-yl)ethanone hydrochloride

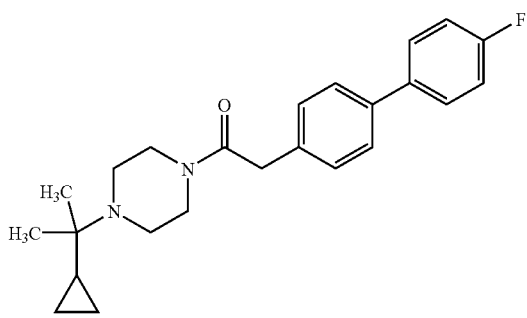

$^1$H NMR (DMSO-d$_6$) δ 0.45–0.60 (m, 4H), 1.22 (m, 7H), 2.97 (m, 2H), 3.23 (m, 1H), 3.52–3.90 (m, 5H), 4.21 (m, 1H), 4.52 (m, 1H), 7.28 (m, 4H), 7.59 (d, J=8 Hz, 2H), 7.68 (m, 2H), 10.80 (br s, 1H); HPLC-MS: m/z 381 (MH$^+$); Rf: 3.63 min.

Example 363

1-(4-Cyclopropylmethylpiperazin-1-yl)-3-(3,4-dichlorophenoxy)propan-1-one hydrochloride

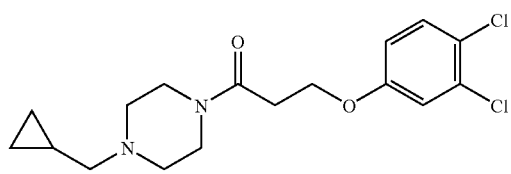

$^1$H NMR (DMSO-d$_6$) δ 0.39 (m, 2H), 0.63 (m, 2H), 1.12 (m, 1H), 2.85–3.20 (m, 7H), 3.50–3.65 (m, 3H), 4.11 (m, 1H), 4.24 (t, J=7 Hz, 2H), 4.46 (m, 1H), 6.97 (dd, J=8 Hz, 1 Hz, 1H), 7.23 (d, J=1 Hz, 1H), 7.52 (d, J=8 Hz, 1H), 11.14 (br s, 1H); HPLC-MS: m/z 357 (MH$^+$); Rf: 3.37 min.

Example 364

1-[4-(1-Ethylpropyl)piperazin-1-yl]-4-(3-fluoro-4-methoxyphenyl)-2-hydroxybutane-1,4-dione hydrochloride

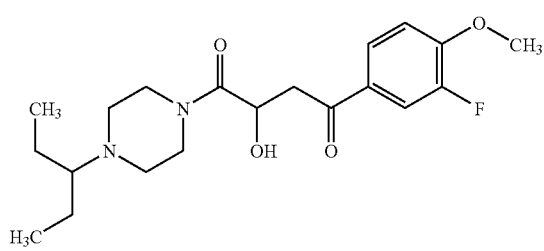

The acid required for this synthesis was prepared as in example 358.

$^1$H NMR (DMSO-d$_6$) δ 0.97 (t, J=7 Hz, 6H), 1.62 (m, 2H), 1.88 (m, 2H), 2.85–3.49 (m, 8H), 3.73 (m, 1H), 3.93 (s, 3H), 4.25–4.43 (m, 2H), 4.88 (m, 1H), 5.16 (br s, 1H), 7.29 (t, J=8 Hz, 1H), 7.72 (dd, J=8 Hz, 1 Hz, 1H), 7.83 (m, 1H), 10.76 (br s, 1H); HPLC-MS: m/z 381 (MH$^+$); Rf: 2.63 min.

Example 365

[4-(1-Ethylpropyl)piperazin-1-yl]-[5-(3-fluoro-4-methoxyphenyl)-2H-pyrazol-3-yl]methanone hydrochloride

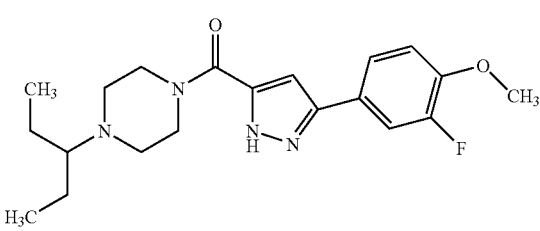

$^1$H NMR (DMSO-d$_6$) δ 0.97 (t, J=7 Hz, 6H), 1.65 (m, 2H), 1.89 (m, 2H), 3.02–3.56 (m, 6H), 3.78 (m, 1H), 3.89 (s, 3H), 4.61 (m, 1H), 5.09 (br s, 1H), 7.08 (br s, 1H), 7.26 (t, J=8 Hz, 1H), 7.62 (brd, J=7 Hz, 1H), 7.72 (brd, J=8 Hz, 1H), 10.53 (br s, 1H), 13.71 (br s, 1H); HPLC-MS: m/z 375 (MH$^+$); Rf: 2.90 min.

Example 366

3-(3,4-Dichlorophenoxy)-1-[4-(tetrahydropyran-4-yl)piperazin-1-yl]propan-1-one hydrochloride

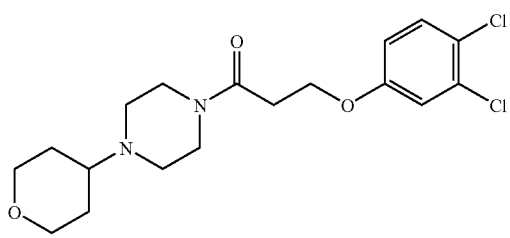

$^1$H NMR (DMSO-d$_6$) δ 1.71 (m, 2H), 2.00 (m, 2H), 2.80–3.68 (m, 11H), 4.00 (m, 2H), 4.12 (m, 1H), 4.25 (t, J=7 Hz, 2H), 4.49 (m, 1H), 7.02 (dd, J=8 Hz, 1 Hz, 1H), 7.25 (d, J=1 Hz, 1H), 7.58 (d, J=8 Hz, 1H), 11.25 (br s, 1H); HPLC-MS: m/z 387 (MH$^+$); Rf: 3.23 min.

Example 367

4-(4-Chlorophenyl)-1-(4-cyclopropylmethylpiperazin-1-yl)butan-1-one hydrochloride

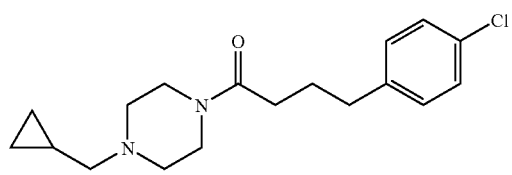

$^1$H NMR (DMSO-d$_6$) δ 0.39 (m, 2H), 0.63 (m, 2H), 1.10 (m, 1H), 1.79 (quint, J=7 Hz, 2H), 2.38 (m, 2H), 2.60 (t, J=7 Hz, 2H), 2.83–3.12 (m, 5H), 3.50 (m, 3H), 4.03 (m, 1H), 4.45 (m, 1H), 7.23 (d, J=8 Hz, 2H), 7.34 (d, J=8 Hz, 2H), 10.65 (br s, 1H); HPLC-MS: m/z 321 (MH$^+$); Rf: 3.23 min.

Example 368

4-(4-Chlorophenyl)-1-[4-(tetrahydropyran-4-yl)piperazin-1-yl]butan-1-one hydrochloride

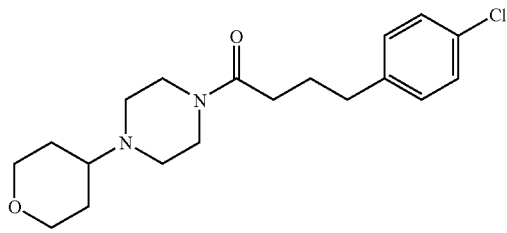

$^1$H NMR (DMSO-d$_6$) δ 1.68 (m, 2H), 1.81 (quint, J=7 Hz, 2H), 1.98 (m, 2H), 2.36 (m, 2H), 2.60 (t, J=7 Hz, 2H), 2.83–3.12 (m, 3H), 3.26–3.55 (m, 6H), 3.94–4.08 (m, 3H), 4.47 (m, 1H), 7.23 (d, J=8 Hz, 2H), 7.35 (d, J=8 Hz, 2H); HPLC-MS: m/z 351 (MH$^+$); Rf: 3.07 min.

Example 369

1-(4-Cyclopropylmethylpiperazin-1-yl)-2-(4'-fluorobiphenyl-4-yl)ethanone hydrochloride

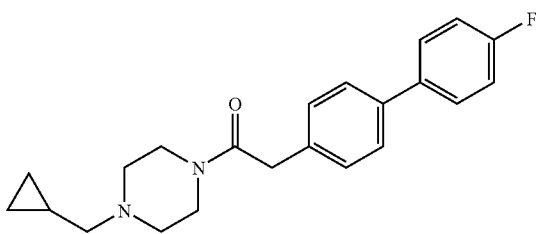

$^1$H NMR (DMSO-d$_6$) δ 0.39 (m, 2H), 0.63 (m, 2H), 1.10 (m, 1H), 2.89–3.22 (m, 5H), 3.53 (m, 3H), 3.79 (d, J=17 Hz, 1H), 3.85 (d, J=17 Hz, 1H), 4.21 (m, 1H), 4.47 (m, 1H), 7.29 (m, 4H), 7.60 (d, J=8 Hz, 2H), 7.69 (m, 2H), 10.20 (br s, 1H); HPLC-MS: m/z 353 (MH$^+$); Rf: 3.47 min.

Example 370

2-(4'-Fluorobiphenyl-4-yl)-1-[4-(tetrahydropyran-4-yl)piperazin-1-yl]ethanone hydrochloride

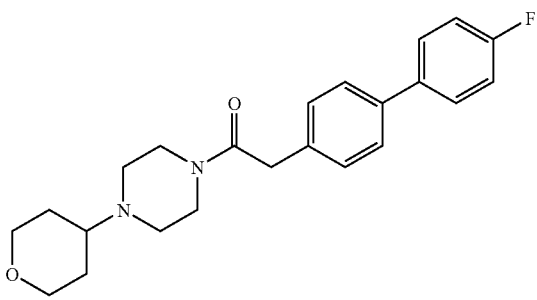

$^1$H NMR (DMSO-d$_6$) δ 1.70 (m, 2H), 2.00 (m, 2H), 2.95 (m, 2H), 3.15–3.70 (m, 7H), 3.75–3.89 (m, 2H), 3.98 (m, 2H), 4.21 (m, 1H), 4.48 (m, 1H), 7.29 (m, 4H), 7.60 (d, J=8 Hz, 2H), 7.69 (m, 2H); HPLC-MS: m/z 383 (MH$^+$); Rf: 3.30 min.

Example 371

1-(4-Cyclopropylmethylpiperazin-1-yl)-4-(3-fluoro-4-methoxyphenyl)butan-1-one hydrochloride

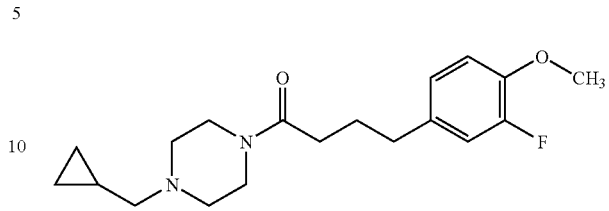

The acid required for this synthesis was prepared from 4-(3-fluoro-4-methoxyphenyl)-4-oxobutyric acid by reduction with triethylsilane/trifluoroacetic acid (70° C., 25 hours, 92% yield).

$^1$H NMR (DMSO-d$_6$) δ 0.39 (m, 2H), 0.63 (m, 2H), 1.10 (m, 1H), 1.79 (quint, J=7 Hz, 2H), 2.38 (m, 2H), 2.60 (t, J=7 Hz, 2H), 2.83–3.12 (m, 5H), 3.50 (m, 3H), 3.76 (s, 3H), 4.03 (m, 1H), 4.45 (m, 1H), 6.94 (br d, J=8 Hz, 1H), 7.05 (m, 2H), 11.05 (br s, 1H); HPLC-MS: m/z 335 (MH$^+$); Rf: 2.80 min.

Example 372

1-[4-(1-Ethylpropyl)piperazin-1-yl]-4-(3-fluoro-4-methoxyphenyl)-2-hydroxybutan-1-one hydrochloride

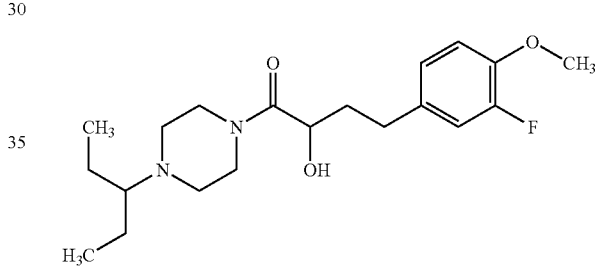

The acid required for this synthesis was prepared from 4-(3-fluoro-4-methoxyphenyl)-2,4-dioxobutyric acid (for preparation, see Example 361) by reduction with triethylsilane/trifluoroacetic acid (70° C., 17 hours, 88% yield).

$^1$H NMR (DMSO-d$_6$) δ 0.97 (t, J=7 Hz, 6H), 1.55–1.92 (m, 6H), 2.60 (m, 2H), 2.88–3.10 (m, 3H), 3.20–3.45 (m, 3H), 3.69 (m, 1H), 3.78 (s, 3H), 4.12–4.29 (m, 2H), 4.40 (m, 1H), 5.25 (br s, 1H), 6.96 (m, 1H), 7.05 (m, 2H), 10.85 (br s, 1H); HPLC-MS: m/z 367 (MH$^+$); Rf: 2.70 min.

Example 373

1-(4-Cyclopent-3-enylpiperazin-1-yl)-4-(3-fluoro-4-methoxyphenyl)butan-1-one hydrochloride

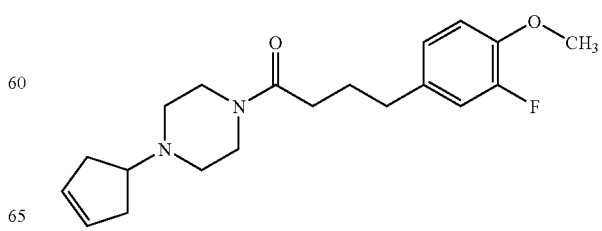

$^1$H NMR (DMSO-d$_6$) δ 1.79 (quint, J=7 Hz, 2H), 2.34 (t, J=7 Hz, 2H), 2.49–3.15 (m, 9H), 3.31–3.60 (m, 3H), 3.80 (s, 3H), 3.89 (m, 1H), 4.01 (m, 1H), 4.47 (m, 1H), 5.73 (s, 2H), 6.94 (br d, J=8 Hz, 1H), 7.05 (m, 2H), 11.61 (br s, 1H); HPLC-MS: m/z 347 (MH$^+$); Rf: 2.87 min.

Example 374

4-(3,4-Dichlorophenyl)-1-[4-(1-ethylpropyl)piperazin-1-yl]but-2-en-1-one hydrochloride

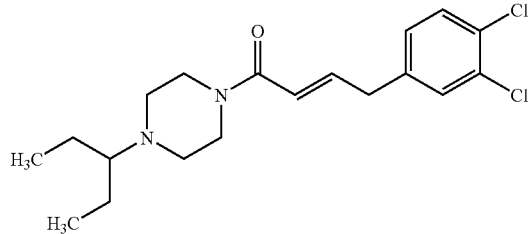

The acid required for this synthesis was prepared from 4-(3,4-dichlorophenyl)-4-oxo-2-butenoic acid (prepared as described in DE 2047806) by reduction with triethylsilane/trifluoroacetic acid (70° C., 24 hours, 41% yield).

$^1$H NMR (DMSO-d$_6$) δ 0.97 (t, J=7 Hz, 6H), 1.60 (m, 2H), 1.85 (m, 2H), 2.91–3.25 (m, 4H), 3.38 (m, 4H), 3.65 (m, 1H), 4.05 (m, 1H), 4.45 (m, 1H), 6.47 (m, 2H), 7.43 (dd, J=8 Hz, 1 Hz, 1H), 7.58 (d, J=8 Hz, 1H), 7.71 (d, J=1 Hz, 1H), 10.50 (br s, 1H); HPLC-MS: m/z 369 (MH$^+$); Rf: 2.95 min.

Example 375

4-(3,4-Dichlorophenyl)-1-[4-(1-ethylpropyl)piperazin-1-yl]-4-hydroxybut-2-en-1-one hydrochloride

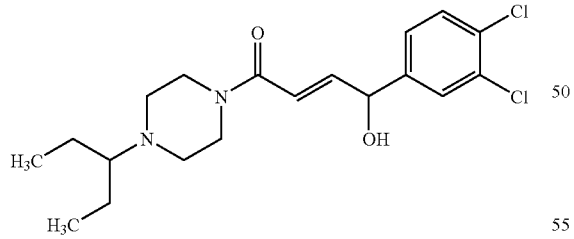

The acid required for this synthesis was prepared from 4-(3,4-dichlorophenyl)-4-oxo-2-butenoic acid (prepared as described in DE 2047806) by reduction with sodium borohydride.

$^1$H NMR (main conformer, DMSO-d$_6$) δ 0.95 (t, J=7 Hz, 6H), 1.60 (m, 2H), 1.85 (m, 2H), 2.88–3.30 (m, 4H), 3.40 (m, 3H), 3.65 (m, 1H), 4.20 (m, 1H), 4.47 (m, 1H), 5.33 (br s, 1H), 6.07 (br s, 1H), 6.72 (s, 2H), 7.34 (m, 1H), 7.60 (m, 2H), 10.40 (br s, 1H); HPLC-MS: m/z 385 (MH$^+$); Rf: 3.10 min.

Example 376

1-(4-Cyclopropylmethylpiperazin-1-yl)-2-(2-fluorobiphenyl-4-yl)ethanone hydrochloride

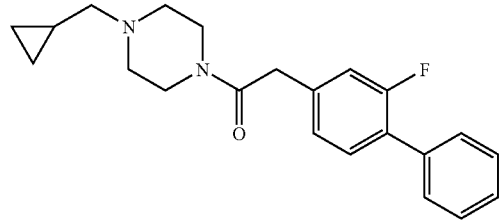

The acid required for this synthesis was prepared according to the literature: NL 6500865.

$^1$H NMR (DMSO-d$_6$) δ 0.39 (m, 2H), 0.63 (m, 2H), 1.10 (m, 1H), 2.89–3.22 (m, 5H), 3.53 (m, 3H), 3.83 (m, 2H), 4.21 (m, 1H), 4.47 (m, 1H), 7.30 (m, 4H), 7.40 (m, 1H), 7.50 (m, 3H), 10.75 (br s, 1H); HPLC-MS: m/z 353 (MH$^+$); Rf: 2.61 min.

Example 377

1-(4-Cyclopropylmethylpiperazin-1-yl)-4-(3,4-dichlorophenyl)but-2-en-1-one hydrochloride

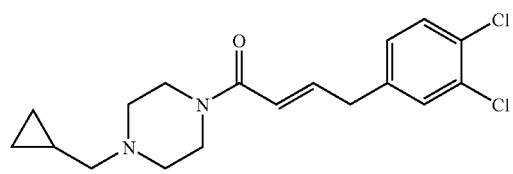

$^1$H NMR (DMSO-d$_6$) δ 0.39 (m, 2H), 0.63 (m, 2H), 1.10 (m, 1H), 2.85–3.25 (m, 4H), 3.30–3.68 (m, 6H), 4.05 (m, 1H), 4.45 (m, 1H), 6.45 (m, 2H), 7.43 (dd, J=8 Hz, 1 Hz, 1H), 7.58 (d, J=8 Hz, 1H), 7.71 (d, J=1 Hz, 1H), 11.15 (br s, 1H); HPLC-MS: m/z 353 (MH$^+$); Rf: 2.66 min.

Example 378

4-(1-Ethylpropyl)piperazine-1-carboxylic acid 3-trifluoromethylphenyl ester hydrochloride

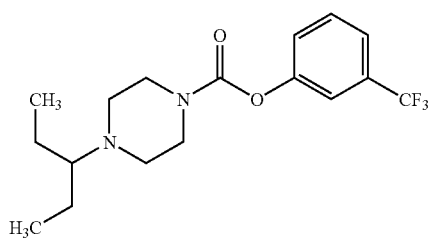

To a stirred mixture of 1-(1-ethylpropyl)piperazine (175 μl, 1.0 mmol) and dry DCM (10 ml) was added 3-trifluoromethylphenyl chloroformate (250 mg, 1.1 mmol). The mixture was stirred overnight at room temperature and then diluted with DCM (50 ml). The reaction mixture was washed with 1 N NaOH (3×25 ml) and water (2×25 ml). The organic solution was concentrated and the residue was dissolved in a 0.5 N HCl solution (15 ml) and a small portion of acetonitrile. The acidic solution was concentrated and stirred with ethyl acetate (15 ml). The solid was isolated and dried to give 330 mg (86%) of the title compound as a solid. M.p. 260–261° C.

$^1$H NMR (400 MHz, DMSO-$d_6$): δ 0.98 (t, 6H), 1.63 (hept, 2H), 1.86–1.98 (m, 2H), 3.03–3.12 (m, 1H), 3.12–3.31 (m, 2H), 3.41–3.49 (m, 2H), 3.52–3.85 (m, 2H), 4.05–4.35 (m, 2H), 7.47–7.70 (m, 4H), 11.0 (brs, 1H).

Example 379

4-(1-Ethylpropyl)piperazine-1-carboxylic acid naphthalen-1-yl ester hydrochloride

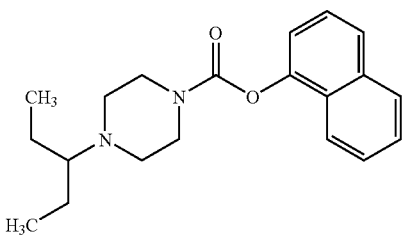

To a stirred mixture of 1-(1-ethylpropyl)piperazine (175 μl, 1.0 mmol) and dry DCM (10 ml) was added 1-napthalenyl chloroformate (225 mg, 1.1 mmol). The mixture was stirred overnight at room temperature and then diluted with DCM (50 ml). The reaction mixture was washed with 1 N NaOH (3×25 ml) and water (2×25 ml). The organic solution was concentrated and the residue was dissolved in a 0.5 N HCl solution (15 ml) and a small portion of acetonitrile. The acidic solution was concentrated and stirred with ethyl acetate (15 ml). The solid was isolated and dried to give 310 mg (85%) of the title compound as a solid.

M.p. 288–290° C.

$^1$H NMR (400 MHz, DMSO-$d_6$): δ 1.00 (t, 6H), 1.63 (hept, 2H), 1.86–2.02 (m, 2H), 3.07–3.18 (m, 1H), 3.18–3.42 (m, 2H), 3.42–3.55 (m, 2H), 3.55–3.73 (m, 1H), 3.78–3.95 (m, 1H), 4.05–4.25 (m, 1H), 4.35–4.55 (m, 1H), 7.35 (d, 1H), 7.53 (t, 1H), 7.56–7.7.61 (m, 2H), 7.85 (d, 1H), 7.90–8.05 (m, 2H), 10.75 (br s, 1H).

Example 380

4-(1-Ethylpropyl)piperazine-1-carboxylic acid 4-fluorophenyl ester hydrochloride

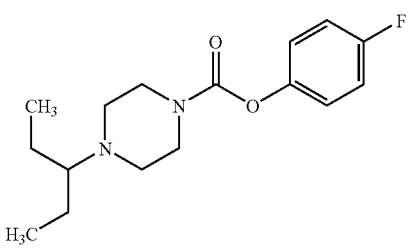

To a stirred mixture of 1-(1-ethylpropyl)piperazine (350 μl, 2.0 mmol) and dry DCM (15 ml) was added 4-fluorophenyl chloroformate (350 mg, 2.0 mmol). The mixture was stirred overnight at room temperature and then diluted with DCM (50 ml). The reaction mixture was washed with 1 N NaOH (3×25 ml) and water (2×25 ml). The organic solution was concentrated and the residue was re-evaporated twice with acetonitrile to give 590 mg of the free base. The hydrochloride salt was prepared from 465 mg free base by addition of a 0.5 N HCl solution (15 ml) and a small portion of acetonitrile. The acidic solution was concentrated and stirred with ethyl acetate (15 ml). The solid was isolated and dried to give 470 mg (90%) of the title compound as a solid. M.p. 275–277° C.

$^1$H NMR (400 MHz, DMSO-$d_6$): δ 0.98 (t, 6H), 1.64 (hept, 2H), 1.85–1.95 (m, 2H), 3.02–3.11 (m, 1H), 3.11–3.28 (m, 2H), 3.38–3.46 (m, 2H), 3.50–3.80 (m, 2H), 4.00–4.30 (m, 2H), 7.18–7.26 (m, 4H), 10.85 (brs, 1H).

Example 381

4-(1-Ethylpropyl)piperazine-1-carboxylic acid 2-nitrophenyl ester hydrochloride

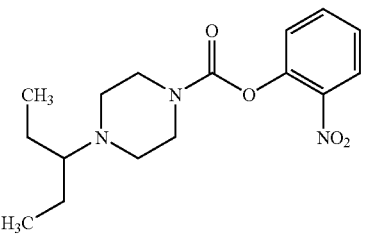

To a stirred mixture of 1-(1-ethylpropyl)piperazine (175 μl, 1.0 mmol) and dry DCM (10 ml) was added 2-nitrophenyl chloroformate (201 mg, 1.0 mmol). The mixture was stirred overnight at room temperature and then diluted with DCM (50 ml). The reaction mixture was washed with 1 N NaOH (3×25 ml) and water (2×25 ml). The organic solution was concentrated and the residue was dissolved in a 0.5 N HCl solution (15 ml). The acidic solution was concentrated and stirred with ethyl acetate (15 ml). The solid was isolated and dried to give 310 mg (86%) of the title compound as a solid. M.p. 251–253° C.

$^1$H NMR (400 MHz, DMSO-$d_6$): δ 0.96 (t, 6H), 1.65 (hept, 2H), 1.83–1.95 (m, 2H), 3.06–3.25 (m, 3H), 3.42–3.53 (m, 2H), 3.53–3.83 (m, 2H), 4.02–4.13 (m, 1H), 4.20–4.34 (m, 1H), 7.50–7.55 (m, 2H), 7.83 (t, 1H), 8.13 (d, 1H), 10.9 (brs, 1H).

Example 382

4-(1-Ethylpropyl)piperazine-1-carboxylic acid 4-methoxycarbonylphenyl ester hydrochloride

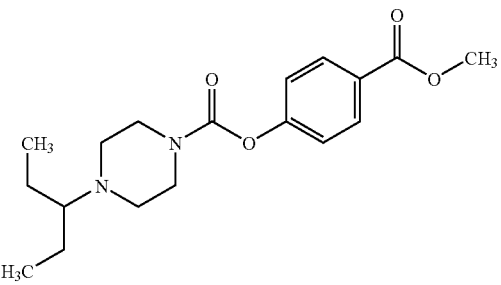

To a stirred mixture of 1-(1-ethylpropyl)piperazine (350 μl, 2.0 mmol) and dry DCM (15 ml) was added 4-methoxycarbonylphenyl chloroformate (430 mg, 2.0 mmol). The

Example 383

4-(1-Ethylpropyl)piperazine-1-carboxylic acid 2-(3,4-dimethoxyphenyl)ethyl ester hydrochloride

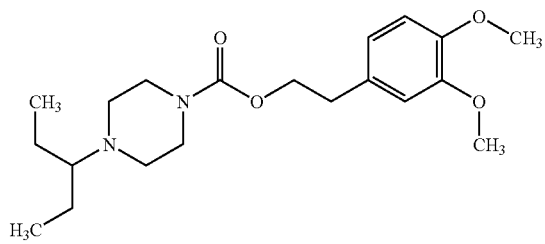

A stirred mixture of 2-(3,4-dimethoxyphenyl)ethanol (1.02 g, 5.6 mmol) and dry DCM (35 ml) was placed on an ice-bath under an atmosphere of nitrogen. 4-Nitrophenyl chloroformate (1.1 g, 5.5 mmol) was added and the mixture was stirred for 15 minutes. Pyridine (0.48 ml) was added and stirring was continued on an ice-bath for 4 hours. The reaction mixture was diluted with DCM (40 ml) and then washed with water (2×30 ml) and then dried (MgSO$_4$). The solvent was evaporated to give an oily residue of crude 2-(3,4-dimethoxyphenyl)ethyl 4-nitrophenylcarbonate.

The above carbonate was dissolved in DCM (25 ml) and 1-(1-ethylpropyl)piperazine (800 mg, 5.1 mmol) was added. The mixture was stirred overnight at room temperature and then diluted with DCM (50 ml). The reaction mixture was washed with 1 N NaOH (3×25 ml) and water (3×25 ml). The organic phase was dried (MgSO$_4$) and the solvent was evaporated. The residue was dissolved into a 1 N HCl solution and the acidic solution was evaporated to give a residue that was re-evaporated several times with acetonitrile. The residue was crystallised from ethyl acetate to give 1.75 g (78%) of the title compound as a solid. M.p. 161–162° C.

$^1$H NMR (400 MHz, DMSO-d$_6$): δ 0.94 (t, 6H), 1.55–1.65 (m, 2H), 1.80–1.92 (m, 2H), 2.82 (t, 2H), 2.92–3.05 (m, 3H), 3.32–3.53 (m, 4H), 3.71 (s, 3H), 3.73 (s, 3H), 3.93–4.05 (m, 2H), 4.21 (t, 2H), 6.72–6.87 (m, 3H), 10.75 (brs, 1H).

mixture was stirred overnight at room temperature and then diluted with DCM (50 ml). The reaction mixture was washed with 1 N NaOH (3×25 ml) and water (2×25 ml). The organic solution was concentrated and re-evaporated twice with acetonitrile. The residue was dissolved in a 0.5 N HCl solution (15 ml) and a small portion of acetonitrile. The acidic solution was concentrated and stirred with ethyl acetate (15 ml). The solid was isolated and dried to give 670 mg (90%) of the title compound as a solid. M.p. 248° C. decomp.

$^1$H NMR (400 MHz, DMSO-d$_6$): δ 0.97 (t, 6H), 1.63 (hept, 2H), 1.85–1.95 (m, 2H), 3.02–3.11 (m, 1H), 3.11–3.30 (m, 2H), 3.40–3.48 (m, 2H), 3.50–3.80 (m, 2H), 3.85 (s, 3H), 4.05–4.33 (m, 2H), 7.33 (d, 2H), 8.00 (d, 2H)), 10.7 (brs, 1H).

Example 384

4-(1-Ethylpropyl)piperazine-1-carboxylic acid 2-(4-methanesulfonylphenoxy)ethyl ester hydrochloride

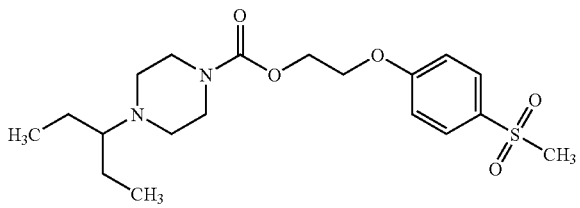

Step 1:

2-(4-Methanesulfonylphenoxy)ethanol

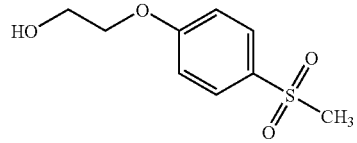

A mixture of 4-methanesulfonylphenol (1.72 g, 10 mmol), DMA (25 ml) and 4 N sodium hydroxide (7 ml) was stirred under an atmosphere of nitrogen. 2-(2-Pyranyloxy)ethylbromide (2.8 g, 14 mmol) was added dropwise and then the mixture was stirred overnight at ambient temperature. The solvent was evaporated in vacuo and the residue was taken up in water (100 ml). The aqueous mixture was extracted with ethyl acetate (2×100 ml) and the combined organic extracts were washed with a 0.5 N sodium hydroxide solution and brine. The organic phase was concentrated to give an oily residue that was dissolved in methanol (50 ml). A solution of 5 N HCl (20 ml) was added and the mixture was stirred at ambient temperature for 2 hours. The reaction mixture was concentrated and a small portion of ice was added followed by 4 N sodium hydroxide until approximately pH 10. The alkaline mixture was extracted with ethyl acetate (3×75 ml) and the combined organic extracts were washed with water and dried (MgSO$_4$). The solvent was evaporated to give 0.82 g (38%) of 2-(4-methanesulfonylphenoxy)ethanol. M.p. 89–90° C.

$^1$H NMR (400 MHz, CDCl$_3$): δ 2.11 (t, 1H), 3.03 (s, 3H), 4.02 (q, 2H), 4.18 (t, 2H), 7.05 (d, 2H), 7.87 (d, 2H).

Step 2:

By a similar procedure as described in Example 333 and starting from 1-(1-ethylpropyl)piperazine (350 mg, 2.2 mmol) and 2-(4-methanesulfonylphenyl)ethanol (540 mg, 2.5 mmol), 875 mg (89%) of the title compound was isolated as a solid.

$^1$H NMR (400 MHz, DMSO-d$_6$) δ 0.94 (t, 6H), 1.53–1.67 (m, 2H), 1.77–1.90 (m, 2H), 2.95–3.08 (m, 3H), 3.17 (s, 3H), 3.30–3.65 (m, 4H), 3.92–4.07 (m, 2H), 4.3–4.4 (m, 4H), 7.19 (d, 1H), 7.84 (d, 1H), 10.7 (brs, 1H).

Pharmacological Methods

The ability of the compounds to interact with the histamine H3 receptor can be determined by the following in vitro binding assays.

Binding Assay I

Rat cerebral cortex is homogenized in ice cold K-Hepes, 5 mM $MgCl_2$ pH 7.1 buffer. After two differential centrifugations the last pellet is resuspended in fresh Hepes buffer containing 1 mg/ml bacitracin. Aliquots of the membrane suspension (400 µg/ml) are incubated for 60 min at 25° C. with 30 pM [$^{125}$I]-iodoproxifan, a known histamine H3 receptor antagonist, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analyzed by nonlinear regression analysis.

Binding Assay II

The H3-receptor agonist ligand R-α-methyl[$^3$H]histamine (RAMHA) is incubated with isolated rat cortex cell-membranes at 25° C. for 1 hour, followed by a filtration of the incubate through Whatman GF/B filters. Radioactivity retained on the filters is measured using a beta counter.

Male Wistar rats (150–200 g) are decapitated and cerebral cortex is quickly dissected out and frozen immediately on dry ice. Tissue is kept at −80° C. until membrane preparation. During the membrane preparation the tissue is kept on ice all the time. Rat cerebral cortex is homogenized in 10 volumes (w/w) ice-cold Hepes buffer (20 mM Hepes, 5 mM $MgCl_2$ pH 7.1 (KOH)+1 mg/ml bacitracin) using an Ultra-Turrax homogenizer for 30 seconds. The homogenate is centrifuged at 140 g in 10 min. The supernatant is transferred to a new test tube and centrifuged for 30 min at 23 000 g. Pellet is resuspended in 5–10 ml Hepes buffer, homogenized and centrifuged for 10 min at 23 000 g. This short centrifugation step is repeated twice. After the last centrifugation the pellet is resuspended in 2–4 ml Hepes buffer and the protein concentration is determined. The membranes are diluted to a protein concentration of 5 mg/ml using Hepes buffer, aliquoted and stored at −80° C. until use.

50 µl test-compound, 100 µl membrane (200 µg/ml), 300 µl Hepes buffer and 50 µl R-α-methyl[$^3$H]histamine (1 nM) are mixed in a test tube. The compounds to be tested are dissolved in DMSO and further diluted in $H_2O$ to the desired concentrations. Radioligand and membranes are diluted in Hepes buffer+1 mg/ml bacitracin. The mixture is incubated for 60 min at 25° C. Incubation is terminated by adding 5 ml ice-cold 0.9% NaCl, followed by rapid filtration through Whatman GF/B filters pre-treated for 1 hour with 0.5% polyethyleneimine. The filters are washed with 2×5 ml ice-cold NaCl. To each filter a 3 ml scintillation cocktail is added and the radioactivity retained is measured with a Packard Tri-Carb beta counter.

$IC_{50}$ values are calculated by non-linear regression analysis of binding curves (6 points minimum) using the windows program GraphPad Prism, GraphPad software, USA.

Binding Assay III

The human H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM (GIBCO-BRL) with glutamax, 10% foetal calf serum, 1% penicillin/streptavidin and 1 mg/ml G 418 at 37° C. and 5% $CO_2$. Before harvesting, the confluent cells are rinsed with PBS and incubated with Versene (proteinase, GIBCO-BRL) for approximately 5 min. The cells are flushed with PBS and DMEM and the cellsuspension collected in a tube and centrifuged for 5–10 min at 1500 rpm in a Heraeus Sepatech Megafuge 1.0. The pellet is resuspended in 10–20 vol. Hepes buffer (20 mM Hepes, 5 mM $MgCl_2$, pH 7.1 (KOH)) and homogenized for 10–20 seconds using an Ultra-Turrax homogenizer. The homogenate is centrifuged for 30 min at 23 000 g. The pellet is resuspended in 5–10 ml Hepes buffer, homogenized 5–10 seconds with the Ultra-Turrax and centrifuged for 10 min at 23 000 g. Following this centrifugation step, the membrane pellet is resuspended in 2–4 ml Hepes buffer, homogenized with a syringe or teflonhomogenizer, and the protein concentration determined. The membranes are diluted to a protein concentration of 1–5 mg/ml in Hepes buffer, aliquoted and kept at −80° C. until use.

Aliquots of the membrane suspension are incubated for 60 min at 25° C. with 30 pM [$^{125}$I]-iodoproxifan, a known compound with high affinity for the H3 receptor, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analysed by nonlinear regression analysis.

When tested, the present compounds of the formula (I) generally show a high binding affinity to the histamine H3 receptor.

Preferably, the compounds according to the invention have an $IC_{50}$ value as determined by one or more of the assays of less than 10 µM, more preferred of less than 1 µM, and even more preferred of less than 500 nM, such as of less than 100 nM.

Functional Assay I

The ability of the compounds to interact with the histamine H3 receptor as agonists, inverse agonists and/or antagonists, is determined by an in vitro functional assay utilizing membranes from HEK 293 cell expressing the human H3 receptors.

The H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM with glutamax, 10% foetal calf serum, 1% penicillin/streptavidin and 1 mg/ml G 418 at 37° C. and 5% $CO_2$.

The H3 receptor expressing cells are washed once with phosphate buffered saline (PBS) and harvested using versene (GIBCO-BRL). PBS is added and the cells are centrifuged for 5 min at 188 g. The cell pellet is resuspended in stimulation buffer to a concentration of $1 \times 10^6$ cells/ml. cAMP accumulation is measured using the Flash Plate® cAMP assay (NEN™ Life Science Products). The assay is generally performed as described by the manufacturer. Briefly, 50 µl cell suspension is added to each well of the Flashplate which also contained 25 µl 40 µM isoprenaline, to stimulate cAMP generation, and 25 µl of test compound (either agonists or inverse agonists alone, or agonist and antagonist in combination). The assay can be run in "agonist-mode" which means that the test compound is added, in increasing concentration, on its own, to the cells, and cAMP is measured. If cAMP goes up, it is an inverse agonist; if cAMP does not change, it is a neutral antagonist, and if cAMP goes down, it is an agonist. The assay can also be run in the "antagonist-mode" which means that a test compound is added, in increasing concentrations, together with increasing concentrations of a known H3 agonist (eg RAMHA). If the compound is an antagonist, increasing concentrations of it cause a right-ward shift in the H3-agonist's dose-response curves. The final volume in each well is 100 µl. Test compounds are dissolved in DMSO and diluted in H$_2$O. The mixture is shaken for 5 min, and allowed to stand for 25 min at room temperature. The reaction is stopped with 100 µl "Detection Mix" per well. The plates are then sealed with plastic, shaken for 30 min, allowed to stand overnight, and finally the radioactivity is counted in the Cobra II auto gamma topcounter. EC$_{50}$ values are calculated by non-linear regression analysis of dose response curves (6 points minimum) using GraphPad Prism. Kb values are calculated by Schild plot analysis.

Functional Assay II

The ability of the present compounds to reduce weight is determined using the in vivo open cage Schedule-fed rat model.

The ability of the compounds to bind and interact with the human, monkey or rat H3 receptor as agonists, inverse agonists and/or antagonists, is determined by a functional assay, named [$^{35}$] GTPγS assay.

The human H3 receptor has the following sequence (SEQ ID NO:1):

Met-Glu-Arg-Ala-Pro-Pro-Asp-Gly-Pro-Leu-Asn-Ala-Ser-Gly-Ala-Leu-Ala-

Gly-Glu-Ala-Ala-Ala-Gly-Gly-Ala-Arg-Gly-Phe-Ser-Ala-Ala-Trp-Thr-

Ala-Val-Leu-Ala-Ala-Leu-Met-Ala-Leu-Leu-Ile-Val-Ala-Thr-Val-Leu-Gly-

Asn-Ala-Leu-Val-Met-Leu-Ala-Phe-Val-Ala-Asp-Ser-Ser-Leu-Arg-Thr-Gln-

Asn-Asn-Phe-Phe-Leu-Leu-Asn-Leu-Ala-Ile-Ser-Asp-Phe-Leu-Val-Gly-Ala-

Phe-Cys-Ile-Pro-Leu-Tyr-Val-Pro-Tyr-Val-Leu-Thr-Gly-Arg-Trp-Thr-Phe-

Gly-Arg-Gly-Leu-Cys-Lys-Leu-Trp-Leu-Val-Val-Asp-Tyr-Leu-Leu-Cys-Thr-

Ser-Ser-Ala-Phe-Asn-Ile-Val-Leu-Ile-Ser-Tyr-Asp-Arg-Phe-Leu-Ser-Val-

Thr-Arg-Ala-Val-Ser-Tyr-Arg-Ala-Gln-Gln-Gly-Asp-Thr-Arg-Arg-Ala-Val-

Arg-Lys-Met-Leu-Leu-Val-Trp-Val-Leu-Ala-Phe-Leu-Leu-Tyr-Gly-Pro-Ala-

Ile-Leu-Ser-Trp-Glu-Tyr-Leu-Ser-Gly-Gly-Ser-Ser-Ile-Pro-Glu-Gly-His-

Cys-Tyr-Ala-Glu-Phe-Phe-Tyr-Asn-Trp-Tyr-Phe-Leu-Ile-Thr-Ala-Ser-Thr-

Leu-Glu-Phe-Phe-Thr-Pro-Phe-Leu-Ser-Val-Thr-Phe-Phe-Asn-Leu-Ser-Ile-

Tyr-Leu-Asn-Ile-Gln-Arg-Arg-Thr-Arg-Leu-Arg-Leu-Asp-Gly-Ala-Arg-Glu-

Ala-Ala-Gly-Pro-Glu-Pro-Pro-Pro-Glu-Ala-Gln-Pro-Ser-Pro-Pro-Pro-Pro-

Pro-Gly-Cys-Trp-Gly-Cys-Trp-Gln-Lys-Gly-His-Gly-Glu-Ala-Met-Pro-Leu-

His-Arg-Tyr-Gly-Val-Gly-Glu-Ala-Ala-Val-Gly-Ala-Glu-Ala-Gly-Glu-Ala-

Thr-Leu-Gly-Gly-Gly-Gly-Gly-Gly-Ser-Val-Ala-Ser-Pro-Thr-Ser-Ser-

Ser-Gly-Ser-Ser-Ser-Arg-Gly-Thr-Glu-Arg-Pro-Arg-Ser-Leu-Lys-Arg-Gly-

Ser-Lys-Pro-Ser-Ala-Ser-Ser-Ala-Ser-Leu-Glu-Lys-Arg-Met-Lys-Met-Val-

Ser-Gln-Ser-Phe-Thr-Gln-Arg-Phe-Arg-Leu-Ser-Arg-Asp-Arg-Lys-Val-Ala-

Lys-Ser-Leu-Ala-Val-Ile-Val-Ser-Ile-Phe-Gly-Leu-Cys-Trp-Ala-Pro-Tyr-

Thr-Leu-Met-Ile-Ile-Arg-Ala-Ala-Cys-His-Gly-His-Cys-Val-Pro-Asp-

Tyr-Trp-Tyr-Glu-Thr-Ser-Phe-Trp-Leu-Leu-Trp-Ala-Asn-Ser-Ala-Val-Asn-

Pro-Val-Leu-Tyr-Pro-Leu-Cys-His-His-Ser-Phe-Arg-Arg-Ala-Phe-Thr-Lys-

Leu-Leu-Cys-Pro-Gln-Lys-Leu-Lys-Ile-Gln-Pro-His-Ser-Ser-Leu-Glu-His-

Cys-Trp-Lys.

The monkey H3 receptor has the following sequence (SEQ ID NO:2):

Met-Glu-Arg-Ala-Pro-Pro-Asp-Gly-Pro-Leu-Asn-Ala-Ser-Gly-Ala-Leu-Ala-
Gly-Glu-Ala-Ala-Ala-Gly-Gly-Ala-Arg-Gly-Phe-Ser-Ala-Ala-Trp-Thr-
Ala-Val-Leu-Ala-Ala-Leu-Met-Ala-Leu-Leu-Ile-Val-Ala-Thr-Val-Leu-Gly-
Asn-Ala-Leu-Val-Met-Leu-Ala-Phe-Val-Ala-Asp-Ser-Ser-Leu-Arg-Thr-Gln-
Asn-Asn-Phe-Phe-Leu-Leu-Asn-Leu-Ala-Ile-Ser-Asp-Phe-Leu-Val-Gly-Ala-
Phe-Cys-Ile-Pro-Leu-Tyr-Val-Pro-Tyr-Val-Leu-Thr-Gly-Arg-Trp-Thr-Phe-
Gly-Arg-Gly-Leu-Cys-Lys-Leu-Trp-Leu-Val-Val-Asp-Tyr-Leu-Leu-Cys-Thr-
Ser-Ser-Ala-Phe-Asn-Ile-Val-Leu-Ile-Ser-Tyr-Asp-Arg-Phe-Leu-Ser-Val-
Thr-Arg-Ala-Val-Ser-Tyr-Arg-Ala-Gln-Gln-Gly-Asn-Thr-Arg-Arg-Ala-Val-
Arg-Lys-Met-Leu-Leu-Val-Trp-Val-Leu-Ala-Phe-Leu-Leu-Tyr-Gly-Pro-Ala-
Ile-Leu-Ser-Trp-Glu-Tyr-Leu-Ser-Gly-Gly-Ser-Ser-Ile-Pro-Glu-Gly-His-
Cys-Tyr-Ala-Glu-Phe-Phe-Tyr-Asn-Trp-Tyr-Phe-Leu-Ile-Thr-Ala-Ser-Thr-
Leu-Glu-Phe-Phe-Thr-Pro-Phe-Leu-Ser-Val-Thr-Phe-Phe-Asn-Leu-Ser-Ile-
Tyr-Leu-Asn-Ile-Gln-Arg-Arg-Thr-Arg-Leu-Arg-Leu-Asp-Gly-Ala-Arg-Glu-
Ala-Gly-Gly-Pro-Glu-Pro-Pro-Pro-Glu-Ala-Gln-Pro-Ser-Pro-Pro-Pro-Pro-
Pro-Gly-Cys-Trp-Gly-Cys-Trp-Gln-Lys-Gly-His-Gly-Glu-Ala-Met-Pro-Leu-
His-Arg-Tyr-Gly-Val-Gly-Glu-Ala-Ala-Ala-Gly-Ala-Glu-Ala-Gly-Glu-Thr-
Ala-Leu-Gly-Gly-Gly-Gly-Gly-Gly-Ser-Ala-Ala-Ser-Pro-Thr-Ser-Ser-
Ser-Gly-Ser-Ser-Ser-Arg-Gly-Thr-Glu-Arg-Pro-Arg-Ser-Leu-Lys-Arg-Gly-
Ser-Lys-Pro-Ser-Ala-Ser-Ser-Ala-Ser-Leu-Glu-Lys-Arg-Met-Lys-Met-Val-
Ser-Gln-Ser-Phe-Thr-Gln-Arg-Phe-Arg-Leu-Ser-Arg-Asp-Arg-Lys-Val-Ala-
Lys-Ser-Leu-Ala-Val-Ile-Val-Ser-Ile-Phe-Gly-Leu-Cys-Trp-Ala-Pro-Tyr-
Thr-Leu-Leu-Met-Ile-Ile-Arg-Ala-Ala-Cys-His-Gly-His-Cys-Val-Pro-Asp-
Tyr-Trp-Tyr-Glu-Thr-Ser-Phe-Trp-Leu-Leu-Trp-Ala-Asn-Ser-Ala-Val-Asn-
Pro-Val-Leu-Tyr-Pro-Leu-Cys-His-His-Ser-Phe-Arg-Arg-Ala-Phe-Thr-Lys-
Leu-Leu-Cys-Pro-Gln-Lys-Leu-Lys-Ile-Gln-Pro-His-Ser-Ser-Leu-Glu-Gln-
Cys-Trp-Lys.

The rat H3 receptor has the following sequence (SEQ ID NO:3):

Met-Glu-Arg-Ala-Pro-Pro-Asp-Gly-Leu-Met-Asn-Ala-Ser-Gly-Thr-Leu-Ala-
Gly-Glu-Ala-Ala-Ala-Gly-Gly-Ala-Arg-Gly-Phe-Ser-Ala-Ala-Trp-Thr-
Ala-Val-Leu-Ala-Ala-Leu-Met-Ala-Leu-Leu-Ile-Val-Ala-Thr-Val-Leu-Gly-
Asn-Ala-Leu-Val-Met-Leu-Ala-Phe-Val-Ala-Asp-Ser-Ser-Leu-Arg-Thr-Gln-
Asn-Asn-Phe-Phe-Leu-Leu-Asn-Leu-Ala-Ile-Ser-Asp-Phe-Leu-Val-Gly-Ala-
Phe-Cys-Ile-Pro-Leu-Tyr-Val-Pro-Tyr-Val-Leu-Thr-Gly-Arg-Trp-Thr-Phe-
Gly-Arg-Gly-Leu-Cys-Lys-Leu-Trp-Leu-Val-Val-Asp-Tyr-Leu-Leu-Cys-Ala-
Ser-Ser-Val-Phe-Asn-Ile-Val-Leu-Ile-Ser-Tyr-Asp-Arg-Phe-Leu-Ser-Val-

-continued
```
Thr-Arg-Ala-Val-Ser-Tyr-Arg-Ala-Gln-Gln-Gly-Asp-Thr-Arg-Ala-Val-
Arg-Lys-Met-Ala-Leu-Val-Trp-Val-Leu-Ala-Phe-Leu-Leu-Tyr-Gly-Pro-Ala-
Ile-Leu-Ser-Trp-Glu-Tyr-Leu-Ser-Gly-Gly-Ser-Ser-Ile-Pro-Glu-Gly-His-
Cys-Tyr-Ala-Glu-Phe-Phe-Tyr-Asn-Trp-Tyr-Phe-Leu-Ile-Thr-Ala-Ser-Thr-
Leu-Glu-Phe-Phe-Thr-Pro-Phe-Leu-Ser-Val-Thr-Phe-Phe-Asn-Leu-Ser-Ile-
Tyr-Leu-Asn-Ile-Gln-Arg-Arg-Thr-Arg-Leu-Arg-Leu-Asp-Gly-Gly-Arg-Glu-
Ala-Gly-Pro-Glu-Pro-Pro-Pro-Asp-Ala-Gln-Pro-Ser-Pro-Pro-Ala-Pro-
Pro-Ser-Cys-Trp-Gly-Cys-Trp-Pro-Lys-Gly-His-Gly-Glu-Ala-Met-Pro-Leu-
His-Arg-Tyr-Gly-Val-Gly-Glu-Ala-Gly-Pro-Gly-Val-Glu-Ala-Gly-Glu-Ala-
Ala-Leu-Gly-Gly-Gly-Ser-Gly-Gly-Gly-Ala-Ala-Ala-Ser-Pro-Thr-Ser-Ser-
Ser-Gly-Ser-Ser-Ser-Arg-Gly-Thr-Glu-Arg-Pro-Arg-Ser-Leu-Lys-Arg-Gly-
Ser-Lys-Pro-Ser-Ala-Ser-Ser-Ala-Ser-Leu-Glu-Lys-Arg-Met-Lys-Met-Val-
Ser-Gln-Ser-Ile-Thr-Gln-Arg-Phe-Arg-Leu-Ser-Arg-Asp-Lys-Lys-Val-Ala-
Lys-Ser-Leu-Ala-Ile-Ile-Val-Ser-Ile-Phe-Gly-Leu-Cys-Trp-Ala-Pro-Tyr-
Thr-Leu-Leu-Met-Ile-Ile-Arg-Ala-Ala-Cys-His-Gly-Arg-Cys-Ile-Pro-Asp-
Tyr-Trp-Tyr-Glu-Thr-Ser-Phe-Trp-Leu-Leu-Trp-Ala-Asn-Ser-Ala-Val-Asn-
Pro-Val-Leu-Tyr-Pro-Leu-Cys-His-Tyr-Ser-Phe-Arg-Arg-Ala-Phe-Thr-Lys-
Leu-Leu-Cys-Pro-Gln-Lys-Leu-Lys-Val-Gln-Pro-His-Gly-Ser-Leu-Glu-Gln-
Cys-Trp-Lys.
```

The assay measures the activation of G proteins by catalyzing the exchange of guanosine 5'-diphosphate (GDP) by guanosine 5'-triphosphate (GTP) at the α-subunit. The GTP-bounded G proteins dissociate into two subunits, $G\alpha_{GTP}$ and $G_{\beta\gamma}$, which in turn regulate intracellular enzymes and ion channels. GTP is rapidly hydrolysed by the Gα-subunit (GTPases) and the G protein is deactivated and ready for a new GTP exchange cycle. To study the function of ligand induced G protein coupled receptor (GPCR) activation by an increase in guanine nucleotide exchange at the G proteins, the binding of [$^{35}$S]-guanosine-5'-O-(3-thio) triphosphate ([$^{35}$S] GTPγS), a non-hydrolysed analogue of GTP, is determined. This process can be monitored in vitro by incubating cell membranes containing the G protein coupled receptor H3 with GDP and [$^{35}$S] GTPγS. Cell membranes are obtained from CHO cells stably expressing the human H3 receptor or from HEK 293 cells stably expressing the rat or monkey H3 receptor. The cells are washed twice in PBS, harvested with PBS+1 mM EDTA, pH 7.4 and centrifuged at 280 g for 5 min. The cell pellet is homogenized in 10 ml ice-cold Hepes buffer (20 mM Hepes, 10 mM EDTA pH 7.4 (NaOH)) using an Ultra-Turrax homogenizer for 30 seconds and centrifuged for 15 min at 30.000 g. Following this centrifugation step, the membrane pellet is resuspended in 10 ml ice-cold Hepes buffer (20 mM Hepes, 0.1 mM EDTA pH 7.4 (NaOH)) and homogenized as describe above. This procedure is repeated twice except for the last homogenization step, the protein concentration is determined and membranes are diluted to a protein concentration of 2 mg/ml, aliquoted and kept at −80° C. until use.

In order to study the presence and the potency of an inverse agonist/antagonist the H3-receptor agonist ligand R-α-methyl histamine (RAMHA) is added. The ability of the test compound to counteract the effect of RAMHA is measured. When studying the effect of an agonist RAMHA is not added to the assay medium. The test compound is diluted in the assay buffer (20 mM HEPES, 120 mM NaCl, 10 mM MgCl$_2$ pH 7.4 (NaOH)) at various concentrations followed by addition of $10^{-8}$ nM RAMHA (only in the case where an inverse agonist/antagonist is examined), 3 μM GDP, 2.5 μg membranes, 0.5 mg SPA beads and 0.1 nM [$^{35}$S] GTPγS and incubated for 2 hours by slightly shaking at room temperature. For the rat and monkey H3 receptor 10 μg membranes including 10 μg/ml saponin are used. The plates are centrifuged at 420 g for 10 min and the radioactivity is measured using a Top-counter. The results are analyzed by non linear regression and the IC$_{50}$ value is determined.

RAMHA and other H3 agonists stimulate the binding of [$^{35}$S] GTPγS to membranes expressing the H3 receptor. In the antagonist/inverse agonist test, the ability of increasing amounts of test compound to inhibit the increased [$^{35}$S] GTPγS binding by $10^{-8}$ M RAMHA is measured as a decrease in radioactivity signal. The IC$_{50}$ value determined for an antagonist is the ability of this compound to inhibit the effect of $10^{-8}$ M RAMHA by 50%. In the agonist test, the ability of increasing amounts of test compound is measured as an increase in radioactivity signal. The EC$_{50}$ value determined for an agonist, is the ability of this compound to increase the signal by 50% of the maximal signal that is obtained by $10^{-5}$ M RAMHA.

Preferably, the antagonists and agonists according to the invention have an IC$_{50}$/EC$_{50}$ value as determined by one or more of the assays of less than 10 μM, more preferred of less than 1 μM, and even more preferred of less than 500 nM, such as of less than 100 nM.

The Open Cage Schedule-Fed Rat Model

Sprague-Dawley (SD) male rats of an age of about 1½ to 2 months and a weight of about 200–250 g are purchased from Møllegård Breeding and Research Centre A/S (Denmark). On arrival they are allowed some days of acclimatisation before being placed in individual open plastic cages. They are habituated to the presence of food (Altromin pelleted rat chow) in their home cage only during 7 hours in the morning from 07.30 to 14.30 all days a week. Water is present ad libitum. As the consumption of food has stabilised after 7 to 9 days, the animals are ready for use.

Each animal is used only once to avoid carry-over effects between treatments. During the test sessions, the test compound is administered intraperitoneally or orally 30 min before the start of the sessions. One group of animals is administered the test compound at different doses and a control group of animals is given a vehicle. Food and water intake are monitored at 1, 2 and 3 hours post administration.

Any side effects may rapidly be discovered (barrel-rolling, bushy fur etc.) since the animals are kept in transparent plastic cages to enable continuous monitoring.

The invention claimed is:
1. A compound of formula (I):

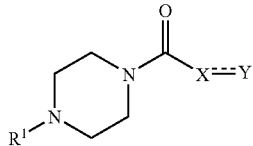

(I)

wherein
- - - - - designates a single bond or a double bond, $R^1$ is $C_{3-8}$-cycloalkyl, $C_{5-8}$-cycloalkenyl, di($C_{3-8}$-cycloalkyl)-$C_{1-6}$-alkyl, $C_{3-8}$-cycloalkyl-$C_{2-6}$-alkenyl, $C_{3-8}$-cycloalkyl-$C_{2-6}$-alkynyl, $C_{5-8}$-cycloalkenyl-$C_{1-6}$-alkyl, $C_{5-8}$-cycloalkenyl-$C_{2-6}$-alkenyl, or $C_{5-8}$-cycloalkenyl-$C_{2-6}$alkynyl, wherein the cyclic moieties may optionally be substituted with one or more substituents selected from the group consisting of $C_{1-6}$-alkyl, halogen, trifluoromethyl, 2,2,2-trifluoroethyl and $C_{3-8}$-cycloalkyl, X is —$(CH_2)$—$(Z)_n$—$(CR^2R^3)_o$—$(CH_2)_p$—$(V)_q$—, p is 0, 1, 2, 3 or 4, n, o and q independently are 0 or 1, Z and V independently are —O—, —C(=O)—, —S—, —S(=O)—, —S(=O)$_2$—, or —C≡C—, $R^2$ and $R^3$ independently are hydrogen, $C_{1-6}$-alkyl or hydroxy, Y is
  aryl which may optionally be substituted with one or more substituents selected from the group consisting of
    halogen, nitro, cyano, hydroxy, $C_{1-7}$-alkanoyl, $C_{1-6}$-alkylthio, $C_{1-6}$-alkylsulfonyl, $C_{1-6}$-alkyl, $C(=O)O$—$C_{1-6}$-alkyl, $C_{3-8}$-cycloalkyl, trifluoromethyl, trifluoromethoxy, —$NR^4R^5$ and —$O(C=O)NR^4R^5$, or wherein two substituents in adjacent positions together form a radical —O—$(CH_2)_{1-3}$—O—,
    wherein $R^4$ and $R^5$ independently are hydrogen, $C_{1-6}$-alkyl, $C_{3-8}$-cycloalkyl, $C_{1-7}$-alkanoyl or aryl, or —$R^4$ and $R^5$ together with the nitrogen atom to which they are attached form a 4 to 7 membered, saturated or unsaturated ring, which in addition to the nitrogen atom consists of carbon atoms as ring members, and
    aryl, aryl-$C_{1-6}$-alkyl, aryloxy and aryl-$C_{1-6}$-alkoxy, wherein the ring moieties optionally may be substituted with one or more substituents selected from the group consisting of
      halogen, nitro, cyano, hydroxy, $C_{1-7}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^6R^7$ and —$O(C=O)NR^6R^7$, or wherein two substituents in adjacent positions together form a radical —O—$(CH_2)_{1-3}$—O—,
      wherein $R^6$ and $R^7$ independently are hydrogen, $C_{1-6}$-alkyl, $C_{3-8}$-cycloalkyl, $C_{1-7}$-alkanoyl or aryl, or —$R^6$ and $R^7$ together with the nitrogen atom to which they are attached form a 4 to 7 membered, saturated or unsaturated ring, which in addition to the nitrogen atom consists of carbon atoms as ring members,
  with the proviso that the sum of n, o, p and q must be at least 1,
  as well as any diastereomer or enantiomer or tautomeric form thereof, mixtures of these or a pharmaceutically acceptable salt thereof.

2. A compound according to claim 1, wherein $R^1$ is $C_{3-8}$ cycloalkyl, which may optionally be substituted with one or two substituents selected from the group consisting of $C_{1-6}$-alkyl and $C_{3-8}$-cycloalkyl.

3. A compound according to claim 2, wherein $R^1$ is 1-ethylcyclopropyl, 1-methylcyclopropyl, cyclopropyl, cyclopentyl or cyclohexyl.

4. A compound according to claim 3, wherein $R^1$ is cyclopropyl, cyclopentyl or cyclohexyl.

5. A compound according to claim 1, wherein $R^1$ is $C_{5-8}$-cycloalkenyl.

6. A compound according to claim 1, wherein X is —$(CH_2)_{2-4}$—, —$(CH_2)_{1-4}$—O—$(CH_2)_{0-4}$—, —$(CH_2)_{1-4}$—S—$(CH_2)_{0-4}$—, —$(CH_2)_{1-4}$—C(=O)—$(CH_2)_{0-4}$—, —$(CH_2)_{1-4}$—CH(OH)—, or —$(CH_2)_{1-4}$—O—$(CH_2)_{1-4}$—O—.

7. A compound according to claim 6, wherein X is —$(CH_2)_{2-4}$—, —$(CH_2)_{1-4}$—O—, —$(CH_2)_{1-4}$—S—$(CH_2)_{1-4}$—$(CH_2)_{1-4}$—S—, or —$(CH_2)_{1-4}$—C(=O)—.

8. A compound according to claim 7, wherein X is —$(CH_2)_2$—, —$(CH_2)_3$—, —$(CH_2)_4$—, —$CH_2$—O—, —$(CH_2)_3$—O—, —$CH_2$—S—$CH_2$—, —$CH_2$—S—, —$(CH_2)_2$—C(=O)— or —$(CH_2)_3$—C(=O)—.

9. A compound according to claim 8, wherein X is —$(CH_2)_3$—, or —$(CH_2)_2$—C(=O)—.

10. A compound according to claim 9, wherein X is —$(CH_2)_3$—.

11. A compound according to claim 9, wherein X is —$(CH_2)_2$—C(=O)—.

12. A compound according to claim 1, wherein Y is phenyl, naphthyl, or indanyl, which may optionally be substituted as defined in claim 1.

13. A compound according to claim 12, wherein Y is phenyl or naphthyl, which may optionally be substituted as defined in claim 1.

14. A compound according to claim 13, wherein Y is phenyl, which may optionally be substituted as defined in claim 1.

15. A compound according to claim 12, wherein Y is unsubstituted or substituted with one or more substituents selected from the group consisting of
  halogen, nitro, cyano, hydroxy, $C_{1-7}$-alkanoyl, $C_{1-6}$-alkylsulfonyl, $C_{1-6}$-alkyl, —$C(=O)O$—$C_{1-6}$-alkyl, $C_{3-8}$-cycloalkyl, trifluoromethyl, trifluoromethoxy, —$NR^4R^5$ and —$O(C=O)NR^4R^5$, or wherein two substituents in adjacent positions together form a radical —O—$(CH_2)_{1-3}$—O—,
    wherein $R^4$ and $R^5$ independently are hydrogen, $C_{1-6}$-alkyl, $C_{3-8}$-cycloalkyl, $C_{1-7}$-alkanoyl or aryl, or —$R^4$ and $R^5$ together with the nitrogen atom to which they are attached form a 4 to 7 membered, saturated or unsaturated ring, which in addition to the nitrogen atom consists of carbon atoms as ring members;
  phenyl, phenoxy and phenyl-$C_{1-6}$-alkoxy, wherein the ring moieties optionally may be substituted with one or more substituents selected from the group consisting of
    halogen, nitro, cyano, hydroxy, $C_{1-7}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^6R^7$ and —$O(C=O)NR^6R^7$, or wherein two substituents in adjacent position form a radical —O—$(CH_2)_{1-3}$—O—,
    wherein $R^6$ and $R^7$ independently are hydrogen, $C_{1-6}$-alkyl, $C_{3-8}$-cycloalkyl, $C_{1-7}$-alkanoyl or aryl, or $R^6$ and $R^7$ together with the nitrogen atom to which they are attached form a 4 to 7 membered, saturated or unsaturated ring, which in addition to the nitrogen atom consists of carbon atoms as ring members.

16. A compound according to claim 15, wherein Y is unsubstituted or substituted with one or more substituents selected from the group consisting of
  halogen, nitro, hydroxy, $C_{1-7}$-alkanoyl, $C_{1-6}$-alkylsulfonyl, $C_{1-6}$-alkyl, $C_{3-8}$-cycloalkyl, trifluoromethyl, trifluoromethoxy, —$NR^4R^5$ and —$O(C=O)NR^4R^5$, or wherein two substituents in adjacent positions together form a radical —O—$(CH_2)_{1-3}$—O—,
    wherein $R^4$ and $R^5$ are $C_{1-6}$alkyl, or —$R^4$ and $R^5$ together with the nitrogen atom to which they are attached form a 4 to 7 membered, saturated or unsaturated ring, which in addition to the nitrogen atom consists of carbon atoms as ring members,
  phenyl and phenyl-$C_{1-6}$-alkoxy, wherein the ring moieties optionally may be substituted with one or more substituents selected from halogen and $C_{1-6}$-alkyl.

17. A compound according to claim 16, wherein Y is unsubstituted or substituted with one to three substituents selected from the group consisting of —$CF_3$, halogen, —$N(C_{1-6}$-alkyl$)_2$, phenyl and 4-fluorophenyl, or wherein two substituents in adjacent positions together form a radical —O—$(CH_2)_{1-3}$—O—.

18. A compound according to claim 17, wherein Y is substituted with one halogen substituent.

19. A compound according to claim 17, wherein Y is substituted with one —$N(C_{1-6}$-alkyl$)_2$ substituent.

20. A pharmaceutical composition comprising, as an active ingredient, at least one compound according to claim 1 together with one or more pharmaceutically acceptable carriers or excipients.

21. A pharmaceutical composition according to claim 20 in unit dosage form, comprising said compound in an amount between about 0.05 mg and about 1000 mg.

22. A pharmaceutical composition according to claim 21, wherein said amount is between about 0.5 mg and about 200 mg.

23. A method for the treatment of a disorder or disease related to the H3 histamine receptor, wherein the disorder or disease is selected from narcolepsy, obesity, and epilepsy, said method comprising administering to a patient in need of such treatment an effective amount for treating said disorder or disease of a compound having the formula (I)

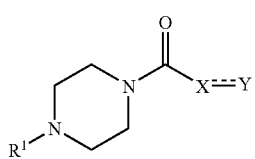

(I)

wherein
- - - - designates a single bond or a double bond, $R^1$ is
$C_{3-8}$-cycloalkyl, $C_{5-8}$-cycloalkenyl, di($C_{3-8}$-cycloalkyl)-$C_{1-6}$-alkyl, $C_{3-8}$-cycloalkyl-$C_{2-6}$-alkenyl, $C_{3-8}$-cycloalkyl-$C_{2-6}$-alkynyl, $C_{5-8}$-cycloalkenyl-$C_{1-6}$-alkyl, $C_{5-8}$-cycloalkenyl-$C_{2-6}$-alkenyl, $C_{5-8}$-cycloalkenyl-$C_{2-6}$alkynyl,
  wherein the cyclic moieties may optionally be substituted with one or more substituents selected from the group consisting of $C_{1-6}$-alkyl, halogen, trifluoromethyl, 2,2,2-trifluoroethyl and $C_{3-8}$-cycloalkyl, X is —$(CH_2)_m$—$(Z)_n$—$(CR^2R^3)_o$—$(CH_2)_p$—$(V)_q$—,
m and p independently are 0, 1, 2, 3 or 4,
n, o and q independently are 0 or 1,
Z and V independently are —O—, —NH—, —C(=O)—, —S—, —S(=O)—, —S(=O)$_2$—, —CH=CH— or —C≡C—,
$R^2$ and $R^3$ independently are hydrogen, $C_{1-6}$-alkyl or hydroxy,
Y is
aryl which may optionally be substituted with one or more substituents selected from the group consisting of
  halogen, nitro, cyano, hydroxy, $C_{1-7}$-alkanoyl, $C_{1-6}$-alkylthio, $C_{1-6}$-alkylsulfonyl, $C_{1-6}$-alkyl, $C_{1-6}$-alkoxy, —C(=O)O—$C_{1-6}$-alkyl, $C_{3-8}$-cycloalkyl, trifluoromethyl, trifluoromethoxy, —$NR^4R^5$ and —O(C=O)$NR^4R^5$, or wherein two substituents in adjacent positions together form a radical —O—$(CH_2)_{1-3}$—O—,
wherein $R^4$ and $R^5$ independently are hydrogen, $C_{1-6}$-alkyl, $C_{3-8}$-cycloalkyl, $C_{1-7}$-alkanoyl or aryl, or —$R^4$ and $R^5$ together with the nitrogen atom to which they are attached form a 4 to 7 membered, saturated or unsaturated ring, which in addition to the nitrogen atom consists of carbon atoms as ring members,
aryl, aryl-$C_{1-6}$-alkyl, aryloxy and aryl-$C_{1-6}$-alkoxy, wherein the ring moieties optionally may be substituted with one or more substituents selected from the group consisting of
  halogen, nitro, cyano, hydroxy, $C_{1-7}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^6R^7$ and —O(C=O)$NR^6R^7$, or wherein two substituents in adjacent positions together form a radical —O—$(CH_2)_{1-3}$—O—,
wherein $R^6$ and $R^7$ independently are hydrogen, $C_{1-6}$-alkyl, $C_{3-8}$-cycloalkyl, $C_{1-7}$-alkanoyl or aryl, or —$R^6$ and $R^7$ together with the nitrogen atom to which they are attached form a 4 to 7 membered, saturated or unsaturated ring, which in addition to the nitrogen atom consists of carbon atoms as ring members, with the proviso that the sum of m, n, o, p and q must be at least 1,
as well as any diastereomer or enantiomer or tautomeric form thereof, mixtures of these or a pharmaceutically acceptable salt thereof.

24. The method according to claim 23, wherein said disorder or disease is obesity.

25. The method according to claim 23, wherein said disorder or disease is narcolepsy.

26. The method according to claim 23 wherein the effective amount is between about 0.05 mg and about 2000 mg per day.

27. The method according to claim 26, wherein the effective amount is between about 0.1 mg and about 1000 mg per day.

28. The method according to claim 27, wherein the effective amount is between about 0.5 mg to about 500 mg per day.

* * * * *

SEQUENCE LISTING

```
<160> NUMBER OF SEQ ID NOS: 3

<210> SEQ ID NO 1
<211> LENGTH: 445
<212> TYPE: PRT
<213> ORGANISM: Homo sapiens

<400> SEQUENCE: 1

Met Glu Arg Ala Pro Pro Asp Gly Pro Leu Asn Ala Ser Gly Ala Leu
1               5                   10                  15

Ala Gly Glu Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
            35                  40                  45

Val Leu Gly Asn Ala Leu Val Met Leu Ala Phe Val Ala Asp Ser Ser
            50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
                100                 105                 110

Val Asp Tyr Leu Leu Cys Thr Ser Ser Ala Phe Asn Ile Val Leu Ile
            115                 120                 125

Ser Tyr Asp Arg Phe Leu Ser Val Thr Arg Ala Val Ser Tyr Arg Ala
130                 135                 140

Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
            180                 185                 190

Phe Tyr Asn Trp Tyr Phe Leu Ile Thr Ala Ser Thr Leu Glu Phe Phe
            195                 200                 205

Thr Pro Phe Leu Ser Val Thr Phe Phe Asn Leu Ser Ile Tyr Leu Asn
        210                 215                 220

Ile Gln Arg Arg Thr Arg Leu Arg Leu Asp Gly Ala Arg Glu Ala Ala
225                 230                 235                 240

Gly Pro Glu Pro Pro Pro Glu Ala Gln Pro Ser Pro Pro Pro Pro Pro
                245                 250                 255

Gly Cys Trp Gly Cys Trp Gln Lys Gly His Gly Glu Ala Met Pro Leu
            260                 265                 270

His Arg Tyr Gly Val Gly Glu Ala Ala Val Gly Ala Glu Ala Gly Glu
```

-continued

```
                 275                 280                 285
Ala Thr Leu Gly Gly Gly Gly Gly Ser Val Ala Ser Pro Thr
    290                 295                 300
Ser Ser Ser Gly Ser Ser Ser Arg Gly Thr Glu Arg Pro Arg Ser Leu
305                 310                 315                 320
Lys Arg Gly Ser Lys Pro Ser Ala Ser Ser Ala Ser Leu Glu Lys Arg
                325                 330                 335
Met Lys Met Val Ser Gln Ser Phe Thr Gln Arg Phe Arg Leu Ser Arg
                340                 345                 350
Asp Arg Lys Val Ala Lys Ser Leu Ala Val Ile Val Ser Ile Phe Gly
            355                 360                 365
Leu Cys Trp Ala Pro Tyr Thr Leu Leu Met Ile Ile Arg Ala Ala Cys
    370                 375                 380
His Gly His Cys Val Pro Asp Tyr Trp Tyr Glu Thr Ser Phe Trp Leu
385                 390                 395                 400
Leu Trp Ala Asn Ser Ala Val Asn Pro Val Leu Tyr Pro Leu Cys His
                405                 410                 415
His Ser Phe Arg Arg Ala Phe Thr Lys Leu Leu Cys Pro Gln Lys Leu
            420                 425                 430
Lys Ile Gln Pro His Ser Ser Leu Glu His Cys Trp Lys
        435                 440                 445

<210> SEQ ID NO 2
<211> LENGTH: 445
<212> TYPE: PRT
<213> ORGANISM: Monkey

<400> SEQUENCE: 2

Met Glu Arg Ala Pro Pro Asp Gly Pro Leu Asn Ala Ser Gly Ala Leu
1               5                   10                  15
Ala Gly Glu Ala Ala Ala Gly Gly Ala Arg Gly Phe Ser Ala Ala
            20                  25                  30
Trp Thr Ala Val Leu Ala Ala Leu Met Ala Leu Leu Ile Val Ala Thr
        35                  40                  45
Val Leu Gly Asn Ala Leu Val Met Leu Ala Phe Val Ala Asp Ser Ser
    50                  55                  60
Leu Arg Thr Gln Asn Asn Phe Phe Leu Leu Asn Leu Ala Ile Ser Asp
65                  70                  75                  80
Phe Leu Val Gly Ala Phe Cys Ile Pro Leu Tyr Val Pro Tyr Val Leu
                85                  90                  95
Thr Gly Arg Trp Thr Phe Gly Arg Gly Leu Cys Lys Leu Trp Leu Val
                100                 105                 110
Val Asp Tyr Leu Leu Cys Thr Ser Ser Ala Phe Asn Ile Val Leu Ile
            115                 120                 125
Ser Tyr Asp Arg Phe Leu Ser Val Thr Arg Ala Val Ser Tyr Arg Ala
        130                 135                 140
Gln Gln Gly Asn Thr Arg Arg Ala Val Arg Lys Met Leu Leu Val Trp
145                 150                 155                 160
Val Leu Ala Phe Leu Leu Tyr Gly Pro Ala Ile Leu Ser Trp Glu Tyr
                165                 170                 175
Leu Ser Gly Gly Ser Ser Ile Pro Glu Gly His Cys Tyr Ala Glu Phe
            180                 185                 190
Phe Tyr Asn Trp Tyr Phe Leu Ile Thr Ala Ser Thr Leu Glu Phe Phe
        195                 200                 205
```

Thr Pro Phe Leu Ser Val Thr Phe Asn Leu Ser Ile Tyr Leu Asn
210                 215                 220

Ile Gln Arg Arg Thr Arg Leu Arg Leu Asp Gly Ala Arg Glu Ala Gly
225                 230                 235                 240

Gly Pro Glu Pro Pro Glu Ala Gln Pro Ser Pro Pro Pro Pro
                245                 250                 255

Gly Cys Trp Gly Cys Trp Gln Lys Gly His Gly Glu Ala Met Pro Leu
                260                 265                 270

His Arg Tyr Gly Val Gly Glu Ala Ala Gly Ala Glu Ala Gly Glu
                275                 280                 285

Thr Ala Leu Gly Gly Gly Gly Gly Ser Ala Ala Ser Pro Thr
290                 295                 300

Ser Ser Ser Gly Ser Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
                325                 330                 335

Met Lys Met Val Ser Gln Ser Phe Thr Gln Arg Phe Arg Leu Ser Arg
                340                 345                 350

Asp Arg Lys Val Ala Lys Ser Leu Ala Val Ile Val Ser Ile Phe Gly
                355                 360                 365

Leu Cys Trp Ala Pro Tyr Thr Leu Leu Met Ile Ile Arg Ala Ala Cys
370                 375                 380

His Gly His Cys Val Pro Asp Tyr Trp Tyr Glu Thr Ser Phe Trp Leu
385                 390                 395                 400

Leu Trp Ala Asn Ser Ala Val Asn Pro Val Leu Tyr Pro Leu Cys His
                405                 410                 415

His Ser Phe Arg Arg Ala Phe Thr Lys Leu Leu Cys Pro Gln Lys Leu
                420                 425                 430

Lys Ile Gln Pro His Ser Ser Leu Glu Gln Cys Trp Lys
                435                 440                 445

<210> SEQ ID NO 3
<211> LENGTH: 445
<212> TYPE: PRT
<213> ORGANISM: Rat

<400> SEQUENCE: 3

Met Glu Arg Ala Pro Pro Asp Gly Leu Met Asn Ala Ser Gly Thr Leu
1               5                   10                  15

Ala Gly Glu Ala Ala Ala Ala Gly Gly Ala Arg Gly Phe Ser Ala Ala
                20                  25                  30

Trp Thr Ala Val Leu Ala Ala Leu Met Ala Leu Leu Ile Val Ala Thr
                35                  40                  45

Val Leu Gly Asn Ala Leu Val Met Leu Ala Phe Val Ala Asp Ser Ser
50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
                100                 105                 110

Val Asp Tyr Leu Leu Cys Ala Ser Ser Val Phe Asn Ile Val Leu Ile
                115                 120                 125

Ser Tyr Asp Arg Phe Leu Ser Val Thr Arg Ala Val Ser Tyr Arg Ala
130                 135                 140

```
Gln Gln Gly Asp Thr Arg Arg Ala Val Arg Lys Met Ala Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
            180                 185                 190

Phe Tyr Asn Trp Tyr Phe Leu Ile Thr Ala Ser Thr Leu Glu Phe Phe
            195                 200                 205

Thr Pro Phe Leu Ser Val Thr Phe Phe Asn Leu Ser Ile Tyr Leu Asn
        210                 215                 220

Ile Gln Arg Arg Thr Arg Leu Arg Leu Asp Gly Gly Arg Glu Ala Gly
225                 230                 235                 240

Pro Glu Pro Pro Pro Asp Ala Gln Pro Ser Pro Pro Pro Ala Pro Pro
                245                 250                 255

Ser Cys Trp Gly Cys Trp Pro Lys Gly His Gly Glu Ala Met Pro Leu
            260                 265                 270

His Arg Tyr Gly Val Gly Glu Ala Gly Pro Gly Val Glu Ala Gly Glu
            275                 280                 285

Ala Ala Leu Gly Gly Gly Ser Gly Gly Gly Ala Ala Ala Ser Pro Thr
        290                 295                 300

Ser Ser Ser Gly Ser Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
                325                 330                 335

Met Lys Met Val Ser Gln Ser Ile Thr Gln Arg Phe Arg Leu Ser Arg
            340                 345                 350

Asp Lys Lys Val Ala Lys Ser Leu Ala Ile Ile Val Ser Ile Phe Gly
        355                 360                 365

Leu Cys Trp Ala Pro Tyr Thr Leu Leu Met Ile Ile Arg Ala Ala Cys
370                 375                 380

His Gly Arg Cys Ile Pro Asp Tyr Trp Tyr Glu Thr Ser Phe Trp Leu
385                 390                 395                 400

Leu Trp Ala Asn Ser Ala Val Asn Pro Val Leu Tyr Pro Leu Cys His
                405                 410                 415

Tyr Ser Phe Arg Arg Ala Phe Thr Lys Leu Leu Cys Pro Gln Lys Leu
            420                 425                 430

Lys Val Gln Pro His Gly Ser Leu Glu Gln Cys Trp Lys
435                 440                 445
```